United States Patent
Buckmelter et al.

(10) Patent No.: US 11,535,618 B2
(45) Date of Patent: Dec. 27, 2022

(54) FUSED PYRROLINES WHICH ACT AS UBIQUITIN-SPECIFIC PROTEASE 30 (USP30) INHIBITORS

(71) Applicant: FORMA Therapeutics, Inc., Watertown, MA (US)

(72) Inventors: Alex J. Buckmelter, Acton, MA (US); Justin Andrew Caravella, Cambridge, MA (US); Hongbin Li, Newtown, CT (US); Matthew W. Martin, Arlington, MA (US); Steven Mischke, Waltham, MA (US); David James Richard, Littleton, MA (US); Angela V. West, Franklin, MA (US)

(73) Assignee: FORMA Therapeutics, Inc., Watertown, MA (US)

( * ) Notice: Subject to any disclaimer, the term of this patent is extended or adjusted under 35 U.S.C. 154(b) by 0 days.

(21) Appl. No.: 17/282,521

(22) PCT Filed: Oct. 4, 2019

(86) PCT No.: PCT/US2019/054803
§ 371 (c)(1),
(2) Date: Apr. 2, 2021

(87) PCT Pub. No.: WO2020/072964
PCT Pub. Date: Apr. 9, 2020

(65) Prior Publication Data
US 2021/0355126 A1 Nov. 18, 2021

Related U.S. Application Data

(60) Provisional application No. 62/741,945, filed on Oct. 5, 2018.

(51) Int. Cl.
| | | |
|---|---|---|
| C07D 471/18 | (2006.01) | |
| C07D 403/12 | (2006.01) | |
| C07D 471/08 | (2006.01) | |
| C07D 487/08 | (2006.01) | |
| C07D 487/18 | (2006.01) | |
| C07D 491/107 | (2006.01) | |

(52) U.S. Cl.
CPC ......... *C07D 471/18* (2013.01); *C07D 403/12* (2013.01); *C07D 471/08* (2013.01); *C07D 487/08* (2013.01); *C07D 487/18* (2013.01); *C07D 491/107* (2013.01)

(58) Field of Classification Search
None
See application file for complete search history.

(56) References Cited

U.S. PATENT DOCUMENTS

| | | |
|---|---|---|
| 6,376,515 B2 | 4/2002 | Zhu et al. |
| 6,576,632 B1 | 6/2003 | Goldstein et al. |
| 6,632,815 B2 | 10/2003 | Zhu et al. |
| 6,835,727 B2 | 12/2004 | Okamoto et al. |
| 7,425,354 B2 | 9/2008 | Yanai et al. |
| 7,687,504 B2 | 3/2010 | Jiaang et al. |
| 7,807,691 B2 | 10/2010 | Gavardinas et al. |
| 7,910,741 B2 | 3/2011 | Nishizawa et al. |
| 8,329,708 B2 | 12/2012 | Sim et al. |
| 8,815,924 B2 | 8/2014 | Dorsch et al. |
| 9,393,244 B2 | 7/2016 | Moussa |
| 9,511,142 B2 | 12/2016 | Burns et al. |
| 9,550,792 B2 | 1/2017 | Lu et al. |
| 9,926,307 B2 | 3/2018 | Jones et al. |
| 9,938,272 B2 | 4/2018 | Ding et al. |
| 9,997,717 B2 | 6/2018 | Kawamura et al. |
| 10,590,109 B2 | 3/2020 | Kong et al. |
| 10,615,343 B2 | 4/2020 | Stoessel et al. |
| 11,247,987 B2 | 2/2022 | Caravella et al. |
| 2003/0191279 A1 | 10/2003 | Goldstein et al. |
| 2009/0264499 A1 | 10/2009 | Deng et al. |
| 2016/0264548 A1 | 9/2016 | Qiu et al. |
| 2017/0247365 A1 | 8/2017 | Jones et al. |
| 2018/0228923 A1 | 8/2018 | Lai et al. |

(Continued)

FOREIGN PATENT DOCUMENTS

| | | |
|---|---|---|
| CN | 101838264 A | 9/2010 |
| CN | 104045552 A | 9/2014 |

(Continued)

OTHER PUBLICATIONS

Ahmed, H.E.A. and Bajorath, J., Methods for Computer-Aided Chemical Biology, Part 5: Rationalizing the Selectivity of Cathepsin Inhibitors on the Basis of Molecular Fragments and Topological Feature Distributions, Chemical Biology & Drug Design, (74): 129-141 (2009).

Bingol, B. et al., The mitochondrial deubiquitinase USP30 opposes parkin—mediated mitophagy, Nature, 510:370-375 (2014).

Buus, R. et al., Deubiquitinase Activities Required for Hepatocyte Growth Factor-Induced Scattering of Epithelial Cells, Current Bio., 19:1463-1466 (2009).

(Continued)

*Primary Examiner* — Samantha L Shterengarts
(74) *Attorney, Agent, or Firm* — Choate, Hall & Stewart LLP; John P. Rearick; Erica M. D'Amato

(57) ABSTRACT

The disclosure relates to USP30 Inhibitor Compounds I, pharmaceutically acceptable salts thereof, pharmaceutical compositions comprising same, and medical uses involving same. (I)

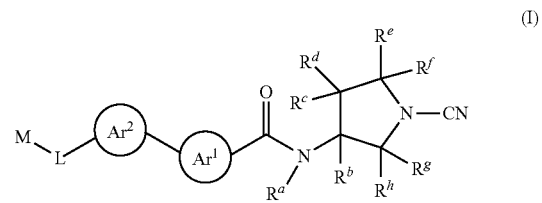

21 Claims, No Drawings

(56) References Cited

U.S. PATENT DOCUMENTS

| | | |
|---|---|---|
| 2020/0317658 A1 | 10/2020 | Caravella et al. |
| 2021/0198263 A1 | 7/2021 | Martin et al. |
| 2022/0185806 A1 | 6/2022 | Caravella et al. |

FOREIGN PATENT DOCUMENTS

| | | |
|---|---|---|
| CN | 104557862 A | 4/2015 |
| CN | 106986859 A | 7/2017 |
| CN | 107619384 A | 1/2018 |
| DE | 102004054666 A1 | 5/2006 |
| EP | 3590931 A1 | 1/2020 |
| GB | 2424881 A | 10/2006 |
| JP | 2009/108152 A | 5/2009 |
| JP | 2009/149754 A | 7/2009 |
| JP | 2010/066630 A | 3/2010 |
| JP | 2011/006360 A | 1/2011 |
| JP | 2011/042606 A | 3/2011 |
| JP | 2012/123292 A | 6/2012 |
| JP | 5057056 B2 | 10/2012 |
| JP | 5219583 B2 | 6/2013 |
| JP | 5443720 B2 | 3/2014 |
| JP | 2014/232188 A | 12/2014 |
| JP | 5899607 B2 | 4/2016 |
| KR | 1077417 B1 | 10/2011 |
| KR | 1715090 B1 | 3/2017 |
| WO | WO-2001/019788 A2 | 3/2001 |
| WO | WO-2001/019798 A2 | 3/2001 |
| WO | WO-2001/029007 A1 | 4/2001 |
| WO | WO-2001/064642 A2 | 9/2001 |
| WO | WO-2001/064643 A2 | 9/2001 |
| WO | WO-2001/077073 A1 | 10/2001 |
| WO | WO-2002/046159 A1 | 6/2002 |
| WO | WO-2002/051831 A1 | 7/2002 |
| WO | WO-2003/007955 A2 | 1/2003 |
| WO | WO-2003/020217 A2 | 3/2003 |
| WO | WO-2004/002481 A1 | 1/2004 |
| WO | WO-2004/014370 A2 | 2/2004 |
| WO | WO-2004/014902 A2 | 2/2004 |
| WO | WO-2004/080966 A1 | 9/2004 |
| WO | WO-2004/085385 A2 | 10/2004 |
| WO | WO-2004/110350 A2 | 12/2004 |
| WO | WO-2005/000300 A1 | 1/2005 |
| WO | WO-2005/019200 A2 | 3/2005 |
| WO | WO-2005/044797 A1 | 5/2005 |
| WO | WO-2005/077345 A1 | 8/2005 |
| WO | WO-2005/077368 A2 | 8/2005 |
| WO | WO-2005/077373 A2 | 8/2005 |
| WO | WO-2005/080379 A1 | 9/2005 |
| WO | WO-2005/112540 A2 | 12/2005 |
| WO | WO-2005/115374 A1 | 12/2005 |
| WO | WO-2005/115382 A1 | 12/2005 |
| WO | WO-2006/014185 A1 | 2/2006 |
| WO | WO-2006/015279 A1 | 2/2006 |
| WO | WO-2006/024034 A1 | 3/2006 |
| WO | WO-2006/027076 A1 | 3/2006 |
| WO | WO-2006/045350 A1 | 5/2006 |
| WO | WO-2006/063113 A2 | 6/2006 |
| WO | WO-2006/074445 A2 | 7/2006 |
| WO | WO-2006/076202 A1 | 7/2006 |
| WO | WO-2006/113261 A2 | 10/2006 |
| WO | WO-2006/129199 A1 | 12/2006 |
| WO | WO-2007/024744 A2 | 3/2007 |
| WO | WO-2007/061923 A2 | 5/2007 |
| WO | WO-2007/144202 A1 | 12/2007 |
| WO | WO-2007/144204 A1 | 12/2007 |
| WO | WO-2007/146838 A2 | 12/2007 |
| WO | WO-2008/028553 A1 | 3/2008 |
| WO | WO-2008/035209 A2 | 3/2008 |
| WO | WO-2008/071456 A2 | 6/2008 |
| WO | WO-2008/073670 A2 | 6/2008 |
| WO | WO-2008/079291 A2 | 7/2008 |
| WO | WO-2008/141976 A1 | 11/2008 |
| WO | WO-2009/010156 A2 | 1/2009 |
| WO | WO-2009/011850 A2 | 1/2009 |
| WO | WO-2009/047105 A1 | 4/2009 |
| WO | WO-2009/078992 A1 | 6/2009 |
| WO | WO-2009/089042 A1 | 7/2009 |
| WO | WO-2009/129371 A1 | 10/2009 |
| WO | WO-2009/158571 A1 | 12/2009 |
| WO | WO-2010/048149 A2 | 4/2010 |
| WO | WO-2010/075376 A2 | 7/2010 |
| WO | WO-2011/025706 A2 | 3/2011 |
| WO | WO-2011/031934 A1 | 3/2011 |
| WO | WO-2011/053825 A2 | 5/2011 |
| WO | WO-2011/103091 A1 | 8/2011 |
| WO | WO-2011/126903 A2 | 10/2011 |
| WO | WO-2011/143495 A1 | 11/2011 |
| WO | WO-2011/161446 A1 | 12/2011 |
| WO | WO-2012/016217 A1 | 2/2012 |
| WO | WO-2012/078855 A1 | 6/2012 |
| WO | WO-2012/083048 A2 | 6/2012 |
| WO | WO-2012/083059 A2 | 6/2012 |
| WO | WO-2012/129562 A2 | 9/2012 |
| WO | WO-2012/139425 A1 | 10/2012 |
| WO | WO-2012/160015 A1 | 11/2012 |
| WO | WO-2012/166951 A1 | 12/2012 |
| WO | WO-2012/177782 A1 | 12/2012 |
| WO | WO-2012/177997 A1 | 12/2012 |
| WO | WO-2013/046136 A1 | 4/2013 |
| WO | WO-2013/052845 A1 | 4/2013 |
| WO | WO-2013/086229 A1 | 6/2013 |
| WO | WO-2013/106678 A1 | 7/2013 |
| WO | WO-2013/130890 A1 | 9/2013 |
| WO | WO-2013/132991 A1 | 9/2013 |
| WO | WO-2013/178816 A1 | 12/2013 |
| WO | WO-2013/182274 A1 | 12/2013 |
| WO | WO-2013/190212 A1 | 12/2013 |
| WO | WO-2014/000846 A1 | 1/2014 |
| WO | WO-2014/041111 A1 | 3/2014 |
| WO | WO-2014/068527 A1 | 5/2014 |
| WO | WO-2014/072261 A1 | 5/2014 |
| WO | WO-2014/108053 A1 | 7/2014 |
| WO | WO-2014/140059 A1 | 9/2014 |
| WO | WO-2014/159733 A1 | 10/2014 |
| WO | WO-2014/165232 A1 | 10/2014 |
| WO | WO-2015/003816 A2 | 1/2015 |
| WO | WO-2015/010297 A1 | 1/2015 |
| WO | WO-2015/011284 A2 | 1/2015 |
| WO | WO-2015/048547 A2 | 4/2015 |
| WO | WO-2015/048662 A2 | 4/2015 |
| WO | WO-2015/058832 A1 | 4/2015 |
| WO | WO-2015/085238 A1 | 6/2015 |
| WO | WO-2015/095104 A1 | 6/2015 |
| WO | WO-2015/106292 A1 | 7/2015 |
| WO | WO-2015/130790 A2 | 9/2015 |
| WO | WO-2015/173225 A1 | 11/2015 |
| WO | WO-2015/176625 A1 | 11/2015 |
| WO | WO-2015/189646 A1 | 12/2015 |
| WO | WO-2015/197028 A1 | 12/2015 |
| WO | WO-2016/007534 A1 | 1/2016 |
| WO | WO-2016/008011 A1 | 1/2016 |
| WO | WO-2016/016366 A1 | 2/2016 |
| WO | WO-2016/034262 A1 | 3/2016 |
| WO | WO-2016/040449 A1 | 3/2016 |
| WO | WO-2016/046530 A1 | 3/2016 |
| WO | WO-2016/109559 A2 | 7/2016 |
| WO | WO-2016/156816 A1 | 10/2016 |
| WO | WO-2016/172631 A2 | 10/2016 |
| WO | WO-2017/002120 A1 | 1/2017 |
| WO | WO-2017/009650 A1 | 1/2017 |
| WO | WO-2017/010399 A1 | 1/2017 |
| WO | WO-2017/019817 A1 | 2/2017 |
| WO | WO-2017/019822 A1 | 2/2017 |
| WO | WO-2017/019830 A1 | 2/2017 |
| WO | WO-2017/040194 A1 | 3/2017 |
| WO | WO-2017/040982 A1 | 3/2017 |
| WO | WO-2017/066705 A1 | 4/2017 |
| WO | WO-2017/093718 A1 | 6/2017 |
| WO | WO-2017/100558 A1 | 6/2017 |
| WO | WO-2017/103614 A1 | 6/2017 |
| WO | WO-2017/109488 A1 | 6/2017 |
| WO | WO-2017/141036 A1 | 8/2017 |
| WO | WO-2017/149313 A1 | 9/2017 |
| WO | WO-2017/158381 A1 | 9/2017 |

(56) References Cited

FOREIGN PATENT DOCUMENTS

| | | |
|---|---|---|
| WO | WO-2017/158388 A1 | 9/2017 |
| WO | WO-2017/161028 A1 | 9/2017 |
| WO | WO-2017/162007 A1 | 9/2017 |
| WO | WO-2017/163078 A1 | 9/2017 |
| WO | WO-2018/005591 A1 | 1/2018 |
| WO | WO-2018/010514 A1 | 1/2018 |
| WO | WO-2018/024188 A1 | 2/2018 |
| WO | WO-2018/039896 A1 | 3/2018 |
| WO | WO-2018/060689 A1 | 4/2018 |
| WO | WO-2018/060691 A1 | 4/2018 |
| WO | WO-2018/060742 A1 | 4/2018 |
| WO | WO-2018/065768 A1 | 4/2018 |
| WO | WO-2018/106818 A1 | 6/2018 |
| WO | WO-2018/106820 A1 | 6/2018 |
| WO | WO-2018/134352 A1 | 7/2018 |
| WO | WO-2018/146116 A1 | 8/2018 |
| WO | WO-2018/157856 A1 | 9/2018 |
| WO | WO-2018/160891 A1 | 9/2018 |
| WO | WO-2018/213150 A1 | 11/2018 |
| WO | WO-2018/220355 A1 | 12/2018 |
| WO | WO-2018/234775 A1 | 12/2018 |
| WO | WO-2019/071073 A1 | 4/2019 |
| WO | WO-2019/171042 A1 | 9/2019 |
| WO | WO-2019/222468 A1 | 11/2019 |
| WO | WO-2020/036940 A1 | 2/2020 |
| WO | WO-2020/072964 A1 | 4/2020 |
| WO | WO-2020/212350 A1 | 10/2020 |
| WO | WO-2020/212351 A1 | 10/2020 |
| WO | WO-2021/043870 A1 | 3/2021 |
| WO | WO-2021/050992 A1 | 3/2021 |

OTHER PUBLICATIONS

Dovlatyan, M. et al., A High-Content Live Imaging Mitophagy Assay to Evaluate Small Molecule Mitophagy Enhancers, Poster Abstract (Board No. B555) presented at ASCB EMBO (Dec. 2017).

Durcan, T. M. and Edward, A. F., The three 'P's of mitophagy: PARKIN, PINK1, and post-translational modifications, Genes and Development, 29:989-999 (2015).

International Search Report for PCT/US2018/054520, 4 pages (dated Feb. 5, 2019).

International Search Report for PCT/US2019/032619, 5 pages (dated Jul. 16, 2019).

International Search Report for PCT/US2019/054803, 6 pages (dated Nov. 27, 2019).

Iwashita, H. et al., Live Cell Imaging of Mitochondrial Autophagy with a Novel Fluorescent Small Molecule, ACS Chem. Biol., 12:2546-2551 (2017).

Ji, Y. et al., Innate C-H Trifluoromethylation of Heterocycles, PNAS, 108(35):14411-14415 (2011).

Kluge, A. F. et al., Novel Highly Selective Inhibitors of Ubiquitin Specific Protease 30 (USP30) Accelerate Mitophagy, Bioorg. and Medic. Chem. Lett., 28(15):2655-2659 (2018).

Lainé, D., et al., Discovery of Novel Cyanamide-Based Inhibitors of Cathepsin C, ACS Med. Chem. Lett., 2:142-147 (2011).

McWilliams, T. G. et al., mit-QC illuminates mitophagy and mitochondrial architecture in vivo, J. Cell Biol., 214:333-345 (2016).

Nakamura, N. and Hirose, S., Regulation of Mitochondrial Morphology by USP30, a Deubiquitinating Enzyme Present in the Mitochondrial Outer Membrane, Mole. Bio. Cell., 19:1903-1911 (2008).

Ndubaku, C. and Tsui, V., Inhibiting the Deubiquitinating Enzymes (DUBs), Jrnl. Med. Chem., 58:1581-1595 (2015).

Pollock, S.R., and Kashatus, D.F., A novel role for RalA during PINK1-Parkin mitophagy, Poster Abstract (Board No. B3252) presented at ASCB EMBO (Dec. 2017).

PubChem CID 116045277, (3-Methylcyclobutyl)cyanamide, 2 pages, Date Created: Jan. 30, 2016, Date Modified: Aug. 8, 2020.

PubChem CID 116214356, (1-Ethylcyclobutyl)cyanamide, 2 pages, Date Created: Jan. 30, 2016, Date Modified: Aug. 8, 2020.

PubChem CID 21516572, (1-Methylcyclopropyl)cyanamide, 7 pages, Date Created: Dec. 5, 2007, Date Modified: Apr. 18, 2020.

Puri, R. et al., Mitochondrial Ubiquitin Ligase Mul1 Mediates an Early Stress Protection of Neuronal Mitochondria From Degradation by Parkin-Mediated Mitophagy, Poster Abstract (Board No. B482) presented at ASCB EMBO (Dec. 2017).

Rusilowicz-Jones, E. et al., A novel USP30 inhibitor recapitulates genetic loss of USP30 and sets the trigger for PINK1-PARKIN amplicfication of mitochondrial ubiquitylation, bioRxiv, doi: https://doi.org/10.1101/2020.04.16.044206, 1-35 (posted Apr. 20, 2020).

Rusilowicz-Jones, E. et al., USP30 sets a trigger threshold for PINK1-PARKIN amplification of mitochondrial ubiquitylation, Life Sci. Alli., 3(8):1-14 (2020).

Rusilowicz-Jones, E. V. et al., Benchmarking a highly selective USP30 inhibitor for enhancement of mitophagy and pexophagy, bioRxiv, doi:https://doi.org/10.1101/2021.04.28.441730, 1-19 (posted Apr. 28, 2021).

Sathe, M. et al., Efficient synthesis of N-cyano $\alpha$ and $\beta$-amino esters, Synthetic Communications: An International Journal for Rapid Communication of Synthetic Organic Chemistry, 38: 1375-1380 (2008).

Seiberlich, V. et al., The small molecule inhibitor PR-619 of deubiquitinating enzymes affects the microtubule network and causes protein aggregate formation in neural cells: Implications for neurodegenerative diseases, Biochem Biophys Acta., 1823 (11):2057-2068 (2012).

Silverman, R., "The Organic Chemistry of Drug Design and Drug Action", NY Elsevier, 29-32 (2004).

Thompson, J. E. et al., Discovery of MF-0094, a potent, selective and cell permeable inhibitor of USP30, Poster (2017).

Deaton, D. N. et al., Novel and potent cyclic cyanamide-based cathepsin K inhibitors, Bioorg. Med. Chem. Lett., 15:1815-1819 (2005).

FUSED PYRROLINES WHICH ACT AS UBIQUITIN-SPECIFIC PROTEASE 30 (USP30) INHIBITORS

CROSS REFERENCE TO RELATED APPLICATIONS

The present application is a U.S. National Stage Application of PCT/US19/54803, filed Oct. 4, 2019, which claims priority to U.S. Provisional Patent Application No. 62/741,945, filed Oct. 5, 2018, the entire contents of each of which are hereby incorporated by reference.

TECHNICAL FIELD

This disclosure relates to inhibiting Ubiquitin-Specific Protease 30 (USP30), including novel compounds and methods for inhibiting USP30. The compounds and related methods are useful in the field of medicine including the development of new therapies (e.g., for the treatment of conditions related to the therapeutic inhibition of USP30 such as Parkinson's Disease (PD)).

BACKGROUND

The ubiquitination system is a highly regulated process which affects a wide variety of cellular activities and physiological processes. Ubiquitination is a reversible process, facilitated by a group of proteins known as deubiquitinating enzymes (DUBs), which deconjugate ubiquitin (Ub) from the substrate. DUBs are encoded by approximately 100 human genes and are divided into six families, with the largest family being the ubiquitin-specific proteases (USPs) with more than 50 members.

Ubiquitination regulates mitochondrial dynamics and biogenesis, affecting the abundance and function of these organelles. Mitochondria serve many functions to maintain cell health in mammals, including generating ATP. As mitochondria age they become damaged, losing their metabolic functionality, and begin releasing pro-apoptotic proteins. Mitochondria self-regulate their quality via the mechanism of mitophagy, which is the selective removal of damaged mitochondria from the cell. Ubiquitination of mitochondrial proteins is believed to contribute to mitochondrial dynamics in mammalian cells, possibly by "flagging" those proteins for inactivation. Ubiquitin-Specific Protease 30 (USP30) is embedded in the outer membrane of mitochondria, where it participates in the maintenance of mitochondrial morphology. It is believed that over-expression of USP30 can lead to a decrease in mitophagy.

Inactivating mutations in PINK1 and Parkin can impair mitophagy and result in accumulation of damaged mitochondria and neuronal toxicity, which has been implicated in Parkinson's Disease. USP30 opposes the ligase activity of Parkin and is a negative regulator of mitophagy. USP30 inhibition is expected to promote mitophagy and restore mitochondrial health.

SUMMARY

The disclosure provides compounds useful for inhibiting USP30, including USP30 Inhibitor Compounds as defined herein. In some embodiments, the disclosure provides a compound of formula (I):

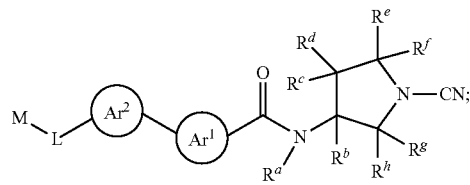

or a pharmaceutically acceptable salt thereof, wherein $R^a$, $R^b$, $R^c$, $R^d$, $R^e$, $R^f$, $R_g$ and $R^h$ are defined as follows:

(i) $R^a$ and $R^b$ form a $C_1$-$C_4$ alkylene group between the atoms to which they are attached, wherein said $C_1$-$C_4$ alkylene group is substituted with 0-4 substituents selected from the group consisting of halogen, $C_1$-$C_3$ alkyl, and $C_1$-$C_3$ haloalkyl; and $R^c$, $R^d$, $R^e$, $R^f$, $R^g$, and $R^h$ are each independently hydrogen, halogen, $C_1$-$C_3$ alkyl, or $C_1$-$C_3$ haloalkyl; or (ii) $R^a$ and $R^e$ form a $C_1$-$C_2$ alkylene group between the atoms to which they are attached, wherein said $C_1$-$C_2$ alkylene group is substituted with 0-4 substituents selected from the group consisting of halogen, $C_1$-$C_3$ alkyl, and $C_1$-$C_3$ haloalkyl; and $R^b$, $R^c$, $R^d$, $R^f$, $R^g$, and $R^h$ are each independently hydrogen, halogen, $C_1$-$C_3$ alkyl, or $C_1$-$C_3$ haloalkyl; or (iii) $R^a$ and $R^g$ form a $C_1$-$C_3$ alkylene group between the atoms to which they are attached, wherein said $C_1$-$C_3$ alkylene group is substituted with 0-4 substituents selected from the group consisting of halogen, $C_1$-$C_3$ alkyl, and $C_1$-$C_3$ haloalkyl; and $R^b$, $R^c$, $R^d$, $R^e$, $R^f$, and $R^h$ are each independently hydrogen, halogen, $C_1$-$C_3$ alkyl, or $C_1$-$C_3$ haloalkyl; or (iv) $R^h$ and $R^c$ form a $C_1$-$C_4$ alkylene group between the atoms to which they are attached, wherein said $C_1$-$C_4$ alkylene group is substituted with 0-4 substituents selected from the group consisting of halogen, $C_1$-$C_3$ alkyl, and $C_1$-$C_3$ haloalkyl; and $R^a$, $R^d$, $R^e$, $R^f$, $R^g$, and $R^h$ are each independently hydrogen, halogen, $C_1$-$C_3$ alkyl, or $C_1$-$C_3$ haloalkyl; or (v) $R^b$ and $R^c$ form a $C_1$-$C_3$ alkylene group between the atoms to which they are attached, wherein said $C_1$-$C_3$ alkylene group is substituted with 0-4 substituents selected from the group consisting of halogen, $C_1$-$C_3$ alkyl, and $C_1$-$C_3$ haloalkyl; and $R^a$, $R^e$, $R^d$, $R^f$, $R^g$, and $R^h$ are each independently hydrogen, halogen, $C_1$-$C_3$ alkyl, or $C_1$-$C_3$ haloalkyl; or (vi) $R^b$ and $R^g$ form a $C_1$-$C_4$ alkylene group between the atoms to which they are attached, wherein said $C_1$-$C_4$ alkylene group is substituted with 0-4 substituents selected from the group consisting of halogen, $C_1$-$C_3$ alkyl, and $C_1$-$C_3$ haloalkyl; and $R^a$, $R^e$, $R^d$, $R^e$, $R^f$, and $R^h$ are each independently hydrogen, halogen, $C_1$-$C_3$ alkyl, or $C_1$-$C_3$ haloalkyl; or (vii) $R^c$ and $R^d$ together with the atom to which they are attached, form a 3-6 membered cycloalkyl or heterocycloalkyl, wherein said 3-6 membered cycloalkyl or heterocycloalkyl is substituted with 0-4 substituents selected from the group consisting of halogen, $C_1$-$C_3$ alkyl, and $C_1$-$C_3$ haloalkyl; and $R^a$, $R^b$, $R^e$, $R^f$, $R^g$, and $R^h$ are each independently hydrogen, halogen, $C_1$-$C_3$ alkyl, or $C_1$-$C_3$ haloalkyl; or (viii) $R^c$ and $R^d$ together form =O; and $R^d$, $R^b$, $R^e$, $R^f$, $R^g$, and $R^h$ are each independently hydrogen, halogen, $C_1$-$C_3$ alkyl, or $C_1$-$C_3$ haloalkyl; or (ix) $R^c$ and $R^e$ form a $C_1$-$C_4$ alkylene group between the atoms to which they are attached, wherein said $C_1$-$C_4$ alkylene group is substituted with 0-4 substituents selected from the group consisting of halogen, $C_1$-$C_3$ alkyl, and $C_1$-$C_3$ haloalkyl; and $R^a$, $R^b$, $R^d$, $R^f$, $R^g$, and $R^h$ are each independently hydrogen, halogen, $C_1$-$C_3$ alkyl, or $C_1$-$C_3$ haloalkyl; or (x) $R^c$ and $R^g$ form a $C_1$-$C_3$ alkylene group between the atoms to which they are attached, wherein said $C_1$-$C_3$ alkylene group is substituted with 0-4 substituents selected from the group consisting of halogen, $C_1$-$C_3$ alkyl, and $C_1$-$C_3$ haloalkyl, and $R^a$, $R^b$, $R^d$, $R^e$, $R^f$, and $R^h$ are each independently hydrogen, halogen, $C_1$-$C_3$ alkyl, or $C_1$-$C_3$ haloalkyl; or (xi) $R^e$ and $R^f$ together with the atom to which they are attached, form a 3-6 membered cycloalkyl or heterocycloalkyl, wherein said 3-6 membered cycloalkyl or heterocycloalkyl is substituted with 0-4 substituents selected from the group consisting of halogen, $C_1$-$C_3$ alkyl, and $C_1$-$C_3$ haloalkyl; and $R^a$, $R^b$, $R^c$, $R^d$, $R^g$, and $R^h$ are each independently hydrogen, halogen, $C_1$-$C_3$ alkyl, or $C_1$-$C_3$ haloalkyl; or (xii) $R^c$ and $R^f$ together form =O; and $R^a$, $R^b$, $R^c$, $R^d$, $R^g$, and $R^h$ are each independently hydrogen, halogen, $C_1$-$C_3$ alkyl, or $C_1$-$C_3$ haloalkyl; or (xiii) $R^e$ and $R^g$ form a $C_1$-$C_3$ alkylene group between the atoms to which they are attached, wherein said $C_1$-$C_3$ alkylene group is substituted with 0-4 substituents selected from the group consisting of halogen, $C_1$-$C_3$ alkyl, and $C_1$-$C_3$ haloalkyl; and $R^a$, $R^b$, $R^c$, $R^d$, $R^f$, and $R^h$ are each independently hydrogen, halogen, $C_1$-$C_3$ alkyl, or $C_1$-$C_3$ haloalkyl; or (xiv) $R^g$ and $R^h$ together with the atom to which they are attached, form a 3-6 membered cycloalkyl or heterocycloalkyl, wherein said 3-6 membered cycloalkyl or heterocycloalkyl is substituted with 0-4 substituents selected from the group consisting of halogen, $C_1$-$C_3$ alkyl, and $C_1$-$C_3$ haloalkyl; and $R^a$, $R^b$, $R^c$, $R^d$, $R^e$, and $R^f$ are each independently hydrogen, halogen, $C_1$-$C_3$ alkyl, or $C_1$-$C_3$ haloalkyl; or (xv) $R^g$ and $R^h$ together form =O; and $R^a$, $R^b$, $R^c$, $R^d$, $R^e$, and $R^f$ are each independently hydrogen, halogen, $C_1$-$C_3$ alkyl, or $C_1$-$C_3$ haloalkyl; and $Ar^1$ is phenylene or 5-6 membered heteroarylene, wherein said phenylene or heteroarylene is substituted with m groups; and $Ar^2$ is phenylene or 5-10 membered heteroarylene, wherein said phenylene or heteroarylene is substituted with n $R^2$ groups;

L is —O—, —S—, —$NR^3$—, —$C(R^4)_2$—, —$S(O)_2$—, or —S(O)—;

M is $C_1$-$C_6$ alkyl, $C_1$-$C_6$ haloalkyl, 3-6 membered cycloalkyl, phenyl, or 5-6 membered heteroaryl, wherein said cycloalkyl, phenyl, or heteroaryl is substituted with p $R^5$ groups;

each occurrence of $R^1$, $R^2$, and $R^5$ is independently halo, cyano, $NO_2$, oxo, hydroxyl, —$R^6$, —$OR^6$, $C_1$-$C_6$ alkyl, $C_1$-$C_6$ haloalkyl, $C_1$-$C_6$ hydroxyalkyl, —$C_1$-$C_6$ alkylene-$R^6$, $C_1$-$C_6$ alkoxy, $C_1$-$C_6$ haloalkoxy, —$C_0$-$C_3$ alkylene-$NR^6R^7$, —$C_0$-$C_3$ alkylene-$NR^7R^8$, —$C_0$-$C_3$ alkylene-$C(O)NR^6R^7$, —$C_0$-$C_3$ alkylene-$C(O)NR^7W$, —$C_0$-$C_3$ alkylene-$NR^7C(O)R^6$, —$C_0$-$C_3$ alkylene-$NR^7C(O)W$, —$C_0$-$C_3$ alkylene-$NR^7S(O)_2R^6$, —$C_0$-$C_3$ alkylene-$C(O)R^6$, —$C_0$-$C_3$ alkylene-$C(O)R^7$, —$C_0$-$C_3$ alkylene-$SR^6$, —$C_0$-$C_3$ alkylene-$S(O)R^6$, —$C_0$-$C_3$ alkylene-$S(O)_2R^6$, —$C_0$-$C_3$ alkylene-$S(O)_2R^7$, —$C_0$-$C_3$ alkylene-$S(O)_2NR^6R^7$, —$C_0$-$C_3$ alkylene-$S(O)_2NR^7R^8$, —$C_0$-$C_3$ alkylene-$NR^7C(O)NR^8R^9$, —$C_0$-$C_3$ alkylene-$NR^7S(O)_2NR^8R^9$, —$C_0$-$C_3$ alkylene-$C(O)OR^7$, —$C_0$-$C_3$ alkylene-$C(O)OR^6$, —$C_0$-$C_3$ alkylene-$OC(O)R^7$, —$C_0$-$C_3$ alkylene-$OC(O)R^6$, —$C_0$-$C_3$ alkylene-$NR^7C(O)OR^8$, or —$C_0$-$C_3$ alkylene-$NR^7S(O)_2R^8$;

$R^3$ is H, $C_1$-$C_6$ alkyl, or $C_1$-$C_6$ haloalkyl;

each $R^4$ is independently H, $C_1$-$C_6$ alkyl, or $C_1$-$C_6$ haloalkyl, or two $R^4$ groups together with the carbon atom to which they are attached form a 3-6 membered cycloalkyl or heterocycloalkyl;

each $R^6$ is independently 5-10 membered heteroaryl, 4-10 membered heterocycloalkyl, 6-10 membered aryl, or 3-8 membered cycloalkyl, wherein said heteroaryl, heterocycloalkyl, aryl, or cycloalkyl is optionally substituted with 1-5 substituents independently selected from the group consisting of halo, oxo, $C_1$-$C_6$ alkyl, $C_1$-$C_6$ haloalkyl, $C_1$-$C_6$ hydroxyalkyl, $C_1$-$C_6$ alkoxy, $C_1$-$C_6$ haloalkoxy, $C_2$-$C_6$ alkenyl, $C_2$-$C_6$ alkynyl, 5-10 membered heteroaryl, 4-10 membered heterocycloalkyl, 6-10 membered aryl, 3-8 membered cycloalkyl, —$NR^{10}C(O)NR^{11}R^{12}$, —$NR^{10}R^{11}$, —$C(O)R^{10}$, —$NR^{10}C(O)R^{11}$, —$NR^{10}C(O)OR^{11}$, —$S(O)_2R^{10}$, —$C(O)NR^{10}R^{11}$, —$C(O)OR^{10}$, —$S(O)_2NR^{10}R^{11}$, —$NR^{10}S(O)_2R^{11}$, —$OR^{10}$, —$OC(O)R^{10}$, —$OS(O)_2R^{10}$, —$OC(O)NR^{10}R^{11}$, —$OC(O)OR^{10}$, —$OS(O)_2NR^{10}R^{11}$, —$C(O)NR^{10}C(O)NR^{11}R^{12}$, —$C(O)C(O)R^{10}$, —$C(O)NR^{10}C(O)R^{11}$, —$C(O)NR^{10}C(O)OR^{11}$, —$C(O)S(O)_2R^{10}$, —$C(O)C(O)NR^{10}R^{11}$, —$C(O)C(O)OR^{10}$, —$C(O)S(O)_2NR^{10}R^{11}$, —$C(O)NR^{10}S(O)_2R^{11}$, —$C_1$-$C_6$ alkylene-$R^{10}$, —$C_1$-$C_6$ alkylene-$NR^{10}C(O)NR^{11}R^{12}$, —$C_1$-$C_6$ alkylene-$NR^{10}NR^{11}$, —$C_1$-$C_6$ alkylene-$C(O)R^{10}$, —$C_1$-$C_6$ alkylene-$NR^{10}C(O)R^{11}$, —$C_1$-$C_6$ alkylene-$NR^{10}C(O)OR^{11}$, —$C_1$-$C_6$ alkylene-$S(O)_2R^{10}$, —$C_1$-$C_6$ alkylene-$C(O)NR^{10}R^{11}$, —$C_1$-$C_6$ alkylene-$C(O)OR^{10}$, —$C_1$-$C_6$ alkylene-$S(O)_2NR^{10}R^{11}$, —$C_1$-$C_6$ alkylene-$NR^{10}S(O)_2R^{11}$, —$C_1$-$C_6$ alkenylene-$R^{10}$, —$C_1$-$C_6$ alkenylene-$NR^{10}C(O)NR^{11}10^2$, —$C_1$-$C_6$ alkenylene-$NR^{10}R^{11}$, —$C_1$-$C_6$ alkenylene-$C(O)R^{10}$, —$C_1$-$C_6$ alkenylene-$NR^{10}C(O)R^{11}$, —$C_1$-$C_6$ alkenylene-$NR^{10}C(O)OR^{11}$, —$C_1$-$C_6$ alkenylene-$S(O)_2R^{10}$, —$C_1$-$C_6$ alkenylene-$C(O)NR^{10}R^{11}$, —$C_1$-$C_6$ alkenylene-$C(O)OR^{10}$, —$C_1$-$C_6$ alkenylene-$S(O)_2NR^{10}R^{11}$, and —$C_1$-$C_6$ alkenylene-$NR^{10}S(O)_2R^{11}$;

each $R^7$, $R^8$, and $R^9$ is independently hydrogen or $C_1$-$C_6$ alkyl;

each $R^{10}$, $R^{11}$, and $R^{12}$ is independently hydrogen, $C_1$-$C_6$ alkyl, 5-10 membered heteroaryl, 4-10 membered heterocycloalkyl, 6-10 membered aryl, or 3-8 membered cycloalkyl;

m is 0-4;

n is 0-4; and p is 0-4.

In some embodiments, the disclosure provides a compound of formula (I-C):

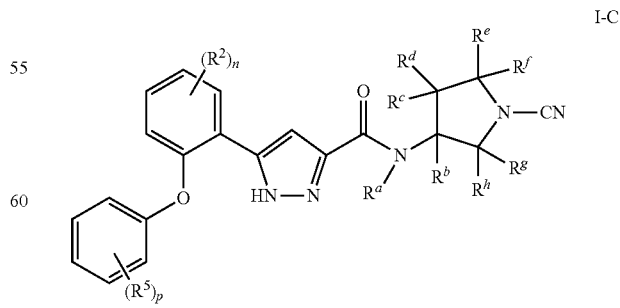

or a pharmaceutically acceptable salt thereof, wherein $R^2$, $R^5$, n, $R^a$, $R^b$, $R^c$, $R^d$, $R^e$, $R^f$, $R^g$, and $R^h$ are all as defined for formula (I) above and described in classes and subclasses herein for formula (I), both singly and in combination.

In some embodiments, a USP30 Inhibitor Compound is a compound selected from the group consisting of:

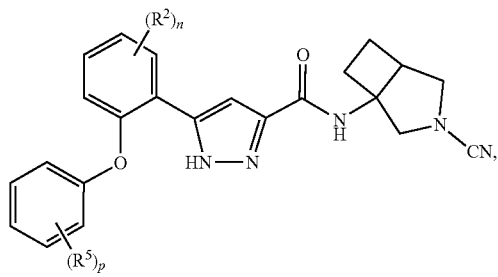

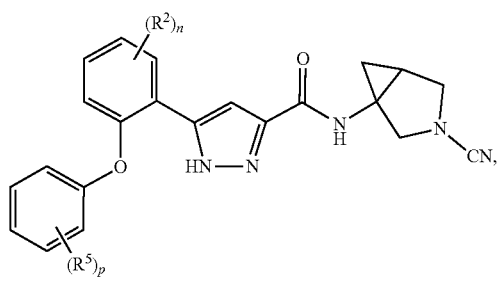

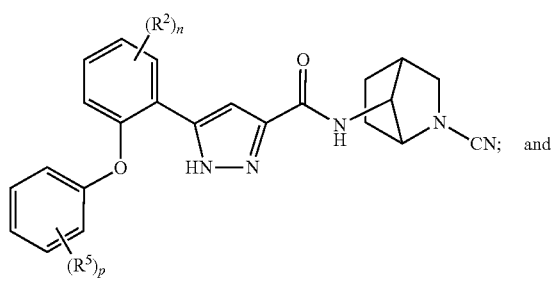 and

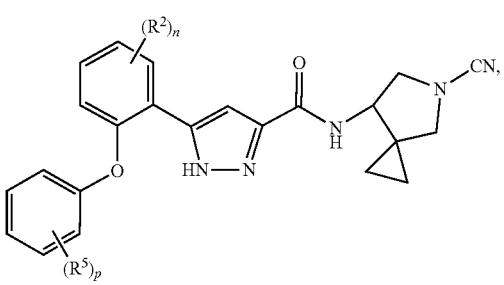

wherein $R^2$, $R^5$, n, and p are as defined with respect to formula (I) herein, or a pharmaceutically acceptable salt thereof, having an $IC_{50}$ value of about ≤1 µM (and preferably ≤0.5 µM or ≤0.1 04) and >0.001 µM as measured in a Ubiquitin-Rhodamine 110 Assay as described in Example 1. In some embodiments, compounds of formula (I-C) are provided where $R^2$ and $R^5$ are both hydrogen.

In some embodiments, a USP30 Inhibitor Compound is a compound of the chemical formula:

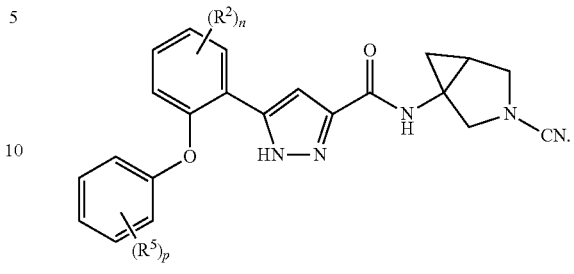

wherein $R^2$, $R^5$, n, and p are as defined with respect to formula (I) herein, or a pharmaceutically acceptable salt thereof, having an $IC_{50}$ value of about ≤1 µM (and preferably ≤0.5 µM or ≤0.1 µM) and >0.001 µM as measured in a Ubiquitin-Rhodamine 110 Assay as described in Example 1.

In some embodiments, a compound is any compound selected from the compounds listed in Table 1 herein.

DETAILED DESCRIPTION

The present disclosure relates to compounds of formula (I), as defined herein, pharmaceutically acceptable salts thereof, pharmaceutical compositions comprising same, and medical uses involving same. In some embodiments, the compounds of formula (I) are USP30 Inhibitor Compounds. In other embodiments, the compounds of formula (I) are useful, for example, as analytical tools and/or control compounds in biological assays (e.g., compounds of any of the following aspects and embodiments that are not USP30 Inhibitor Compounds).

USP30 Inhibitor Compounds are useful in the development of new therapies for Parkinson's disease (PD), and in methods of treating diseases or conditions by inhibiting USP30 (such as PD). Parkin (E3 ubiquitin ligase) and PINK1 (kinase) are key regulators of mitophagy. In healthy mitochondria, PINK1 localization to the mitochondrial outer membrane (MOM) and exposure to the cytosol is limited by rapid import to the mitochondrial inner membrane (MIM). Once localized to the MIM, PINK1 is processed by several proteases, such as presenilin associated rhomboid-like protease (PARL), to yield a truncated version of PINK1 which is subsequently degraded by the proteasome (Meissner et al., Autophagy. 2015, 11(9), 1484-1498). Upon mitochondrial depolarization or dysfunction, PINK1 accumulates in the MOM, recruiting and activating Parkin via PINK1-dependent phosphorylation of both ubiquitin and Parkin. Consequently, activated Parkin ubiquitinates MOM proteins like TOMM20 to trigger mitophagy (Pickrell et al., Neuron. 2015, 85(2), 257-273). USP30 is embedded in the MOM with its catalytic DUB domain oriented towards the cytosol and has been shown to antagonize Parkin-mediated ubiquitination of common substrates, consequently opposing Parkin-mediated mitophagy. Genetic silencing of USP30 results in increased ubiquitination of several Parkin substrates followed by increased mitophagy. In model organisms, USP30 depletion is able to rescue mitophagy defects caused by pathogenic Parkin mutations, as well as restore mitochondria morphology and function, and dopamine levels. (Nakamura, et al., Mol Biol Cell. 2008, 19(5), 1903-1911; Bingol, et al., Nature 2014, 510(7505):370-5). Therefore, inhibition of USP30 with a compound disclosed herein could present a novel treatment paradigm for PD by promoting mitochondrial turnover.

Definitions

As used herein, the term "alkyl" means a substituted or unsubstituted hydrocarbon chain that is completely saturated, including straight-chain alkyl groups and branched-chain alkyl groups, and that has a single point of attachment to the rest of the molecule. In some embodiments, a straight chain or branched chain alkyl has about 1-20 carbon atoms in its backbone (e.g., $C_1$-$C_{20}$ for straight chain, $C_2$-$C_{20}$ for branched chain), and alternatively, about 1-10. In some embodiments, an alkyl has about 1-8 carbon atoms. In some embodiments, an alkyl has about 1-6 carbon atoms. In some embodiments, an alkyl has about 1-5 carbon atoms. In some embodiments, an alkyl has about 1-4 carbon atoms. In some embodiments, an alkyl has about 1-3 carbon atoms. In some embodiments, an alkyl has about 1-2 carbon atoms.

As used herein, the term "alkylene" refers to a bivalent alkyl group. Exemplary alkylenes include —$CH_2$—, —$CH_2CH_2$—, —$CH(CH_3)$—, —$CH_2CH(CH_3)$—, —$CH(CH_3)CH_3)$—, etc. In some embodiments, an "alkylene chain" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent.

As used herein, the term "alkenyl" refers to an alkyl group, as defined herein, having one or more double bonds.

As used herein, the term "alkenylene" refers to a bivalent alkenyl group. A substituted alkenylene chain is a polymethylene group containing at least one double bond in which one or more hydrogen atoms are replaced with a substituent.

As used herein, the term "alkynyl" refers to an alkyl group, as defined herein, having one or more triple bonds.

The term "aryl" refers to ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present disclosure, "aryl" refers to an aromatic ring system and exemplary groups include phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The term "arylene" refers to a bivalent aryl group (e.g., phenylene).

As used herein, the term "cycloalkyl" refers to a cyclic alkyl group (e.g., a monocyclic alkyl group or a bicyclic alkyl group). In some embodiments, "cycloalkyl" refers to a monocyclic $C_3$-$C_8$ cycloalkyl group. In some embodiments, "cycloalkyl" refers to a monocyclic $C_3$-$C_6$ cycloalkyl group.

The terms "halogen" or "halo" mean F, Cl, Br, or I.

The term "heteroaryl" refer to groups having 5 to 10 ring atoms, preferably 5, 6, or 9 ring atoms; having 6, 10, or 14 π electrons shared in a cyclic array; and having, in addition to carbon atoms, from one to five heteroatoms wherein the term "heteroatom" refers to nitrogen, oxygen, or sulfur, and includes any oxidized form of nitrogen or sulfur, and any quaternized form of a basic nitrogen. Exemplary heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The term "heteroaryl", as used herein, also includes groups in which a heteroaromatic ring is fused to one or more aryl, cycloaliphatic, or heterocyclyl rings, where the radical or point of attachment is on the heteroaromatic ring. Examplary groups include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted.

The term "heteroarylene" refers to a bivalent heteroaryl group.

As used herein, the term "heterocycloalkyl" refers to a stable 3- to 7-membered monocyclic or 7- to 10-membered bicyclic cyclic moiety that is saturated and having, in addition to carbon atoms, one or more, preferably one to four, heteroatoms independently selected from nitrogen, oxygen, and sulfur, including any oxidized form of nitrogen or sulfur, and any quaternized form of a basic nitrogen. As an example, in a saturated ring having 1-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl). A heterocycloalkyl ring can be attached to its pendant group at any heteroatom or carbon atom that results in a stable structure and any of the ring atoms can be optionally substituted. Examples of such heterocycloalkyl radicals include tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The term "heterocycloalkyl" also includes groups in which a heterocycloalkyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocycloalkyl ring.

As used herein, a "USP30 Inhibitor Compound" refers to a compound having an IC50 of about 1 micromolar or less (i.e., an $IC_{50}$ value of ≤1 μM and >0.001 μM) in the Ubiquitin-Rhodamine 110 Assay for USP30 as described in Example 1 herein. For example, a USP30 Inhibitor can be a compound of formula (I) having an $IC_{50}$ value of ≤0.5 μM and >0.001 μM when tested in the Biochemical Assay of Example 1. In some embodiments, a USP30 Inhibitor is a compound of formula (I) having an $IC_{50}$ value of ≤0.1 μM and >0.001 μM when tested in the Biochemical Assay of Example 1.

As used herein, the term "pharmaceutically acceptable salt" refers to salts of such compounds that are appropriate for use in pharmaceutical contexts, i.e., salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977).

Unless otherwise stated, all chemical structures and chemical names depicted herein without stereochemical descriptors shall be understood to include all stereoisomeric (e.g., enantiomeric or diastereomeric) forms of the compound depicted by the structure or name, as well as all geometric and conformational isomeric forms of the compound; for example, the R and S configurations for each stereocenter. Unless otherwise stated, such structures and names shall be understood to include a stereochemically pure form of the compound and any mixture of enantiomers, diastereomers, or geometric (or conformational) isomers. Unless otherwise stated, all tautomeric forms of the compounds of the disclosure are within the scope of the disclosure.

Unless otherwise stated, all chemical structures and chemical names depicted herein with stereochemical descriptors (i.e., hash and wedge bonds in the chemical structures; (R)- and (S)-designators in the chemical names) shall be understood to refer to a compound having the relative stereochemistry (but not necessarily the absolute stereochemistry) indicated by the stereochemical descriptors. Unless otherwise stated, such structures and names shall be understood to include an enantiomerically pure form of the compound having the relative stereochemistry indicated by the stereochemical descriptors or any mixture of enantiomers. In some embodiments, the enantiomers are present in a racemic mixture. In other embodiments, the enantiomer having the absolute stereochemistry suggested by the stereochemical descriptors is present in substantially enantiomerically pure form. In other embodiments, the enantiomer having the absolute stereochemistry opposite to that suggested by the stereochemical descriptors is present in substantially enantiomerically pure form.

Unless otherwise stated, all chemical structures and chemical names depicted herein with stereochemical descriptors (i.e., hash and wedge bonds in the chemical structures; (R)- and (S)-designators in the chemical names) and an "absolute" descriptor ("abs") shall be understood to refer to a compound having the absolute stereochemistry indicated by the stereochemical descriptors. Unless otherwise stated, such structures and names shall be understood to include the compound in enantiomerically pure form or in a mixture with its enantiomer. In some embodiments, the enantiomers are present in a racemic mixture. In other embodiments, the enantiomer having the absolute stereochemistry indicated by the stereochemical descriptors is present in substantially enantiomerically pure form.

Unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this disclosure.

It will be appreciated that throughout the present disclosure, unless otherwise indicated, reference to a compound of formula (I) is intended to also include formulas I-1, I-2, I-3, I-4, I-A, I-A-1, I-A-2, I-A-3, I-A-4, I-B, I-B-1, I-B-2, I-B-3, I-B-4, I-C, I-C-1, I-C-2, I-C-3, I-C-4, I-C-a, I-C-b, I-C-c, I-C-d, I-C-e, I-C-f, I-D, I-E, I-E-1, I-E-2, I-E-3, I-E-4, I-F-1, I-F-2, I-G-1, I-G-2, I-H-1, I-H-2, I-J-1, I-J-2, I-K-1, I-K-2, I-L-1, I-L-2, I-M, I-M-1, I-M-2, I-M-3, and I-M-4, and compound species of such formulas disclosed herein.

Compounds of the Disclosure

In one aspect, the disclosure relates to a compound of formula (I):

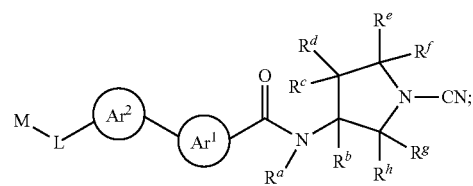

or a pharmaceutically acceptable salt thereof, wherein $Ar^1$, $Ar^2$, M, L, $R^a$, $R^b$, $R^c$, $R^d$, $R^e$, $R^f$, $R^g$, and $R^h$ are all as defined for formula (I) above.

In some embodiments, the present disclosure provides compounds, or pharmaceutically acceptable salts thereof, of formula (I-1):

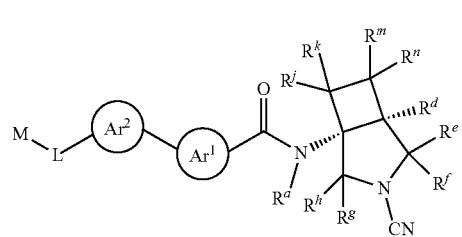

wherein $Ar^1$, $Ar^2$, M, L, $R^a$, $R^d$, $R^e$, $R^f$, $R^g$, and $R^h$ are all as defined for formula (I) above and described in classes and subclasses herein for formula (I), both singly and in combination, and wherein $R^j$, $R^k$, $R^l$, and Rn are each independently hydrogen, halogen, $C_1$-$C_3$ alkyl, or $C_1$-$C_3$ haloalkyl.

In some embodiments, the present disclosure provides compounds, or pharmaceutically acceptable salts thereof, of formula (I-2):

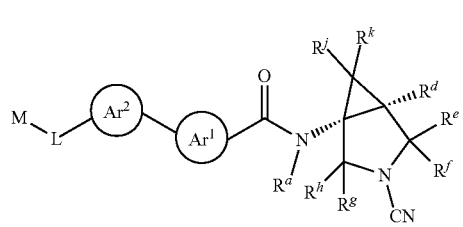

wherein $Ar^1$, $Ar^2$, M, L, $R^a$, $R^d$, $R^e$, $R^f$, $R^g$, and $R^h$ are all as defined for formula (I) above and described in classes and subclasses herein for formula (I), both singly and in combination, and wherein $R^j$ and $R^k$ are each independently hydrogen, halogen, $C_1$-$C_3$ alkyl, or $C_1$-$C_3$ haloalkyl.

In some embodiments, the present disclosure provides compounds, or pharmaceutically acceptable salts thereof, of formula (I-3)

I-3 wherein $Ar^1$, $Ar^2$, M, L, $R^a$, $R^d$, $R^e$, $R^f$, $R^g$, and $R^h$ are all as defined for formula (I) above and described in classes and subclasses herein for formula (I), both singly and in combination, and wherein $R^j$, $R^k$, $R^m$, $R^n$, $R^o$, and $R^p$ are each independently hydrogen, halogen, $C_1$-$C_3$ alkyl, or $C_1$-$C_3$ haloalkyl.

In some embodiments, the present disclosure provides compounds, or pharmaceutically acceptable salts thereof, of formula (I-4)

I-4 wherein $Ar^1$, $Ar^2$, M, L, $R^a$, $R^b$, $R^d$, $R^f$, $R_g$ and $R^h$ are all as defined for formula (I) above and described in classes and subclasses herein for formula (I), both singly and in combination, and wherein $R^q$ and $R^r$ are each independently hydrogen, halogen, $C_1$-$C_3$ alkyl, or $C_1$-$C_3$ haloalkyl.

In another aspect, the disclosure relates to a compound of formula (I-A):

I-A or a pharmaceutically acceptable salt thereof, wherein:
$X^1$ is C or N;
$X^2$ is CH, $CR^1$, O, S, N, NH, or $NR^1$, as valency permits;
$X^3$ is CH, $CR^1$, O, S, N, NH, or $NR^1$, as valency permits;
$X^4$ is C or N;
$X^5$ is a bond, CH, $CR^1$, O, S, N, NH, or $NR^1$, as valency permits;

$X^6$ is CH, $CR^1$, O, S, N, NH, or $NR^1$, as valency permits;
$Y^1$ is C or N;
$Y^2$ is C or N;
$Y^3$ is CH, $CR^2$, O, S, N, NH, or $NR^2$, as valency permits;
$Y^4$ is a bond, CH, $CR^2$, O, S, N, NH, or $NR^2$, as valency permits;
$Y^5$ is CH, $CR^2$, O, S, N, NH, or $NR^2$, as valency permits;
$Y^6$ is CH, $CR^2$, O, S, N, NH, or $NR^2$, as valency permits,
provided that the ring comprising $X^1$, $X^2$, $X^3$, $X^4$, $X^5$, and $X^6$ is aromatic, and
that the ring comprising $Y^1$, $Y^2$, $Y^3$, $Y^4$, $Y^5$ and $Y^6$ is aromatic;

and wherein L, M, $R^1$, $R^2$, $R^5$, $R^a$, $R^b$, $R^c$, $R^d$, $R^e$, $R^f$, $R^g$, and $R^h$ are are all as defined for formula (I) above and described in classes and subclasses herein for formula (I), both singly and in combination.

In some embodiments, the present disclosure provides compounds, or pharmaceutically acceptable salts thereof, of formula (I-A-1):

I-A-1 wherein M, L, $X^1$, $X^2$, $X^3$, $X^4$, $X^5$, $X^6$, $Y^1$, $Y^2$, $Y^3$, $Y^4$, $Y^5$, $R^a$, $R^d$, $R^e$, $R^f$, $R^g$, and $R^h$ are all as defined for formula (I-A) above and described in classes and subclasses herein for formula (I-A), both singly and in combination, and wherein $R^j$, $R^k$, $R^m$, and $R^n$ are each independently hydrogen, halogen, $C_1$-$C_3$ alkyl, or $C_1$-$C_3$ haloalkyl.

In some embodiments, the present disclosure provides compounds, or pharmaceutically acceptable salts thereof, of formula (I-A-2):

I-A-2 wherein M, L, $X^1$, $X^2$, $X^3$, $X^4$, $X^5$, $X^6$, $Y^1$, $Y^2$, $Y^3$, $Y^4$, $Y^5$, $Y^6$, $R^a$, $R^d$, $R^e$, $R^f$, $R^g$ and $R^h$ are all as defined for formula (I-A) above and described in classes and subclasses herein for formula (I-A), both singly and in combination, and wherein $R^j$ and $R^k$ are each independently hydrogen, halogen, $C_1$-$C_3$ alkyl, or $C_1$-$C_3$ haloalkyl.

In some embodiments, the present disclosure provides compounds, or pharmaceutically acceptable salts thereof, of formula (I-A-3):

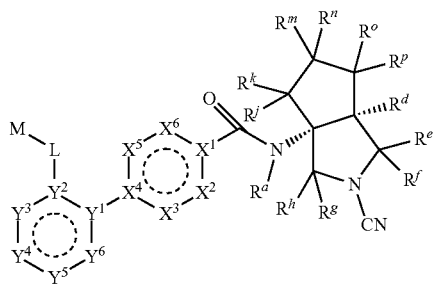

I-A-3 wherein M, L, $X^1$, $X^2$, $X^3$, $X^4$, $X^5$, $X^6$, $Y^1$, $Y^2$, $Y^3$, $Y^4$, $Y^5$, $Y^6$, $R^a$, $R^d$, $R^e$, $R^f$, $R^g$, and $R^h$ are all as defined for formula (I-A) above and described in classes and subclasses herein for formula (I-A), both singly and in combination, and wherein $R^j$, $R^k$, $R^m$, $R^n$, $R^o$, and $R^p$ are each independently hydrogen, halogen, $C_1$-$C_3$ alkyl, or $C_1$-$C_3$ haloalkyl.

In some embodiments, the present disclosure provides compounds, or pharmaceutically acceptable salts thereof, of formula (I-A-4):

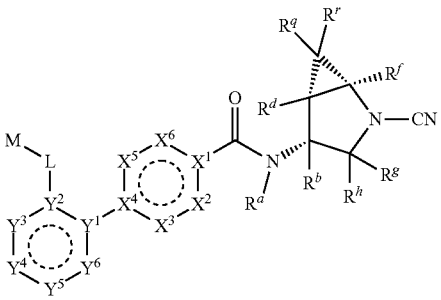

I-A-4 wherein M, L, $X^1$, $X^2$, $X^3$, $X^4$, $X^5$, $X^6$, $Y^1$, $Y^2$, $Y^4$, $Y^6$, $R^a$, $R^b$, $R^d$, $R^f$, $R^g$ and $R^h$ are all as defined for formula (I-A) above and described in classes and subclasses herein for formula (I-A), both singly and in combination, and wherein $R^q$ and $R^r$ are each independently hydrogen, halogen, $C_1$-$C_3$ alkyl, or $C_1$-$C_3$ haloalkyl.

In another aspect, the disclosure relates to a compound of formula (I-B):

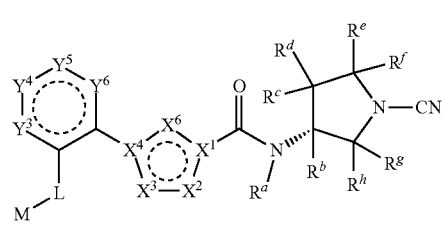

I-B or a pharmaceutically acceptable salt thereof, wherein:

$Y^3$ is CH, $CR^2$, or N;

$Y^4$ is CH, $CR^2$, or N;

$Y^5$ is CH, $CR^2$, or N;

$Y^6$ is CH, $CR^2$, or N; and wherein $X^1$, $X^2$, $X^3$, $X^4$, $X^6$, L, M, $R^a$, $R^b$, $R^c$, $R^d$, $R^e$, $R^f$, $R^g$ and $R^h$ are all as defined for formula (I) above and described in classes and subclasses herein for formula (I-A), both singly and in combination.

In some embodiments, the present disclosure provides compounds, or pharmaceutically acceptable salts thereof, of formula (I-B-1):

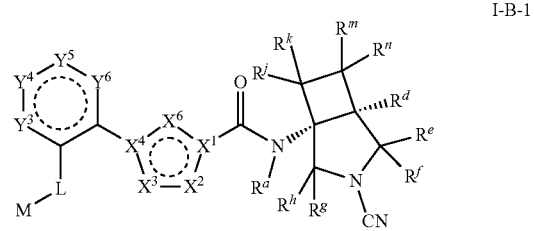

I-B-1 wherein M, L, $X^1$, $X^2$, $X^3$, $X^4$, $X^6$, $Y^3$, $Y^4$, $Y^5$, $Y^6$, $R^a$, $R^d$, $R^e$, $R^f$, $R^g$, and $R^h$ are all as defined for formula (I-B) above and described in classes and subclasses herein for formula (I-B), both singly and in combination, and wherein $R^j$, $R^k$, $R^m$, and $R^n$ are each independently hydrogen, halogen, $C_1$-$C_3$ alkyl, or $C_1$-$C_3$ haloalkyl.

In some embodiments, the present disclosure provides compounds, or pharmaceutically acceptable salts thereof, of formula (I-B-2):

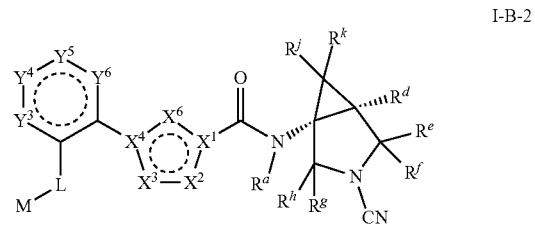

I-B-2 wherein M, L, $X^1$, $X^2$, $X^3$, $X^4$, $X^6$, $Y^3$, $Y^4$, $Y^5$, $Y^6$, $R^a$, $R^d$, $R^e$, $R^f$, $R^g$, and $R^h$ are all as defined for formula (I-B) above and described in classes and subclasses herein for formula (I-B), both singly and in combination, and wherein $R^j$ and $R^k$ are each independently hydrogen, halogen, $C_1$-$C_3$ alkyl, or $C_1$-$C_3$ haloalkyl.

In some embodiments, the present disclosure provides compounds, or pharmaceutically acceptable salts thereof, of formula (I-B-3):

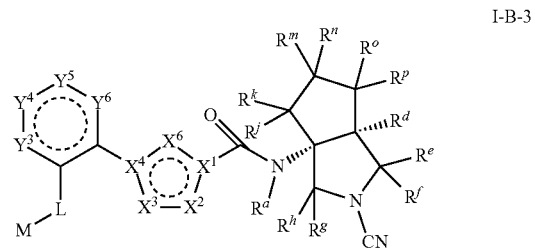

I-B-3 wherein M, L, $X^1$, $X^2$, $X^3$, $X^4$, $X^6$, $Y^3$, $Y^4$, $Y^5$, $Y^6$, $R^a$, $R^d$, $R^e$, $R^f$, $R^g$, and $R^h$ are all as defined for formula (I-B) above and described in classes and subclasses herein for formula (I-B), both singly and in combination, and wherein $R^j$, $R^k$, $R^m$, $R^n$, $R^o$, and $R^p$ are each independently hydrogen, halogen, $C_1$-$C_3$ alkyl, or $C_1$-$C_3$ haloalkyl.

In some embodiments, the present disclosure provides compounds, or pharmaceutically acceptable salts thereof, of formula (I-B-4):

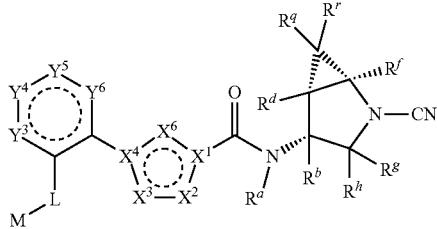

I-B-4 wherein M, L, $X^1$, $X^2$, $X^3$, $X^4$, $X^6$, $Y^3$, $Y^4$, $Y^5$, $Y^6$, $R^a$, $R^d$, $R^e$, $R^f$, $R^g$, and $R^h$ are all as defined for formula (I-B) above and described in classes and subclasses herein for formula (I-B), both singly and in combination, and wherein $R^q$ and $R^r$ are each independently hydrogen, halogen, $C_1$-$C_3$ alkyl, or $C_1$-$C_3$ haloalkyl.

In another aspect, the disclosure relates to a compound of formula (I-C):

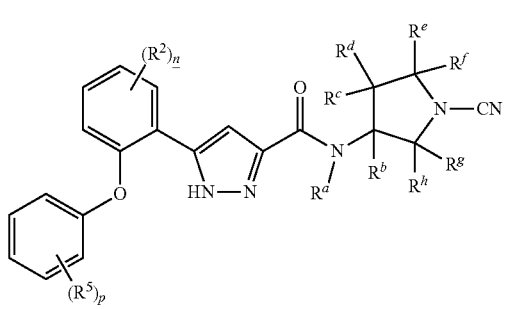

I-C or a pharmaceutically acceptable salt thereof, wherein $R^2$, $R^5$, n, p, $R^a$, $R^b$, $R^c$, $R^d$, $R^e$, $R^f$, $R^g$ and $R^h$ are all as defined for formula (I) above and described in classes and subclasses herein for formula (I), both singly and in combination.

In some embodiments, the present disclosure provides compounds, or pharmaceutically acceptable salts thereof, of formula (I-C-1):

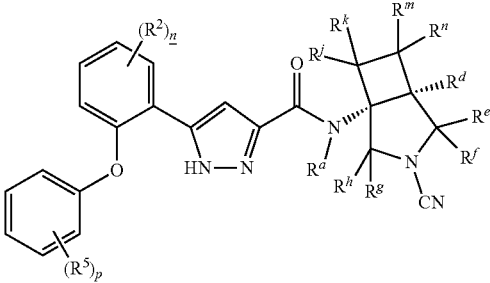

I-C-1 wherein $R^2$, $R^5$, n, p, $R^a$, $R^d$, $R^e$, $R^f$, $R^g$, and $R^h$ are all as defined for formula (I-C) above and described in classes and subclasses herein for formula (I-C), both singly and in combination, and wherein $R^j$, $R^k$, $R^m$, and $R^n$ are each independently hydrogen, halogen, $C_1$-$C_3$ alkyl, or $C_1$-$C_3$ haloalkyl.

In some embodiments, the present disclosure provides compounds, or pharmaceutically acceptable salts thereof, of formula (I-C-2):

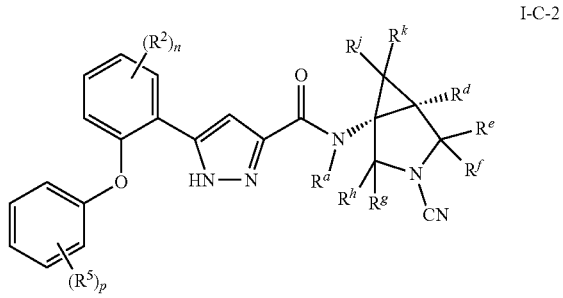

I-C-2 wherein $R^2$, $R^5$, n, p, $R^a$, $R^d$, $R^e$, $R^f$, $R^g$, and $R^h$ are all as defined for formula (I-C) above and described in classes and subclasses herein for formula (I-C), both singly and in combination, and wherein $R^j$ and $R^k$ are each independently hydrogen, halogen, $C_1$-$C_3$ alkyl, or $C_1$-$C_3$ haloalkyl.

In some embodiments, the present disclosure provides compounds, or pharmaceutically acceptable salts thereof, of formula (I-C-3):

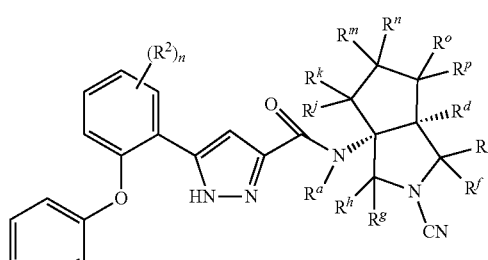

I-C-3 wherein $R^2$, $R^5$, n, p, $R^a$, $R^d$, $R^e$, $R^f$, $R^g$, and $R^h$ are all as defined for formula (I-C) above and described in classes and subclasses herein for formula (I-C), both singly and in combination, and wherein $R^j$, $R^k$, $R^m$, $R^n$, $R^o$, and $R^p$ are each independently hydrogen, halogen, $C_1$-$C_3$ alkyl, or $C_1$-$C_3$ haloalkyl.

In some embodiments, the present disclosure provides compounds, or pharmaceutically acceptable salts thereof, of formula (I-C-4):

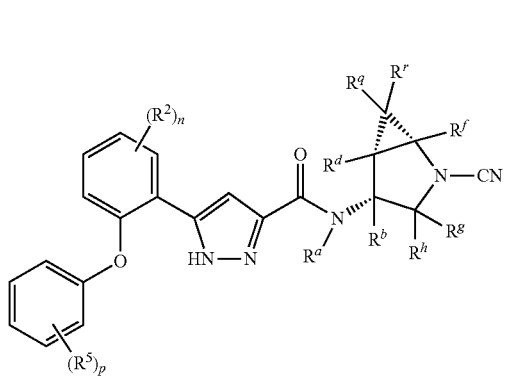

I-C-4 wherein $R^2$, $R^5$, n, p, $R^a$, $R^b$, $R^d$, $R^f$, $R^g$, and $R^h$ are all as defined for formula (I-C) above and described in classes and subclasses herein for formula (I-C), both singly and in combination, and
wherein $R^q$ and $R^r$ are each independently hydrogen, halogen, $C_1$-$C_3$ alkyl, or $C_1$-$C_3$ haloalkyl.

In some embodiments, the disclosure relates to a compound of formula (I-C), or a pharmaceutically acceptable salt thereof, wherein the compound is of formula (I-C-a):

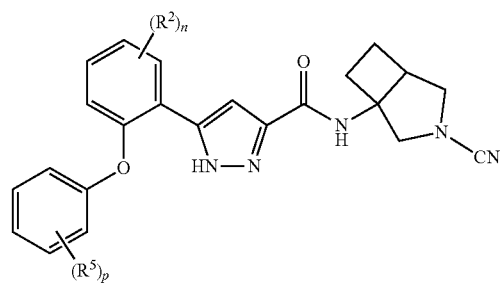

I-C-a wherein $R^2$, $R^5$, n, and p are all as defined for formula (I-C) above and described in classes and subclasses herein for formula (I-C), both singly and in combination.

In some embodiments, the disclosure relates to a compound of formula (I-C), or a pharmaceutically acceptable salt thereof, wherein the compound is of formula (I-C-b):

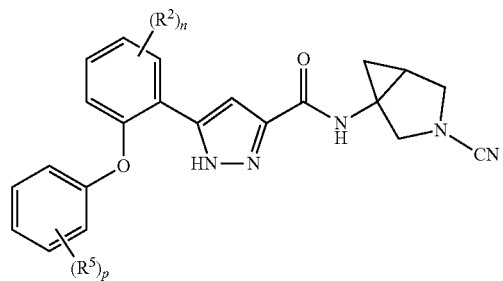

I-C-b wherein $R^2$, $R^5$, n, and p are all as defined for formula (I-C) above and described in classes and subclasses herein for formula (I-C), both singly and in combination.

In some embodiments, the disclosure relates to a compound of formula (I-C), or a pharmaceutically acceptable salt thereof, wherein the compound is of formula (I-C-c):

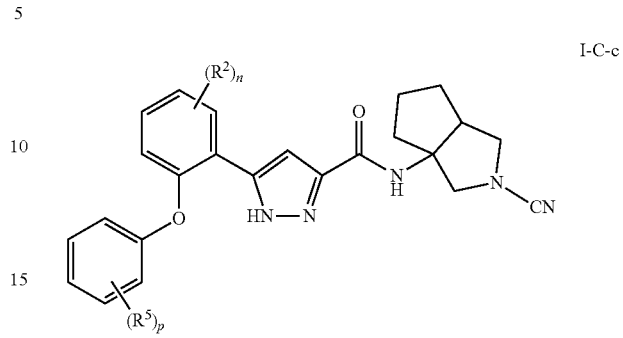

I-C-c wherein $R^2$, $R^5$, n, and p are all as defined for formula (I-C) above and described in classes and subclasses herein for formula (I-C), both singly and in combination.

In some embodiments, the disclosure relates to a compound of formula (I-C), or a pharmaceutically acceptable salt thereof, wherein the compound is of formula (I-C-d):

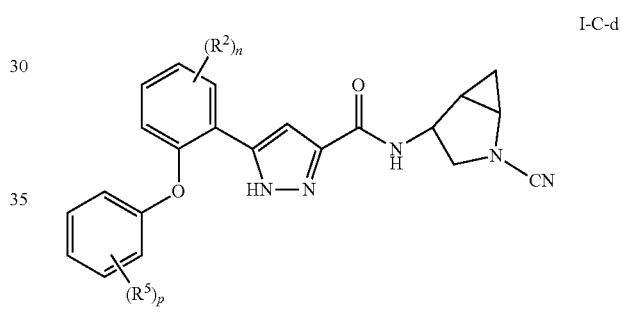

I-C-d wherein $R^2$, $R^5$, n, and p are all as defined for formula (I-C) above and described in classes and subclasses herein for formula (I-C), both singly and in combination.

In some embodiments, the disclosure relates to a compound of formula (I-C), or a pharmaceutically acceptable salt thereof, wherein the compound is of formula (I-C-e):

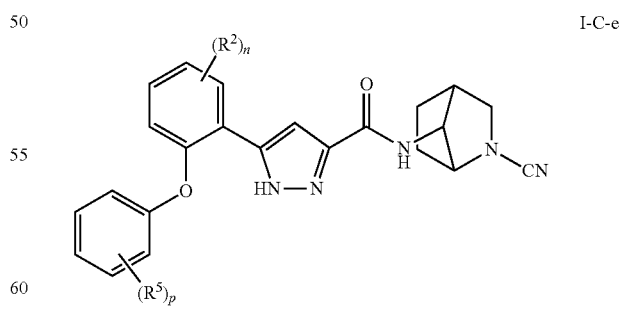

I-C-e wherein $R^2$, $R^5$, n, and p are all as defined for formula (I-C) above and described in classes and subclasses herein for formula (I-C), both singly and in combination.

In some embodiments, the disclosure relates to a compound of formula (I-C), or a pharmaceutically acceptable salt thereof, wherein the compound is of formula (I-C-f):

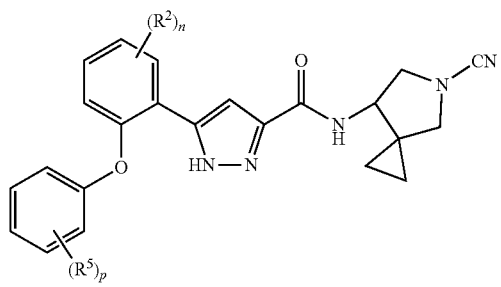

I-C-f wherein $R^2$, $R^5$, n, and p are all as defined for formula (I-C) above and described in classes and subclasses herein for formula (I-C), both singly and in combination.

In another aspect, the disclosure relates to a compound of formula (I-D):

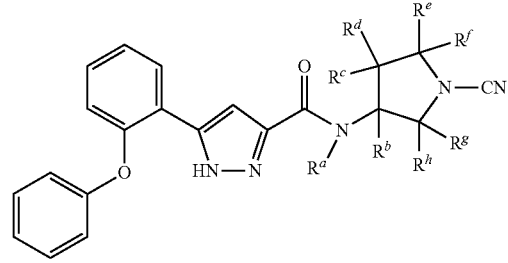

I-D or a pharmaceutically acceptable salt thereof, wherein $R^a$, $R^b$, $R^c$, $R^d$, $R^e$, $R^f$, $R^g$ and $R^h$ are all as defined for formula (I) above and described in classes and subclasses herein for formula (I), both singly and in combination.

In another aspect, the disclosure relates to a compound of formula (I-E):

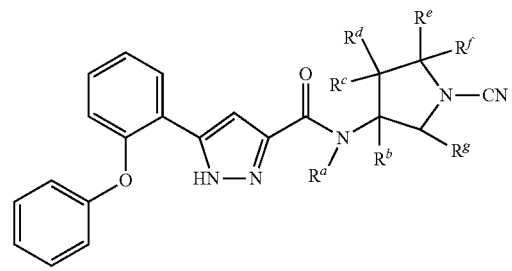

I-E or a pharmaceutically acceptable salt thereof, wherein $R^a$, $R^b$, $R^c$, $R^d$, $R^e$, $R^f$ and $R^g$ are all as defined for formula (I) above and described in classes and subclasses herein for formula (I), both singly and in combination. In some embodiments, the present disclosure provides compounds, or pharmaceutically acceptable salts thereof, of formula (I-E-1):

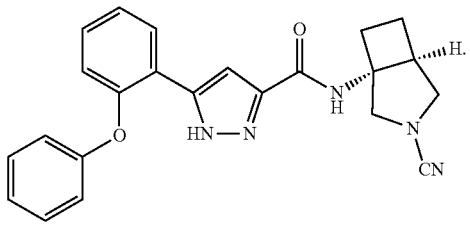

I-E-1

In some embodiments, the compound of formula (I-E-1) has the absolute stereochemistry of the first eluting isomer when a racemic mixture of the compound of formula (I-E-1) is separated by the procedure described in Example 3, Step 6. In some embodiments, the compound of formula (I-E-1) has the absolute stereochemistry of the second eluting isomer when a racemic mixture of the compound of formula (I-E-1) is separated by the procedure described in Example 3, Step 6.

In some embodiments, the compound of formula (I-E-1) is:

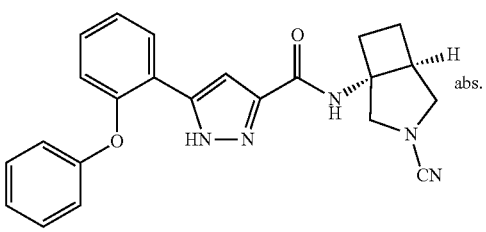 [SMILES: N#CN1C[C@@H]2CC[C@]2(NC(=O)c2cc(-c3ccccc3Oc3ccccc3)[nH]n2)C1]

In some embodiments, the compound of formula (I-E-1) is:

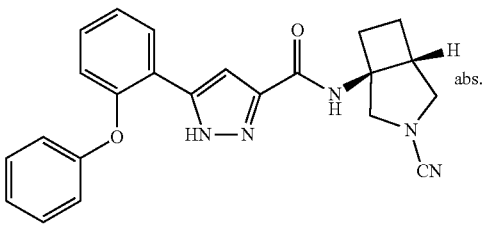 [SMILES: N#CN1C[C@H]2CC[C@@]2(NC(=O)c2cc(-c3ccccc3Oc3ccccc3)[nH]n2)C1]

In some embodiments, the present disclosure provides compounds, or pharmaceutically acceptable salts thereof, of formula (I-E-2):

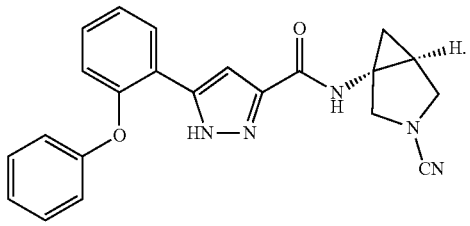

I-E-2

In some embodiments, the compound of formula (I-E-2) has the absolute stereochemistry of the first eluting isomer when a racemic mixture of the compound of formula (I-E-2)

is separated by the procedure described in Example 4, Step 6. In some embodiments, the compound of formula (I-E-2) has the absolute stereochemistry of the second eluting isomer when a racemic mixture of the compound of formula (I-E-2) is separated by the procedure described in Example 4, Step 6.

In some embodiments, the compound of formula (I-E-2) is:

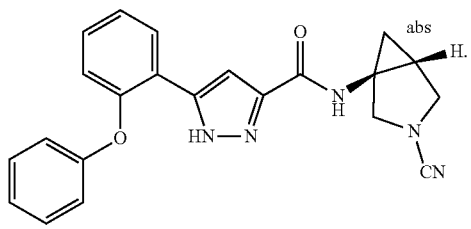

In some embodiments, the compound of formula (I-E-2) is:

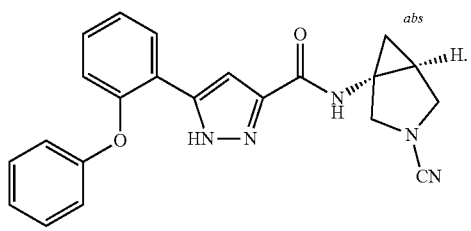

In some embodiments, the present disclosure provides compounds, or pharmaceutically acceptable salts thereof, of formula (I-E-3):

I-E-3

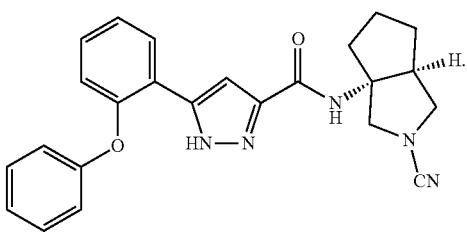

In some embodiments, the compound of formula (I-E-3) has the absolute stereochemistry of the first eluting isomer when a racemic mixture of the compound of formula (I-E-3) is separated by the procedure described in Example 2, Step 7. In some embodiments, the compound of formula (I-E-3) has the absolute stereochemistry of the second eluting isomer when a racemic mixture of the compound of formula (I-E-3) is separated by the procedure described in Example 2, Step 7.

In some embodiments, the compound of formula (I-E-3) is:

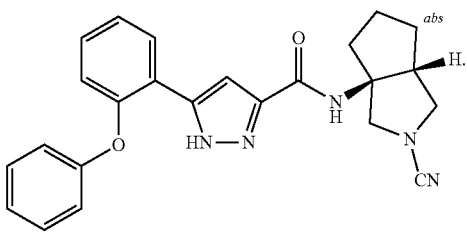

In some embodiments, the compound of formula (I-E-3) is:

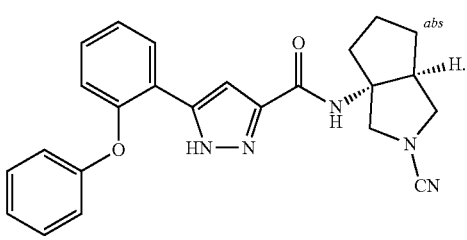

In some embodiments, the present disclosure provides compounds, or pharmaceutically acceptable salts thereof, of formula (I-E-4):

I-E-4

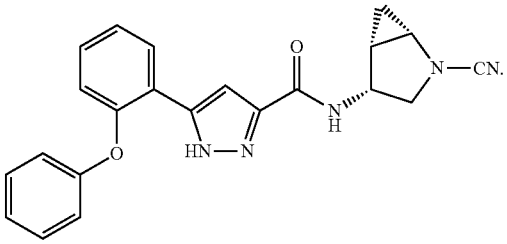

In some embodiments, the compound of formula (I-E-4) has the absolute stereochemistry of the first eluting isomer when a racemic mixture of the compound of formula (I-E-4) is separated by the procedure described in Example 2, Step 7. In some embodiments, the compound of formula (I-E-4) has the absolute stereochemistry of the second eluting isomer when a racemic mixture of the compound of formula (I-E-4) is separated by the procedure described in Example 2, Step 7.

In some embodiments, the compound of formula (I-E-4) is:

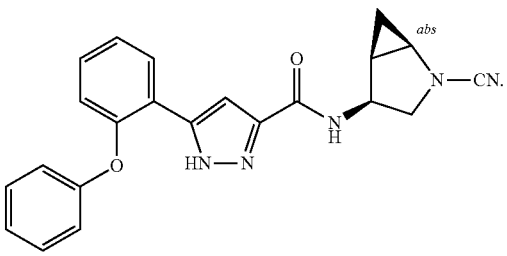 [SMILES: N#CN1C[C@@H](NC(=O)c2cc(-c3ccccc3Oc3ccccc3)[nH]n2)[C@H]2C[C@H]21]

In some embodiments, the compound of formula (I-E-4) is:

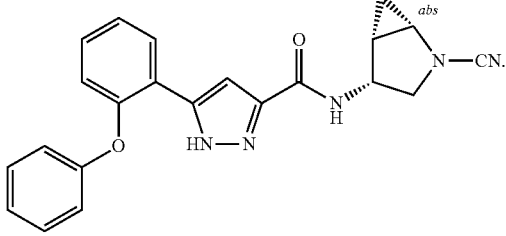

In another aspect, the disclosure relates to a compound of formula (I-F-1) or (I-F-2):

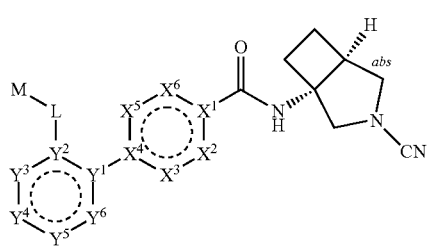

I-F-1

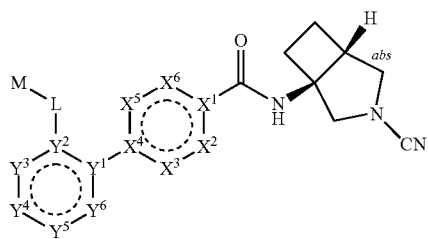

I-F-2 or a pharmaceutically acceptable salt thereof, wherein $X^1$, $X^2$, $X^3$, $X^4$, $X^5$, $X^6$, $Y^1$, $Y^2$, $Y^3$, $Y^4$, $Y^5$, $Y^6$, L, and M are all as defined for formula (I-A) above and described in classes and subclasses herein for formula (I-A), both singly and in combination.

In some embodiments, the compounds of formula (I-F-1) and (I-F-2) are present in a racemic mixture. In other embodiments, the compound of formula (I-F-1) or (I-F-2) is present in substantially enantiomerically pure form. The compounds of formula (I-F-1) and (I-F-2) can be separated from one another by chiral HPLC, such as by the procedure described in Example 2, Step 7 or Example 3, Step 6.

In another aspect, the disclosure relates to a compound of formula (I-G-1) or (I-G-2):

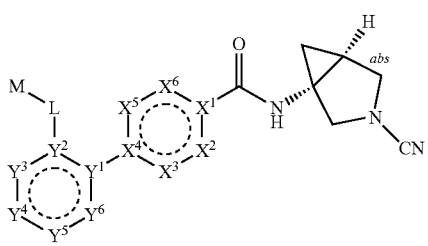

I-G-1

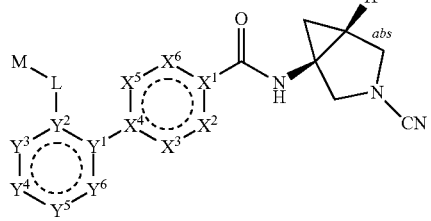

I-G-2 or a pharmaceutically acceptable salt thereof, wherein $X^1$, $X^2$, $X^3$, $X^4$, $X^5$, $X^6$, $Y^1$, $Y^2$, $Y^3$, $Y^4$, $Y^5$, $Y^6$, L, and M are all as defined for formula (I-A) above and described in classes and subclasses herein for formula (I-A), both singly and in combination.

In some embodiments, the compounds of formula (I-G-1) and (I-G-2) are present in a racemic mixture. In other embodiments, the compound of formula (I-G-1) or (I-G-2) is present in substantially enantiomerically pure form. The compounds of formula (I-G-1) and (I-G-2) can be separated from one another by chiral HPLC, such as by the procedure described in Example 2, Step 7, or Example 4, Step 6.

In another aspect, the disclosure relates to a compound of formula (I-H-1) or (I-H-2):

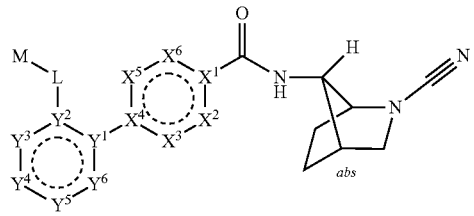

I-H-1

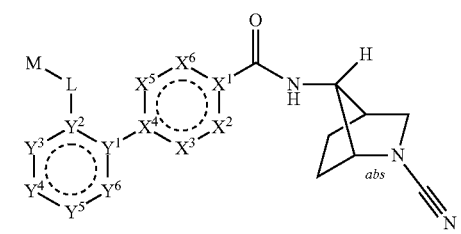

I-H-2 or a pharmaceutically acceptable salt thereof, wherein $X^1$, $X^2$, $X^3$, $X^4$, $X^5$, $X^6$, $Y^1$, $Y^2$, $Y^3$, $Y^4$, $Y^5$, $Y^6$, L, and M are all as defined for formula (I-A) above and described in classes and subclasses herein for formula (I-A), both singly and in combination.

In some embodiments, the compounds of formula (I-H-1) and (I-H-2) are present in a racemic mixture. In other embodiments, the compound of formula (I-H-1) or (I-H-2) is present in substantially enantiomerically pure form. The compounds of formula (I-H-1) and (I-H-2) can be separated from one another by chiral HPLC, such as by the procedure described in Example 2, Step 7.

In another aspect, the disclosure relates to a compound of formula (I-J-1) or (I-J-2):

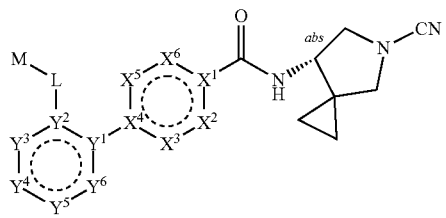

I-J-1

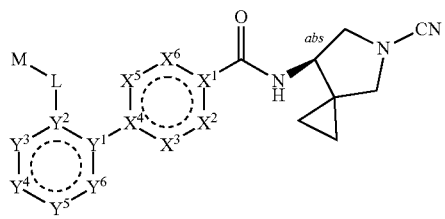

I-J-2 or a pharmaceutically acceptable salt thereof, wherein $X^1$, $X^2$, $X^3$, $X^4$, $X^5$, $X^6$, $Y^1$, $Y^2$, $Y^4$, $Y^5$, $Y^6$, L, and M are all as defined for formula (I-A) above and described in classes and subclasses herein for formula (I-A), both singly and in combination.

In some embodiments, the compounds of formula (I-J-1) and (I-J-2) are present in a racemic mixture. In other embodiments, the compound of formula (I-J-1) or (I-J-2) is present in substantially enantiomerically pure form. The compounds of formula (I-J-1) and (I-J-2) can be separated from one another by chiral HPLC, such as by the procedure described in Example 2, Step 7.

In some embodiments, the present disclosure provides compounds, or pharmaceutically acceptable salts thereof, of formula (I-K-1) or (I-K-2):

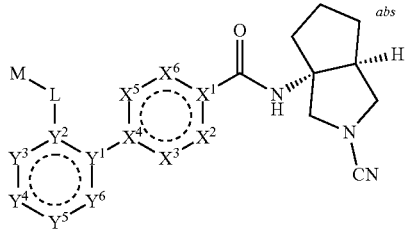

I-K-1

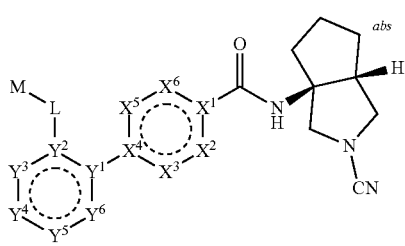

I-K-2 wherein M, L, $X^1$, $X^2$, $X^3$, $X^4$, $X^5$, $X^6$, $Y^1$, $Y^2$, $Y^3$, $Y^4$, $Y^5$, and $Y^6$ are all as defined for formula (I-A) above and described in classes and subclasses herein for formula (I-A), both singly and in combination.

In some embodiments, the present disclosure provides compounds, or pharmaceutically acceptable salts thereof, of formula (I-L-1) or (I-L-2):

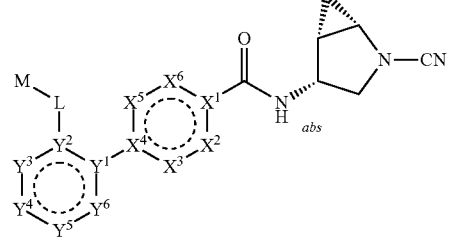

I-L-1

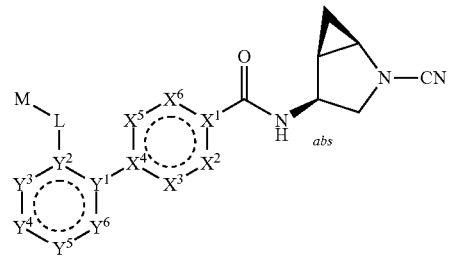

I-L-2 wherein M, L, $X^1$, $X^2$, $X^3$, $X^4$, $X^5$, $X^6$, $Y^1$, $Y^2$, $Y^3$, $Y^4$, $Y^5$, and $Y^6$ are all as defined for formula (I-A) above and described in classes and subclasses herein for formula (I-A), both singly and in combination.

In some embodiments, the present disclosure provides compounds, or pharmaceutically acceptable salts thereof, of formula (I-M):

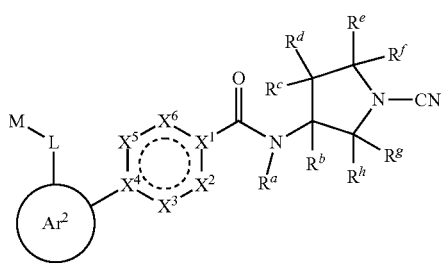

I-M wherein M, L, $X^1$, $X^2$, $X^3$, $X^4$, $X^5$, $X^6$, $R^a$, $R^b$, $R^c$, $R^d$, $R^e$, $R^f$, $R^g$, and $R^h$ are all as defined for formula (I) and (I-A) above and described in classes and subclasses herein for formula (I) and (I-A), both singly and in combination.

In some embodiments, the present disclosure provides compounds, or pharmaceutically acceptable salts thereof, of formula (I-M-1):

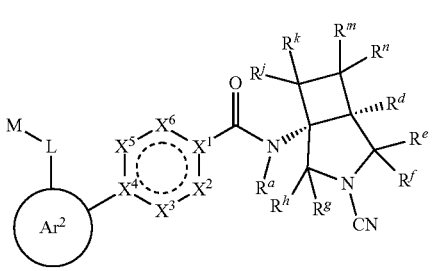

I-M-1 wherein M, L, $X^1$, $X^2$, $X^3$, $X^4$, $X^5$, $X^6$, $R^a$, $R^d$, $R^e$, $R^f$, $R^g$, and $R^h$ are all as defined for formula (I-M) above and described in classes and subclasses herein for formula (I-M), both singly and in combination, and wherein $R^j$, $R^k$, $R^m$, and $R^n$ are each independently hydrogen, halogen, $C_1$-$C_3$ alkyl, or $C_1$-$C_3$ haloalkyl.

In some embodiments, the present disclosure provides compounds, or pharmaceutically acceptable salts thereof, of formula (I-M-2):

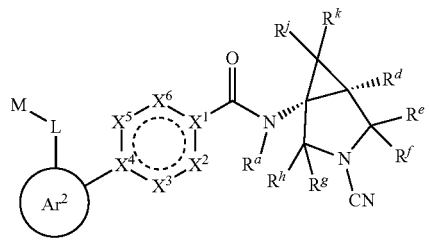

I-M-2 wherein M, L, $X^1$, $X^2$, $X^3$, $X^4$, $X^5$, $R^a$, $R^d$, $R^e$, $R^f$, $R^g$, and $R^h$ are all as defined for formula (I-M) above and described in classes and subclasses herein for formula (I-M), both singly and in combination, and wherein $R^j$ and $R^k$ are each independently hydrogen, halogen, $C_1$-$C_3$ alkyl, or $C_1$-$C_3$ haloalkyl.

In some embodiments, the present disclosure provides compounds, or pharmaceutically acceptable salts thereof, of formula (I-M-3):

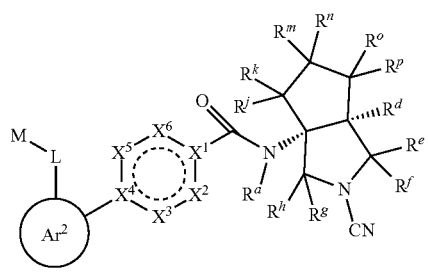

I-M-3 wherein M, L, $X^1$, $X^2$, $X^3$, $X^4$, $X^5$, $R^a$, $R^d$, $R^e$, $R^f$, $R^g$, and $R^h$ are all as defined for formula (I-M) above and described in classes and subclasses herein for formula (I-M), both singly and in combination, and wherein $R^j$, $R^k$, $R^m$, $R^n$, $R^o$, and $R^p$ are each independently hydrogen, halogen, $C_1$-$C_3$ alkyl, or $C_1$-$C_3$ haloalkyl.

In some embodiments, the present disclosure provides compounds, or pharmaceutically acceptable salts thereof, of formula (I-M-4):

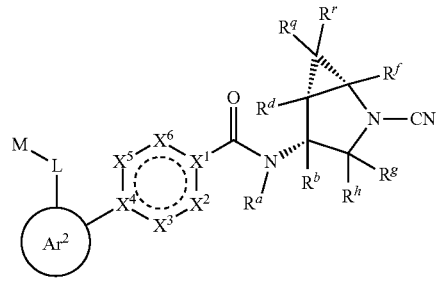

I-M-4 wherein M, L, $X^1$, $X^2$, $X^3$, $X^5$, $X^6$, $R^a$, $R^b$, $R^d$, $R^f$, $R^g$, and $R^h$ are all as defined for formula (I-M) above and described in classes and subclasses herein for formula (I-M), both singly and in combination, and wherein $R^q$ and $R^r$ are each independently hydrogen, halogen, $C_1$-$C_3$ alkyl, or $C_1$-$C_3$ haloalkyl.

In some embodiments, the disclosure relates to a compound of formula (I), (I-1), (I-2), (I-3), or (I-4), or a pharmaceutically acceptable salt thereof, wherein $Ar^1$ is independently phenylene or 5-6 membered heteroarylene, wherein said phenylene or heteroarylene is substituted with m $R^1$ groups. In some embodiments, $Ar^1$ is phenylene substituted with m $R^1$ groups. In some embodiments, $Ar^1$ is phenylene substituted with 1-2 $R^1$ groups selected from the group consisting of halo, cyano, hydroxyl, $C_1$-$C_6$ alkyl, $C_1$-$C_6$ alkoxy, $C_1$-$C_6$ haloalkyl, and $C_1$-$C_6$ hydroxyalkyl. In some embodiments, $Ar^1$ is phenylene. In some embodiments, $Ar^1$ is 5-6 membered heteroarylene substituted with m $R^1$ groups. In some embodiments, $Ar^1$ is 5-6 membered heteroarylene substituted with 1-2 $R^1$ groups selected from the group consisting of halo, cyano, hydroxyl, $C_1$-$C_6$ alkyl, $C_1$-$C_6$ alkoxy, $C_1$-$C_6$ haloalkyl, and $C_1$-$C_6$ hydroxyalkyl. In some embodiments, $Ar^1$ is 5-membered heteroarylene substituted with m $R^1$ groups. In some embodiments, $Ar^1$ is pyrazole. In some embodiments, $Ar^1$ is thiazole. In some embodiments, $Ar^1$ is 6-membered heteroarylene substituted with m $R^1$ groups.

In some embodiments, the disclosure relates to a compound of formula (I), (I-1), (I-2), (I-3), (I-4), (I-M), (I-M-1), (I-M-2), (I-M-3), or (I-M-4), or a pharmaceutically acceptable salt thereof, wherein $Ar^2$ is independently phenylene or 5-10 membered heteroarylene, wherein said phenylene or heteroarylene is substituted with n $R^2$ groups. In some embodiments, $Ar^2$ is phenylene or 5-6 membered heteroarylene, wherein said phenylene or heteroarylene is substituted with n $R^2$ groups. In some embodiments, $Ar^2$ is phenylene substituted with n $R^2$ groups. In some embodiments, $Ar^2$ is phenylene substituted with 1-2 $R^2$ groups selected from the group consisting of halo, cyano, hydroxyl, $C_1$-$C_6$ alkyl, $C_1$-$C_6$ alkoxy, $C_1$-$C_6$ haloalkyl, and $C_1$-$C_6$ hydroxyalkyl. In some embodiments, $Ar^2$ is phenylene. In some embodiments, $Ar^2$ is 5-10 membered heteroarylene substituted with n $R^2$ groups. In some embodiments, $Ar^2$ is 5-6 membered heteroarylene substituted with n $R^2$ groups. In some embodiments, $Ar^2$ is 5-6 membered heteroarylene substituted with 1-2 $R^2$ groups selected from the group consisting of halo, cyano, hydroxyl, $C_1$-$C_6$ alkyl, $C_1$-$C_6$ alkoxy, $C_1$-$C_6$ haloalkyl, and $C_1$-$C_6$ hydroxyalkyl. In some embodiments, $Ar^2$ is 5-membered heteroarylene substituted with n $R^2$ groups. In some embodiments, $Ar^2$ is 6-membered heteroarylene substituted with n $R^2$ groups. In some embodiments, $Ar^2$ is pyridine. In some embodiments, $Ar^2$ is 7-membered heteroarylene substituted with n $R^2$ groups. In some embodiments, $Ar^2$ is 8-membered heteroarylene substituted with n $R^2$ groups. In some embodiments, $Ar^2$ is 9-membered heteroarylene substituted with n $R^2$ groups. In some embodiments, $Ar^2$ is 10-membered heteroarylene substituted with n $R^2$ groups.

In some embodiments, the disclosure relates to a compound of formula (I), (I-1), (I-2), (I-3), (I-4), (I-A), (I-A-1), (I-A-2), (I-A-3), (I-A-4), (I-B), (I-B-1), (I-B-2), (I-B-3), (I-B-4), (I-F-1), (I-F-2), (I-G-1), (I-G-2), (I-H-1), (I-H-2), (I-J-1), (I-J-2), (I-K-1), (I-K-2), (I-L-1), (I-L-2), (I-M), (I-M-1), (I-M-2), (I-M-3), or (I-M-4), or a pharmaceutically acceptable salt thereof, wherein L is —O—, —S—, —NR$^3$—, —C(R$^4$)$_2$—, —S(O)$_2$—, or —S(O)—. In some embodiments, L is —O—, —S—, or —NH—. In some embodiments, L is —O—. In some embodiments, L is —S—. In some embodiments, L is —NR$^3$—. In some embodiments, L is —NH—. In some embodiments, L is —C(R$^4$)$_2$—. In some embodiments, L is —CH$_2$—. In some embodiments, L is —S(O)$_2$—. In some embodiments, L is —S(O)—.

In some embodiments, the disclosure relates to a compound of formula (I), (I-1), (I-2), (I-3), (I-4), (I-A), (I-A-1), (I-A-2), (I-A-3), (I-A-4), (I-B), (I-B-1), (I-B-2), (I-B-3), (I-B-4), (I-F-1), (I-F-2), (I-G-1), (I-G-2), (I-H-1), (I-H-2), (I-J-1), (I-J-2), (I-K-1), (I-K-2), (I-L-1), (I-L-2), (I-M), (I-M-1), (I-M-2), (I-M-3), or (I-M-4), or a pharmaceutically acceptable salt thereof, wherein M is $C_1$-$C_6$ alkyl, $C_1$-$C_6$ haloalkyl, 3-6 membered cycloalkyl, phenyl, or 5-6 membered heteroaryl, wherein said cycloalkyl, phenyl, or heteroaryl is substituted with p $R^5$ groups. In some embodiments, M is 3-6 membered cycloalkyl, phenyl, or 5-6 membered heteroaryl, wherein said cycloalkyl, phenyl, or heteroaryl is substituted with p $R^5$ groups. In some embodiments, M is $C_1$-$C_6$ alkyl. In some embodiments, M is $C_1$-$C_6$ haloalkyl. In some embodiments, M is 3-6 membered cycloalkyl substituted with p $R^5$ groups. In some embodiments, M is 3-6 membered cycloalkyl. In some embodiments, M is 3-6 membered cycloalkyl substituted with 1-2 $R^5$ groups selected from the group consisting of halo, cyano, hydroxyl, $C_1$-$C_6$ alkyl, $C_1$-$C_6$ haloalkyl, and $C_1$-$C_6$ hydroxyalkyl. In some embodiments, M is phenyl substituted with p $R^5$ groups. In some embodiments, M is phenyl. In some embodiments, M is phenyl substituted with 1-2 $R^5$ groups selected from the group consisting of halo, cyano, hydroxyl, $C_1$-$C_6$ alkyl, $C_1$-$C_6$ haloalkyl, $C_1$-$C_6$ alkoxy, and $C_1$-$C_6$ hydroxyalkyl. In some embodiments, M is phenyl substituted with fluoro. In some embodiments, M is 5-6 membered heteroaryl substituted with p $R^5$ groups. In some embodiments, M is 5-6 membered heteroaryl. In some embodiments, M is 5-6 membered heteroaryl substituted with 1-2 $R^5$ groups selected from the group consisting of halo, cyano, hydroxyl, $C_1$-$C_6$ alkyl, $C_1$-$C_6$ alkoxy, $C_1$-$C_6$ haloalkyl, and $C_1$-$C_6$ hydroxyalkyl.

In some embodiments, the disclosure relates to a compound of formula (I), (I-1), (I-2), (I-3), (I-4), (I-A), (I-A-1), (I-A-2), (I-A-3), (I-A-4), (I-B), (I-B-1), (I-B-2), (I-B-3), (I-B-4), (I-C), (I-C-1), (I-C-2), (I-C-3), (I-C-4), (I-C-a), (I-C-b), (I-C-c), (I-C-d), (I-C-e), (I-C-f), (I-F-1), (I-F-2), (I-G-1), (I-G-2), (I-H-1), (I-H-2), (I-J-1), (I-J-2), (I-K-1), (I-K-2), (I-L-1), (I-L-2), (I-M), (I-M-1), (I-M-2), (I-M-3), or (I-M-4), or a pharmaceutically acceptable salt thereof, wherein each occurrence of $R^1$, $R^2$, and $R^5$ is independently halo, cyano, NO$_2$, oxo, hydroxyl, —R$^6$, —OR$^6$, $C_1$-$C_6$ alkyl, $C_1$-$C_6$ haloalkyl, $C_1$-$C_6$ hydroxyalkyl, —$C_1$-$C_6$ alkylene-R$^6$, $C_1$-$C_6$ alkoxy, $C_1$-$C_6$ haloalkoxy, —$C_0$-$C_3$ alkylene-NR$^6$R$^7$, —$C_0$-$C_3$ alkylene-NR$^7$R$^8$, —$C_0$-$C_3$ alkylene-C(O)NR$^6$R$^7$, —$C_0$-$C_3$ alkylene-C(O)NR$^7$R$^8$, —$C_0$-$C_3$ alkylene-NR$^7$C(O) R$^6$, —$C_0$-$C_3$ alkylene-NR$^7$C(O)R$^8$, —$C_0$-$C_3$ alkylene-NR$^7$S(O)$_2$R$^6$, —$C_0$-$C_3$ alkylene-C(O)R$^6$, —$C_0$-$C_3$ alkylene-C(O) R$^7$, —$C_0$-$C_3$ alkylene-SR$^6$, —$C_0$-$C_3$ alkylene-S(O)R$^6$, —$C_0$-$C_3$ alkylene-S(O)$_2$R$^6$, —$C_0$-$C_3$ alkylene-S(O)$_2$R$^7$, —$C_0$-$C_3$ alkylene-S(O)$_2$NR$^6$R$^7$, —$C_0$-$C_3$ alkylene-S(O)$_2$NR$^7$R$^8$, —$C_0$-$C_3$ alkylene-NR$^7$C(O)NR$^8$R$^9$, —$C_0$-$C_3$ alkylene- NR$^7$S(O)$_2$NR$^8$R$^9$, —$C_0$-$C_3$ alkylene-C(O)OR$^7$, —$C_0$-$C_3$ alkylene-C(O)OR$^6$, —$C_0$-$C_3$ alkylene-OC(O)R$^7$, —$C_0$-$C_3$ alkylene-OC(O)R$^6$, —$C_0$-$C_3$ alkylene-NR$^7$C(O)OR$^8$, or —$C_0$-$C_3$ alkylene-NR$^7$S(O)$_2$R$^8$. In some embodiments, each occurrence of $R^1$ is independently halo, cyano, hydroxyl, $C_1$-$C_6$ alkyl, $C_1$-$C_6$ alkoxy, $C_1$-$C_6$ haloalkyl, and $C_1$-$C_6$ hydroxyalkyl. In some embodiments, each occurrence of $R^1$ is independently halo (e.g., fluoro, chloro, bromo, or iodo). In some embodiments, each occurrence of $R^1$ is fluoro. In some embodiments, each occurrence of $R^1$ is cyano. In some embodiments, each occurrence of $R^1$ is hydroxyl. In some embodiments, each occurrence of $R^1$ is $C_1$-$C_6$ alkyl. In some embodiments, each occurrence of $R^1$ is $C_1$-$C_6$ alkoxy. In some embodiments, each occurrence of $R^1$ is $C_1$-$C_6$ haloalkyl. In some embodiments, each occurrence of $R^1$ is $C_1$-$C_6$ hydroxyalkyl. In some embodiments, each occurrence of $R^2$ is independently halo, cyano, hydroxyl, $C_1$-$C_6$ alkyl, $C_1$-$C_6$ alkoxy, $C_1$-$C_6$ haloalkyl, and $C_1$-$C_6$ hydroxyalkyl. In some embodiments, each occurrence of $R^2$ is independently halo (e.g., fluoro, chloro, bromo, or iodo). In some embodiments, each occurrence of $R^2$ is fluoro. In some embodiments, each occurrence of $R^2$ is cyano. In some embodiments, each occurrence of $R^2$ is hydroxyl. In some embodiments, each occurrence of $R^2$ is $C_1$-$C_6$ alkyl. In some embodiments, each occurrence of $R^2$ is $C_1$-$C_6$ alkoxy. In some embodiments, each occurrence of $R^2$ is $C_1$-$C_6$ haloalkyl. In some embodiments, each occurrence of $R^2$ is $C_1$-$C_6$ hydroxyalkyl. In some embodiments, each occurrence of $R^5$ is independently halo, cyano, hydroxyl, $C_1$-$C_6$ alkyl, $C_1$-$C_6$ alkoxy, $C_1$-$C_6$ haloalkyl, and $C_1$-$C_6$ hydroxyalkyl. In some embodiments, each occurrence of $R^5$ is independently halo (e.g., fluoro, chloro, bromo, or iodo). In some embodiments, each occurrence of $R^5$ is fluoro. In some embodiments, each occurrence of $R^5$ is cyano. In some embodiments, each occurrence of $R^5$ is hydroxyl. In some embodiments, each occurrence of $R^5$ is $C_1$-$C_6$ alkyl. In some embodiments, each occurrence of $R^5$ is $C_1$-$C_6$ alkoxy. In some embodiments, each occurrence of $R^5$ is $C_1$-$C_6$ haloalkyl. In some embodiments, each occurrence of $R^5$ is $C_1$-$C_6$ hydroxyalkyl.

In some embodiments, the disclosure relates to a compound of formula (I), (I-1), (I-2), (I-3), (I-4), (I-A), (I-A-1), (I-A-2), (I-A-3), (I-A-4), (I-B), (I-B-1), (I-B-2), (I-B-3), (I-B-4), (I-F-1), (I-F-2), (I-G-1), (I-G-2), (I-H-1), (I-H-2), (I-J-1), (I-J-2), (I-K-1), (I-K-2), (I-L-1), (I-L-2), (I-M), (I-M-1), (I-M-2), (I-M-3), or (I-M-4), or a pharmaceutically acceptable salt thereof, wherein $R^3$ is H, $C_1$-$C_6$ alkyl, or $C_1$-$C_6$ haloalkyl. In some embodiments, $R^3$ is H. In some embodiments, $R^3$ is $C_1$-$C_6$ alkyl. In some embodiments, $R^3$ is $C_1$-$C_6$ haloalkyl.

In some embodiments, the disclosure relates to a compound of formula (I), (I-1), (I-2), (I-3), (I-4), (I-A), (I-A-1), (I-A-2), (I-A-3), (I-A-4), (I-B), (I-B-1), (I-B-2), (I-B-3), (I-B-4), (I-F-1), (I-F-2), (I-G-1), (I-G-2), (I-H-1), (I-H-2), (I-J-1), (I-J-2), (I-K-1), (I-K-2), (I-L-1), (I-L-2), (I-M), (I-M-1), (I-M-2), (I-M-3), or (I-M-4), or a pharmaceutically acceptable salt thereof, wherein each $R^4$ is independently H, $C_1$-$C_6$ alkyl, or $C_1$-$C_6$ haloalkyl, or two $R^4$ groups together with the carbon atom to which they are attached form a 3-6 membered cycloalkyl or heterocycloalkyl. In some embodiments, each $R^4$ is H. In some embodiments, two $R^4$ groups together with the carbon atom to which they are attached form a 3-6 membered cycloalkyl. In some embodiments, two $R^4$ groups together with the carbon atom to which they are attached form a 3-6 membered heterocycloalkyl.

In some embodiments, the disclosure relates to a compound of formula (I), (I-1), (I-2), (I-3), (I-4), (I-A), (I-A-1), (I-A-2), (I-A-3), (I-A-4), (I-B), (I-B-1), (I-B-2), (I-B-3), (I-B-4), (I-C), (I-C-1), (I-C-2), (I-C-3), (I-C-4), (I-C-a), (I-C-b), (I-C-c), (I-C-d), (I-C-e), (I-C-f), (I-F-2), (I-G-1), (I-G-2), (I-H-1), (I-H-2), (I-J-1), (I-J-2), (I-K-1), (I-K-2), (I-L-1), (I-L-2), (I-M), (I-M-1), (I-M-2), (I-M-3), or (I-M-4), or a pharmaceutically acceptable salt thereof, wherein each $R^6$ is 5-10 membered heteroaryl, 4-10 membered heterocycloalkyl, 6-10 membered aryl, or 3-8 membered cycloalkyl, wherein said heteroaryl, heterocycloalkyl, aryl, or cycloalkyl is optionally substituted with 1-5 substituents independently selected from the group consisting of halo, oxo, $C_1$-$C_6$ alkyl, $C_1$-$C_6$ haloalkyl, $C_1$-$C_6$ hydroxyalkyl, $C_1$-$C_6$ alkoxy, $C_1$-$C_6$ haloalkoxy, $C_2$-$C_6$ alkenyl, $C_2$-$C_6$ alkynyl, 5-10 membered heteroaryl, 4-10 membered heterocycloalkyl, 6-10 membered aryl, 3-8 membered cycloalkyl, —$NR^{10}C(O)NR^{11}R^{12}$, —$NR^{10}R^{11}$, —$C(O)R^{10}$, —$NR^{10}C(O)R^{11}$, —$NR^{10}C(O)OR^{11}$, —$S(O)_2R^{10}$, —$C(O)NR^{10}R^{11}$, —$C(O)OR^{10}$, —$S(O)_2NR^{10}R^{11}$, —$NR^{10}S(O)_2R^{11}$, —$OR^{10}$, —$OC(O)R^{10}$, —$OC(O)OR^{10}$, —$OS(O)_2R^{10}$, —$OC(O)NR^{10}R^{11}$, —$OC(O)OR^{10}$, —$OS(O)_2NR^{10}R^{11}$, —$C(O)NR^{10}C(O)NR^{11}R^{12}$, —$C(O)C(O)R^{10}$, —$C(O)NR^{10}C(O)R^{11}$, —$C(O)NR^{10}C(O)OR^{11}$, —$C(O)S(O)_2R^{10}$, —$C(O)C(O)NR^{10}R^{11}$, —$C(O)C(O)OR^{10}$, —$C(O)S(O)_2NR^{10}R^{11}$, —$C(O)NR^{10}S(O)_2R^{11}$, —$C_1$-$C_6$ alkylene-$R^{10}$, —$C_1$-$C_6$ alkylene-$NR^{10}C(O)NR^{11}R^{12}$, —$C_1$-$C_6$ alkylene-$NR^{10}R^{11}$, —$C_1$-$C_6$ alkylene-$C(O)R^{10}$, —$C_1$-$C_6$ alkylene-$NR^{10}C(O)R^{11}$, —$C_1$-$C_6$ alkylene-$NR^{10}C(O)OR^{11}$, —$C_1$-$C_6$ alkylene-$S(O)_2R^{19}$, —$C_1$-$C_6$ alkylene-$C(O)NR^{10}R^{11}$, —$C_1$-$C_6$ alkylene-$C(O)OR^{10}$, —$C_1$-$C_6$ alkylene-$S(O)_2NR^{10}R^{11}$, —$C_1$-$C_6$ alkylene-$NR^{10}S(O)_2R^{11}$, —$C_1$-$C_6$ alkenylene-$R^{10}$, —$C_1$-$C_6$ alkenylene-$NR^{10}C(O)NR^{11}R^{12}$, —$C_1$-$C_6$ alkenylene-$NR^{10}R^{11}$, —$C_1$-$C_6$ alkenylene-$C(O)R^{10}$, —$C_1$-$C_6$ alkenylene-$NR^{10}C(O)R^{11}$, —$C_1$-$C_6$ alkenylene-$NR^{10}C(O)OR^{11}$, —$C_1$-$C_6$ alkenylene-$S(O)_2R^{10}$, —$C_1$-$C_6$ alkenylene-$C(O)NR^{10}R^{11}$, —$C_1$-$C_6$ alkenylene-$C(O)OR^{10}$, —$C_1$-$C_6$ alkenylene-$S(O)_2NR^{10}R^{11}$, and —$C_1$-$C_6$ alkenylene-$NR^{19}S(O)_2R^{11}$. In some embodiments, each $R^6$ is independently optionally substituted 5-10 membered heteroaryl. In some embodiments, each $R^6$ is independently optionally substituted 4-10 membered heterocycloalkyl. In some embodiments, each $R^6$ is independently optionally substituted 6-10 membered aryl. In some embodiments, each $R^6$ is independently optionally substituted 3-8 membered cycloalkyl.

In some embodiments, the disclosure relates to a compound of formula (I), (I-1), (I-2), (I-3), (I-4), (I-A), (I-A-1), (I-A-2), (I-A-3), (I-A-4), (I-B), (I-B-1), (I-B-2), (I-B-3), (I-B-4), (I-C), (I-C-1), (I-C-2), (I-C-3), (I-C-4), (I-C-a), (I-C-b), (I-C-c), (I-C-d), (I-C-e), (I-C-f), (I-F-1), (I-F-2), (I-G-1), (I-G-2), (I-H-1), (I-H-2), (I-J-1), (I-J-2), (I-K-1), (I-K-2), (I-L-1), (I-L-2), (I-M), (I-M-1), (I-M-2), (I-M-3), or (I-M-4), or a pharmaceutically acceptable salt thereof, wherein each $R^7$, $R^8$, and $R^9$ is independently hydrogen or $C_1$-$C_6$ alkyl. In some embodiments, each $R^7$, $R^8$, and $R^9$ is independently hydrogen.

In some embodiments, the disclosure relates to a compound of formula (I), (I-1), (I-2), (I-3), (I-4), (I-A), (I-A-1), (I-A-2), (I-A-3), (I-A-4), (I-B), (I-B-1), (I-B-2), (I-B-3), (I-B-4), (I-C), (I-C-1), (I-C-2), (I-C-3), (I-C-4), (I-C-a), (I-C-b), (I-C-c), (I-C-d), (I-C-e), (I-C-f), (I-F-1), (I-F-2), (I-G-1), (I-G-2), (I-H-1), (I-H-2), (I-J-1), (I-J-2), (I-K-1), (I-K-2), (I-L-1), (I-L-2), (I-M), (I-M-1), (I-M-2), (I-M-3), or (I-M-4), or a pharmaceutically acceptable salt thereof, wherein each $R^{10}$, $R^{11}$, and $R^{12}$ is independently hydrogen, $C_1$-$C_6$ alkyl, 5-10 membered heteroaryl, 4-10 membered heterocycloalkyl, 6-10 membered aryl, or 3-8 membered cycloalkyl. In some embodiments, each $R^{1-9}$, $R^H$, and $R^{12}$ is independently hydrogen.

In some embodiments, the disclosure relates to a compound of formula (I), (I-1), (I-2), (I-3), or (I-4), or a pharmaceutically acceptable salt thereof, wherein m is 0-4 (i.e., m is 0, 1, 2, 3, or 4). In some embodiments, m is 0. In some embodiments, m is 1. In some embodiments, m is 2. In some embodiments, m is 3. In some embodiments, in is 4. In some embodiments, in is 0, 1, or 2. In some embodiments, m is 1 or 2.

In some embodiments, the disclosure relates to a compound of formula (I), (I-1), (I-2), (I-3), (I-4), (I-C), (I-C-1), (I-C-2), (I-C-3), (I-C-4), (I-C-a), (I-C-b), (I-C-c), (I-C-d), (I-C-e), (I-C-f), (I-M), (I-M-1), (I-M-2), (I-M-3), or (I-M-4), or a pharmaceutically acceptable salt thereof, wherein n is 0-4 (i.e., n is 0, 1, 2, 3, or 4). In some embodiments, n is 0. In some embodiments, n is 1. In some embodiments, n is 2. In some embodiments, n is 3. In some embodiments, n is 4. In some embodiments, n is 0, 1, or 2. In some embodiments, n is 1 or 2.

In some embodiments, the disclosure relates to a compound of formula (I), (I-1), (I-2), (I-3), (I-4), (I-A), (I-A-1), (I-A-2), (I-A-3), (I-A-4), (I-B), (I-B-1), (I-B-2), (I-B-3), (I-B-4), (I-C), (I-C-1), (I-C-2), (I-C-3), (I-C-4), (I-C-a), (I-C-b), (I-C-c), (I-C-d), (I-C-e), (I-C-f), (I-F-1), (I-F-2), (I-G-1), (I-G-2), (I-H-1), (I-H-2), (I-J-1), (I-J-2), (I-K-1), (I-K-2), (I-L-1), (I-L-2), (I-M), (I-M-1), (I-M-2), (I-M-3), or (I-M-4), or a pharmaceutically acceptable salt thereof, wherein p is 0-4 (i.e., p is 0, 1, 2, 3, or 4). In some embodiments, p is 0. In some embodiments, p is 1. In some embodiments, p is 2. In some embodiments, p is 3. In some embodiments, p is 4. In some embodiments, p is 0, 1, or 2. In some embodiments, p is 1 or 2. In some embodiments, n and p are both 0. In some embodiments, m and n are both 0. In some embodiments, m and n are both 0. In some embodiments, m, n, and p are 0. In some embodiments, in and n are 0, and p is 1.

In some embodiments, the disclosure relates to a compound of formula (I), (I-A), (I-B), (I-C), (I-D), (I-E), or (I-M), or a pharmaceutically acceptable salt thereof, wherein $R^a$ and $R^b$ form a $C_1$-$C_4$ alkylene group between the atoms to which they are attached, wherein said $C_1$-$C_4$ alkylene group is substituted with 0-4 substituents selected from the group consisting of halogen, $C_1$-$C_3$ alkyl, and $C_1$-$C_3$ haloalkyl. In some embodiments, $R^a$ and $R^b$ form a $C_1$-$C_4$ alkylene group between the atoms to which they are attached; and $R^c$, $R^d$, $R^e$, $R^f$, $R^g$, and $R^h$ are each hydrogen. In some embodiments, $R^a$ and $R^b$ form a $C_1$ alkylene group between the atoms to which they are attached; and $R^c$, $R^d$, $R^e$, $R^f$, $R^g$, and $R^h$ are each hydrogen. In some embodiments, $R^a$ and $R^b$ form a $C_2$ alkylene group between the atoms to which they are attached; and $R^c$, $R^d$, $R^e$, $R^f$, $R^g$, and $R^h$ are each hydrogen. In some embodiments, $R^a$ and $R^b$ form a $C_3$ alkylene group between the atoms to which they are attached; and $R^c$, $R^d$, $R^e$, $R^f$, $R^g$, and $R^h$ are each hydrogen. In some embodiments, $R^a$ and $R^b$ form a $C_4$ alkylene group between the atoms to which they are attached; and $R^c$, $R^d$, $R^e$, $R^f$, $R^g$, and $R^h$ are each hydrogen.

In some embodiments, the disclosure relates to a compound of formula (I), (I-A), (I-B), (I-C), (I-D), (I-E), or (I-M), or a pharmaceutically acceptable salt thereof, wherein $R^a$ and $R^e$ form a $C_1$-$C_2$ alkylene group between the atoms to which they are attached, wherein said $C_1$-$C_2$ alkylene group is substituted with 0-4 substituents selected from the group consisting of halogen, $C_1$-$C_3$ alkyl, and $C_1$-$C_3$ haloalkyl. In some embodiments, $R^a$ and $R^e$ form a $C_1$-$C_2$ alkylene group between the atoms to which they are attached; and $R^b$, $R^c$, $R^d$, $R^f$, $R^g$, and $R^h$ are each hydrogen. In some embodiments, $R^a$ and $R^e$ form a $C_1$ alkylene group between the atoms to which they are attached; and $R^b$, $R^c$, $R^d$, $R^f$, $R^g$, and $R^h$ are each hydrogen. In some embodiments, $R^a$ and $R^e$ form a $C_2$ alkylene group between the atoms to which they are attached; and $R^b$, $R^c$, $R^d$, $R^f$, $R^g$, and $R^h$ are each hydrogen.

In some embodiments, the disclosure relates to a compound of formula (I), (I-A), (I-B), (I-C), (I-D), (I-E), or (I-M), or a pharmaceutically acceptable salt thereof, wherein $R^a$ and $R^g$ form a $C_1$-$C_3$ alkylene group between the atoms to which they are attached, wherein said $C_1$-$C_3$ alkylene group is substituted with 0-4 substituents selected from the group consisting of halogen, $C_1$-$C_3$ alkyl, and $C_1$-$C_3$ haloalkyl. In some embodiments, $R^a$ and $R^g$ form a $C_1$-$C_3$ alkylene group between the atoms to which they are attached; and $R^b$, $R^c$, $R^d$, $R^e$, $R^f$, and $R^h$ are each hydrogen. In some embodiments, $R^a$ and $R^g$ form a $C_1$ alkylene group between the atoms to which they are attached; and $R^b$, $R^c$, $R^d$, $R^e$, $R^f$, and $R^h$ are each hydrogen. In some embodiments, $R^a$ and $R^g$ form a $C_2$ alkylene group between the atoms to which they are attached; and $R^b$, $R^c$, $R^d$, $R^e$, $R^f$, and $R^h$ are each hydrogen. In some embodiments, $R^a$ and $R^g$ form a $C_3$ alkylene group between the atoms to which they are attached; and $R^b$, $R^c$, $R^d$, $R^e$, $R^f$, and $R^h$ are each hydrogen.

In some embodiments, the disclosure relates to a compound of formula (I), (I-A), (I-B), (I-C), (I-D), (I-E), or (I-M), or a pharmaceutically acceptable salt thereof, wherein $R^b$ and $R^c$ form a $C_1$-$C_4$ alkylene group between the atoms to which they are attached, wherein said $C_1$-$C_4$ alkylene group is substituted with 0-4 substituents selected from the group consisting of halogen, $C_1$-$C_3$ alkyl, and $C_1$-$C_3$ haloalkyl. In some embodiments, $R^b$ and $R^c$ form a $C_1$-$C_4$ alkylene group between the atoms to which they are attached; and $R^a$, $R^d$, $R^e$, $R^f$, $R^g$, and $R^h$ are each hydrogen.

In some embodiments, $R^b$ and $R^c$ form a $C_1$-$C_3$ alkylene group between the atoms to which they are attached; and $R^a$, $R^d$, $R^e$, $R^f$, $R^g$, and $R^h$ are each hydrogen. In some embodiments, $R^b$ and $R^c$ form a $C_1$ alkylene group between the atoms to which they are attached; and $R^a$, $R^d$, $R^e$, $R^f$, $R^g$, and $R^h$ are each hydrogen. In some embodiments, $R^b$ and $R^c$ form a $C_2$ alkylene group between the atoms to which they are attached; and $R^a$, $R^d$, $R^e$, $R^f$, $R^g$, and $R^h$ are each hydrogen. In some embodiments, $R^b$ and $R^c$ form a $C_3$ alkylene group between the atoms to which they are attached; and $R^a$, $R^d$, $R^e$, $R^f$, $R^g$, and $R^h$ are each hydrogen. In some embodiments, $R^b$ and $R^c$ form a $C_4$ alkylene group between the atoms to which they are attached; and $R^a$, $R^d$, $R^e$, $R^f$, $R^g$, and $R^h$ are each hydrogen.

In some embodiments, the disclosure relates to a compound of formula (I), (I-A), (I-B), (I-C), (I-D), (I-E), or (I-M), or a pharmaceutically acceptable salt thereof, wherein $R^b$ and $R^e$ form a $C_1$-$C_3$ alkylene group between the atoms to which they are attached, wherein said $C_1$-$C_3$ alkylene group is substituted with 0-4 substituents selected from the group consisting of halogen, $C_1$-$C_3$ alkyl, and $C_1$-$C_3$ haloalkyl. In some embodiments, $R^b$ and $R^e$ form a $C_1$-$C_3$ alkylene group between the atoms to which they are attached; and $R^a$, $R^c$, $R^d$, $R^f$, $R^g$, and $R^h$ are each hydrogen. In some embodiments, $R^b$ and $R^e$ form a $C_1$ alkylene group between the atoms to which they are attached; and $R^a$, $R^c$, $R^d$, $R^f$, $R^g$, and $R^h$ are each hydrogen. In some embodiments, $R^b$ and $R^e$ form a $C_2$ alkylene group between the atoms to which they are attached; and $R^a$, $R^c$, $R^d$, $R^f$, $R^g$, and $R^h$ are each hydrogen. In some embodiments, $R^b$ and $R^e$ form a $C_3$ alkylene group between the atoms to which they are attached; and $R^a$, $R^c$, $R^d$, $R^f$, $R^g$, and $R^h$ are each hydrogen.

In some embodiments, the disclosure relates to a compound of formula (I), (I-A), (I-B), (I-C), (I-D), (I-E), or (I-M), or a pharmaceutically acceptable salt thereof, wherein $R^b$ and $R^g$ form a $C_1$-$C_4$ alkylene group between the atoms to which they are attached, wherein said $C_1$-$C_4$ alkylene group is substituted with 0-4 substituents selected from the group consisting of halogen, $C_1$-$C_3$ alkyl, and $C_1$-$C_3$ haloalkyl. In some embodiments, $R^b$ and $R^g$ form a $C_1$-$C_4$ alkylene group between the atoms to which they are attached; and $R^a$, $R^c$, $R^d$, $R^e$, $R^f$, and $R^h$ are each hydrogen. In some embodiments, $R^b$ and $R^g$ form a $C_1$ alkylene group between the atoms to which they are attached; and $R^a$, $R^c$, $R^d$, $R^e$, $R^f$, and $R^h$ are each hydrogen. In some embodiments, $R^b$ and $R^g$ form a $C_2$ alkylene group between the atoms to which they are attached; and $R^a$, $R^c$, $R^d$, $R^e$, $R^f$, and $R^h$ are each hydrogen. In some embodiments, $R^b$ and $R^g$ form a $C_3$ alkylene group between the atoms to which they are attached; and $R^a$, $R^c$, $R^d$, $R^e$, $R^f$, and $R^h$ are each hydrogen. In some embodiments, $R^b$ and $R^g$ form a $C_4$ alkylene group between the atoms to which they are attached; and $R^a$, $R^c$, $R^d$, $R^e$, $R^f$, and $R^h$ are each hydrogen.

In some embodiments, the disclosure relates to a compound of formula (I), (I-A), (I-B), (I-C), (I-D), (I-E), or (I-M), or a pharmaceutically acceptable salt thereof, wherein $R^c$ and $R^d$ together with the atom to which they are attached, form a 3-6 membered cycloalkyl or heterocycloalkyl, wherein said 3-6 membered cycloalkyl or heterocycloalkyl is substituted with 0-4 substituents selected from the group consisting of halogen, $C_1$-$C_3$ alkyl, and $C_1$-$C_3$ haloalkyl. In some embodiments, $R^c$ and $R^d$ together with the atom to which they are attached, form a 3-6 membered cycloalkyl or heterocycloalkyl; and $R^a$, $R^b$, $R^e$, $R^f$, $R^g$, and $R^h$ are each hydrogen. In some embodiments, $R^c$ and $R^d$ together with the atom to which they are attached, form a 3 membered cycloalkyl or a 4 membered heterocycloalkyl; and $R^a$, $R^b$, $R^e$, $R^f$, $R^g$, and $R^h$ are each hydrogen. In some embodiments, $R^c$ and $R^d$ together with the atom to which they are attached, form a 3-6 membered cycloalkyl; and $R^a$, $R^b$, $R^e$, $R^f$, $R^g$, and $R^h$ are each hydrogen. In some embodiments, $R^c$ and $R^d$ together with the atom to which they are attached, form a 3 membered cycloalkyl; and $R^a$, $R^b$, $R^e$, $R^f$, $R_g$ and $R^h$ are each hydrogen. In some embodiments, $R^c$ and $R^d$ together with the atom to which they are attached, form a 4 membered cycloalkyl; and $R^a$, $R^b$, $R^e$, $R^f$, $R^g$, and $R^h$ are each hydrogen. In some embodiments, $R^c$ and $R^d$ together with the atom to which they are attached, form a 5 membered cycloalkyl; and $R^a$, $R^b$, $R^e$, $R^f$, $R^g$, and $R^h$ are each hydrogen. In some embodiments, $R^c$ and $R^d$ together with the atom to which they are attached, form a 6 membered cycloalkyl; and $R^a$, $R^b$, $R^e$, $R^f$, $R^g$, and $R^h$ are each hydrogen. In some embodiments, $R^c$ and $R^d$ together with the atom to which they are attached, form a 3-6 membered heterocycloalkyl ring; and $R^a$, $R^b$, $R^e$, $R^f$, $R^g$, and $R^h$ are each hydrogen. In some embodiments, $R^c$ and $R^d$ together with the atom to which they are attached, form a 3-6 membered heterocycloalkyl ring, wherein the 3-6 membered heterocycloalkyl ring contains O, S, or NH; and $R^a$, $R^b$, $R^e$, $R^f$, $R^g$, and $R^h$ are each hydrogen. In some embodiments, $R^c$ and $R^d$ together with the atom to which they are attached, form a 3 membered heterocycloalkyl ring; and $R^a$, $R^b$, $R^e$, $R^f$, $R^g$, and $R^h$ are each hydrogen. In some embodiments, $R^c$ and $R^d$ together with the atom to which they are attached, form a 4 membered heterocycloalkyl ring; and $R^a$, $R^b$, $R^e$, $R^f$, $R^g$, and $R^h$ are each hydrogen. In some embodiments, $R^c$ and $R^d$ together with the atom to which they are attached, form an oxetane ring; and $R^a$, $R^b$, $R^e$, $R^f$, $R^g$, and $R^h$ are each hydrogen. In some embodiments, $R^c$ and $R^d$ together with the atom to which they are attached, form a 5 membered heterocycloalkyl ring; and $R^a$, $R^b$, $R^e$, $R^f$, $R^g$, and $R^h$ are each hydrogen. In some embodiments, $R^c$ and $R^d$ together with the atom to which they are attached, form a 6 membered heterocycloalkyl ring; and $R^a$, $R^b$, $R^e$, $R^f$, $R^g$, and $R^h$ are each hydrogen. In some embodiments, $R^c$ and $R^d$ together form =O. In some embodiments, $R^c$ and $R^d$ together form =O; and $R^a$, $R^b$, $R^e$, $R^f$, $R^g$, and $R^h$ are each hydrogen.

In some embodiments, the disclosure relates to a compound of formula (I), (I-A), (I-B), (I-C), (I-D), (I-E), or (I-M), or a pharmaceutically acceptable salt thereof, wherein $R^c$ and $R^e$ form a $C_1$-$C_4$ alkylene group between the atoms to which they are attached, wherein said $C_1$-$C_4$ alkylene group is substituted with 0-4 substituents selected from the group consisting of halogen, $C_1$-$C_3$ alkyl, and $C_1$-$C_3$ haloalkyl. In some embodiments, $R^c$ and $R^e$ form a $C_1$-$C_4$ alkylene group between the atoms to which they are attached; and $R^a$, $R^b$, $R^d$, $R^f$, $R^g$, and $R^h$ are each hydrogen. In some embodiments, $R^c$ and $R^e$ form a $C_1$ alkylene group between the atoms to which they are attached; and $R^a$, $R^b$, $R^d$, $R^f$, $R^g$, and $R^h$ are each hydrogen. In some embodiments, $R^c$ and $R^e$ form a $C_2$ alkylene group between the atoms to which they are attached; and $R^a$, $R^b$, $R^d$, $R^f$, $R^g$, and $R^h$ are each hydrogen. In some embodiments, $R^c$ and $R^e$ form a $C_3$ alkylene group between the atoms to which they are attached; and $R^a$, $R^b$, $R^d$, $R^f$, $R^g$, and $R^h$ are each hydrogen. In some embodiments, $R^c$ and $R^e$ form a $C_4$ alkylene group between the atoms to which they are attached; and $R^a$, $R^b$, $R^d$, $R^f$, $R^g$, and $R^h$ are each hydrogen.

In some embodiments, the disclosure relates to a compound of formula (I), (I-A), (I-B), (I-C), (I-D), (I-E), or (I-M), or a pharmaceutically acceptable salt thereof, wherein $R^c$ and $R^g$ form a $C_1$-$C_3$ alkylene group between the atoms to which they are attached, wherein said $C_1$-$C_3$ alkylene group is substituted with 0-4 substituents selected from the group consisting of halogen, $C_1$-$C_3$ alkyl, and $C_1$-$C_3$ haloalkyl. In some embodiments, $R^c$ and $R^g$ form a $C_1$-$C_3$ alkylene group between the atoms to which they are attached; and $R^a$, $R^b$, $R^d$, $R^e$, $R^f$, and $R^h$ are each hydrogen. In some embodiments, $R^c$ and $R^g$ form a $C_1$-$C_2$ alkylene group between the atoms to which they are attached; and $R^a$, $R^b$, $R^d$, $R^e$, $R^f$, and $R^h$ are each hydrogen. In some embodiments, $R^c$ and $R^g$ form a $C_1$ alkylene group between the atoms to which they are attached; and $R^a$, $R^b$, $R^d$, $R^e$, $R^f$, and $R^h$ are each hydrogen. In some embodiments, $R^c$ and $R^g$ form a $C_2$ alkylene group between the atoms to which they are attached; and $R^a$, $R^b$, $R^d$, $R^e$, $R^f$, and $R^h$ are each hydrogen. In some embodiments, $R^c$ and $R^g$ form a $C_3$ alkylene group between the atoms to which they are attached; and $R^a$, $R^b$, $R^d$, $R^e$, $R^f$, and $R^h$ are each hydrogen.

In some embodiments, the disclosure relates to a compound of formula (I), (I-A), (I-B), (I-C), (I-D), (I-E), or (I-M), or a pharmaceutically acceptable salt thereof, wherein $R^e$ and $R^f$ together with the atom to which they are attached, form a 3-6 membered cycloalkyl or heterocycloalkyl, wherein said 3-6 membered cycloalkyl or heterocycloalkyl is substituted with 0-4 substituents selected from the group consisting of halogen, $C_1$-$C_3$ alkyl, and $C_1$-$C_3$ haloalkyl. In some embodiments, $R^e$ and $R^f$ together with the atom to which they are attached, form a 3-6 membered cycloalkyl or heterocycloalkyl; and $R^a$, $R^b$, $R^c$, $R^d$, $R^g$, and $R^h$ are each hydrogen. In some embodiments, $R^e$ and $R^f$ together with the atom to which they are attached, form a 3-6 membered cycloalkyl; and $R^a$, $R^b$, $R^c$, $R^d$, $R^g$, and $R^h$ are each hydrogen. In some embodiments, $R^e$ and $R^f$ together with the atom to which they are attached, form a 3 membered cycloalkyl; and $R^a$, $R^b$, $R^c$, $R^d$, $R^g$, and $R^h$ are each hydrogen. In some embodiments, $R^e$ and $R^f$ together with the atom to which they are attached, form a 4 membered cycloalkyl; and $R^a$, $R^b$, $R^e$, $R^d$, $R^g$, and $R^h$ are each hydrogen. In some embodiments, $R^e$ and $R^f$ together with the atom to which they are attached, form a 5 membered cycloalkyl; and $R^a$, $R^b$, $R^c$, $R^d$, $R^g$, and $R^h$ are each hydrogen. In some embodiments, $R^e$ and $R^f$ together with the atom to which they are attached, form a 6 membered cycloalkyl; and $R^a$, $R^b$, $R^c$, $R^d$, $R^g$, and $R^h$ are each hydrogen. In some embodiments, $R^e$ and $R^f$ together with the atom to which they are attached, form a 3-6 membered heterocycloalkyl ring; and $R^a$, $R^b$, $R^c$, $R^d$, $R^g$, and $R^h$ are each hydrogen. In some embodiments, $R^e$ and $R^f$ together with the atom to which they are attached, form a 3-6 membered heterocycloalkyl ring, wherein the 3-6 membered heterocycloalkyl ring contains O, S, or NH; and $R^a$, $R^b$, $R^c$, $R^d$, $R^g$, and $R^h$ are each hydrogen. In some embodiments, $R^e$ and $R^f$ together with the atom to which they are attached, form a 3 membered heterocycloalkyl ring; and $R^a$, $R^b$, $R^c$, $R^d$, $R^g$, and $R^h$ are each hydrogen. In some embodiments, $R^e$ and $R^f$ together with the atom to which they are attached, form a 4 membered heterocycloalkyl ring; and $R^a$, $R^b$, $R^c$, $R^d$, $R^g$, and $R^h$ are each hydrogen. In some embodiments, $R^e$ and $R^f$ together with the atom to which they are attached, form an oxetane ring; and $R^a$, $R^b$, $R^c$, $R^d$, $R^g$, and $R^h$ are each hydrogen. In some embodiments, $R^e$ and $R^f$ together with the atom to which they are attached, form a 5 membered heterocycloalkyl ring; and $R^a$, $R^b$, $R^c$, $R^d$, $R^g$, and $R^h$ are each hydrogen. In some embodiments, $R^e$ and $R^f$ together with the atom to which they are attached, form a 6 membered heterocycloalkyl ring; and $R^a$, $R^b$, $R^c$, $R^d$, $R^g$, and $R^h$ are each hydrogen. In some embodiments, $R^e$ and $R^f$ together form =O. In some embodiments, $R^e$ and $R^f$ together form =O; and $R^a$, $R^b$, $R^c$, $R^d$, $R^g$, and $R^h$ are each hydrogen.

In some embodiments, the disclosure relates to a compound of formula (I), (I-A), (I-B), (I-C), (I-D), (I-E), or (I-M), or a pharmaceutically acceptable salt thereof, wherein $R^e$ and $R^g$ form a $C_1$-$C_3$ alkylene group between the atoms to which they are attached, wherein said $C_1$-$C_3$ alkylene group is substituted with 0-4 substituents selected from the group consisting of halogen, $C_1$-$C_3$ alkyl, and $C_1$-$C_3$ haloalkyl. In some embodiments, $R^e$ and $R^g$ form a $C_1$-$C_3$ alkylene group between the atoms to which they are attached; and $R^a$, $R^b$, $R^c$, $R^d$, $R^f$, and $R^h$ are each hydrogen. In some embodiments, $R^e$ and $R^g$ form a $C_1$ alkylene group between the atoms to which they are attached; and $R^a$, $R^b$, $R^c$, $R^d$, $R^f$, and $R^h$ are each hydrogen. In some embodiments, $R^e$ and $R^g$ form a $C_2$ alkylene group between the atoms to which they are attached; and $R^a$, $R^b$, $R^c$, $R^d$, $R^f$, and $R^h$ are each hydrogen. In some embodiments, $R^e$ and $R^g$ form a $C_3$ alkylene group between the atoms to which they are attached; and $R^a$, $R^b$, $R^c$, $R^d$, $R^f$, and $R^h$ are each hydrogen.

In some embodiments, the disclosure relates to a compound of formula (I), (I-A), (I-B), (I-C), (I-D), (I-E), or (I-M), or a pharmaceutically acceptable salt thereof, wherein $R^g$ and $R^h$ together with the atom to which they are attached, form a 3-6 membered cycloalkyl or heterocycloalkyl, wherein said 3-6 membered cycloalkyl or heterocycloalkyl is substituted with 0-4 substituents selected from the group consisting of halogen, $C_1$-$C_3$ alkyl, and $C_1$-$C_3$ haloalkyl. In some embodiments, $R^g$ and $R^h$ together with the atom to which they are attached, form a 3-6 membered cycloalkyl or heterocycloalkyl; and $R^a$, $R^b$, $R^c$, $R^d$, $R^e$, and $R^f$ are each hydrogen. In some embodiments, $R^g$ and $R^h$ together with the atom to which they are attached, form a 3-6 membered cycloalkyl; and $R^a$, $R^b$, $R^c$, $R^d$, $R^e$, and $R^f$ are each hydrogen. In some embodiments, $R^g$ and $R^h$ together with the atom to which they are attached, form a 3 membered cycloalkyl; and $R^a$, $R^b$, $R^c$, $R^d$, $R^e$, and $R^f$ are each hydrogen. In some embodiments, $R^g$ and $R^h$ together with the atom to which they are attached, form a 4 membered cycloalkyl; and $R^a$, $R^b$, $R^c$, $R^d$, $R^e$, and $R^f$ are each hydrogen. In some embodiments, $R^g$ and $R^h$ together with the atom to which they are attached, form a 5 membered cycloalkyl; and $R^a$, $R^b$, $R^c$, $R^d$, $R^e$, and $R^f$ are each hydrogen. In some embodiments, $R^g$ and $R^h$ together with the atom to which they are attached, form a 6 membered cycloalkyl; and $R^a$, $R^b$, $R^c$, $R^d$, $R^e$, and $R^f$ are each hydrogen. In some embodiments, $R^g$ and $R^h$ together with the atom to which they are attached, form a 3-6 membered heterocycloalkyl ring; and $R^a$, $R^b$, $R^c$, $R^d$, $R^e$, and $R^f$ are each hydrogen. In some embodiments, $R^g$ and $R^h$ together with the atom to which they are attached, form a 3-6 membered heterocycloalkyl ring, wherein the 3-6 membered heterocycloalkyl ring contains O, S, or NH; and $R^a$, $R^b$, $R^c$, $R^d$, $R^e$, and $R^f$ are each hydrogen. In some embodiments, $R^g$ and $R^h$ together with the atom to which they are attached, form a 3 membered heterocycloalkyl ring; and $R^a$, $R^b$, $R^c$, $R^d$, $R^e$, and $R^f$ are each hydrogen. In some embodiments, $R^g$ and $R^h$ together with the atom to which they are attached, form a 4 membered heterocycloalkyl ring; and $R^a$, $R^b$, $R^c$, $R^d$, $R^e$, and $R^f$ are each hydrogen. In some embodiments, $R^g$ and $R^h$ together with the atom to which they are attached, form an oxetane ring; and $R^a$, $R^b$, $R^c$, $R^d$, $R^e$, and $R^f$ are each hydrogen. In some embodiments, $R^g$ and $R^h$ together with the atom to which they are attached, form a 5 membered heterocycloalkyl ring; and $R^a$, $R^b$, $R^c$, $R^d$, $R^e$, and $R^f$ are each hydrogen. In some embodiments, $R^g$ and $R^h$ together with the atom to which they are attached, form a 6 membered heterocycloalkyl ring; and $R^a$, $R^b$, $R^c$, $R^d$, $R^e$, and $R^f$ are each hydrogen. In some embodiments, $R^g$ and $R^h$ together form =O. In some embodiments, $R^g$ and $R^h$ together form =O; and $R^a$, $R^b$, $R^c$, $R^d$, $R^e$, and $R^f$ are each hydrogen.

In some embodiments, the disclosure relates to a compound of formula (I), (I-A), (I-B), (I-C), (I-D), (I-E), or (I-M), or a pharmaceutically acceptable salt thereof, wherein $R^a$, $R^b$, $R^c$, $R^d$, $R^e$, $R^f$, $R^g$, and $R^h$ are defined as follows:

(ii) $R^a$ and $R^e$ form a $C_1$-$C_2$ alkylene group between the atoms to which they are attached, wherein said $C_1$-$C_2$ alkylene group is substituted with 0-4 substituents selected from the group consisting of halogen, $C_1$-$C_3$ alkyl, and $C_1$-$C_3$ haloalkyl; and $R^b$, $R^c$, $R^d$, $R^f$, $R^g$, and $R^h$ are each independently hydrogen, halogen, $C_1$-$C_3$ alkyl, or $C_1$-$C_3$ haloalkyl; or (iv) $R^b$ and $R^c$ form a $C_1$-$C_4$ alkylene group between the atoms to which they are attached, wherein said $C_1$-$C_4$ alkylene group is substituted with 0-4 substituents selected from the group consisting of halogen, $C_1$-$C_3$ alkyl, and $C_1$-$C_3$ haloalkyl; and $R^a$, $R^d$, $R^e$, $R^f$, $R^g$, and $R^h$ are each independently hydrogen, halogen, $C_1$-$C_3$ alkyl, or $C_1$-$C_3$ haloalkyl; or (vii) $R^c$ and $R^d$ together with the atom to which they are attached, form a 3-6 membered cycloalkyl or heterocycloalkyl, wherein said 3-6 membered cycloalkyl or heterocycloalkyl is substituted with 0-4 substituents selected from the group consisting of halogen, $C_1$-$C_3$ alkyl, and $C_1$-$C_3$ haloalkyl; and $R^a$, $R^b$, $R^e$, $R^f$, $R^g$, and $R^h$ are each independently hydrogen, halogen, $C_1$-$C_3$ alkyl, or $C_1$-$C_3$ haloalkyl; or (viii) Re and $R^d$ together form =O; and $R^a$, $R^b$, $R^e$, $R^f$, $R^g$, and $R^h$ are each independently hydrogen, halogen, $C_1$-$C_3$ alkyl, or $C_1$-$C_3$ haloalkyl; or (ix) $R^c$ and $R^e$ form a $C_1$-$C_4$ alkylene group between the atoms to which they are attached, wherein said $C_1$-$C_4$ alkylene group is substituted with 0-4 substituents selected from the group consisting of halogen, $C_1$-$C_3$ alkyl, and $C_1$-$C_3$ haloalkyl, and $R^a$, $R^b$, $R^d$, $R^f$, $R^g$, and $R^h$ are each independently hydrogen, halogen, $C_1$-$C_3$ alkyl, or $C_1$-$C_3$ haloalkyl; or (x) $R^c$ and $R^g$ form a $C_1$-$C_3$ alkylene group between the atoms to which they are attached, wherein said $C_1$-$C_3$ alkylene group is substituted with 0-4 substituents selected from the group consisting of halogen, $C_1$-$C_3$ alkyl, and $C_1$-$C_3$ haloalkyl, and $R^a$, $R^b$, $R^d$, $R^e$, $R^f$, and $R^h$ are each independently hydrogen, halogen, $C_1$-$C_3$ alkyl, or $C_1$-$C_3$ haloalkyl; or (xi) $R^e$ and $R^f$ together with the atom to which they are attached, form a 3-6 membered cycloalkyl or heterocycloalkyl, wherein said 3-6 membered cycloalkyl or heterocycloalkyl is substituted with 0-4 substituents selected from the group consisting of halogen, $C_1$-$C_3$ alkyl, and $C_1$-$C_3$ haloalkyl; and $R^a$, $R^b$, $R^c$, $R^d$, $R^g$, and $R^h$ are each independently hydrogen, halogen, $C_1$-$C_3$ alkyl, or $C_1$-$C_3$ haloalkyl; or (xiii) $R^e$ and $R^g$ form a $C_1$-$C_3$ alkylene group between the atoms to which they are attached, wherein said $C_1$-$C_3$ alkylene group is substituted with 0-4 substituents selected from the group consisting of halogen, $C_1$-$C_3$ alkyl, and $C_1$-$C_3$ haloalkyl; and $R^a$, $R^b$, $R^c$, $R^d$, $R^f$, and $R^h$ are each independently hydrogen, halogen, $C_1$-$C_3$ alkyl, or $C_1$-$C_3$ haloalkyl; or (xv) $R^g$ and $R^h$ together form =O; and $R^a$, $R^b$, $R^c$, $R^d$, $R^e$, and $R^f$ are each independently hydrogen, halogen, $C_1$-$C_3$ alkyl, or $C_1$-$C_3$ haloalkyl.

In some embodiments, the disclosure relates to a compound of formula (I), (I-A), (I-B), (I-C), (I-D), (I-E), or (I-M), or a pharmaceutically acceptable salt thereof, wherein $R^a$, $R^b$, $R^c$, $R^d$, $R^e$, $R^f$, $R^g$, and $R^h$ are defined as follows:

(ii) $R^a$ and $R^e$ form a $C_1$-$C_2$ alkylene group between the atoms to which they are attached; and $R^b$, $R^c$, $R^d$, $R^f$, $R^g$, and $R^h$ are each hydrogen; or (iv) $R^b$ and $R^c$ form a $C_1$-$C_4$ alkylene group between the atoms to which they are attached; and $R^a$, $R^d$, $R^e$, $R^f$, $R^g$, and $R^h$ are each hydrogen; or (vii) $R^c$ and $R^d$ together with the atom to which they are attached, form a 3-6 membered cycloalkyl or heterocycloalkyl; and $R^a$, $R^b$, $R^e$, $R^f$, $R^g$, and $R^h$ are each hydrogen; or (viii) $R^c$ and $R^d$ together form =O; and $R^a$, $R^b$, $R^e$, $R^f$, $R^g$, and $R^h$ are each hydrogen; or (ix) $R^c$ and $R^e$ form a $C_1$-$C_4$ alkylene group between the atoms to which they are attached; and $R^a$, $R^b$, $R^d$, $R^f$, $R^g$, and $R^h$ are each hydrogen; or (x) $R^c$ and $R^g$ form a $C_1$-$C_3$ alkylene group between the atoms to which they are attached; and $R^a$, $R^b$, $R^d$, $R^e$, $R^f$, and $R^h$ are each hydrogen; or (xi) $R^e$ and $R^f$ together with the atom to which they are attached, form a 3-6 membered cycloalkyl or heterocycloalkyl; and $R^a$, $R^b$, $R^c$, $R^d$, $R^g$, and $R^h$ are each hydrogen; or (xiii) $R^e$ and $R^g$ form a $C_1$-$C_3$ alkylene group between the atoms to which they are attached; and $R^a$, $R^b$, $R^c$, $R^d$, $R^f$, and $R^h$ are each independently hydrogen; or (xv) $R^g$ and $R^h$ together form =O; and $R^a$, $R^b$, $R^c$, $R^d$, $R^e$, and $R^f$ are each hydrogen.

In some embodiments, the disclosure relates to a compound of formula (I), (I-A), (I-B), (I-C), (I-D), (I-E), or (I-M), or a pharmaceutically acceptable salt thereof, wherein $R^a$, $R^b$, $R^c$, $R^d$, $R^e$, $R^f$, $R^g$, and $R^h$ are defined as follows:

(ii) $R^a$ and $R^e$ form a $C_1$-$C_2$ alkylene group between the atoms to which they are attached; and $R^b$, $R^c$, $R^d$, $R^f$, $R^g$, and $R^h$ are each hydrogen; or (iv) $R^b$ and $R^c$ form a $C_1$-$C_3$ alkylene group between the atoms to which they are attached, and $R^a$, $R^d$, $R^e$, $R^f$, $R_g$ and $R^h$ are each hydrogen; or (vii) $R^c$ and $R^d$ together with the atom to which they are attached, form a 3-membered cycloalkyl or a 4-membered heterocycloalkyl; and $R^a$, $R^b$, $R^e$, $R^f$, $R^g$, and $R^h$ are each hydrogen; or (viii) $R^c$ and $R^d$ together form =O; and $R^a$, $R^b$, $R^e$, $R^f$, $R^g$, and $R^h$ are each hydrogen; or (ix) $R^c$ and $R^e$ form a $C_1$ alkylene group between the atoms to which they are attached; and $R^a$, $R^b$, $R^d$, $R^f$, $R^g$, and $R^h$ are each hydrogen; or (x) $R^c$ and $R^g$ form a $C_1$-$C_2$ alkylene group between the atoms to which they are attached; and $R^a$, $R^b$, $R^d$, $R^e$, $R^f$, and $R^h$ are each hydrogen; or (xi) $R^e$ and $R^f$ together with the atom to which they are attached, form a 4-membered heterocycloalkyl; and $R^a$, $R^b$, $R^c$, $R^d$, $R^g$, and $R^h$ are each hydrogen; or (xiii) $R^e$ and $R^g$ form a $C_2$ alkylene group between the atoms to which they are attached; and $R^a$, $R^b$, $R^c$, $R^d$, $R^f$, and $R^h$ are each independently hydrogen; or (xv) $R^g$ and $R^h$ together form =O; and $R^a$, $R^b$, $R^c$, $R^d$, $R^e$, and $R^f$ are each hydrogen.

In some embodiments, the disclosure relates to a compound of formula (I), (I-A), (I-B), (I-C), (I-D), (I-E), or (I-M), or a pharmaceutically acceptable salt thereof, wherein $R^a$, $R^b$, $R^c$, $R^d$, $R^e$, $R^f$, $R^g$, and $R^h$ are defined as follows:

(ii) $R^a$ and $R^e$ form a $C_1$-$C_2$ alkylene group between the atoms to which they are attached; and $R^b$, $R^c$, $R^d$, $R^f$, and $R^g$ are each hydrogen; or (iv) $R^b$ and $R^c$ form a $C_1$-$C_2$ alkylene group between the atoms to which they are attached; and $R^a$, $R^c$, $R^d$, $R^f$, and $R^g$ are each hydrogen; or (vii) $R^c$ and $R^d$ together with the atom to which they are attached, form a 3 membered cycloalkyl; and $R^a$, $R^b$, $R^e$, $R^f$, and $R^g$ are each hydrogen; or (x) $R^c$ and $R^g$ form a $C_1$-$C_2$ alkylene group between the atoms to which they are attached; and $R^a$, $R^b$, $R^d$, $R^e$, and $R^g$ are each hydrogen; or (xi) $R^e$ and $R^f$ together with the atom to which they are attached, form a 4 membered heterocycloalkyl; and $R^a$, $R^b$, $R^c$, $R^d$, and $R^g$ are each hydrogen; or (xiii) $R^e$ and $R^g$ form a $C_2$ alkylene group between the atoms to which they are attached; and $R^a$, $R^b$, $R^c$, $R^d$, and $R^f$ are each independently hydrogen.

In some embodiments, the disclosure relates to a compound of formula (I), (I-A), (I-B), (I-C), (I-D), (I-E), or (I-M), or a pharmaceutically acceptable salt thereof, wherein

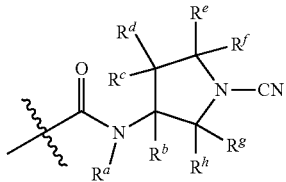

is selected from:

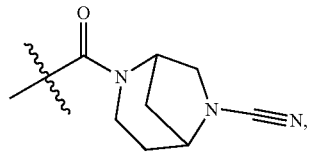

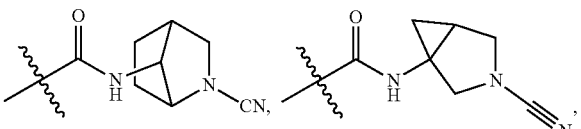

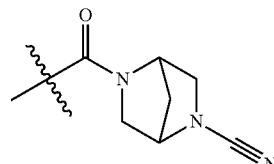

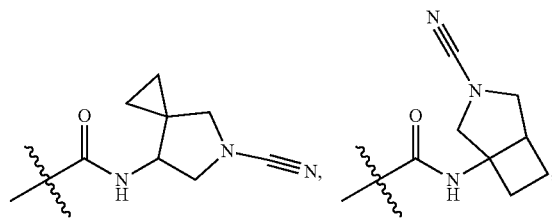

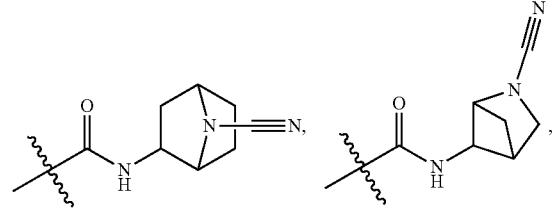

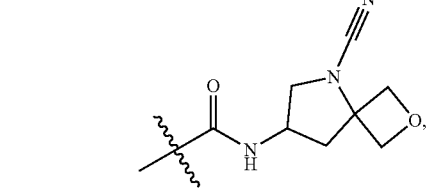

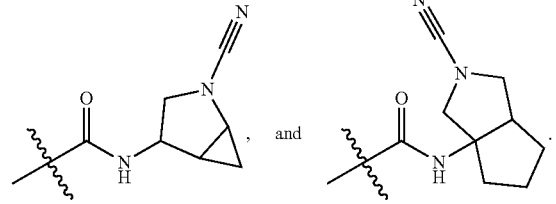

In some embodiments,

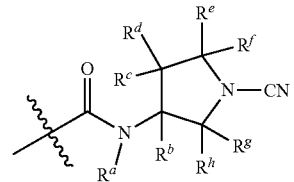

is

-continued
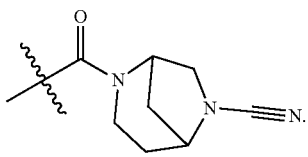
In some embodiments.
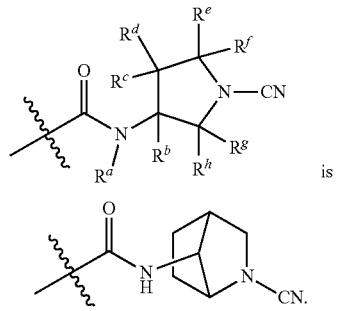
is
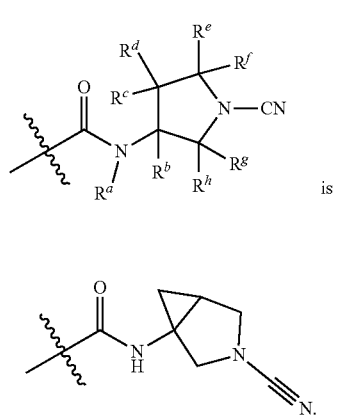
In some embodiments,
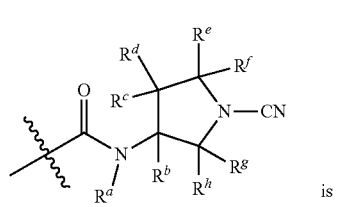
is
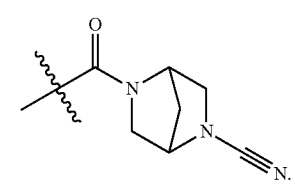
In some embodiments,
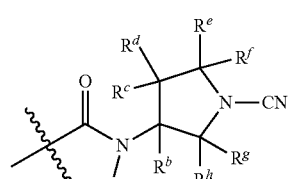
is
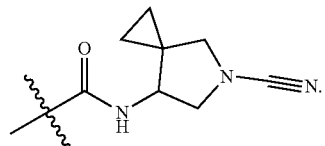
In some embodiments,
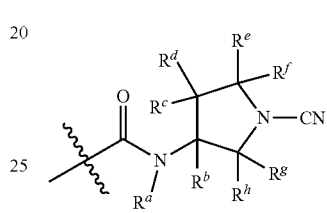 is .
In some embodiments,
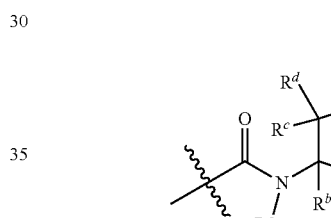
is
In some embodiments,
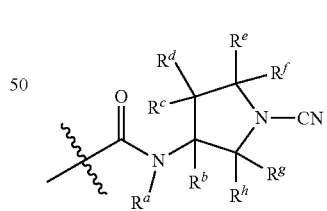
is
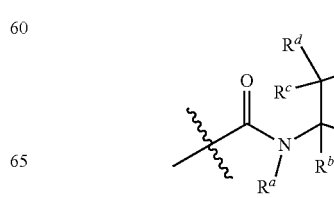
In some embodiments,
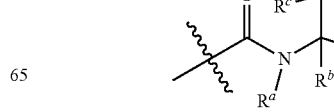 is -continued In some embodiments,

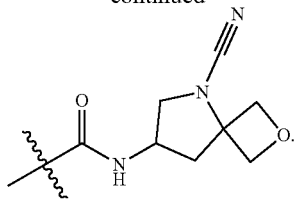

In some embodiments,

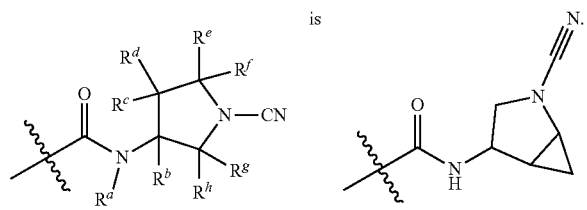 is 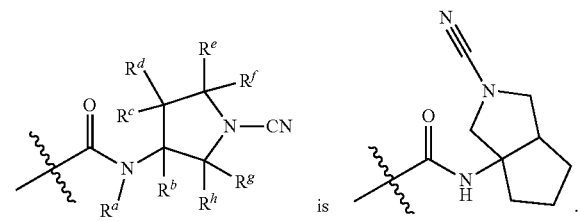.

In some embodiments, the disclosure relates to a compound of formula (I-A), (I-A-1), (I-A-2), (I-A-3), (I-A-4), (I-B), (I-B-1), (I-B-2), (I-B-3), (I-B-4), (I-F-1), (I-F-2), (I-G-1), (I-G-2), (I-H-1), (I-H-2), (I-J-1), (I-J-2), (I-K-1), (I-K-2), (I-L-1), (I-L-2), (I-M), (I-M-1), (I-M-2), (I-M-3), or (I-M-4), or a pharmaceutically acceptable salt thereof, wherein $X^1$ is C or N. In some embodiments, $X^1$ is C. In some embodiments, $X^1$ is N.

In some embodiments, the disclosure relates to a compound of formula (I-A), (I-A-1), (I-A-2), (I-A-3), (I-A-4), (I-B), (I-B-1), (I-B-2), (I-B-3), (I-B-4), (I-F-1), (I-F-2), (I-G-1), (I-G-2), (I-H-1), (I-H-2), (I-J-1), (I-J-2), (I-K-1), (I-K-2), (I-L-1), (I-L-2), (I-M), (I-M-1), (I-M-2), (I-M-3), or (I-M-4), or a pharmaceutically acceptable salt thereof, wherein $X^2$ is CH, $CR^1$, O, S, N, NH, or $NR^1$, as valency permits. In some embodiments, $X^2$ is CH. In some embodiments, $X^2$ is $CR^1$. In some embodiments, $X^2$ is O. In some embodiments, $X^2$ is S. In some embodiments, $X^2$ is N. In some embodiments, $X^2$ is NH. In some embodiments, $X^2$ is $NR^1$.

In some embodiments, the disclosure relates to a compound of formula (I-A), (I-A-1), (I-A-2), (I-A-3), (I-A-4), (I-B), (I-B-1), (I-B-2), (I-B-3), (I-B-4), (I-F-1), (I-F-2), (I-G-1), (I-G-2), (I-H-1), (I-H-2), (I-J-1), (I-J-2), (I-K-1), (I-K-2), (I-L-1), (I-L-2), (I-M), (I-M-1), (I-M-2), (I-M-3), or (I-M-4), or a pharmaceutically acceptable salt thereof, wherein $X^3$ is CH, $CR^1$, O, S, N, NH, or $NR^1$, as valency permits. In some embodiments, $X^3$ is CH. In some embodiments, $X^3$ is $CR^1$. In some embodiments, $X^3$ is O. In some embodiments, $X^3$ is S. In some embodiments, $X^3$ is N. In some embodiments, $X^3$ is NH. In some embodiments, $X^3$ is $NR^1$.

In some embodiments, the disclosure relates to a compound of formula (I-A), (I-A-1), (I-A-2), (I-A-3), (I-A-4), (I-B), (I-B-1), (I-B-2), (I-B-3), (I-B-4), (I-F-1), (I-F-2), (I-G-1), (I-G-2), (I-H-1), (I-H-2), (I-J-1), (I-J-2), (I-K-1), (I-K-2), (I-L-1), (I-L-2), (I-M), (I-M-1), (I-M-2), (I-M-3), or (I-M-4), or a pharmaceutically acceptable salt thereof, wherein $X^4$ is C or N. In some embodiments, $X^4$ is C. In some embodiments, $X^4$ is N.

In some embodiments, the disclosure relates to a compound of formula (I-A), (I-A-1), (I-A-2), (I-A-3), (I-A-4), (I-F-1), (I-F-2), (I-G-1), (I-G-2), (I-H-1), (I-H-2), (I-J-1), (I-J-2), (I-K-1), (I-K-2), (I-L-1), (I-L-2), (I-M), (I-M-1), (I-M-2), (I-M-3), or (I-M-4), or a pharmaceutically acceptable salt thereof, wherein $X^5$ is a bond, CH, $CR^1$, O, S, N, NH, or $NR^1$, as valency permits. In some embodiments, $X^5$ is a bond. In some embodiments, $X^5$ is CH. In some embodiments, $X^5$ is $CR^1$. In some embodiments, $X^5$ is O. In some embodiments, $X^5$ is S. In some embodiments, $X^5$ is N. In some embodiments, $X^5$ is NH. In some embodiments, $X^5$ is $NR^1$.

In some embodiments, the disclosure relates to a compound of formula (I-A), (I-A-1), (I-A-2), (I-A-3), (I-A-4), (I-B), (I-B-1), (I-B-2), (I-B-3), (I-B-4), (I-F-1), (I-F-2), (I-G-1), (I-G-2), (I-H-1), (I-H-2), (I-J-1), (I-J-2), (I-K-1), (I-K-2), (I-L-1), (I-L-2), (I-M), (I-M-1), (I-M-2), (I-M-3), or (I-M-4), or a pharmaceutically acceptable salt thereof, wherein $X^6$ is CH, $CR^1$, O, S, N, NH, or $NR^1$, as valency permits. In some embodiments, $X^6$ is CH. In some embodiments, $X^6$ is $CR^1$. In some embodiments, $X^6$ is O. In some embodiments, $X^6$ is S. In some embodiments, $X^6$ is N. In some embodiments, $X^6$ is NH. In some embodiments, $X^6$ is $NR^1$.

In some embodiments, the disclosure relates to a compound of formula (I-A), (I-A-1), (I-A-2), (I-A-3), (I-A-4), (I-F-1), (I-F-2), (I-G-1), (I-G-2), (I-H-1), (I-H-2), (I-J-1), (I-J-2), (I-K-1), (I-K-2), (I-L-1), (I-L-2), (I-M), (I-M-1), (I-M-2), (I-M-3), or (I-M-4), or a pharmaceutically acceptable salt thereof, wherein $X^1$ is C; $X^2$ is N; $X^3$ is NH; $X^4$ is C; $X^5$ is a bond; and $X^6$ is CH.

In some embodiments, the disclosure relates to a compound of formula (I-A), (I-A-1), (I-A-2), (I-A-3), (I-A-4), (I-F-1), (I-F-2), (I-G-1), (I-G-2), (I-H-1), (I-H-2), (I-J-1), (I-J-2), (I-K-1), (I-K-2), (I-L-1), (I-L-2), (I-M), (I-M-1), (I-M-2), (I-M-3), or (I-M-4), or a pharmaceutically acceptable salt thereof, wherein $X^1$ is C; $X^2$ is N; $X^3$ is CH; $X^4$ is C; $X^5$ is a bond; and $X^6$ is S.

In some embodiments, the disclosure relates to a compound of formula (I-A), (I-A-1), (I-A-2), (I-A-3), (I-A-4), (I-F-1), (I-F-2), (I-G-1), (I-G-2), (I-H-1), (I-H-2), (I-J-1), (I-J-2), (I-K-1), (I-K-2), (I-L-1), (I-L-2), (I-M), (I-M-1), (I-M-2), (I-M-3), or (I-M-4), or a pharmaceutically acceptable salt thereof, wherein $X^1$ is C; $X^2$ is CH; $X^3$ is CH; $X^4$ is C; $X^5$ is CH; and $X^6$ is C.

In some embodiments, the disclosure relates to a compound of formula (I-A), (I-A-1), (I-A-2), (I-A-3), (I-A-4), (I-F-1), (I-F-2), (I-G-1), (I-G-2), (I-H-1), (I-H-2), (I-J-1), (I-J-2), (I-K-1), (I-K-2), (I-L-1), or (I-L-2), or a pharmaceutically acceptable salt thereof, wherein $Y^1$ is C or N. In some embodiments, $Y^1$ is C. In some embodiments, $Y^1$ is N.

In some embodiments, the disclosure relates to a compound of formula (I-A), (I-A-1), (I-A-2), (I-A-3), (I-A-4), (I-F-1), (I-F-2), (I-G-1), (I-G-2), (I-H-1), (I-H-2), (I-J-1), (I-J-2), (I-K-1), (I-K-2), (I-L-1), or (I-L-2), or a pharmaceutically acceptable salt thereof, wherein $Y^2$ is C or N. In some embodiments, $Y^2$ is C. In some embodiments, $Y^2$ is N.

In some embodiments, the disclosure relates to a compound of formula (I-A), (I-A-1), (I-A-2), (I-A-3), (I-A-4), (I-B), (I-B-1), (I-B-2), (I-B-3), (I-B-4), (I-F-1), (I-F-2), (I-G-1), (I-G-2), (I-H-1), (I-H-2), (I-J-1), (I-J-2), (I-K-1), (I-K-2), (I-L-1), or (I-L-2), or a pharmaceutically acceptable salt thereof, wherein $Y^3$ is CH, $CR^2$, O, S, N, NH, or $NR^2$, as valency permits. In some embodiments, $Y^3$ is CH. In some embodiments, $Y^3$ is $CR^2$. In some embodiments, $Y^3$ is O. In some embodiments, $Y^3$ is S. In some embodiments, $Y^3$ is N. In some embodiments, $Y^3$ is NH. In some embodiments, $Y^3$ is $NR^2$.

In some embodiments, the disclosure relates to a compound of formula (I-A), (I-A-1), (I-A-2), (I-A-3), (I-A-4), (I-B), (I-B-1), (I-B-2), (I-B-3), (I-B-4), (I-F-1), (I-F-2), (I-G-1), (I-G-2), (I-H-1), (I-H-2), (I-J-1), (I-J-2), (I-K-1), (I-K-2), (I-L-1), or (I-L-2), or a pharmaceutically acceptable salt thereof, wherein $Y^4$ is a bond, CH, $CR^2$, O, S, N, NH, or $NR^2$, as valency permits. In some embodiments, $Y^4$ is a bond. In some embodiments, $Y^4$ is CH. In some embodiments, $Y^4$ is $CR^2$. In some embodiments, $Y^4$ is O. In some embodiments, $Y^4$ is S. In some embodiments, $Y^4$ is N. In some embodiments, $Y^4$ is NH. In some embodiments, $Y^4$ is $NR^2$.

In some embodiments, the disclosure relates to a compound of formula (I-A), (I-A-1), (I-A-2), (I-A-3), (I-A-4), (I-B), (I-B-1), (I-B-2), (I-B-3), (I-B-4), (I-F-1), (I-F-2), (I-G-1), (I-G-2), (I-H-1), (I-H-2), (I-J-1), (I-J-2), (I-K-1), (I-K-2), (I-L-1), or (I-L-2), or a pharmaceutically acceptable salt thereof, wherein $Y^5$ is CH, $CR^2$, O, S, N, NH, or $NR^2$, as valency permits. In some embodiments, $Y^5$ is CH. In some embodiments, $Y^5$ is $CR^2$. In some embodiments, $Y^5$ is O. In some embodiments, $Y^5$ is S. In some embodiments, $Y^5$ is N. In some embodiments, $Y^5$ is NH. In some embodiments, $Y^5$ is $NR^2$.

In some embodiments, the disclosure relates to a compound of formula (I-A), (I-A-1), (I-A-2), (I-A-3), (I-A-4), (I-B), (I-B-1), (I-B-2), (I-B-3), (I-B-4), (I-F-1), (I-F-2), (I-G-1), (I-G-2), (I-H-1), (I-H-2), (I-J-1), (I-J-2), (I-K-1), (I-K-2), (I-L-1), or (I-L-2), or a pharmaceutically acceptable salt thereof, wherein $Y^6$ is CH, $CR^2$, O, S, N, NH, or $NR^2$, as valency permits. In some embodiments, $Y^6$ is CH. In some embodiments, $Y^6$ is $CR^2$. In some embodiments, $Y^6$ is O. In some embodiments, $Y^6$ is S. In some embodiments, $Y^6$ is N. In some embodiments, $Y^6$ is NH. In some embodiments, $Y^6$ is $NR^2$.

In some embodiments, the disclosure relates to a compound of formula (I-A), (I-A-1), (I-A-2), (I-A-3), (I-A-4), (I-F-1), (I-F-2), (I-G-1), (I-G-2), (I-H-1), (I-H-2), (I-J-1), (I-J-2), (I-K-1), (I-K-2), (I-L-1), or (I-L-2), or a pharmaceutically acceptable salt thereof, wherein $Y^1$ is C; $Y^2$ is C; $Y^3$ is CH; $Y^4$ is CH; $Y^5$ is CH; and $Y^6$ is CH.

In some embodiments, the disclosure relates to a compound of formula (I-A), (I-A-1), (I-A-2), (I-A-3), (I-A-4), (I-F-1), (I-F-2), (I-G-1), (I-G-2), (I-H-1), (I-H-2), (I-J-1), (I-J-2), (I-K-1), (I-K-2), (I-L-1), or (I-L-2), or a pharmaceutically acceptable salt thereof, wherein $Y^1$ is C; $Y^2$ is C; $Y^3$ is $CR^2$; $Y^4$ is CH; $Y^5$ is CH; and $Y^6$ is CH.

In some embodiments, the disclosure relates to a compound of formula (I-A), (I-A-1), (I-A-2), (I-A-3), (I-A-4), (I-F-1), (I-F-2), (I-G-1), (I-G-2), (I-H-1), (I-H-2), (I-J-1), (I-J-2), (I-K-1), (I-K-2), (I-L-1), or (I-L-2), or a pharmaceutically acceptable salt thereof, wherein $Y^1$ is C; $Y^2$ is C; $Y^3$ is CH; $Y^4$ is $CR^2$; $Y^5$ is CH; and $Y^6$ is CH.

In some embodiments, the disclosure relates to a compound of formula (I-A), (I-A-1), (I-A-2), (I-A-3), (I-A-4), (I-F-1), (I-F-2), (I-G-1), (I-G-2), (I-H-1), (I-H-2), (I-J-1), (I-J-2), (I-K-1), (I-K-2), (I-L-1), or (I-L-2), or a pharmaceutically acceptable salt thereof, wherein $Y^1$ is C; $Y^2$ is C; $Y^3$ is CH; $Y^4$ is CH; $Y^5$ is $CR^2$; and $Y^6$ is CH.

In some embodiments, the disclosure relates to a compound of formula (I-A), (I-A-1), (I-A-2), (I-A-3), (I-A-4), (I-F-1), (I-F-2), (I-G-1), (I-G-2), (I-H-1), (I-H-2), (I-J-1), (I-J-2), (I-K-1), (I-K-2), (I-L-1), or (I-L-2), or a pharmaceutically acceptable salt thereof, wherein $Y^1$ is C; $Y^2$ is C; $Y^3$ is N; $Y^4$ is CH; $Y^5$ is CH; and $Y^6$ is $CR^2$. In some embodiments, the disclosure relates to a compound of formula (I-A), or a pharmaceutically acceptable salt thereof, wherein $Y^1$ is C; $Y^2$ is C; $Y^3$ is N; $Y^4$ is CH; $Y^5$ is CH; and $Y^6$ is CH.

In some embodiments, the disclosure relates to a compound of formula (I-A), (I-A-1), (I-A-2), (I-A-3), (I-A-4), (I-F-1), (I-F-2), (I-G-1), (I-G-2), (I-H-1), (I-H-2), (I-J-1), (I-J-2), (I-K-1), (I-K-2), (I-L-1), or (I-L-2), or a pharmaceutically acceptable salt thereof, wherein $Y^1$ is C; $Y^2$ is C; $Y^3$ is CH; $Y^4$ is N; $Y^5$ is CH; and $Y^6$ is CH.

In some embodiments, the disclosure relates to a compound of formula (I-A), (I-A-1), (I-A-2), (I-A-3), (I-A-4), (I-F-1), (I-F-2), (I-G-1), (I-G-2), (I-H-1), (I-H-2), (I-J-1), (I-J-2), (I-K-1), (I-K-2), (I-L-1), or (I-L-2), or a pharmaceutically acceptable salt thereof, wherein $Y^1$ is C; $Y^2$ is C; $Y^3$ is CH; $Y^4$ is CH; $Y^5$ is N; and $Y^6$ is CH.

In some embodiments, the disclosure relates to a compound of formula (I-A), (I-A-1), (I-A-2), (I-A-3), (I-A-4), (I-F-1), (I-F-2), (I-G-1), (I-G-2), (I-H-1), (I-H-2), (I-J-1), (I-J-2), (I-K-1), (I-K-2), (I-L-1), or (I-L-2), or a pharmaceutically acceptable salt thereof, wherein $Y^1$ is C; $Y^2$ is C; $Y^3$ is CH; $Y^4$ is CH; $Y^5$ is CH; and $Y^6$ is N.

In some embodiments, the disclosure relates to a compound of formula (I-A-1), (I-A-2), (I-A-3), (I-A-4), (I-B-1), (I-B-2), (I-B-3), (I-B-4), (I-C-1), (I-C-2), (I-C-3), (I-C-4), (I-M-1), (I-M-2), (I-M-3), or (I-M-4), or a pharmaceutically acceptable salt thereof, wherein $R^j$, $R^k$, $R^m$, $R^n$, $R^o$, $R^p$, $R^q$, and $R^r$, when present, are each independently hydrogen, halogen, $C_1$-$C_3$ alkyl, or $C_1$-$C_3$ haloalkyl. In some embodiments, $R^j$, $R^k$, $R^m$, $R^n$, $R^o$, $R^p$, $R^q$, and $R^r$, when present, are each hydrogen.

In some embodiments, the disclosure relates to a compound of formula (I-B), (I-B-1), (I-B-2), (I-B-3), or (I-B-4), or a pharmaceutically acceptable salt thereof, wherein $X^1$ is C; $X^2$ is N; $X^3$ is NH; $X^4$ is C; and $X^6$ is CH.

In some embodiments, the disclosure relates to a compound of formula (I-B), (I-B-1), (I-B-2), (I-B-3), or (I-B-4), or a pharmaceutically acceptable salt thereof, wherein $X^1$ is C; $X^2$ is N; $X^3$ is CH; $X^4$ is C; and $X^6$ is S.

In some embodiments, the disclosure relates to a compound of formula (I-B), (I-B-1), (I-B-2), (I-B-3), or (I-B-4), or a pharmaceutically acceptable salt thereof, wherein $Y^3$ is CH; $Y^4$ is CH; $Y^5$ is CH; and $Y^6$ is CH.

In some embodiments, the disclosure relates to a compound of formula (I-B), (I-B-1), (I-B-2), (I-B-3), or (I-B-4), or a pharmaceutically acceptable salt thereof, wherein $Y^3$ is $CR^2$; $Y^4$ is CH; $Y^5$ is CH; and $Y^6$ is CH.

In some embodiments, the disclosure relates to a compound of formula (I-B), (I-B-1), (I-B-2), (I-B-3), or (I-B-4), or a pharmaceutically acceptable salt thereof, wherein $Y^3$ is CH; $Y^4$ is $CR^2$; $Y^5$ is CH; and $Y^6$ is CH.

In some embodiments, the disclosure relates to a compound of formula (I-B), (I-B-1), (I-B-2), (I-B-3), or (I-B-4), or a pharmaceutically acceptable salt thereof, wherein $Y^3$ is CH; $Y^4$ is CH; $Y^5$ is $CR^2$; and $Y^6$ is CH In some embodiments, the disclosure relates to a compound of formula (I-B), (I-B-1), (I-B-2), (I-B-3), or (I-B-4), or a pharmaceutically acceptable salt thereof, wherein $Y^3$ is CH; $Y^4$ is CH; $Y^5$ is CH; and $Y^6$ is $CR^2$.

In some embodiments, the disclosure relates to a compound of formula (I-B), (I-B-1), (I-B-2), (I-B-3), or (I-B-4), or a pharmaceutically acceptable salt thereof, wherein $Y^3$ is N; $Y^4$ is CH; $Y^5$ is CH; and $Y^6$ is CH.

In some embodiments, the disclosure relates to a compound of formula (I-B), (I-B-1), (I-B-2), (I-B-3), or (I-B-4), or a pharmaceutically acceptable salt thereof, wherein $Y^3$ is CH; $Y^4$ is N; $Y^5$ is CH, and $Y^6$ is CH.

In some embodiments, the disclosure relates to a compound of formula (I-B), (I-B-1), (I-B-2), (I-B-3), or (I-B-4), or a pharmaceutically acceptable salt thereof, wherein $Y^3$ is CH; $Y^4$ is CH; $Y^5$ is N, and $Y^6$ is CH.

In some embodiments, the disclosure relates to a compound of formula (I-B), (I-B-1), (I-B-2), (I-B-3), or (I-B-4), or a pharmaceutically acceptable salt thereof, wherein $Y^3$ is CH; $Y^4$ is CH; $Y^5$ is CH; and $Y^6$ is N.

In some embodiments, the disclosure relates to a compound provided herein, or a pharmaceutically acceptable salt thereof, that is a USP30 Inhibitor Compound having an IC50 value of ≤1 μM and >0.001 μM as measured in a Ubiquitin-Rhodamine 110 Assay as described in Example 1.

In another aspect, the disclosure relates to a compound selected from Table 1, or a pharmaceutically acceptable salt thereof. Each pair of compounds listed in Table 1 (i.e., compounds 1-a and 1-b, compounds 2-a and 2-b, etc.) was obtained as a racemic mixture, and were then separated by chiral HPLC according to the procedure described in Example 2, Step 7, or a similar method, to obtain the individual compounds in substantially enantiomerically pure form. For each pair of compounds, the first compound (i.e., compounds 1-a, 2-a, etc.) was the first eluting isomer, and the second compound (i.e., compounds 1-b, 2-b, etc.) was the second eluting isomer. The stereochemical descriptors reflect the relative stereochemistry of each compound. The absolute stereochemistry of each compound was arbitrarily assigned. In some embodiments, the compound selected from Table 1, or a pharmaceutically acceptable salt thereof, is present in a racemic mixture. In some embodiments, the compound selected from Table 1, or a pharmaceutically acceptable salt thereof, is present in substantially enantiomerically pure form.

TABLE 1

Compounds of the Disclosure

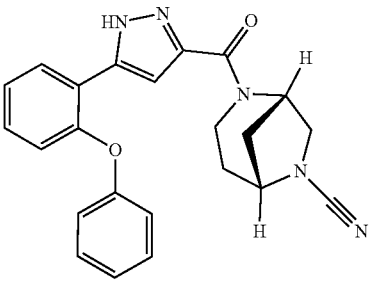

| Compound Number | Compound Structure and Chemical Name |
|---|---|
| 1-a | (1S,5R)-2-(5-(2-phenoxyphenyl)-1H-pyrazole-3-carbonyl)-2,6-diazabicyclo[3.2.1]octane-6-carbonitrile |
| 1-b | (1R,5S)-2-(5-(2-phenoxyphenyl)-1H-pyrazole-3-carbonyl)-2,6-diazabicyclo[3.2.1]octane-6-carbonitrile |
| 2-a | N-((1S,4S,7S)-2-cyano-2-azabicyclo[2.2.1]heptan-7-yl)-5-(2-phenoxyphenyl)-1H-pyrazole-3-carboxamide |
| 2-b | N-((1R,4R,7R)-2-cyano-2-azabicyclo[2.2.1]heptan-7-yl)-5-(2-phenoxyphenyl)-1H-pyrazole-3-carboxamide |
| 3-a | N-((1S,5R)-3-cyano-3-azabicyclo[3.1.0]hexan-1-yl)-5-(2-phenoxyphenyl)-1H-pyrazole-3-carboxamide |

TABLE 1-continued

Compounds of the Disclosure

| Compound Number | Compound Structure and Chemical Name |
|---|---|
| 3-b | 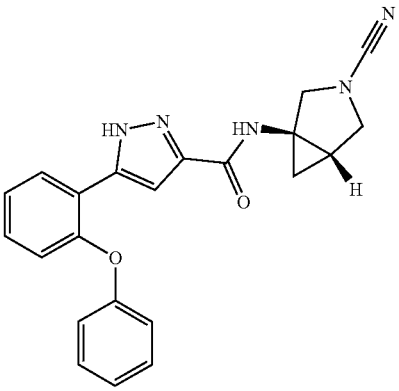<br>N-((1R,5S)-3-cyano-3-azabicyclo[3.1.0]hexan-1-yl)-5-(2-phenoxyphenyl)-1H-pyrazole-3-carboxamide |
| 4-a | 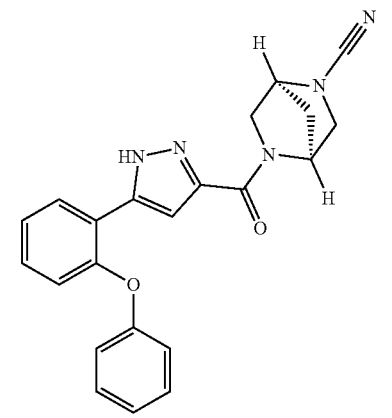<br>(1S,4S)-5-(5-(2-phenoxyphenyl)-1H-pyrazole-3-carbonyl)-2,5-diazabicyclo[2.2.1]heptane-2-carbonitrile |
| 4-b | 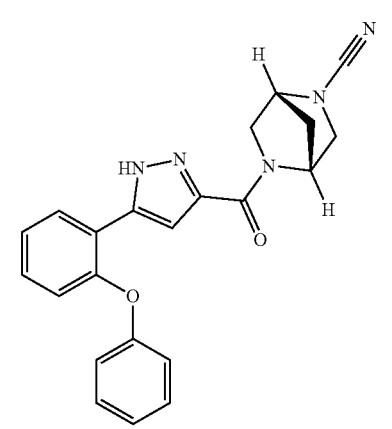<br>(1R,4R)-5-(5-(2-phenoxyphenyl)-1H-pyrazole-3-carbonyl)-2,5-diazabicyclo[2.2.1]heptane-2-carbonitrile |
| 5-a | 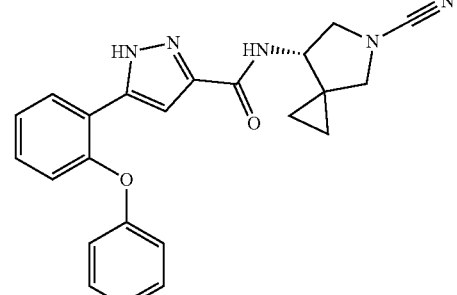<br>(S)-N-(5-cyano-5-azaspiro[2.4]heptan-7-yl)-5-(2-phenoxyphenyl)-1H-pyrazole-3-carboxamide |
| 5-b | 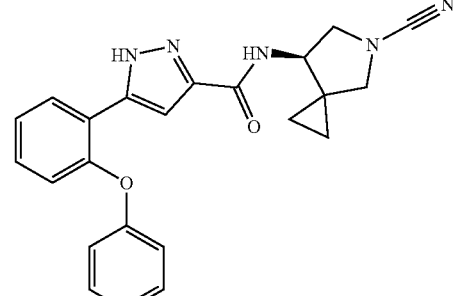<br>(R)-N-(5-cyano-5-azaspiro[2.4]heptan-7-yl)-5-(2-phenoxyphenyl)-1H-pyrazole-3-carboxamide |
| 6-a | 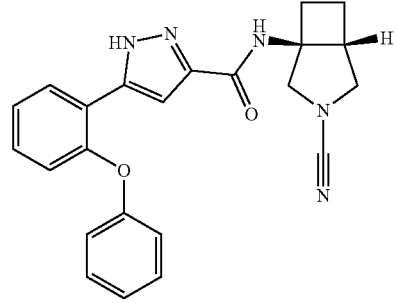<br>N-((1R,5S)-3-cyano-3-azabicyclo[3.2.0]heptan-1-yl)-5-(2-phenoxyphenyl)-1H-pyrazole-3-carboxamide |
| 6-b | 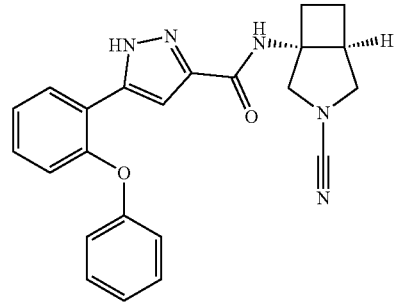<br>N-((1S,5R)-3-cyano-3-azabicyclo[3.2.0]heptan-1-yl)-5-(2-phenoxyphenyl)-1H-pyrazole-3-carboxamide |

TABLE 1-continued

Compounds of the Disclosure

| Compound Number | Compound Structure and Chemical Name |
|---|---|
| 7-a | 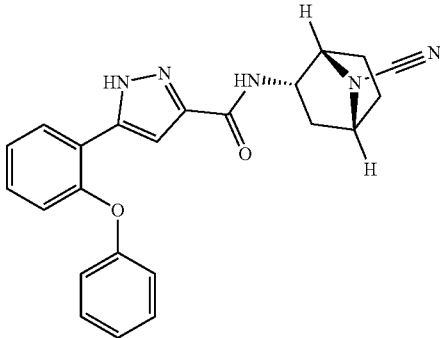<br>N-((1S,2S,4R)-7-cyano-7-azabicyclo[2.2.1]heptan-2-yl)-5-(2-phenoxyphenyl)-1H-pyrazole-3-carboxamide |
| 7-b | 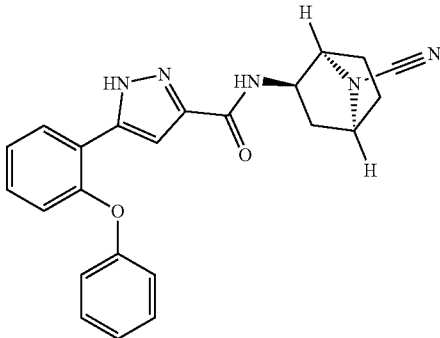<br>N-((1R,2R,4S)-7-cyano-7-azabicyclo[2.2.1]heptan-2-yl)-5-(2-phenoxyphenyl)-1H-pyrazole-3-carboxamide |
| 8-a | 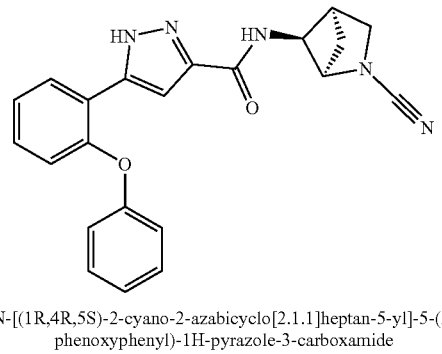<br>N-[(1R,4R,5S)-2-cyano-2-azabicyclo[2.1.1]heptan-5-yl]-5-(2-phenoxyphenyl)-1H-pyrazole-3-carboxamide |
| 8-b | 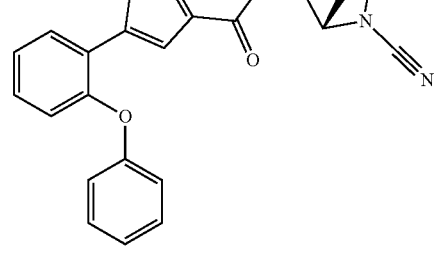<br>N-[(1S,4S,5R)-2-cyano-2-azabicyclo[2.1.1]heptan-5-yl]-5-(2-phenoxyphenyl)-1H-pyrazole-3-carboxamide |
| 9-a | 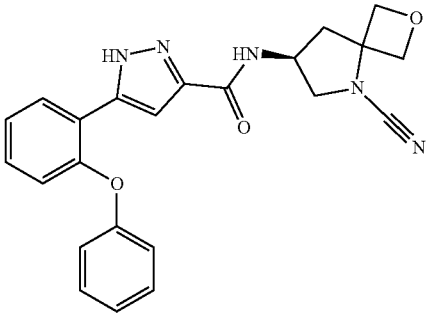<br>(S)-N-(5-cyano-2-oxa-5-azaspiro[3.4]octan-7-yl)-5-(2-phenoxyphenyl)-1H-pyrazole-3-carboxamide |
| 9-b | 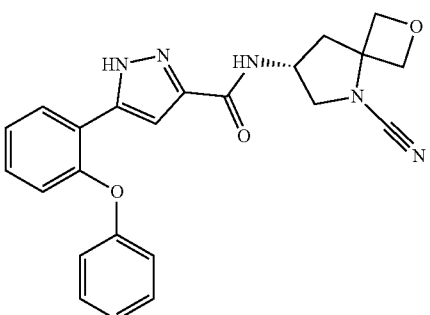<br>(R)-N-(5-cyano-2-oxa-5-azaspiro[3.4]octan-7-yl)-5-(2-phenoxyphenyl)-1H-pyrazole-3-carboxamide |
| 13-a | 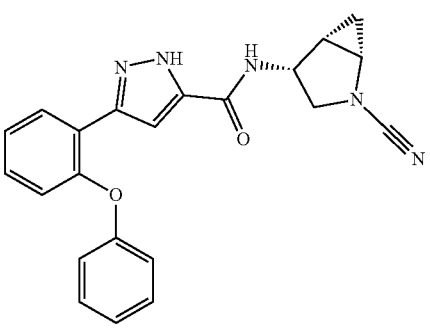<br>N-((1S,4R,5S)-2-cyano-2-azabicyclo[3.1.0]hexan-4-yl)-3-(2-phenoxyphenyl)-1H-pyrazole-5-carboxamide |

TABLE 1-continued

Compounds of the Disclosure

| Compound Number | Compound Structure and Chemical Name |
|---|---|
| 13-b | 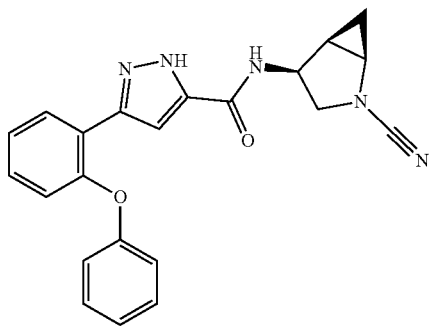<br>N-((1R,4S,5R)-2-cyano-2-azabicyclo[3.1.0]hexan-4-yl)-3-(2-phenoxyphenyl)-1H-pyrazole-5-carboxamide |
| 20-a | 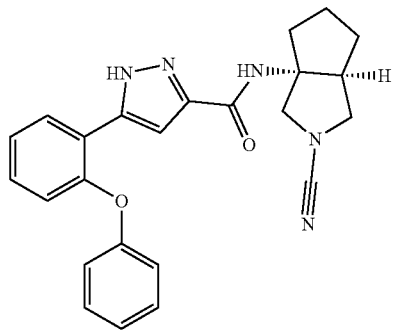<br>N-((3aR,6aS)-2-cyanohexahydrocyclopenta[c]pyrrol-3a(1H)-yl)-5-(2-phenoxyphenyl)-1H-pyrazole-3-carboxamide |

TABLE 1-continued

Compounds of the Disclosure

| Compound Number | Compound Structure and Chemical Name |
|---|---|
| 20-b | 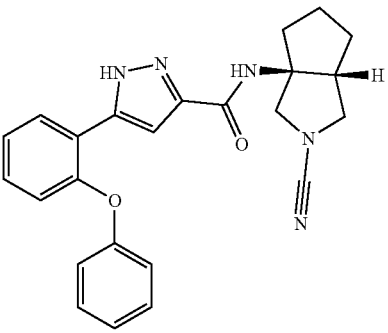<br>N-((3aS,6aR)-2-cyanohexahydrocyclopenta[c]pyrrol-3a(1H)-yl)-5-(2-phenoxyphenyl)-1H-pyrazole-3-carboxamide |

In another aspect, the disclosure relates to a compound selected from Table 2, or a pharmaceutically acceptable salt thereof. In some embodiments, the compound, or a pharmaceutically acceptable salt thereof, is present in a racemic mixture with its enantiomer. In some embodiments, the compound, or a pharmaceutically acceptable salt thereof, is present in substantially enantiomerically pure form.

In another aspect, the disclosure relates to the enantiomer of a compound selected from Table 2, or a pharmaceutically acceptable salt thereof. In some embodiments, the enantiomer, or a pharmaceutically acceptable salt thereof, is present in a racemic mixture. In some embodiments, the enantiomer, or a pharmaceutically acceptable salt thereof, is present in substantially enantiomerically pure form.

TABLE 2

Compounds of the Disclosure

| Compound Number | Compound Structure and Chemical Name |
|---|---|
| 10 | 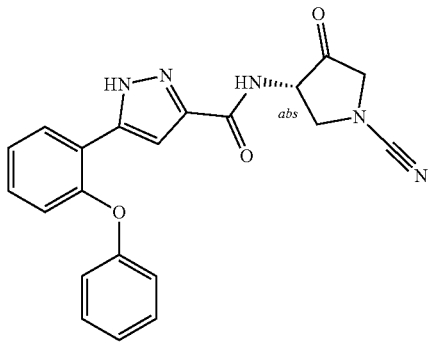<br>(S)-N-(1-cyano-4-oxopyrrolidin-3-yl)-5-(2-phenoxyphenyl)-1H-pyrazole-3-carboxamide |

TABLE 2-continued

Compounds of the Disclosure

| Compound Number | Compound Structure and Chemical Name |
|---|---|
| 11 | 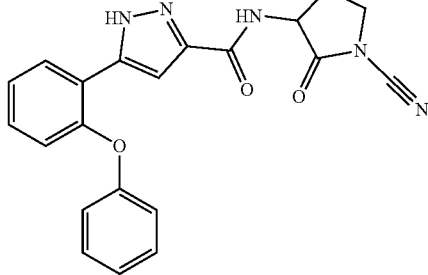<br>N-(1-cyano-2-oxopyrrolidin-3-yl)-5-(2-phenoxyphenyl)-1H-pyrazole-3-carboxamide |
| 12 | 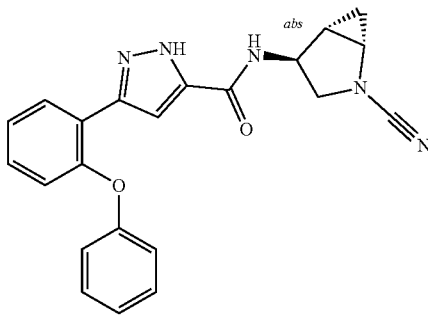<br>N-((1S,4S,5S)-2-cyano-2-azabicyclo[3.1.0]hexan-4-yl)-3-(2-phenoxyphenyl)-1H-pyrazole-5-carboxamide |
| 13 | 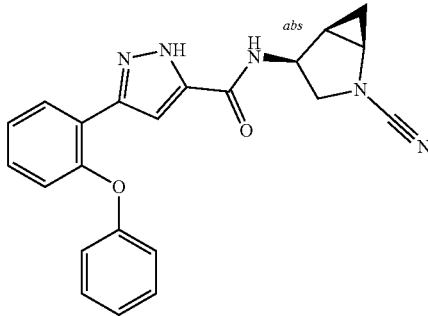<br>N-((1R,4S,5R)-2-cyano-2-azabicyclo[3.1.0]hexan-4-yl)-3-(2-phenoxyphenyl)-1H-pyrazole-5-carboxamide |
| 14 | 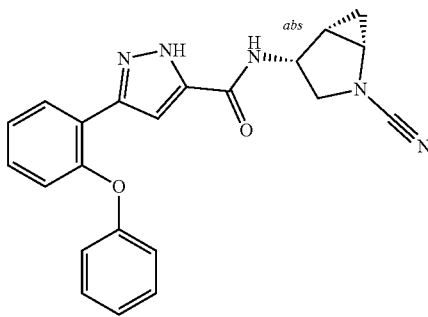<br>N-((1S,4R,5S)-2-cyano-2-azabicyclo[3.1.0]hexan-4-yl)-3-(2-phenoxyphenyl)-1H-pyrazole-5-carboxamide |

TABLE 2-continued
Compounds of the Disclosure
| Compound Number | Compound Structure and Chemical Name |
|---|---|
| 15 | 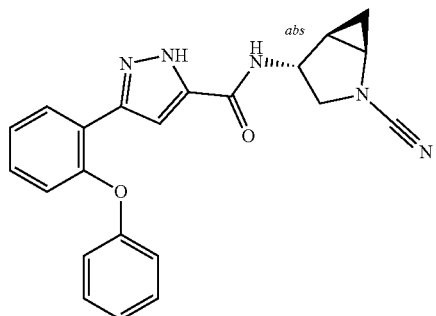<br>N-((1R,4R,5S)-2-cyano-2-azabicyclo[3.1.0]hexan-4-yl)-3-(2-phenoxyphenyl)-1H-pyrazole-5-carboxamide |
| 16 | 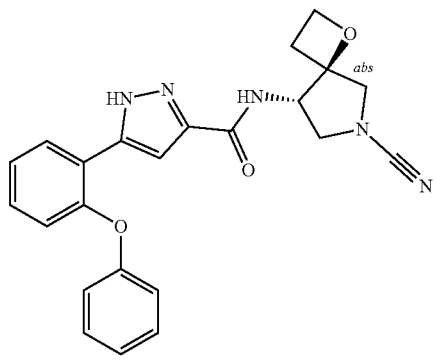<br>N-((4S,8S)-6-cyano-1-oxa-6-azaspiro[3.4]octan-8-yl)-5-(2-phenoxyphenyl)-1H-pyrazole-3-carboxamide |
| 17 | 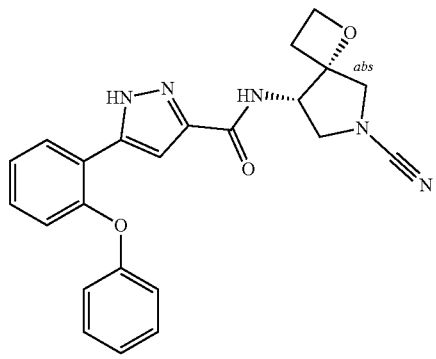<br>N-((4R,8S)-6-cyano-1-oxa-6-azaspiro[3.4]octan-8-yl)-5-(2-phenoxyphenyl)-1H-pyrazole-3-carboxamide |

TABLE 2-continued
Compounds of the Disclosure
| Compound Number | Compound Structure and Chemical Name |
|---|---|
| 18 | 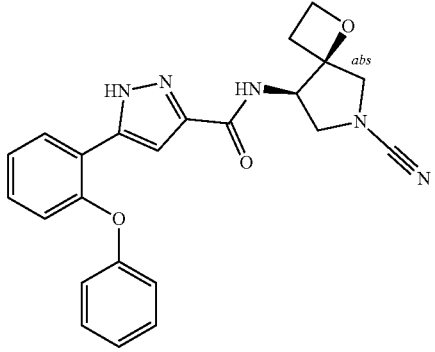<br>N-((4S,8R)-6-cyano-1-oxa-6-azaspiro[3.4]octan-8-yl)-5-(2-phenoxyphenyl)-1H-pyrazole-3-carboxamide |
| 19 | 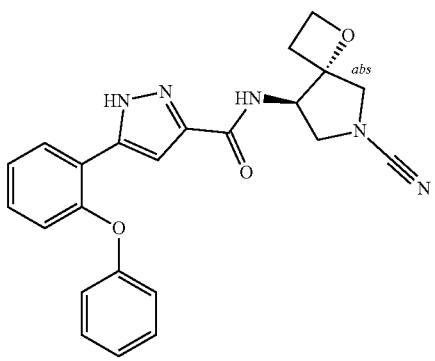<br>N-((4R,8R)-6-cyano-1-oxa-6-azaspiro[3.4]octan-8-yl)-5-(2-phenoxyphenyl)-1H-pyrazole-3-carboxamide |
| 20 | 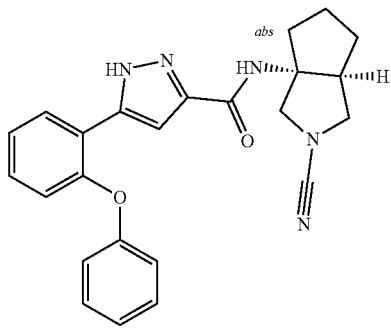<br>N-((3aR,6aS)-2-cyanohexahydrocyclopenta[c]pyrrol-3a(1H)-yl)-5-(2-phenoxyphenyl)-1H-pyrazole-3-carboxamide |

TABLE 2-continued
Compounds of the Disclosure
| Compound Number | Compound Structure and Chemical Name |
|---|---|
| 21 | 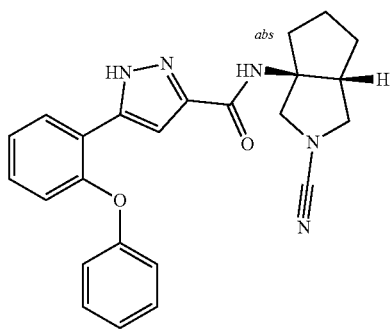<br>N-((3aR,6aS)-2-cyanohexahydrocyclopenta[c]pyrrol-3a(1H)-yl)-5-(2-phenoxyphenyl)-1H-pyrazole-3-carboxamide |
| 22 | 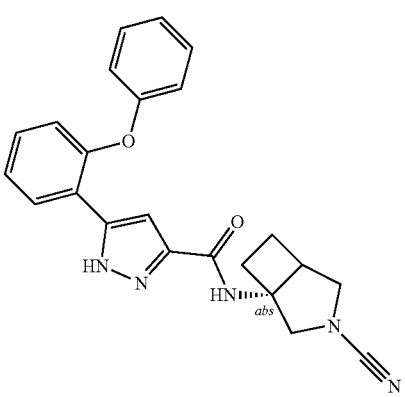<br>N-((1R)-3-cyano-3-azabicyclo[3.2.0]heptan-1-yl)-5-(2-phenoxyphenyl)-1H-pyrazole-3-carboxamide |
| 23 | 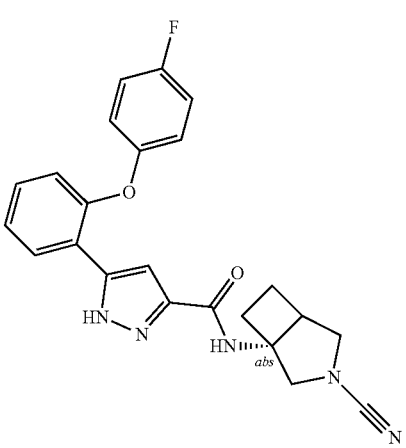<br>N-((1R)-3-cyano-3-azabicyclo[3.2.0]heptan-1-yl)-5-(2-(4-fluorophenoxy)phenyl)-1H-pyrazole-3-carboxamide |

TABLE 2-continued
Compounds of the Disclosure
| Compound Number | Compound Structure and Chemical Name |
|---|---|
| 24 | 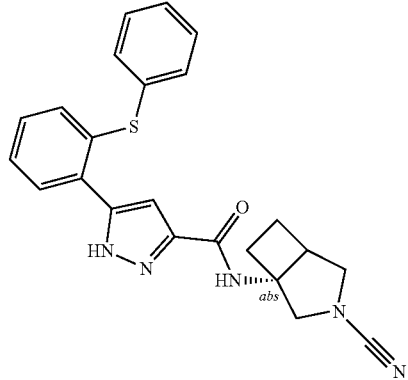<br>N-((1R)-3-cyano-3-azabicyclo[3.2.0]heptan-1-yl)-5-(2-(phenylthio)phenyl)-1H-pyrazole-3-carboxamide |
| 25 | 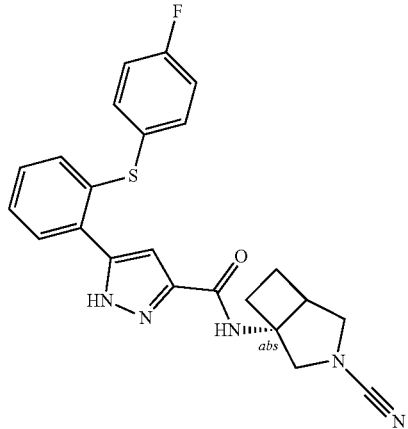<br>N-((1R)-3-cyano-3-azabicyclo[3.2.0]heptan-1-yl)-5-(2-((4-fluorophenyl)thio)phenyl)-1H-pyrazole-3-carboxamide |
| 26 | 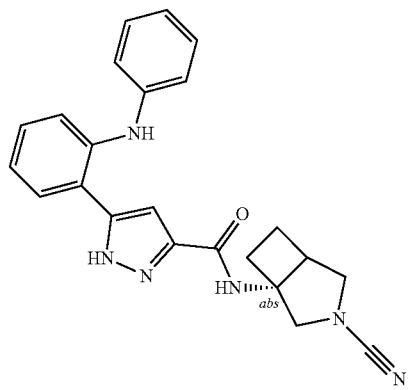<br>N-((1R)-3-cyano-3-azabicyclo[3.2.0]heptan-1-yl)-5-(2-(phenylamino)phenyl)-1H-pyrazole-3-carboxamide |

TABLE 2-continued
Compounds of the Disclosure
| Compound Number | Compound Structure and Chemical Name |
|---|---|
| 27 | 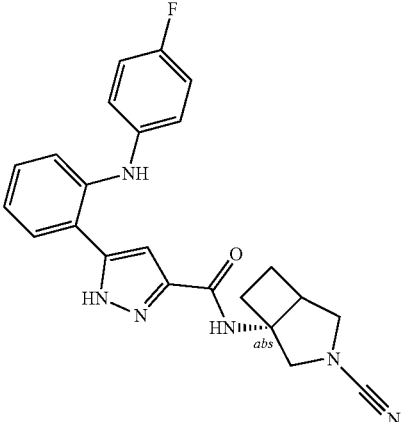<br>N-((1R)-3-cyano-3-azabicyclo[3.2.0]heptan-1-yl)-5-(2-((4-fluorophenyl)amino)phenyl)-1H-pyrazole-3-carboxamide |
| 28 | 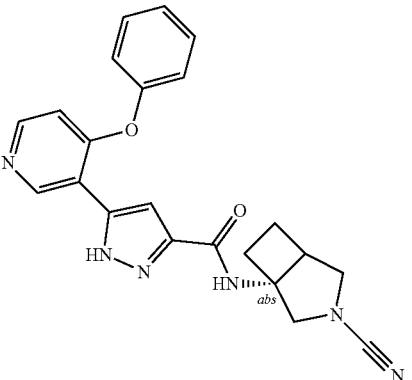<br>N-((1R)-3-cyano-3-azabicyclo[3.2.0]heptan-1-yl)-5-(4-phenoxypyridin-3-yl)-1H-pyrazole-3-carboxamide |
| 29 | 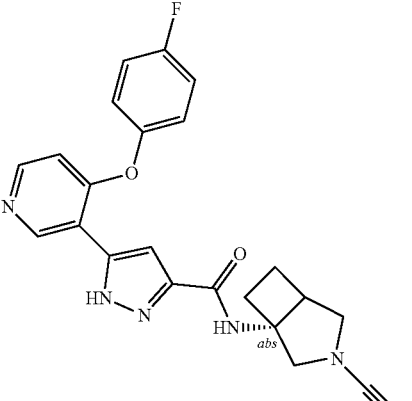<br>N-((1R)-3-cyano-3-azabicyclo[3.2.0]heptan-1-yl)-5-(4-(4-fluorophenoxy)pyridin-3-yl)-1H-pyrazole-3-carboxamide |

TABLE 2-continued
Compounds of the Disclosure
| Compound Number | Compound Structure and Chemical Name |
|---|---|
| 30 | 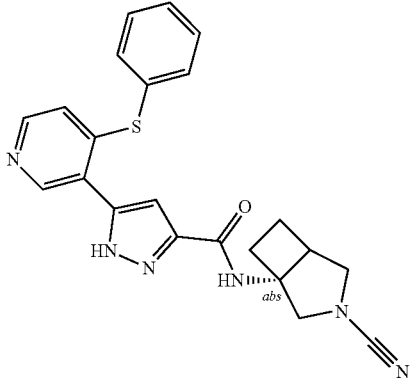<br>N-((1R)-3-cyano-3-azabicyclo[3.2.0]heptan-1-yl)-5-(4-(phenylthio)pyridin-3-yl)-1H-pyrazole-3-carboxamie |
| 31 | 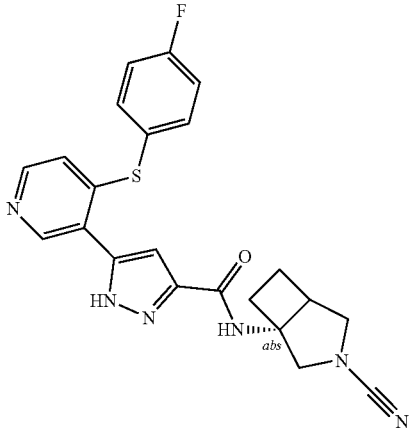<br>N-((1R)-3-cyano-3-azabicyclo[3.2.0]heptan-1-yl)-5-(4-((4-fluorophenyl)thio)pyridin-3-yl)-1H-pyrazole-3-carboxamide |
| 32 | 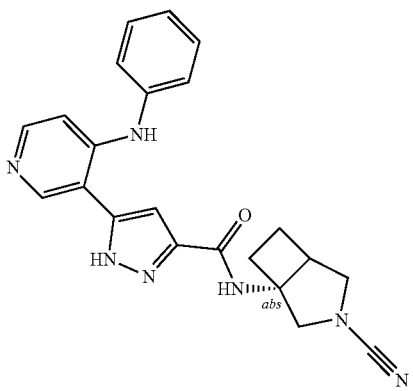<br>N-((1R)-3-cyano-3-azabicyclo[3.2.0]heptan-1-yl)-5-(4-(phenylamino)pyridin-3-yl)-1H-pyrazole-3-carboxamide |

TABLE 2-continued
Compounds of the Disclosure
| Compound Number | Compound Structure and Chemical Name |
|---|---|
| 33 | 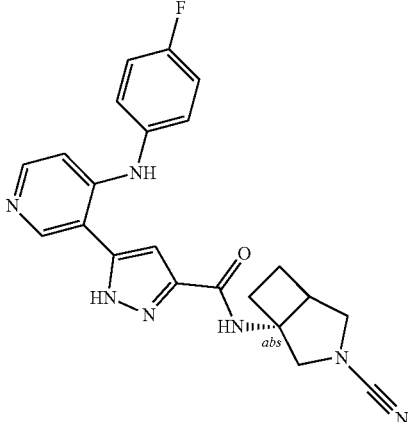<br>N-((1R)-3-cyano-3-azabicyclo[3.2.0]heptan-1-yl)-5-(4-((4-fluorophenyl)amino)pyridin-3-yl)-1H-pyrazole-3-carboxamide |
| 34 | 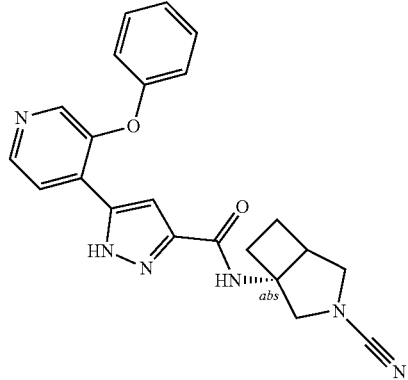<br>N-((1R)-3-cyano-3-azabicyclo[3.2.0]heptan-1-yl)-5-(3-phenoxypyridin-4-yl)-1H-pyrazole-3-carboxamide |
| 35 | 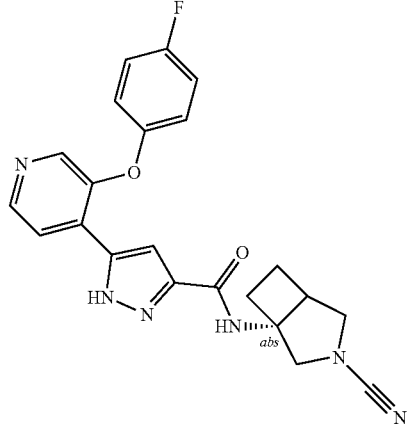<br>N-((1R)-3-cyano-3-azabicyclo[3.2.0]heptan-1-yl)-5-(3-(4-fluorophenoxy)pyridin-4-yl)-1H-pyrazole-3-carboxamide |

TABLE 2-continued
Compounds of the Disclosure
| Compound Number | Compound Structure and Chemical Name |
|---|---|
| 36 | 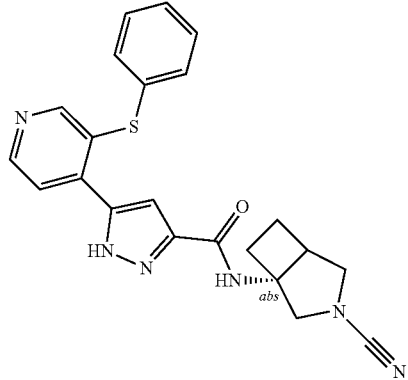<br>N-((1R)-3-cyano-3-azabicyclo[3.2.0]heptan-1-yl)-5-(3-(phenylthio)pyridin-4-yl)-1H-pyrazole-3-carboxamie |
| 37 | 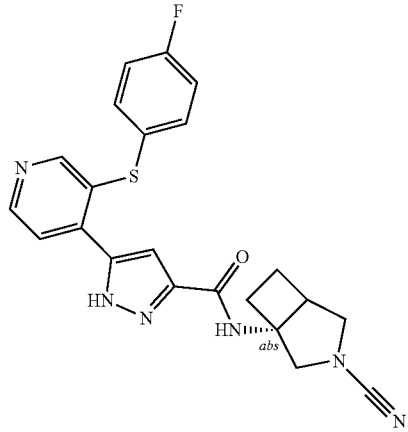<br>N-((1R)-3-cyano-3-azabicyclo[3.2.0]heptan-1-yl)-5-(3-((4-fluorophenyl)thio)pyridin-4-yl)-1H-pyrazole-3-carboxamide |
| 38 | 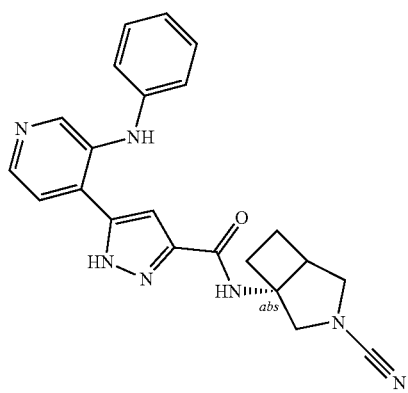<br>N-((1R)-3-cyano-3-azabicyclo[3.2.0]heptan-1-yl)-5-(3-(phenylamino)pyridin-4-yl)-1H-pyrazole-3-carboxamide |

TABLE 2-continued
Compounds of the Disclosure
| Compound Number | Compound Structure and Chemical Name |
|---|---|
| 39 | 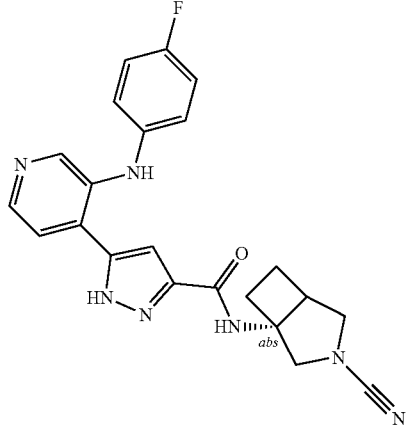<br>N-((1R)-3-cyano-3-azabicyclo[3.2.0]heptan-1-yl)-5-(3-((4-fluorophenyl)amino)pyridin-4-yl)-1H-pyrazole-3-carboxamide |
| 40 | 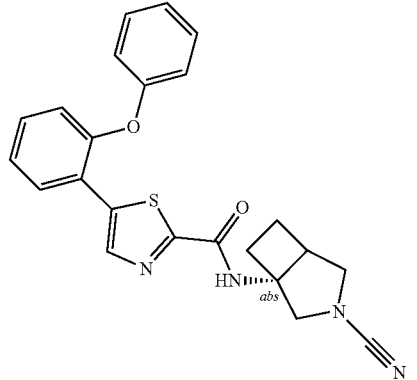<br>N-((1R)-3-cyano-3-azabicyclo[3.2.0]heptan-1-yl)-5-(2-phenoxyphenyl)thiazole-2-carboxamide |
| 41 | 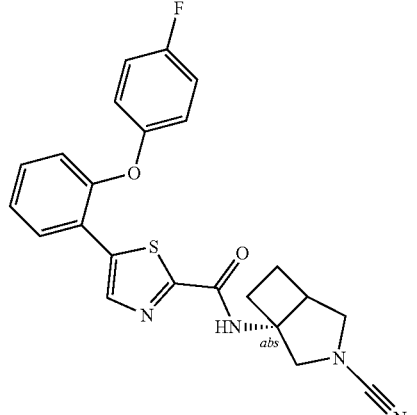<br>N-((1R)-3-cyano-3-azabicyclo[3.2.0]heptan-1-yl)-5-(2-(4-fluorophenoxy)phenyl)thiazole-2-carboxamide |

TABLE 2-continued
Compounds of the Disclosure
| Compound Number | Compound Structure and Chemical Name |
|---|---|
| 42 | 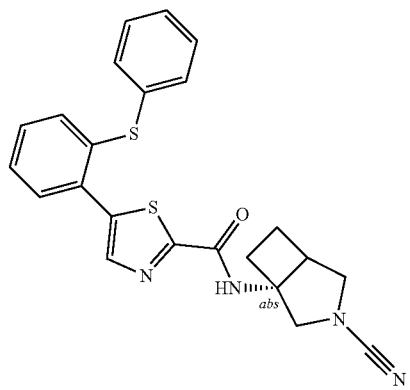<br>N-((1R)-3-cyano-3-azabicyclo[3.2.0]heptan-1-yl)-5-(2-(phenylthio)phenyl)thiazole-2-carboxamide |
| 43 | 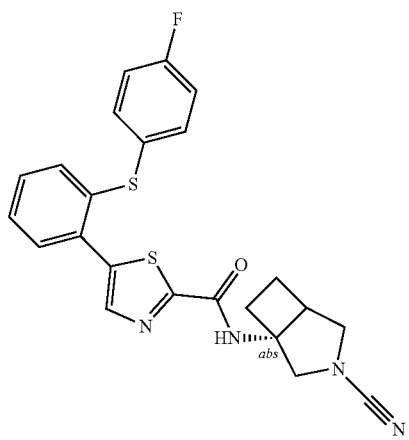<br>N-((1R)-3-cyano-3-azabicyclo[3.2.0]heptan-1-yl)-5-(2-((4-fluorophenyl)thio)phenyl)thiazole-2-carboxamide |
| 44 | 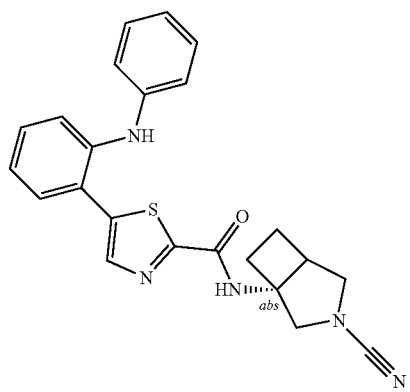<br>N-((1R)-3-cyano-3-azabicyclo[3.2.0]heptan-1-yl)-5-(2-(phenylamino)phenyl)thiazole-2-carboxamide |

TABLE 2-continued
Compounds of the Disclosure
| Compound Number | Compound Structure and Chemical Name |
|---|---|
| 45 | 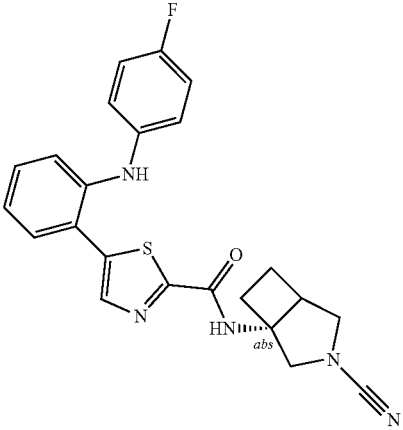<br>N-((1R)-3-cyano-3-azabicyclo[3.2.0]heptan-1-yl)-5-(2-((4-fluorophenyl)amino)phenyl)thiazole-2-carboxamide |
| 46 | 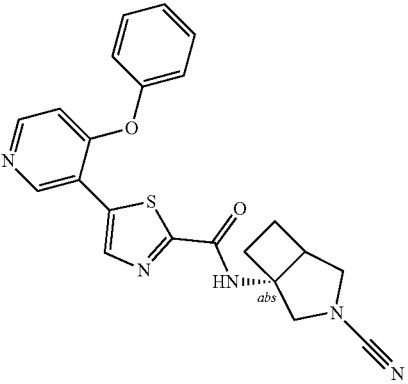<br>N-((1R)-3-cyano-3-azabicyclo[3.2.0]heptan-1-yl)-5-(4-(phenoxypyridin-3-yl)thiazole-2-carboxamide |
| 47 | 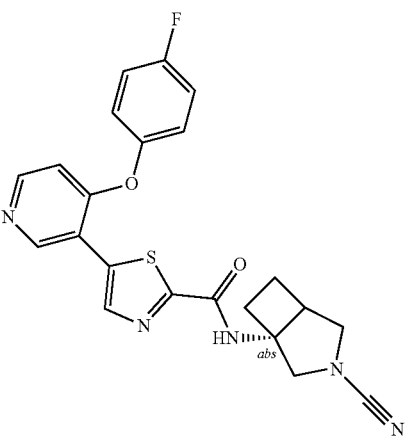<br>N-((1R)-3-cyano-3-azabicyclo[3.2.0]heptan-1-yl)-5-(4-(4-fluorophenoxy)pyridin-3-yl)thiazole-2-carboxamide |

TABLE 2-continued
Compounds of the Disclosure
| Compound Number | Compound Structure and Chemical Name |
|---|---|
| 48 | 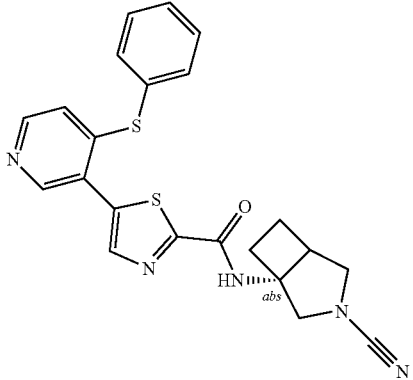<br>N-((1R)-3-cyano-3-azabicyclo[3.2.0]heptan-1-yl)-5-(4-(phenylthio)pyridin-3-yl)thiazole-2-carboxamide |
| 49 | 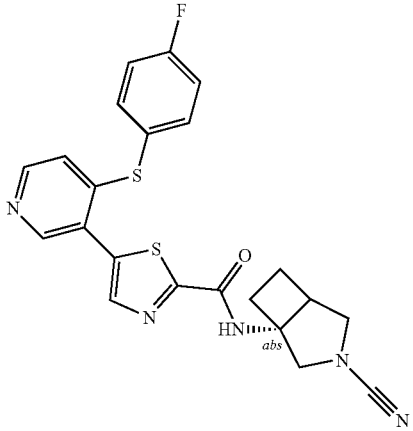<br>N-((1R)-3-cyano-3-azabicyclo[3.2.0]heptan-1-yl)-5-(4-((4-fluorophenyl)thio)pyridin-3-yl)thiazole-2-carboxamide |
| 50 | 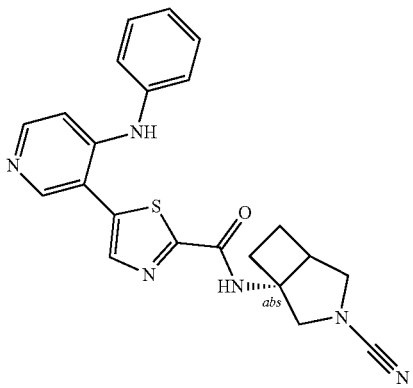<br>N-((1R)-3-cyano-3-azabicyclo[3.2.0]heptan-1-yl)-5-(4-(phenylamino)pyridin-3-yl)thiazole-2-carboxamide |

TABLE 2-continued
Compounds of the Disclosure
| Compound Number | Compound Structure and Chemical Name |
|---|---|
| 51 | 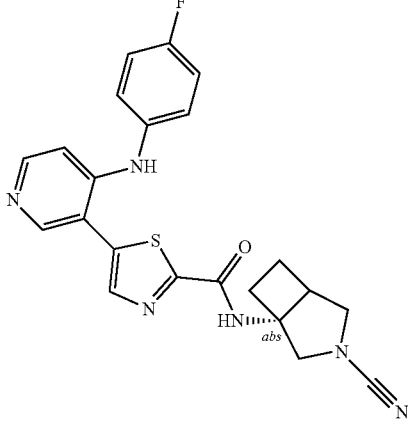  N-((1R)-3-cyano-3-azabicyclo[3.2.0]heptan-1-yl)-5-(4-((4-fluorophenyl)amino)pyridin-3-yl)thiazole-2-carboxamide |
| 52 | 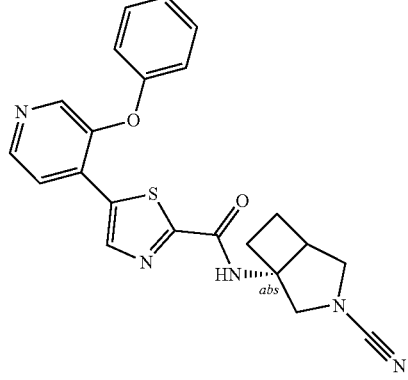  N-((1R)-3-cyano-3-azabicyclo[3.2.0]heptan-1-yl)-5-(3-phenoxypyridin-4-yl)thiazole-2-carboxamide |
| 53 | 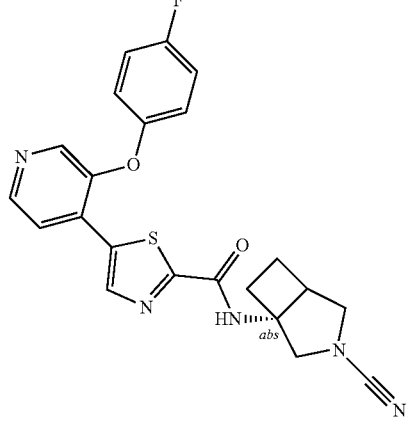  N-((1R)-3-cyano-3-azabicyclo[3.2.0]heptan-1-yl)-5-(3-(4-fluorophenoxy)pyridin-4-yl)thiazole-2-carboxamide |

TABLE 2-continued
Compounds of the Disclosure
| Compound Number | Compound Structure and Chemical Name |
|---|---|
| 54 | 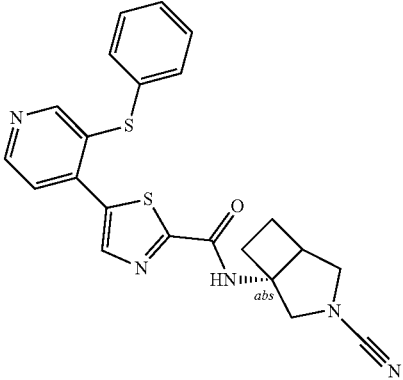<br>N-((1R)-3-cyano-3-azabicyclo[3.2.0]heptan-1-yl)-5-(3-(phenylthio)pyridin-4-yl)thiazole-2-carboxamide |
| 55 | 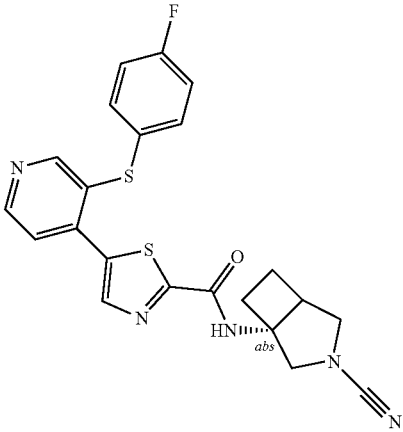<br>N-((1R)-3-cyano-3-azabicyclo[3.2.0]heptan-1-yl)-5-(3-((4-fluorophenyl)thio)pyridin-4-yl)thiazole-2-carboxamide |
| 56 | 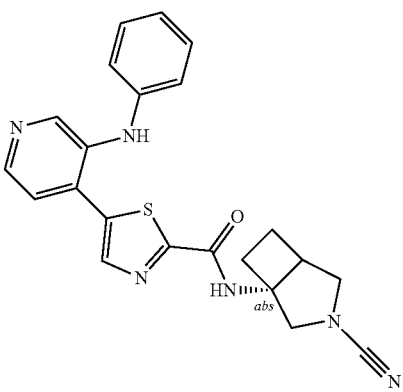<br>N-((1R)-3-cyano-3-azabicyclo[3.2.0]heptan-1-yl)-5-(3-(phenylamino)pyridin-4-yl)thiazole-2-carboxamide |

TABLE 2-continued
Compounds of the Disclosure
| Compound Number | Compound Structure and Chemical Name |
|---|---|
| 57 | 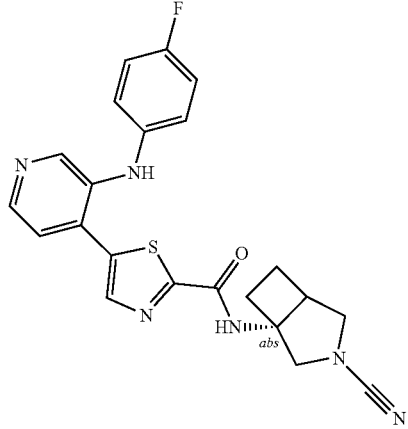<br>N-((1R)-3-cyano-3-azabicyclo[3.2.0]heptan-1-yl)-5-(3-((4-fluorophenyl)amino)pyridin-4-yl)thiazole-2-carboxamide |
| 58 | 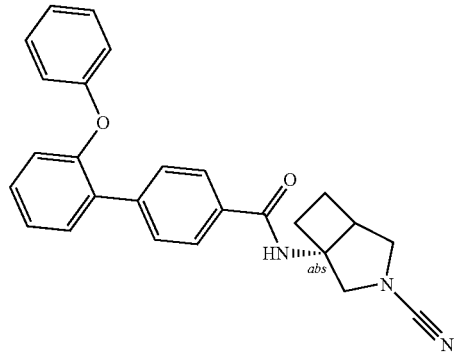<br>N-((1R)-3-cyano-3-azabicyclo[3.2.0]heptan-1-yl)-2'-phenoxy-[1,1'-biphenyl]-4-carboxamide |
| 59 | 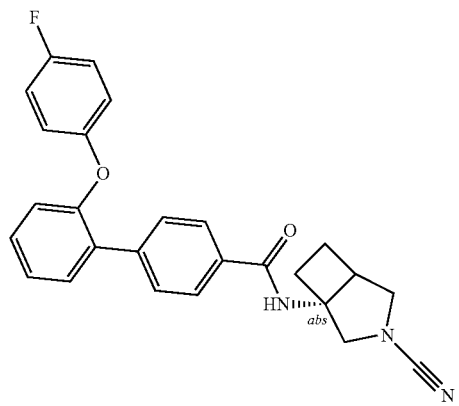<br>N-((1R)-3-cyano-3-azabicyclo[3.2.0]heptan-1-yl)-2'-(4-fluorophenoxy)-[1,1'-biphenyl]-4-carboxamide |

TABLE 2-continued
Compounds of the Disclosure
| Compound Number | Compound Structure and Chemical Name |
|---|---|
| 60 | 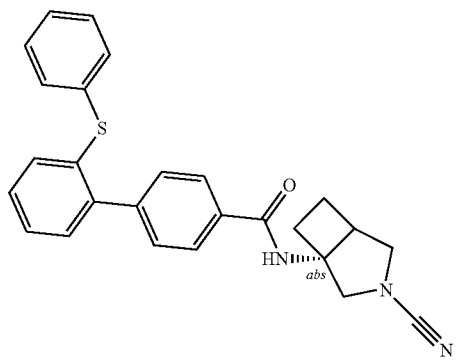<br>N-((1R)-3-cyano-3-azabicyclo[3.2.0]heptan-1-yl)-2'-(phenylthio)-[1,1'-biphenyl]-4-carboxamide |
| 61 | 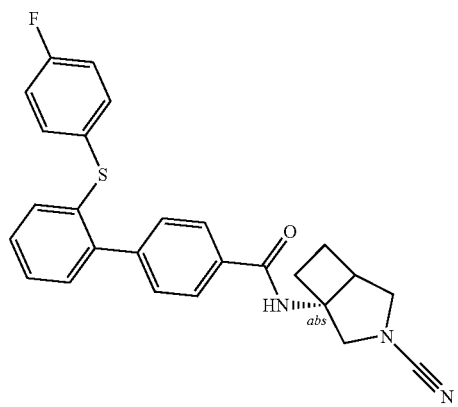<br>N-((1R)-3-cyano-3-azabicyclo[3.2.0]heptan-1-yl)-2'-((4-fluorophenyl)thio-[1,1'-biphenyl]-4-carboxamide |
| 62 | 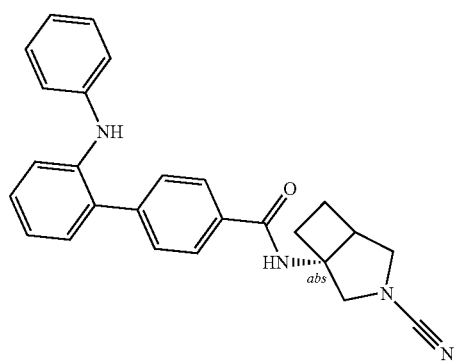<br>N-((1R)-3-cyano-3-azabicyclo[3.2.0]heptan-1-yl)-2'-(phenylamino)-[1,1'-biphenyl]-4-carboxamide |

TABLE 2-continued
Compounds of the Disclosure
| Compound Number | Compound Structure and Chemical Name |
|---|---|
| 63 | 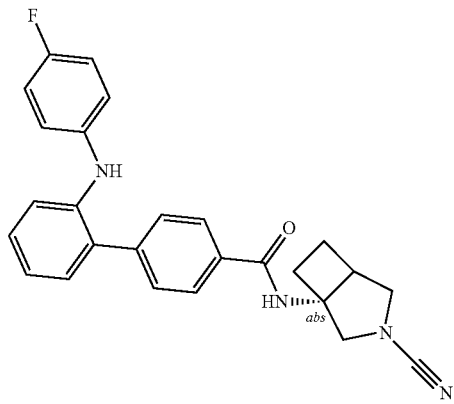<br>N-((1R)-3-cyano-3-azabicyclo[3.2.0]heptan-1-yl)-2'-((4-fluorophenyl)amino)-[1,1'-biphenyl]-4-carboxamide |
| 64 | 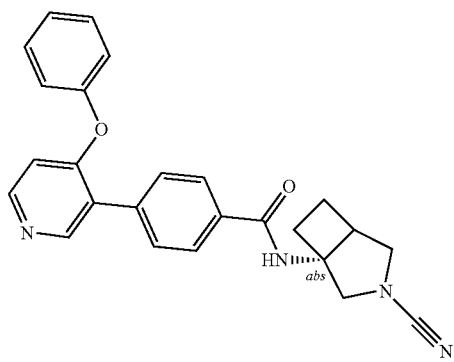<br>N-((1R)-3-cyano-3-azabicyclo[3.2.0]heptan-1-yl)-4-(4-phenoxypyridin-3-yl)benzamide |
| 65 | 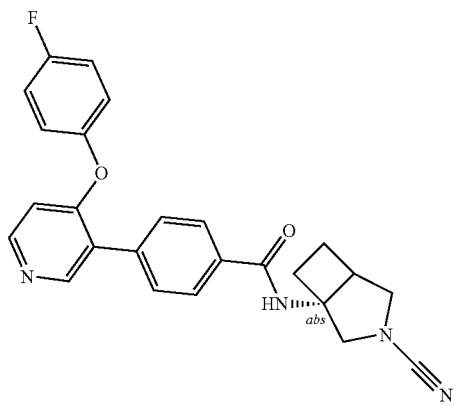<br>N-((1R)-3-cyano-3-azabicyclo[3.2.0]heptan-1-yl)-4-(4-(4-fluorophenoxy)pyridin-3-yl)benzamide |

TABLE 2-continued
Compounds of the Disclosure
| Compound Number | Compound Structure and Chemical Name |
|---|---|
| 66 | 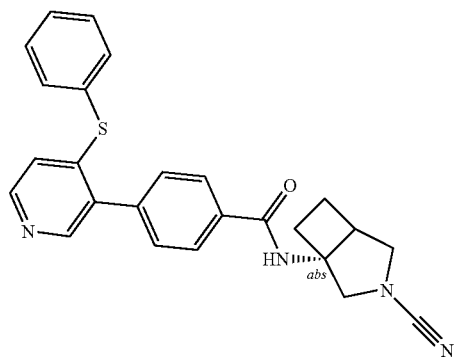<br>N-((1R)-3-cyano-3-azabicyclo[3.2.0]heptan-1-yl)-4-(4-(phenylthio)pyridin-3-yl)benzamide |
| 67 | 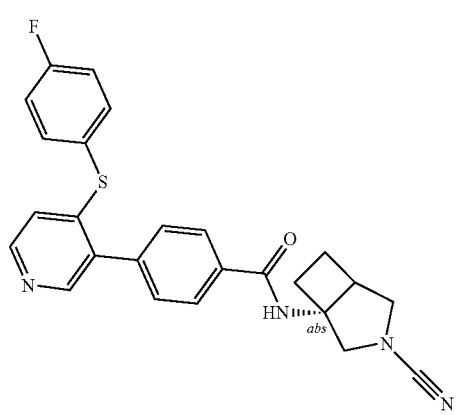<br>N-((1R)-3-cyano-3-azabicyclo[3.2.0]heptan-1-yl)-4-(4-((4-fluorophenyl)thio)pyridin-3-yl)benzamide |
| 68 | 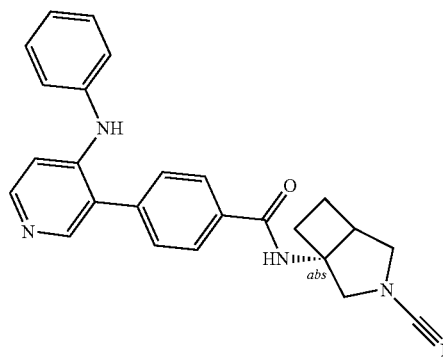<br>N-((1R)-3-cyano-3-azabicyclo[3.2.0]heptan-1-yl)-4-(4-(phenylamino)pyridin-3-yl)benzamide |

TABLE 2-continued
Compounds of the Disclosure
| Compound Number | Compound Structure and Chemical Name |
|---|---|
| 69 | 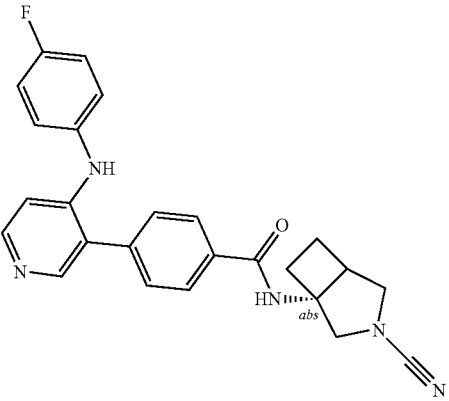<br>N-((1R)-3-cyano-3-azabicyclo[3.2.0]heptan-1-yl)-4-(4-((4-fluorophenyl)amino)pyridin-3-yl)benzamide |
| 70 | 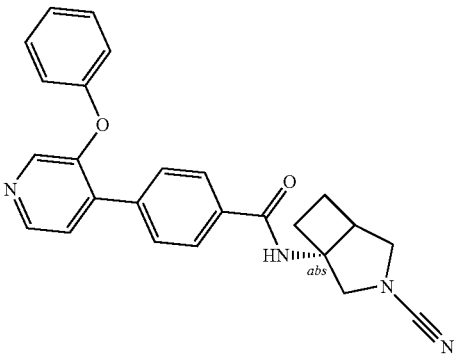<br>N-((1R)-3-cyano-3-azabicyclo[3.2.0]heptan-1-yl)-4-(3-phenoxypiridin-4-yl)benzamide |
| 71 | 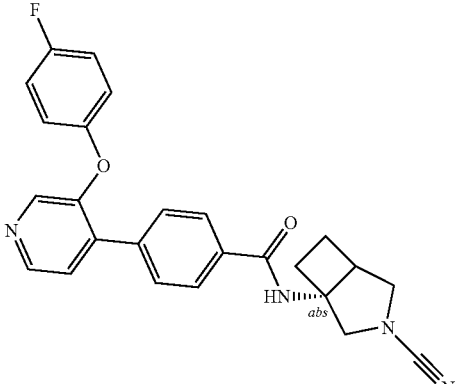<br>N-((1R)-3-cyano-3-azabicyclo[3.2.0]heptan-1-yl)-4-(3-(4-fluorophenoxy)pyridin-4-yl)benzamide |

TABLE 2-continued
Compounds of the Disclosure
| Compound Number | Compound Structure and Chemical Name |
|---|---|
| 72 | 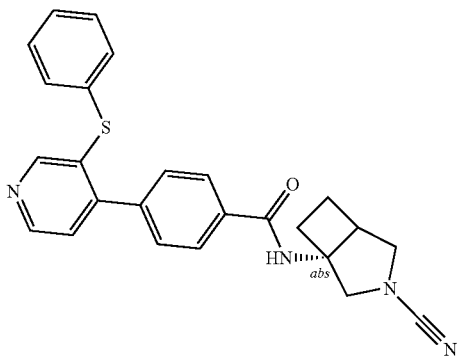<br>N-((1R)-3-cyano-3-azabicyclo[3.2.0]heptan-1-yl)-4-<br>(3-(phenylthio)pyridin-4-yl)benzamide |
| 73 | 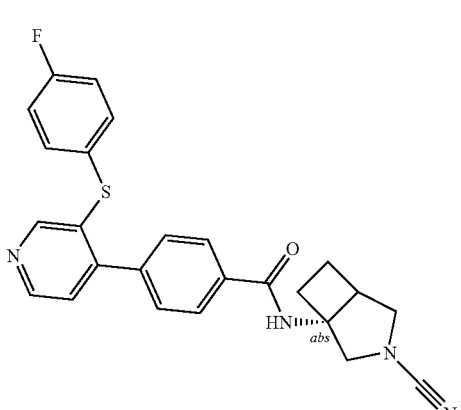<br>N-((1R)-3-cyano-3-azabicyclo[3.2.0]heptan-1-yl)-4-<br>(3-((4-fluorophenyl)thio)pyridin-4-yl)benzamide |
| 74 | 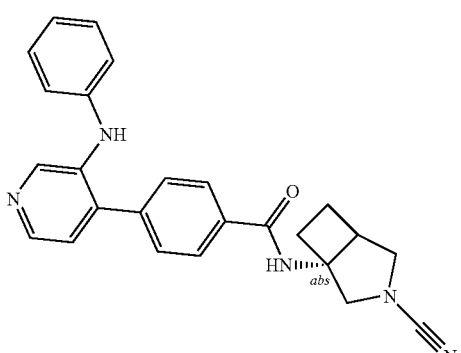<br>N-((1R)-3-cyano-3-azabicyclo[3.2.0]heptan-1-yl)-4-<br>(3-(phenylamino)pyridin-4-yl)benzamide |

TABLE 2-continued
Compounds of the Disclosure
| Compound Number | Compound Structure and Chemical Name |
|---|---|
| 75 | 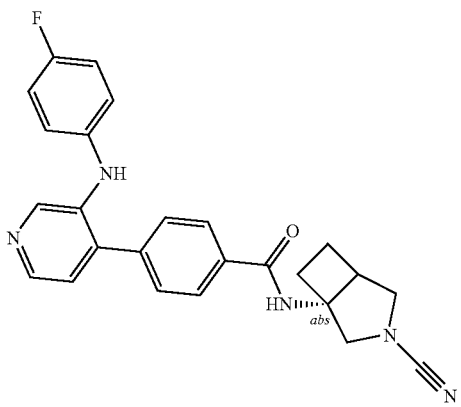  N-((1R)-3-cyano-3-azabicyclo[3.2.0]heptan-1-yl)-4-(3-((4-fluorophenyl)amino)pyridin-4-yl)benzamide |
| 76 | 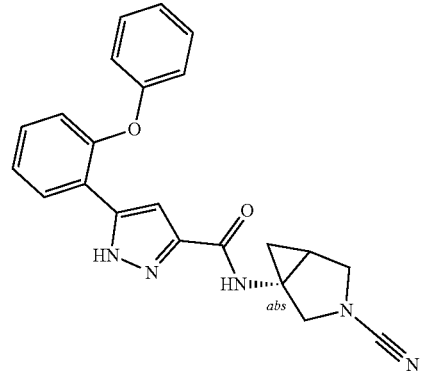  N-((1R)-3-cyano-3-azabicyclo[3.1.0]hexan-1-yl)-5-(2-phenoxyphenyl)-1H-pyrazole-3-carboxamide |
| 77 | 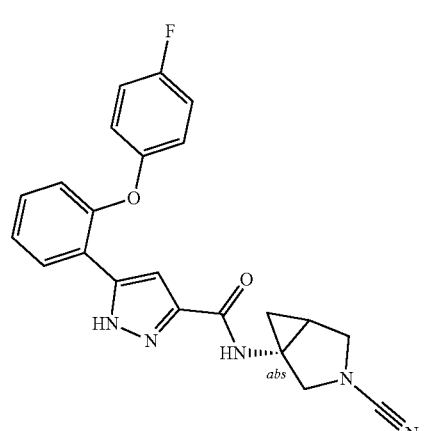  N-((1R)-3-cyano-3-azabicyclo[3.1.0]hexan-1-yl)-5-(2-(4-fluorophenoxy)phenyl)-1H-pyrazole-3-carboxamide |

TABLE 2-continued
Compounds of the Disclosure
| Compound Number | Compound Structure and Chemical Name |
|---|---|
| 78 | 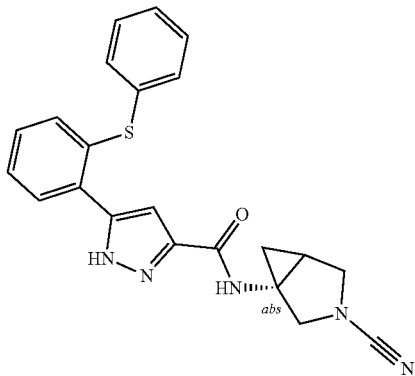<br>N-((1R)-3-cyano-3-azabicyclo[3.1.0]hexan-1-yl)-5-(2-(phenylthio)phenyl)-1H-pyrazole-3-carboxamide |
| 79 | 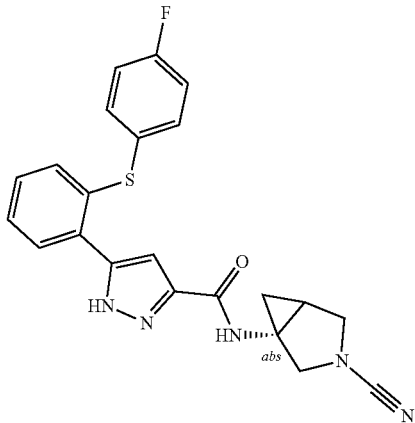<br>N-((1R)-3-cyano-3-azabicyclo[3.1.0]hexan-1-yl)-5-(2-((4-fluorophenyl)thio)phenyl)-1H-pyrazole-3-carboxamide |
| 80 | 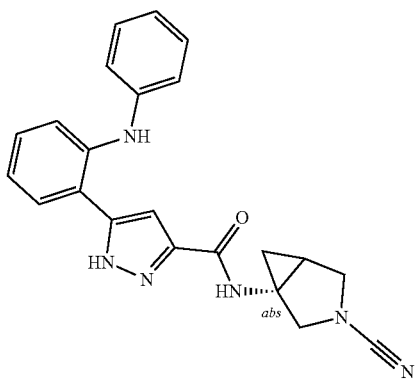<br>N-((1R)-3-cyano-3-azabicyclo[3.1.0]hexan-1-yl)-5-(2-(phenylamino)phenyl)-1H-pyrazole-3-carboxamide |

TABLE 2-continued
Compounds of the Disclosure
| Compound Number | Compound Structure and Chemical Name |
|---|---|
| 81 | 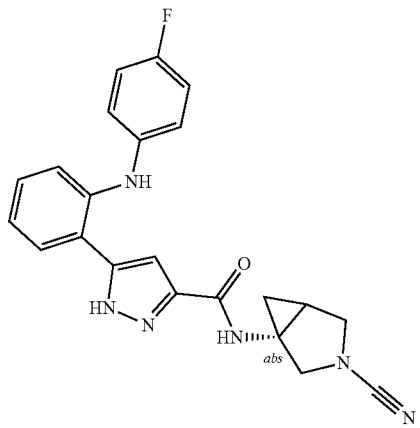 N-((1R)-3-cyano-3-azabicyclo[3.1.0]hexan-1-yl)-5-(2-((4-fluorophenyl)amino)phenyl)-1H-pyrazole-3-carboxamide |
| 82 | 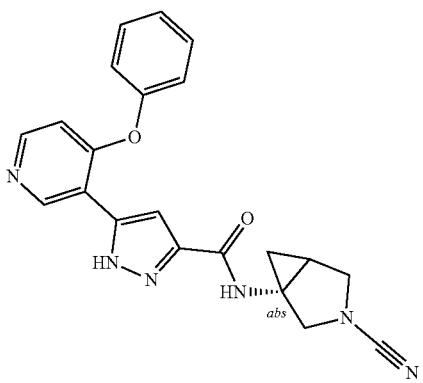 N-((1R)-3-cyano-3-azabicyclo[3.1.0]hexan-1-yl)-5-(4-phenoxypyridin-3-yl)-1H-pyrazole-3-carboxamide |
| 83 | 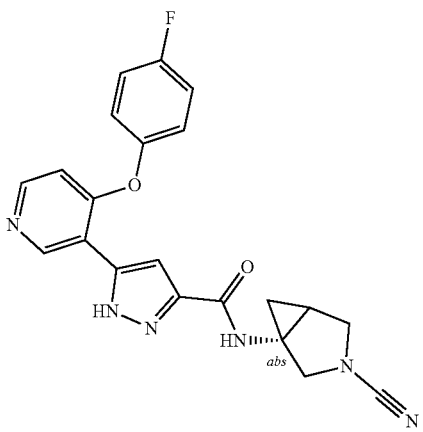 N-((1R)-3-cyano-3-azabicyclo[3.1.0]hexan-1-yl)-5-(4-(4-fluorophenoxy)pyridin-3-yl)-1H-pyrazole-3-carboxamide |

TABLE 2-continued
Compounds of the Disclosure
| Compound Number | Compound Structure and Chemical Name |
|---|---|
| 84 | 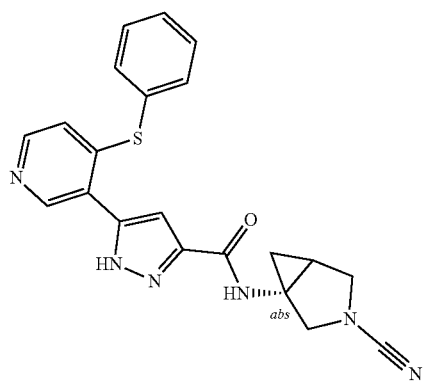<br>N-((1R)-3-cyano-3-azabicyclo[3.1.0]hexan-1-yl)-5-(4-(phenylthio)pyridin-3-yl)-1H-pyrazole-3-carboxamide |
| 85 | 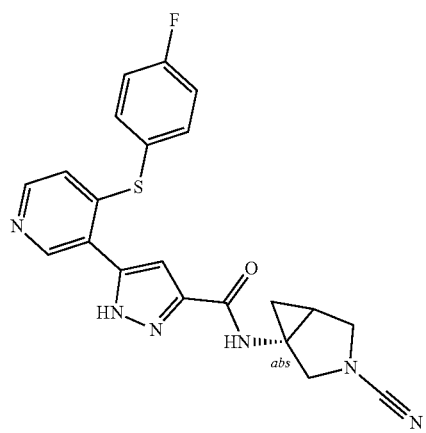<br>N-((1R)-3-cyano-3-azabicyclo[3.1.0]hexan-1-yl)-5-(4-((4-fluorophenyl)thio)pyridin-3-yl)-1H-pyrazole-3-carboxamide |
| 86 | 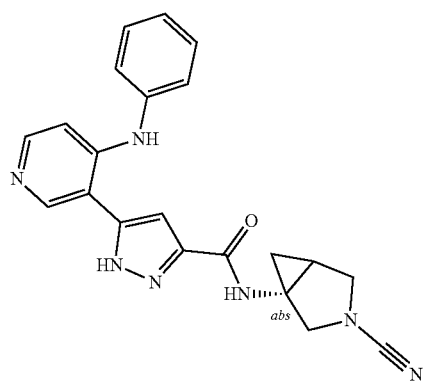<br>N-((1R)-3-cyano-3-azabicyclo[3.1.0]hexan-1-yl)-5-(4-(phenylamino)pyridin-3-yl)-1H-pyrazole-3-carboxamide |

TABLE 2-continued
Compounds of the Disclosure
| Compound Number | Compound Structure and Chemical Name |
|---|---|
| 87 | 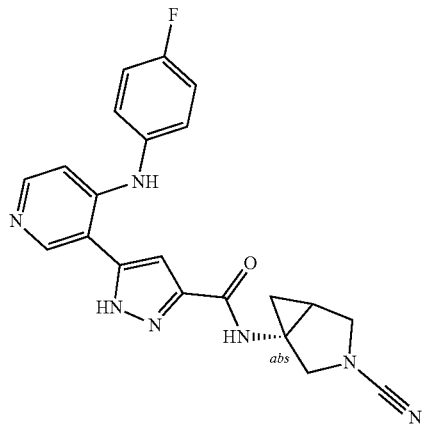<br>N-((1R)-3-cyano-3-azabicyclo[3.1.0]hexan-1-yl)-5-(4-((4-fluorophenyl)amino)pyridin-3-yl)-1H-pyrazole-3-carboxamide |
| 88 | 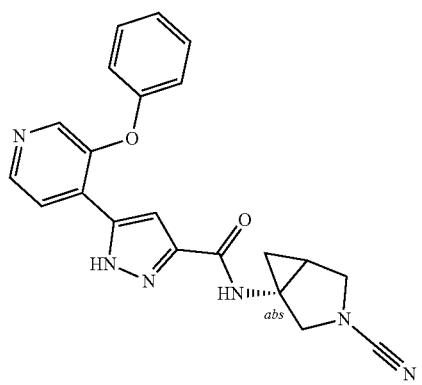<br>N-((1R)-3-cyano-3-azabicyclo[3.1.0]hexan-1-yl)-5-(3-phenoxypyridin-4-yl)-1H-pyrazole-3-carboxamide |
| 89 | 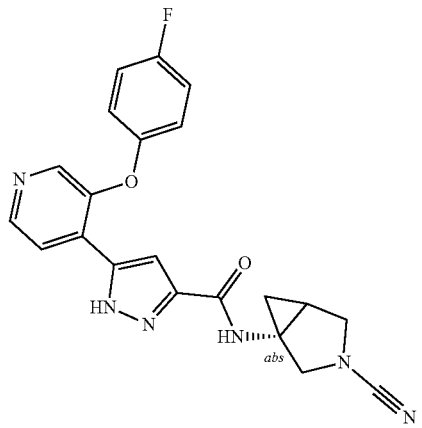<br>N-((1R)-3-cyano-3-azabicyclo[3.1.0]hexan-1-yl)-5-(3-(4-fluorophenoxy)pyridin-4-yl)-1H-pyrazole-3-carboxamide |

TABLE 2-continued
Compounds of the Disclosure
| Compound Number | Compound Structure and Chemical Name |
|---|---|
| 90 | 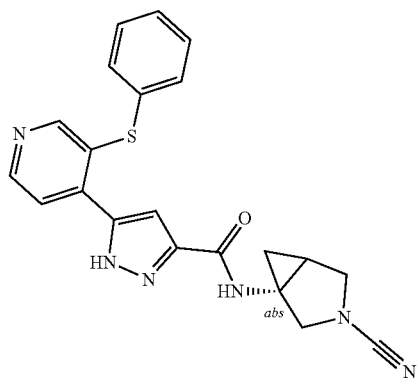<br>N-((1R)-3-cyano-3-azabicyclo[3.1.0]hexan-1-yl)-5-(3-(phenylthio)pyridin-4-yl)-1H-pyrazole-3-carboxamide |
| 91 | 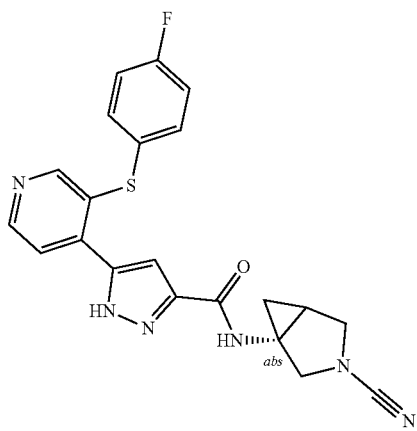<br>N-((1R)-3-cyano-3-azabicyclo[3.1.0]hexan-1-yl)-5-(3-((4-fluorophenyl)thio)pyridin-4-yl)-1H-pyrazole-3-carboxamide |
| 92 | 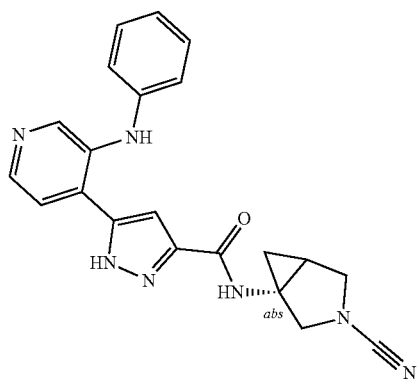<br>N-((1R)-3-cyano-3-azabicyclo[3.1.0]hexan-1-yl)-5-(3-(phenylamino)pyridin-4-yl)-1H-pyrazole-3-carboxamide |

109
TABLE 2-continued
Compounds of the Disclosure
| Compound Number | Compound Structure and Chemical Name |
|---|---|
| 93 | 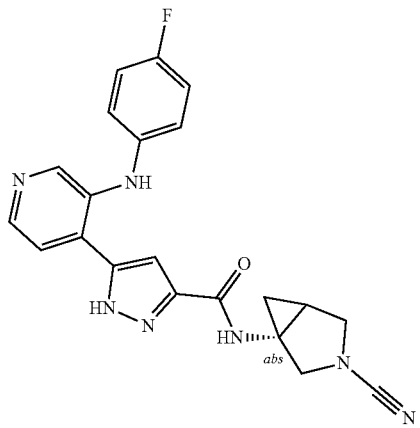<br>N-((1R)-3-cyano-3-azabicyclo[3.1.0]hexan-1-yl)-5-(3-((4-fluorophenyl)amino)pyridin-4-yl)-1H-pyrazole-3-carboxamide |
| 94 | 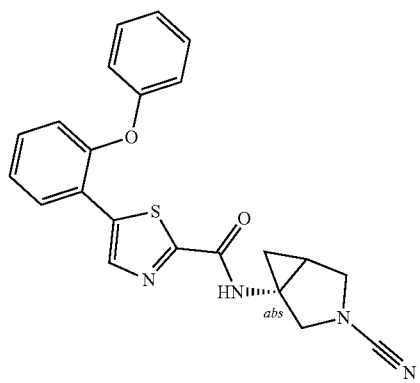<br>N-((1R)-3-cyano-3-azabicyclo[3.1.0]hexan-1-yl)-5-(2-phenoxyphenyl)thiazole-2-carboxamide |
| 95 | 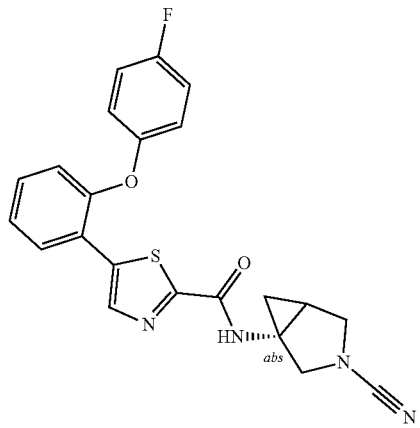<br>N-((1R)-3-cyano-3-azabicyclo[3.1.0]hexan-1-yl)-5-(2-(4-fluorophenoxy)phenyl)thiazole-2-carboxamide |

TABLE 2-continued
Compounds of the Disclosure
| Compound Number | Compound Structure and Chemical Name |
|---|---|
| 96 | 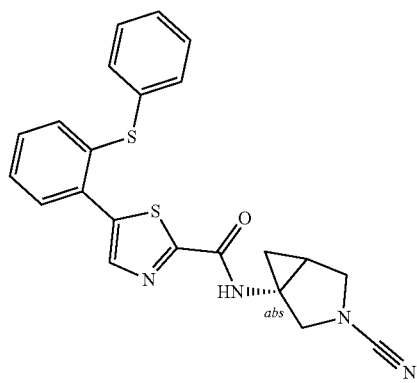<br>N-((1R)-3-cyano-3-azabicyclo[3.1.0]hexan-1-yl)-5-(2-(phenylthio)phenyl)thiazole-2-carboxamide |
| 97 | 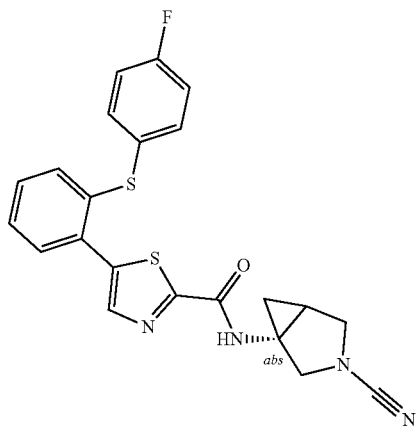<br>N-((1R)-3-cyano-3-azabicyclo[3.1.0]hexan-1-yl)-5-(2-((4-fluorophenyl)thio)phenyl)thiazole-2-carboxamide |
| 98 | 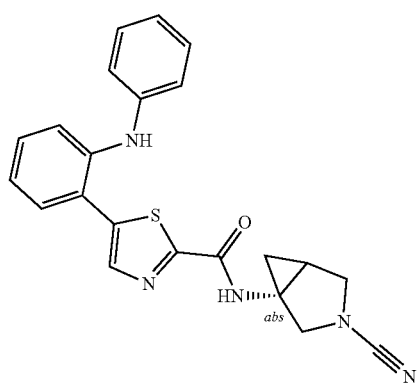<br>N-((1R)-3-cyano-3-azabicyclo[3.1.0]hexan-1-yl)-5-(2-(phenylamino)phenyl)thiazole-2-carboxamide |

TABLE 2-continued
Compounds of the Disclosure
| Compound Number | Compound Structure and Chemical Name |
|---|---|
| 99 | 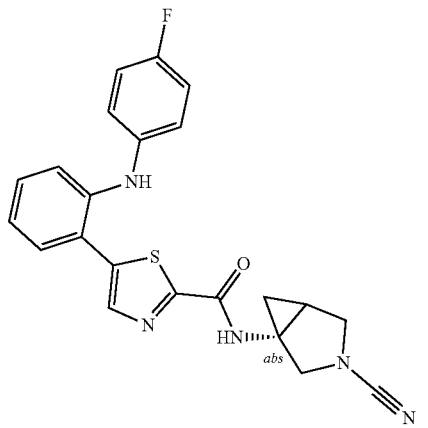<br>N-((1R)-3-cyano-3-azabicyclo[3.1.0]hexan-1-yl)-5-(2-((4-fluorophenyl)amino)phenyl)thiazole-2-carboxamide |
| 100 | 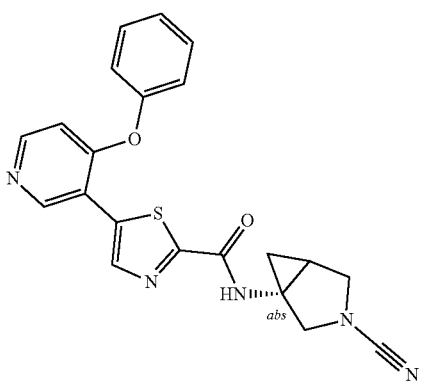<br>N-((1R)-3-cyano-3-azabicyclo[3.1.0]hexan-1-yl)-5-(4-phenoxypyridin-3-yl)thiazole-2-carboxamide |
| 101 | 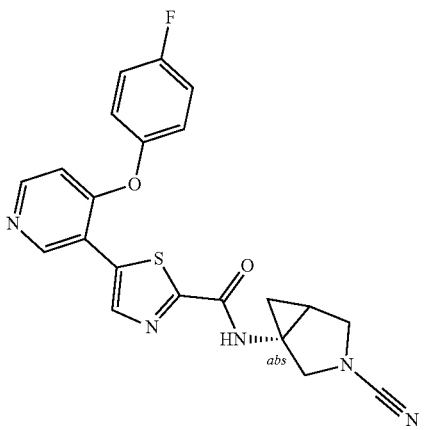<br>N-((1R)-3-cyano-3-azabicyclo[3.1.0]hexan-1-yl)-5-(4-(4-fluorophenoxy)pyridin-3-yl)thiazole-2-carboxamide |

TABLE 2-continued
Compounds of the Disclosure
| Compound Number | Compound Structure and Chemical Name |
|---|---|
| 102 | 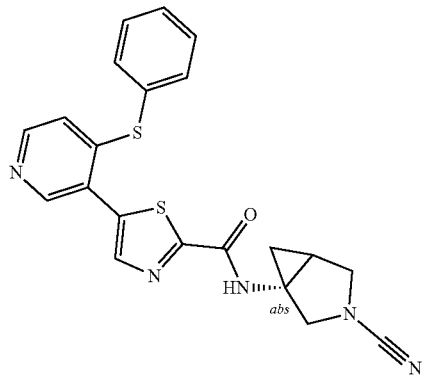<br>N-((1R)-3-cyano-3-azabicyclo[3.1.0]hexan-1-yl)-5-(4-(phenylthio)pyridin-3-yl)thiazole-2-carboxamide |
| 103 | 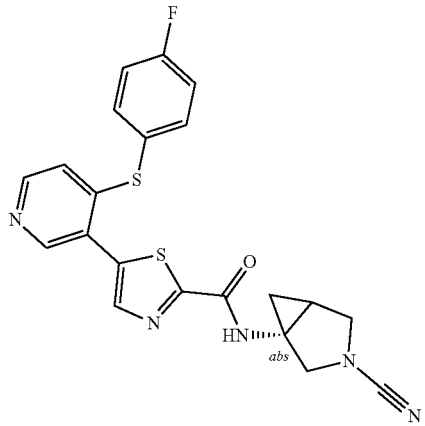<br>N-((1R)-3-cyano-3-azabicyclo[3.1.0]hexan-1-yl)-5-(4-((4-fluorophenyl)thio)pyridin-3-yl)thiazole-2-carboxamide |
| 104 | 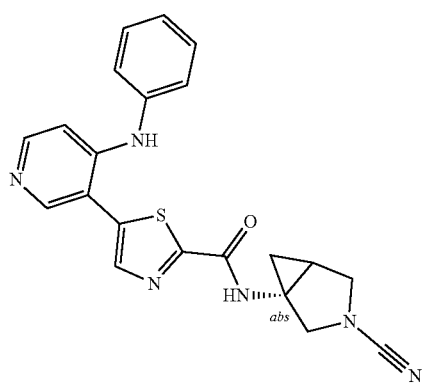<br>N-((1R)-3-cyano-3-azabicyclo[3.1.0]hexan-1-yl)-5-(4-phenylamino)pyridin-3-yl)thiazole-2-carboxamide |

TABLE 2-continued
Compounds of the Disclosure
| Compound Number | Compound Structure and Chemical Name |
|---|---|
| 105 | 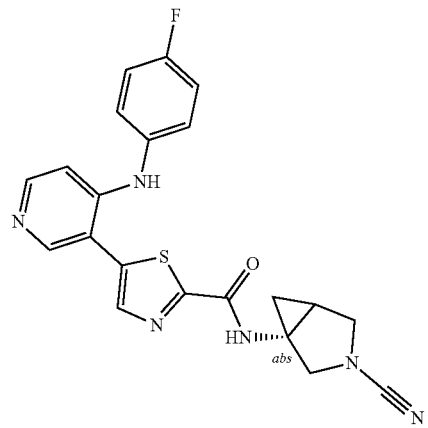  N-((1R)-3-cyano-3-azabicyclo[3.1.0]hexan-1-yl)-5-(4-((4-fluorophenyl)amino)pyridin-3-yl)thiazole-2-carboxamide |
| 106 | 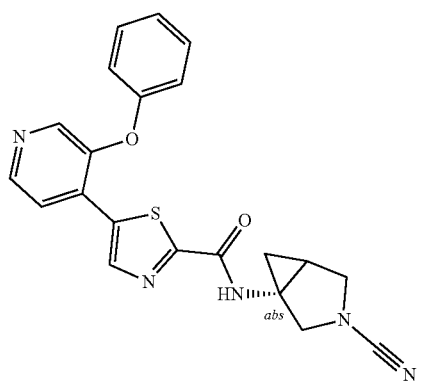  N-((1R)-3-cyano-3-azabicyclo[3.1.0]hexan-1-yl)-5-(3-phenoxypyridin-4-yl)thiazole-2-carboxamide |
| 107 | 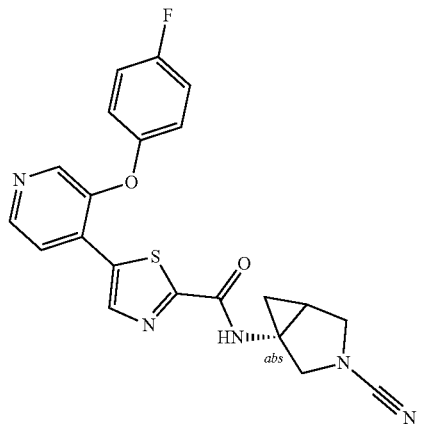  N-((1R)-3-cyano-3-azabicyclo[3.1.0]hexan-1-yl)-5-(3-(4-fluorophenoxy)pyridin-4-yl)thiazole-2-carboxamide |

TABLE 2-continued
Compounds of the Disclosure
| Compound Number | Compound Structure and Chemical Name |
|---|---|
| 108 | 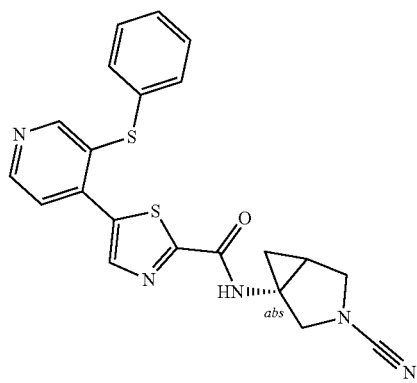
N-((1R)-3-cyano-3-azabicyclo[3.1.0]hexan-1-yl)-5-(3-(phenylthio)pyridin-4-yl)thiazole-2-carboxamide |
| 109 | 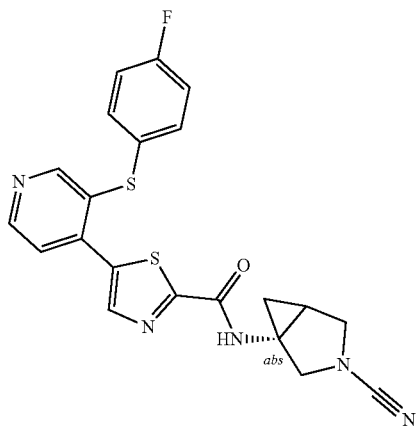
N-((1R)-3-cyano-3-azabicyclo[3.1.0]hexan-1-yl)-5-(3-((4-fluorophenyl)thio)pyridin-4-yl)thiazole-2-carboxamide |
| 110 | 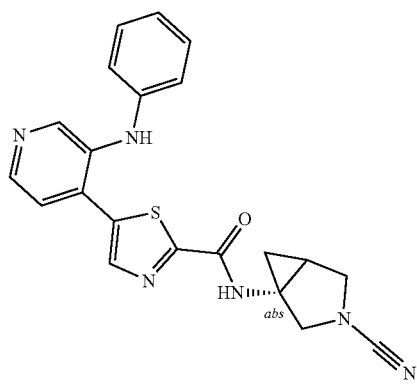
N-((1R)-3-cyano-3-azabicyclo[3.1.0]hexan-1-yl)-5-(3-(phenylamino)pyridin-4-yl)thiazole-2-carboxamide |

TABLE 2-continued
Compounds of the Disclosure
| Compound Number | Compound Structure and Chemical Name |
|---|---|
| 111 | 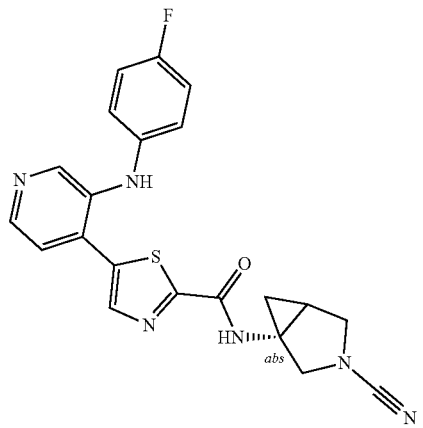<br>N-((1R)-3-cyano-3-azabicyclo[3.1.0]hexan-1-yl)-5-(3-((4-fluorophenyl)amino)pyridin-4-yl)thiazole-2-carboxamide |
| 112 | 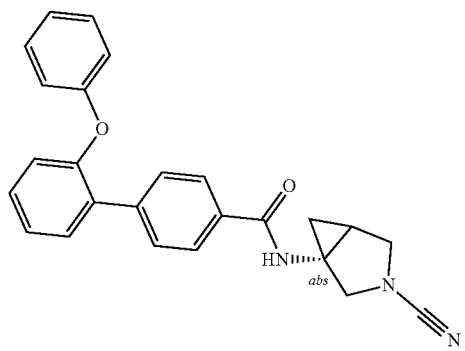<br>N-((1R)-3-cyano-3-azabicyclo[3.1.0]hexan-1-yl)-2'-phenoxy-[1,1'-biphenyl]-4-carboxamide |
| 113 | 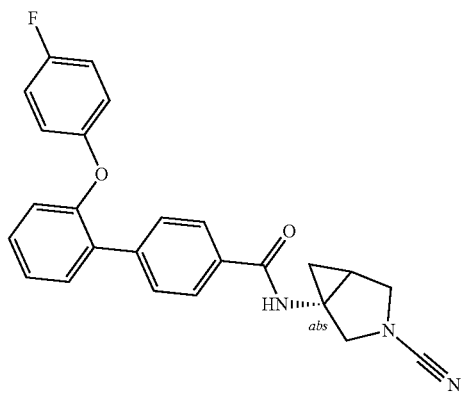<br>N-((1R)-3-cyano-3-azabicyclo[3.1.0]hexan-1-yl)-2'-(4-fluorophenoxy)-[1,1'-biphenyl]-4-carboxamide |

TABLE 2-continued
Compounds of the Disclosure
| Compound Number | Compound Structure and Chemical Name |
|---|---|
| 114 | 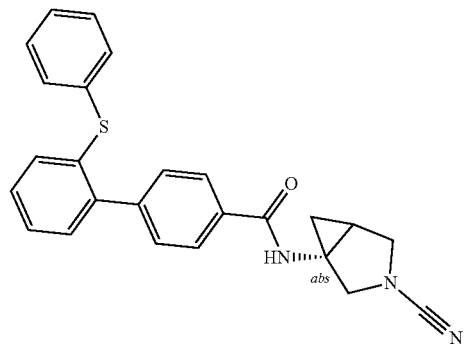 N-((1R)-3-cyano-3-azabicyclo[3.1.0]hexan-1-yl)-2'-(phenylthio)-[1,1'-biphenyl]-4-carboxamide |
| 115 | 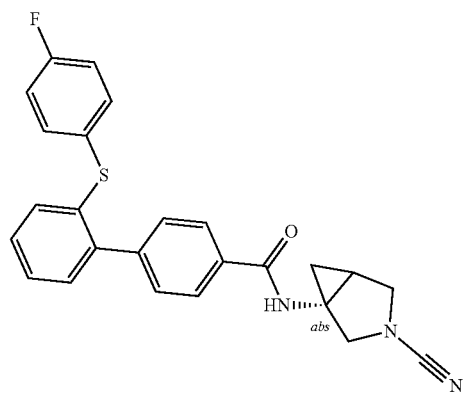 N-((1R)-3-cyano-3-azabicyclo[3.1.0]hexan-1-yl)-2'-((4-fluorophenyl)thio)-[1,1'-biphenyl]-4-carboxamide |
| 116 | 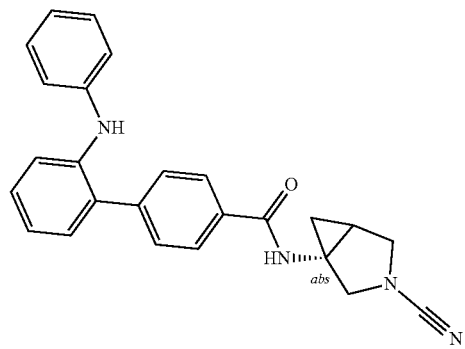 N-((1R)-3-cyano-3-azabicyclo[3.1.0]hexan-1-yl)-2'-(phenylamino)-[1,1'-biphenyl]-4-carboxamide |

TABLE 2-continued
Compounds of the Disclosure
| Compound Number | Compound Structure and Chemical Name |
|---|---|
| 117 | 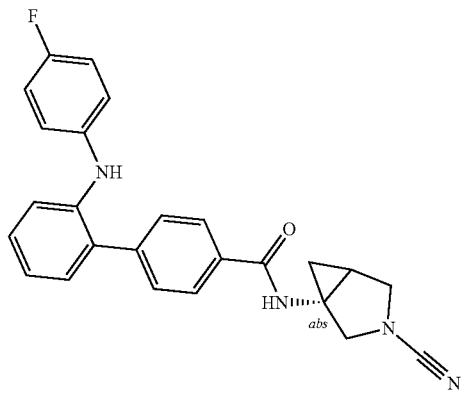<br>N-((1R)-3-cyano-3-azabicyclo[3.1.0]hexan-1-yl)-2'-((4-fluorophenyl)amino)-[1,1'-biphenyl]-4-carboxamide |
| 118 | 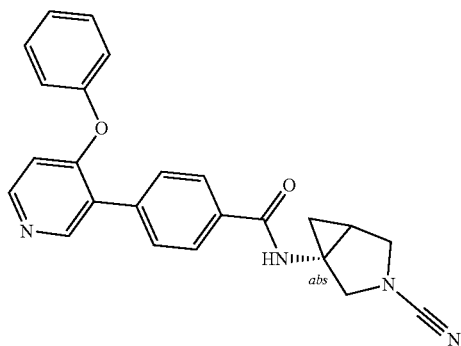<br>N-((1R)-3-cyano-3-azabicyclo[3.1.0]hexan-1-yl)-4-(4-phenoxypyridin-3-yl)benzamide |
| 119 | 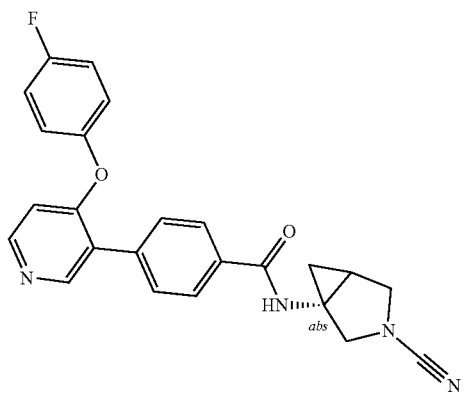<br>N-((1R)-3-cyano-3-azabicyclo[3.1.0]hexan-1-yl)-4-(4-(4-fluorophenoxy)pyridin-3-yl)benzamide |

TABLE 2-continued
Compounds of the Disclosure
| Compound Number | Compound Structure and Chemical Name |
|---|---|
| 120 | 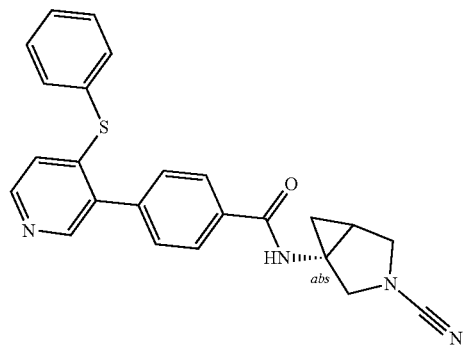<br>N-((1R)-3-cyano-3-azabicyclo[3.1.0]hexan-1-yl)-4-(4-(phenylthio)pyridin-3-yl)benzamide |
| 121 | 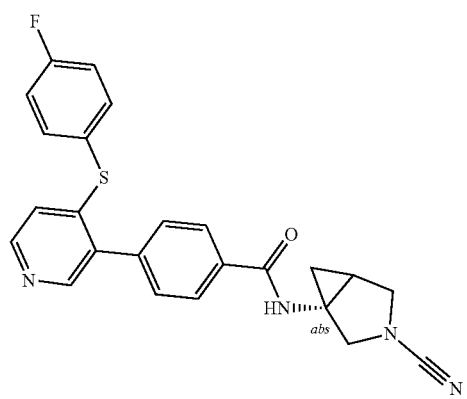<br>N-((1R)-3-cyano-3-azabicyclo[3.1.0]hexan-1-yl)-4-(4-((4-fluorophenyl)thio)pyridin-3-yl)benzamide |
| 122 | 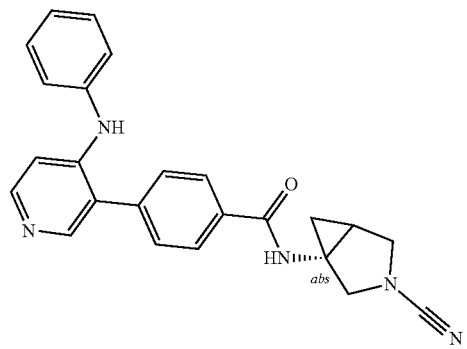<br>N-((1R)-3-cyano-3-azabicyclo[3.1.0]hexan-1-yl)-4-(4-(phenylamino)pyridin-3-yl)benzamide |

TABLE 2-continued
Compounds of the Disclosure
| Compound Number | Compound Structure and Chemical Name |
|---|---|
| 123 | 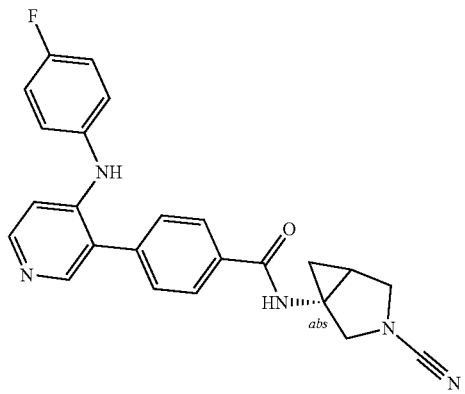<br>N-((1R)-3-cyano-3-azabicyclo[3.1.0]hexan-1-yl)-4-(4-((4-fluorophenyl)amino)pyridin-3-yl)benzamide |
| 124 | 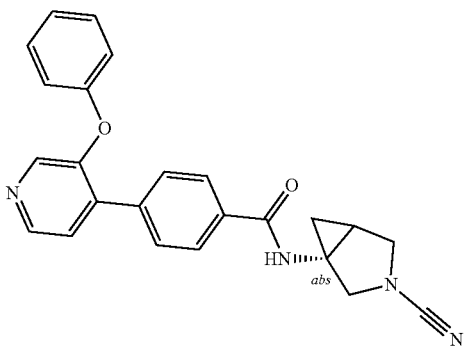<br>N-((1R)-3-cyano-3-azabicyclo[3.1.0]hexan-1-yl)-4-(3-phenoxypyridin-4-yl)benzamide |
| 125 | 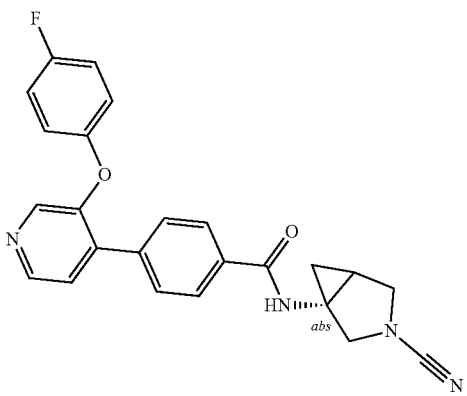<br>N-((1R)-3-cyano-3-azabicyclo[3.1.0]hexan-1-yl)-4-(3-(4-fluorophenoxy)pyridin-4-yl)benzamide |

TABLE 2-continued
Compounds of the Disclosure
| Compound Number | Compound Structure and Chemical Name |
|---|---|
| 126 | 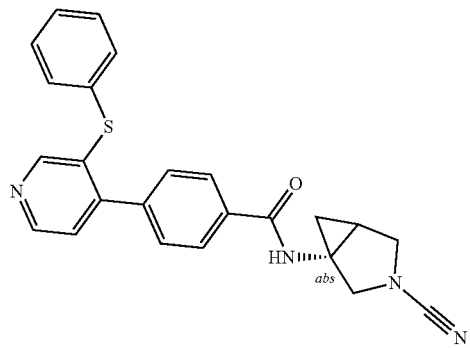<br>N-((1R)-3-cyano-3-azabicyclo[3.1.0]hexan-1-yl)-4-(3-(phenylthio)pyridin-4-yl)benzamide |
| 127 | 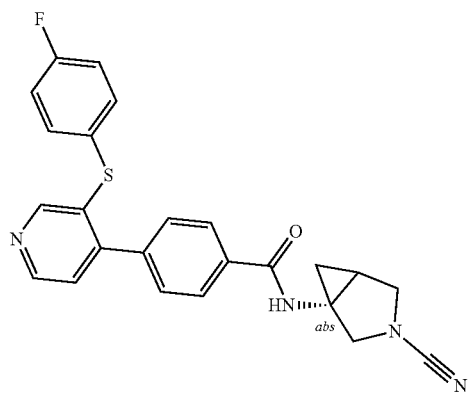<br>N-((1R)-3-cyano-3-azabicyclo[3.1.0]hexan-1-yl)-4-(3-((4-fluorophenyl)thio)pyridin-4-yl)benzamide |
| 128 | 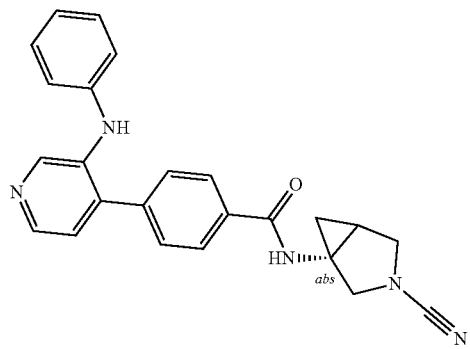<br>N-((1R)-3-cyano-3-azabicyclo[3.1.0]hexan-1-yl)-4-(3-(phenylamino)pyridin-4-yl)benzamide |

TABLE 2-continued
Compounds of the Disclosure
| Compound Number | Compound Structure and Chemical Name |
| --- | --- |
| 129 | 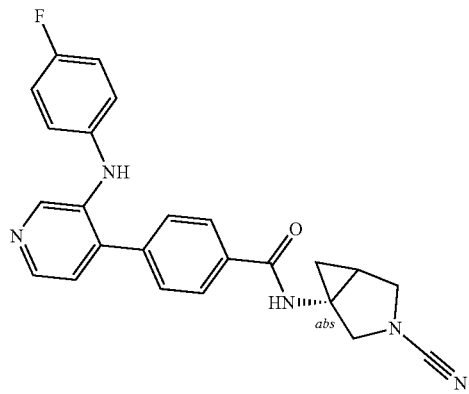<br>N-((1R)-3-cyano-3-azabicyclo[3.1.0]hexan-1-yl)-4-(3-((4-fluorophenyl)amino)pyridin-4-yl)benzamide |
| 130 | 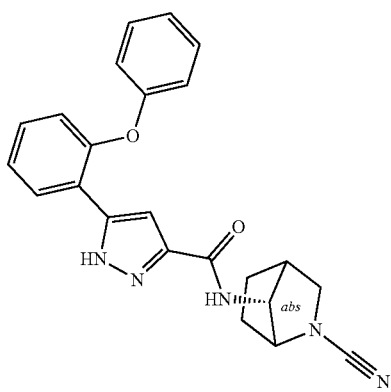<br>N-((7R)-2-cyano-2-azabicyclo[2.2.1]heptan-7-yl)-5-(2-phenoxyphenyl)-1H-pyrazole-3-carboxamide |
| 131 | 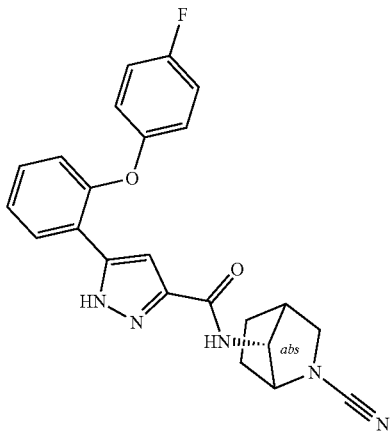<br>N-((7R)-2-cyano-2-azabicyclo[2.2.1]heptan-7-yl)-5-(2-(4-fluorophenoxy)phenyl)-1H-pyrazole-3-carboxamide |

TABLE 2-continued
Compounds of the Disclosure
| Compound Number | Compound Structure and Chemical Name |
|---|---|
| 132 | 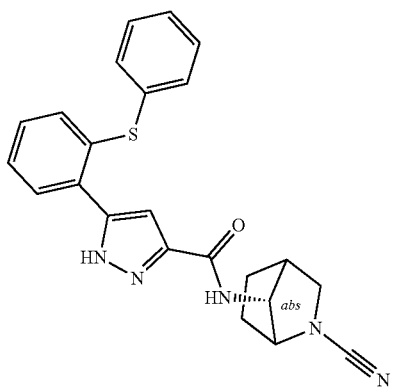<br>N-((7R)-2-cyano-2-azabicyclo[2.2.1]heptan-7-yl)-5-(2-(phenylthio)phenyl)-1H-pyrazole-3-carboxamide |
| 133 | 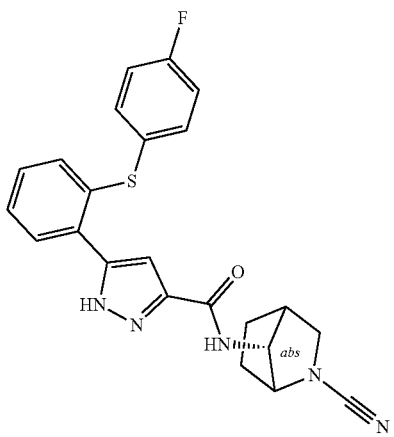<br>N-((7R)-2-cyano-2-azabicyclo[2.2.1]heptan-7-yl)-5-(2-((4-fluorophenyl)thio)phenyl)-1H-pyrazole-3-carboxamide |
| 134 | 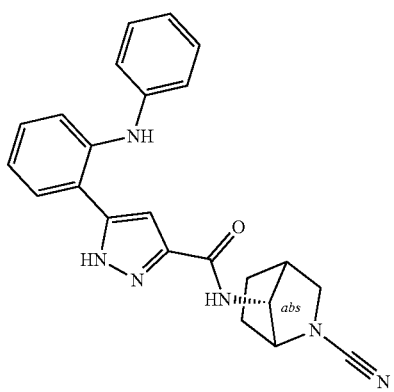<br>N-((7R)-2-cyano-2-azabicyclo[2.2.1]heptan-7-yl)-5-(2-(phenylamino)phenyl)-1H-pyrazole-3-carboxamide |

TABLE 2-continued
Compounds of the Disclosure
| Compound Number | Compound Structure and Chemical Name |
|---|---|
| 135 | 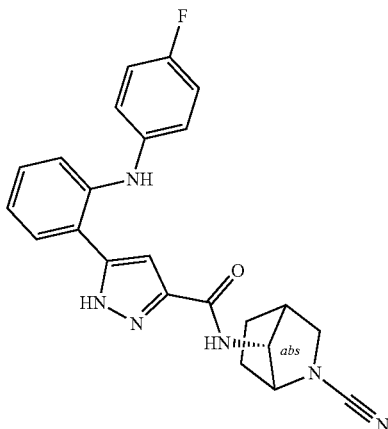<br>N-((7R)-2-cyano-2-azabicyclo[2.2.1]heptan-7-yl)-5-(2-((4-fluorophenyl)amino)phenyl)-1H-pyrazole-3-carboxamide |
| 136 | 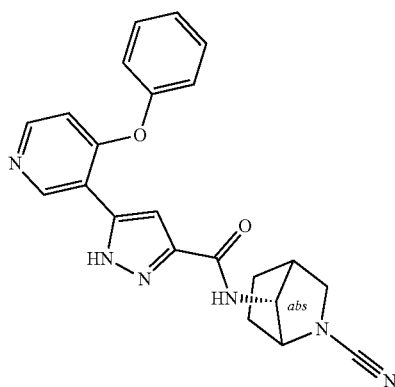<br>N-((7R)-2-cyano-2-azabicyclo[2.2.1]heptan-7-yl)-5-(4-phenoxypyridin-3-yl)-1H-pyrazole-3-carboxamide |
| 137 | 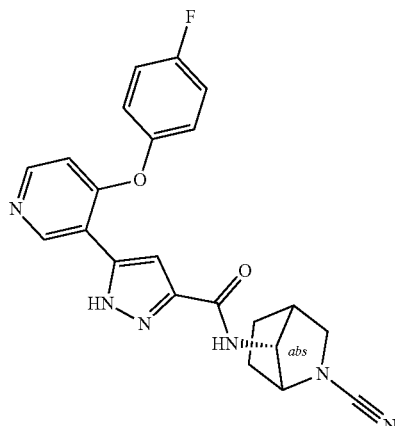<br>N-((7R)-2-cyano-2-azabicyclo[2.2.1]heptan-7-yl)-5-(4-(4-fluorophenoxy)pyridin-3-yl)-1H-pyrazole-3-carboxamide |

TABLE 2-continued
Compounds of the Disclosure
| Compound Number | Compound Structure and Chemical Name |
|---|---|
| 138 | 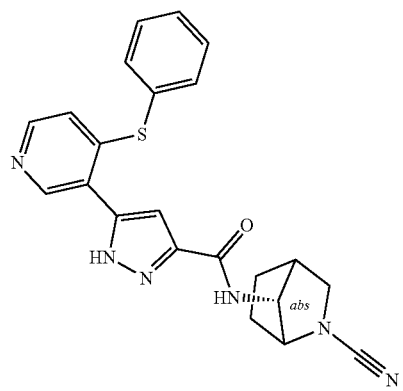  N-((7R)-2-cyano-2-azabicyclo[2.2.1]heptan-7-yl)-5-(4-(phenylthio)pyridin-3-yl)-1H-pyrazole-3-carboxamide |
| 139 | 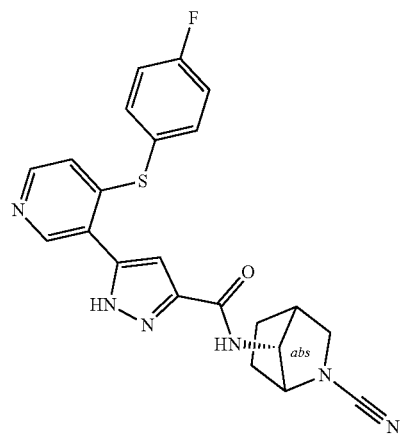  N-((7R)-2-cyano-2-azabicyclo[2.2.1]heptan-7-yl)-5-(4-((4-fluorophenyl)thio)pyridin-3-yl)-1H-pyrazole-3-carboxamide |
| 140 | 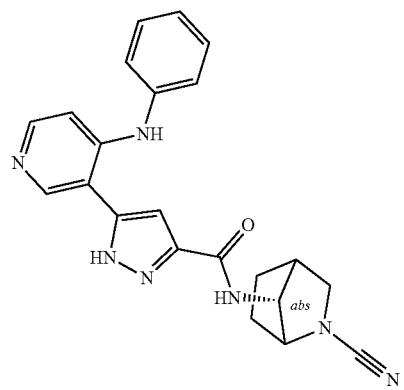  N-((7R)-2-cyano-2-azabicyclo[2.2.1]heptan-7-yl)-5-(4-(phenylamino)pyridin-3-yl)-1H-pyrazole-3-carboxamide |

TABLE 2-continued
Compounds of the Disclosure
| Compound Number | Compound Structure and Chemical Name |
|---|---|
| 141 | 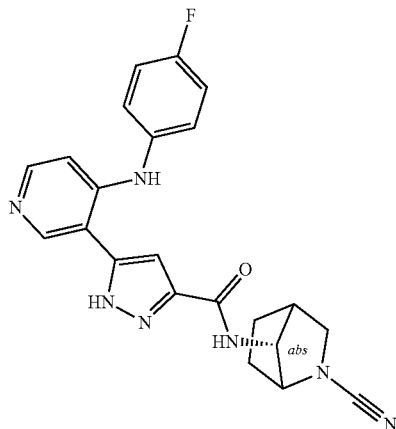  N-((7R)-2-cyano-2-azabicyclo[2.2.1]heptan-7-yl)-5-(4-((4-fluorophenyl)amino)pyridin-3-yl)-1H-pyrazole-3-carboxamide |
| 142 | 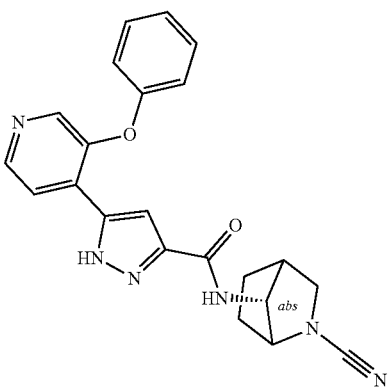  N-((7R)-2-cyano-2-azabicyclo[2.2.1]heptan-7-yl)-5-(3-phenoxypyridin-4-yl)-1H-pyrazole-3-carboxamide |
| 143 | 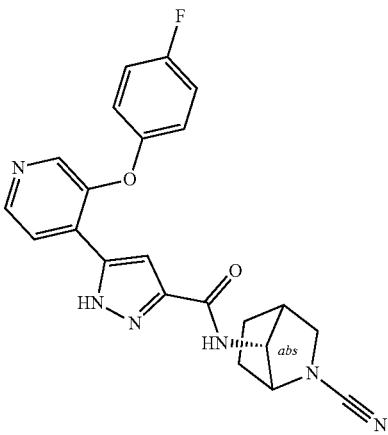  N-((7R)-2-cyano-2-azabicyclo[2.2.1]heptan-7-yl)-5-(3-(4-fluorophenoxy)pyridin-4-yl)-1H-pyrazole-3-carboxamide |

TABLE 2-continued
Compounds of the Disclosure
| Compound Number | Compound Structure and Chemical Name |
|---|---|
| 144 | 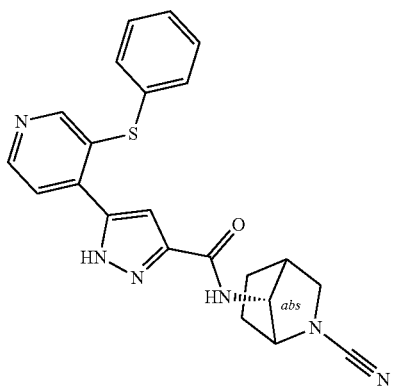<br>N-((7R)-2-cyano-2-azabicyclo[2.2.1]heptan-7-yl)-5-(3-(phenylthio)pyridin-4-yl)-1H-pyrazole-3-carboxamide |
| 145 | 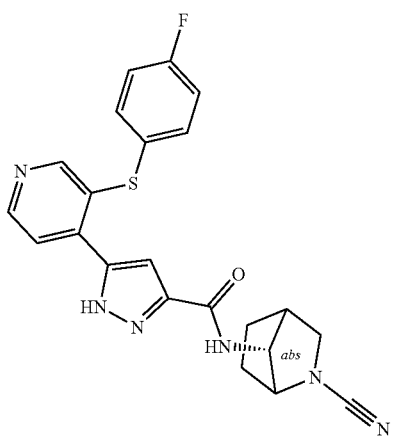<br>N-((7R)-2-cyano-2-azabicyclo[2.2.1]heptan-7-yl)-5-(3-((4-fluorophenyl)thio)pyridin-4-yl)-1H-pyrazole-3-carboxamide |
| 146 | 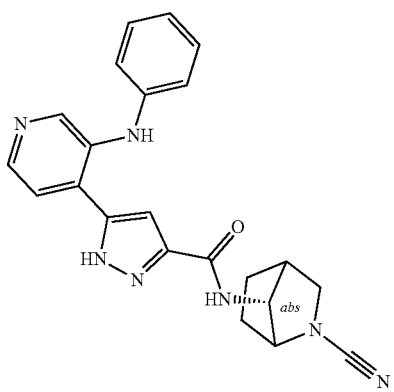<br>N-((7R)-2-cyano-2-azabicyclo[2.2.1]heptan-7-yl)-5-(3-(phenylamino)pyridin-4-yl)-1H-pyrazole-3-carboxamide |

TABLE 2-continued
Compounds of the Disclosure
| Compound Number | Compound Structure and Chemical Name |
|---|---|
| 147 | 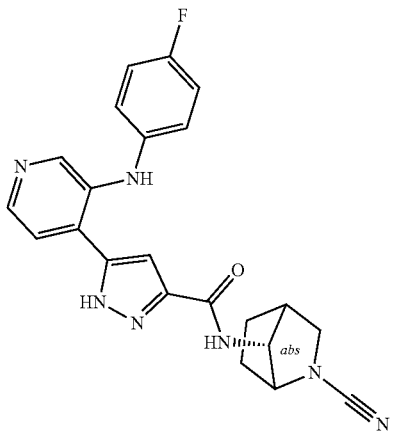<br>N-((7R)-2-cyano-2-azabicyclo[2.2.1]heptan-7-yl)-5-(3-((4-fluorophenyl)amino)pyridin-4-yl)-1H-pyrazole-3-carboxamide |
| 148 | 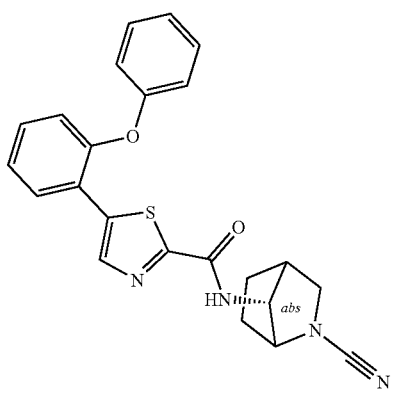<br>N-((7R)-2-cyano-2-azabicyclo[2.2.1]heptan-7-yl)-5-(2-phenoxyphenyl)thiazole-2-carboxamide |
| 149 | 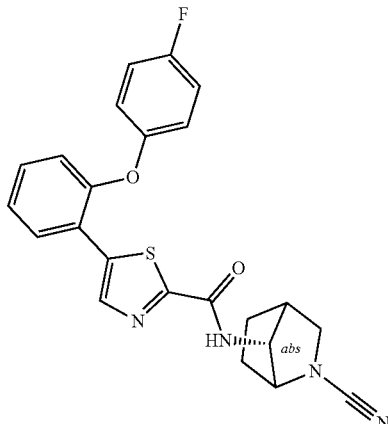<br>N-((7R)-2-cyano-2-azabicyclo[2.2.1]heptan-7-yl)-5-(2-(4-fluorophenoxy)phenyl)thiazole-2-carboxamide |

TABLE 2-continued
Compounds of the Disclosure
| Compound Number | Compound Structure and Chemical Name |
|---|---|
| 150 | 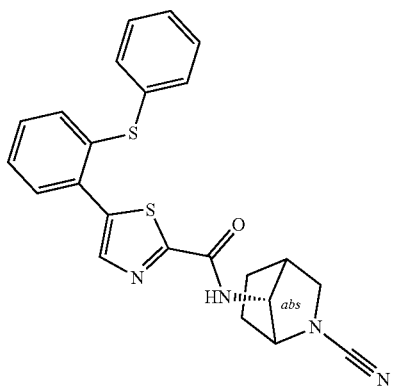<br>N-((7R)-2-cyano-2-azabicyclo[2.2.1]heptan-7-yl)-5-(2-(phenylthio)phenyl)thiazole-2-carboxamide |
| 151 | 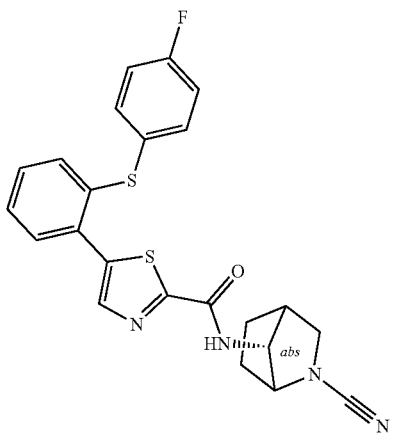<br>N-((7R)-2-cyano-2-azabicyclo[2.2.1]heptan-7-yl)-5-(2-((4-fluorophenyl)thio)phenyl)thiazole-2-carboxamide |
| 152 | 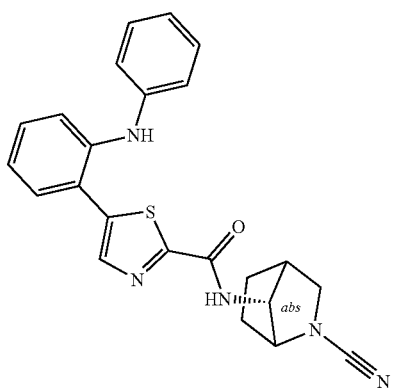<br>N-((7R)-2-cyano-2-azabicyclo[2.2.1]heptan-7-yl)-5-(2-(phenylamino)phenyl)thiazole-2-carboxamide |

TABLE 2-continued
Compounds of the Disclosure
| Compound Number | Compound Structure and Chemical Name |
|---|---|
| 153 | 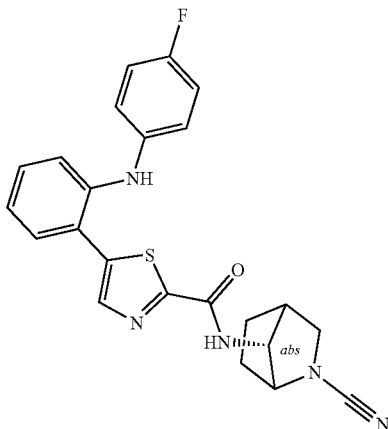<br>N-((7R)-2-cyano-2-azabicyclo[2.2.1]heptan-7-yl)-5-(2-((4-fluorophenyl)amino)phenyl)thiazole-2-carboxamide |
| 154 | 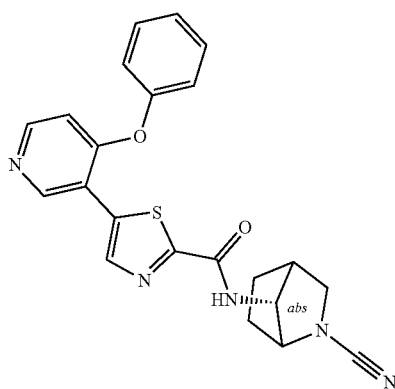<br>N-((7R)-2-cyano-2-azabicyclo[2.2.1]heptan-7-yl)-5-(4-phenoxypyridin-3-yl)thiazole-2-carboxamide |
| 155 | 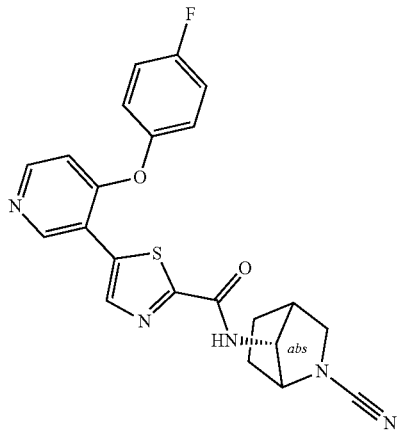<br>N-((7R)-2-cyano-2-azabicyclo[2.2.1]heptan-7-yl)-5-(4-(4-fluorophenoxy)pyridin-3-yl)thiazole-2-carboxamide |

TABLE 2-continued
Compounds of the Disclosure
| Compound Number | Compound Structure and Chemical Name |
|---|---|
| 156 | 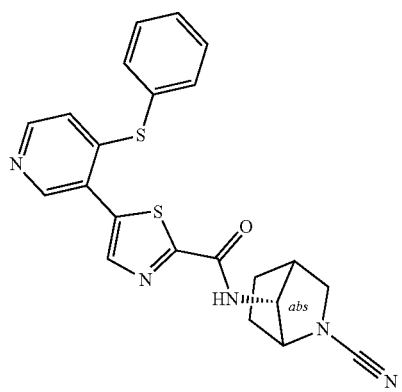 N-((7R)-2-cyano-2-azabicyclo[2.2.1]heptan-7-yl)-5-(4-(phenylthio)pyridin-3-yl)thiazole-2-carboxamide |
| 157 | 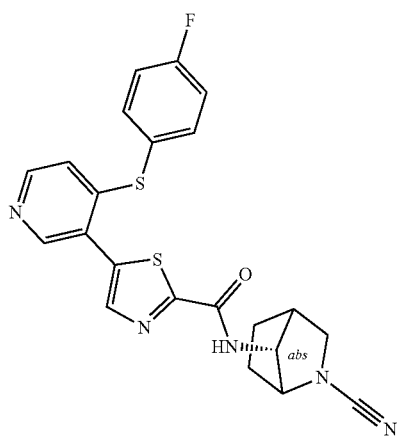 N-((7R)-2-cyano-2-azabicyclo[2.2.1]heptan-7-yl)-5-(4-((4-fluorophenyl)thio)pyridin-3-yl)thiazole-2-carboxamide |
| 158 | 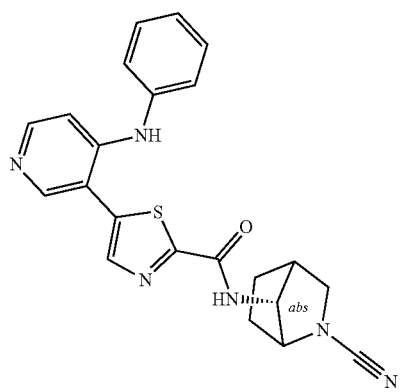 N-((7R)-2-cyano-2-azabicyclo[2.2.1]heptan-7-yl)-5-(4-(phenylamino)pyridin-3-yl)thiazole-2-carboxamide |

TABLE 2-continued
Compounds of the Disclosure
| Compound Number | Compound Structure and Chemical Name |
|---|---|
| 159 | 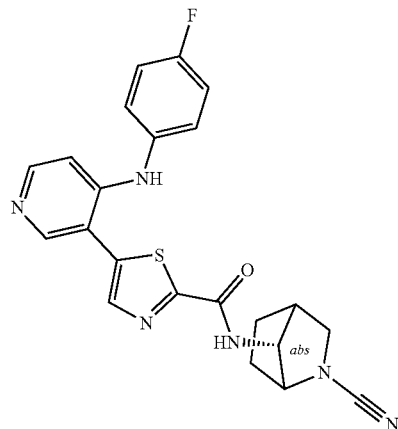<br>N-((7R)-2-cyano-2-azabicyclo[2.2.1]heptan-7-yl)-5-(4-((4-fluorophenyl)amino)pyridin-3-yl)thiazole-2-carboxamide |
| 160 | 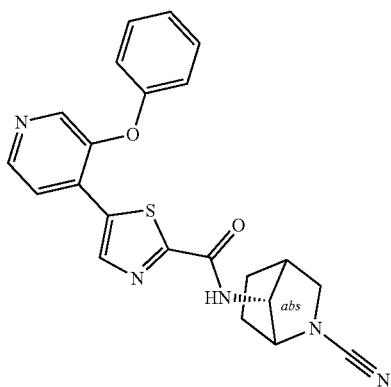<br>N-((7R)-2-cyano-2-azabicyclo[2.2.1]heptan-7-yl)-5-(3-phenoxypyridin-4-yl)thiazole-2-carboxamide |
| 161 | 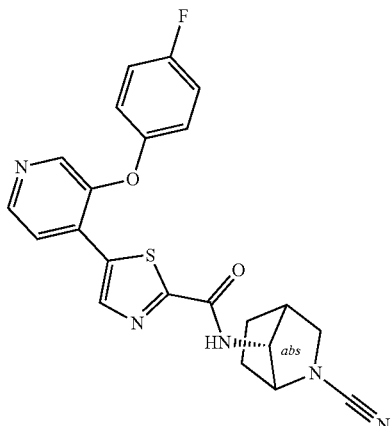<br>N-((7R)-2-cyano-2-azabicyclo[2.2.1]heptan-7-yl)-5-(3-(4-fluorophenoxy)pyridin-4-yl)thiazole-2-carboxamide |

TABLE 2-continued
Compounds of the Disclosure
| Compound Number | Compound Structure and Chemical Name |
|---|---|
| 162 | 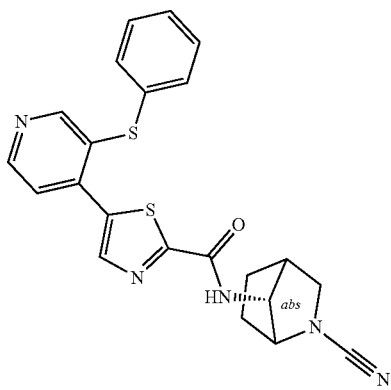<br>N-((7R)-2-cyano-2-azabicyclo[2.2.1]heptan-7-yl)-5-(3-(phenylthio)pyridin-4-yl)thiazole-2-carboxamide |
| 163 | 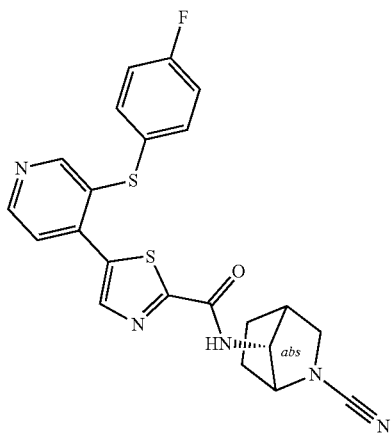<br>N-((7R)-2-cyano-2-azabicyclo[2.2.1]heptan-7-yl)-5-(3-((4-fluorophenyl)thio)pyridin-4-yl)thiazole-2-carboxamide |
| 164 | 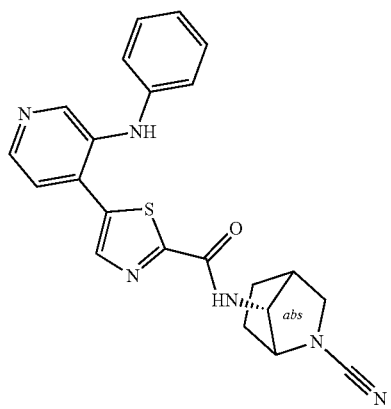<br>N-((7R)-2-cyano-2-azabicyclo[2.21]heptan-7-yl)-5-(3-phenylamino)pyridin-4-yl)thiazole-2-carboxamide |

TABLE 2-continued
Compounds of the Disclosure
| Compound Number | Compound Structure and Chemical Name |
|---|---|
| 165 | 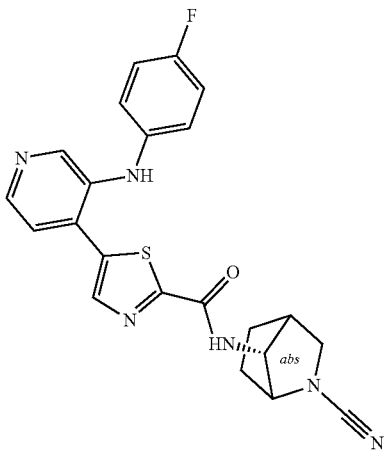 N-((7R)-2-cyano-2-azabicyclo[2.2.1]heptan-7-yl)-5-(3-((4-fluorophenyl)amino)pyridin-4-yl)thiazole-2-carboxamide |
| 166 | 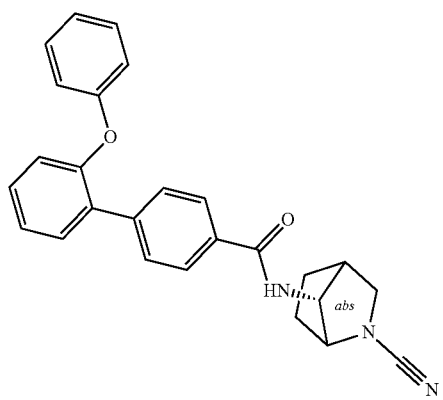 N-((7R)-2-cyano-2-azabicyclo[2.2.1]heptan-7-yl)-2'-phenoxy-[1,1'-biphenyl]-4-carboxamide |
| 167 | 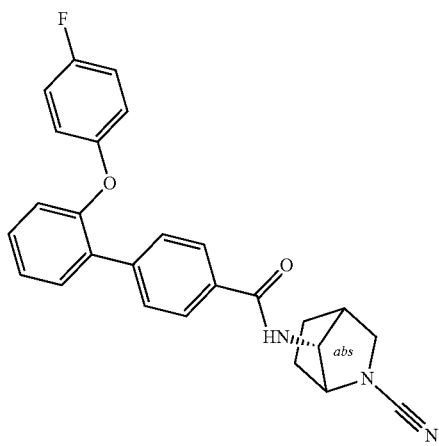 N-((7R)-2-cyano-2-azabicyclo[2.2.1]heptan-7-yl)-2'-(4-fluorophenoxy)-[1,1'-biphenyl]-4-carboxamide |

TABLE 2-continued
Compounds of the Disclosure
| Compound Number | Compound Structure and Chemical Name |
|---|---|
| 168 | 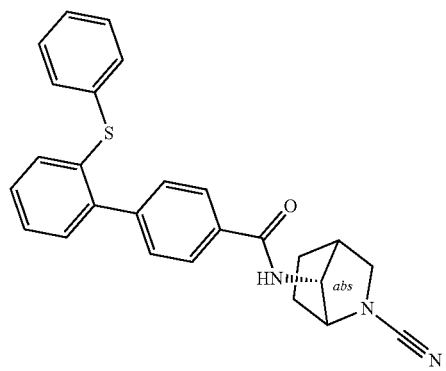
N-((7R)-2-cyano-2-azabicyclo[2.2.1]heptan-7-yl)-2'-(phenylthio)-[1,1'-biphenyl]-4-carboxamide |
| 169 | 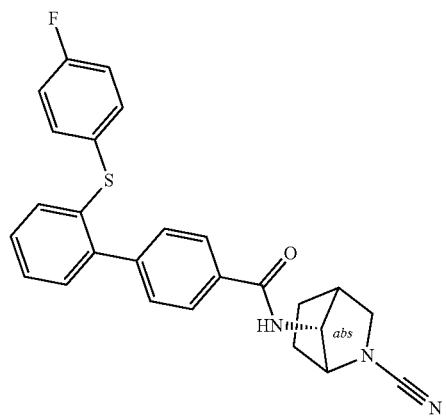
N-((7R)-2-cyano-2-azabicyclo[2.2.1]heptan-7-yl)-2'-((4-fluorophenyl)thio)-[1,1'-biphenyl]-4-carboxamide |
| 170 | 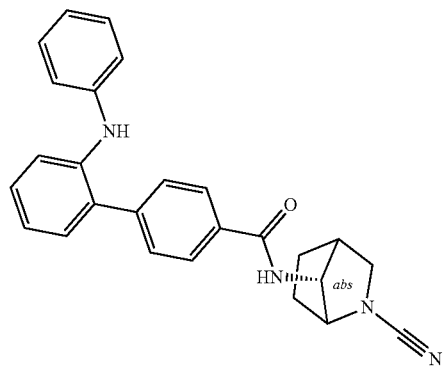
N-((7R)-2-cyano-2-azabicyclo[2.2.1]heptan-7-yl)-2'-(phenylamino)-[1,1'-biphenyl]-4-carboxamide |

TABLE 2-continued
Compounds of the Disclosure
| Compound Number | Compound Structure and Chemical Name |
|---|---|
| 171 | 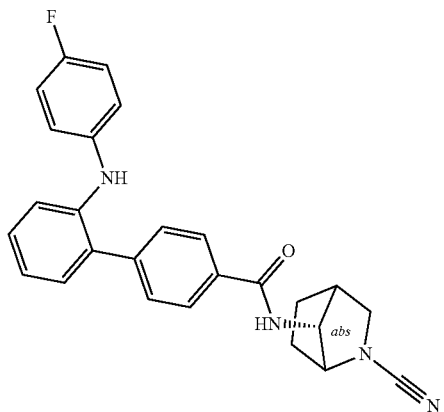<br>N-((7R)-2-cyano-2-azabicyclo[2.2.1]heptan-7-yl)-2'-((4-fluorophenyl)amino)-[1,1'-biphenyl]-4-carboxamide |
| 172 | 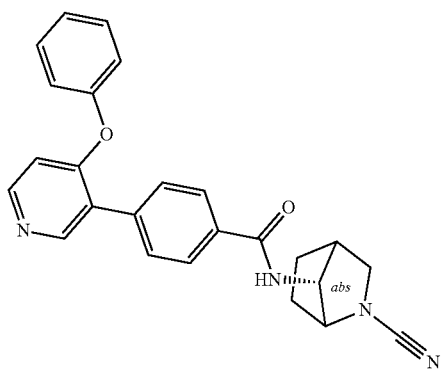<br>N-((7R)-2-cyano-2-azabicyclo[2.2.1]heptan-7-yl)-4-(4-phenoxypyridin-3-yl)benzamide |
| 173 | 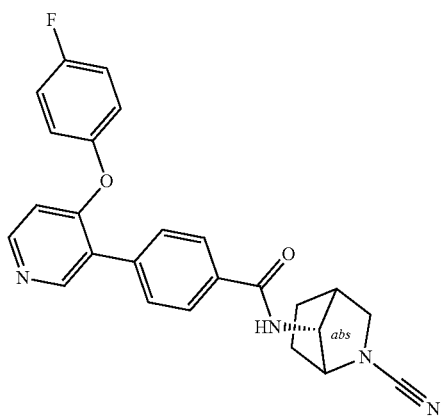<br>N-((7R)-2-cyano-2-azabicyclo[2.2.1]heptan-7-yl)-4-(4-(4-fluorophenoxy)pyridin-3-yl)benzamide |

TABLE 2-continued
Compounds of the Disclosure
| Compound Number | Compound Structure and Chemical Name |
|---|---|
| 174 | 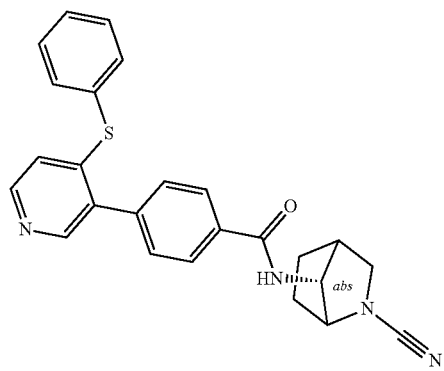<br>N-((7R)-2-cyano-2-azabicyclo[2.2.1]heptan-7-yl)-4-(4-(phenylthio)pyridin-3-yl)benzamide |
| 175 | 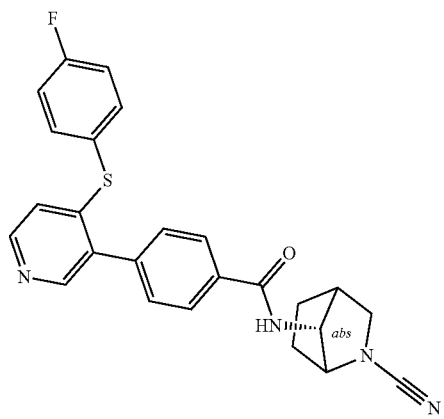<br>N-((7R)-2-cyano-2-azabicyclo[2.2.1]heptan-7-yl)-4-(4-((4-fluorophenyl)thio)pyridin-3-yl)benzamide |
| 176 | 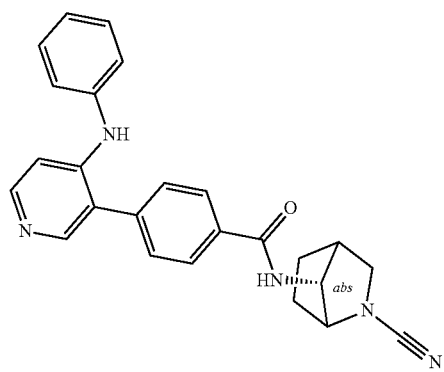<br>N-((7R)-2-cyano-2-azabicyclo[2.2.1]heptan-7-yl)-4-(4-(phenylamino)pyridin-3-yl)benzamide |

TABLE 2-continued
Compounds of the Disclosure
| Compound Number | Compound Structure and Chemical Name |
|---|---|
| 177 | 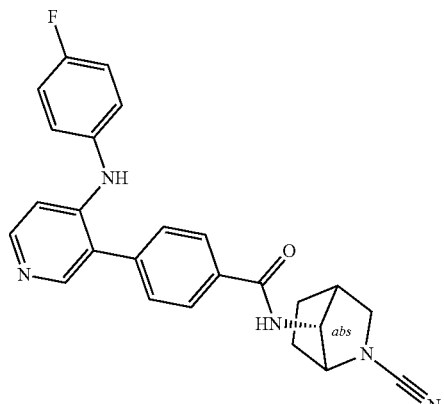<br>N-((7R)-2-cyano-2-azabicyclo[2.2.1]heptan-7-yl)-4-(4-((4-fluorophenyl)amino)pyridin-3-yl)benzamide |
| 178 | 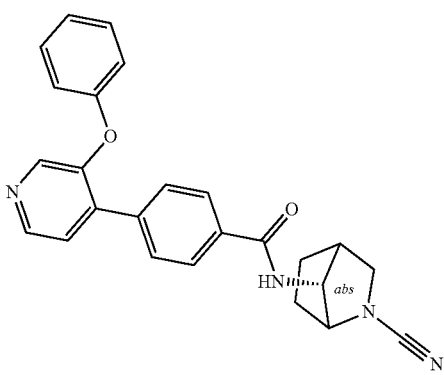<br>N-((7R)-2-cyano-2-azabicyclo[2.2.1]heptan-7-yl)-4-(3-phenoxypyridin-4-yl)benzamide |
| 179 | 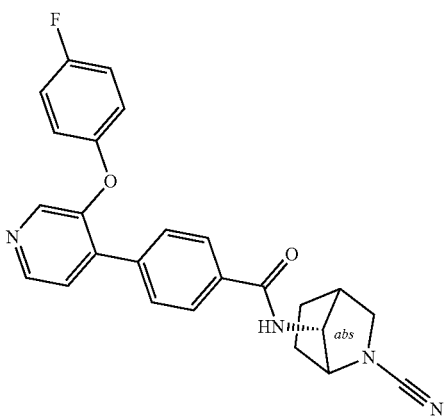<br>N-((7R)-2-cyano-2-azabicyclo[2.2.1]heptan-7-yl)-4-(3-(4-fluorophenoxy)pyridin-4-yl)benzamide |

TABLE 2-continued
Compounds of the Disclosure
| Compound Number | Compound Structure and Chemical Name |
|---|---|
| 180 | 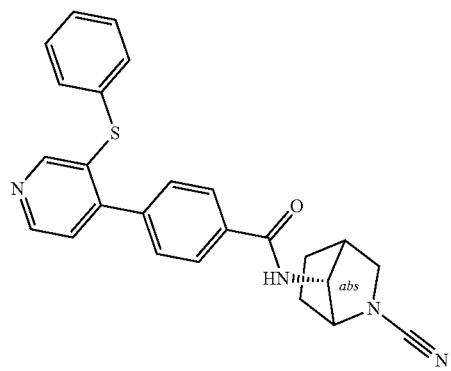<br>N-((7R)-2-cyano-2-azabicyclo[2.2.1]heptan-7-yl)-4-(3-(phenylthio)pyridin-4-yl)benzamide |
| 181 | 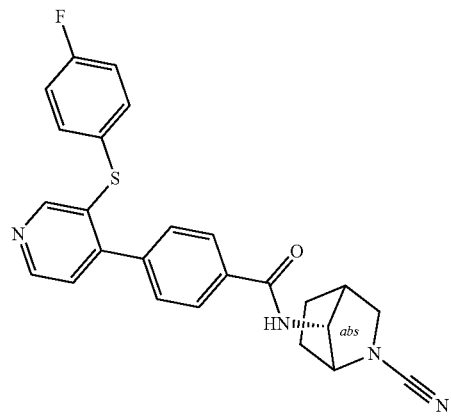<br>N-((7R)-2-cyano-2-azabicyclo[2.2.1]heptan-7-yl)-4-(3-((4-fluorophenyl)thio)pyridin-4-yl)benzamide |
| 182 | 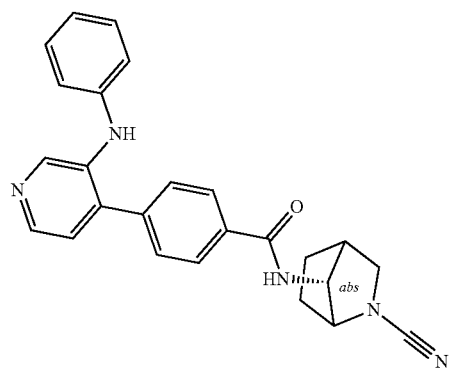<br>N-((7R)-2-cyano-2-azabicyclo[2.2.1]heptan-7-yl)-4-(3-(phenylamino)pyridin-4-yl)benzamide |

TABLE 2-continued

Compounds of the Disclosure

| Compound Number | Compound Structure and Chemical Name |
|---|---|
| 183 | 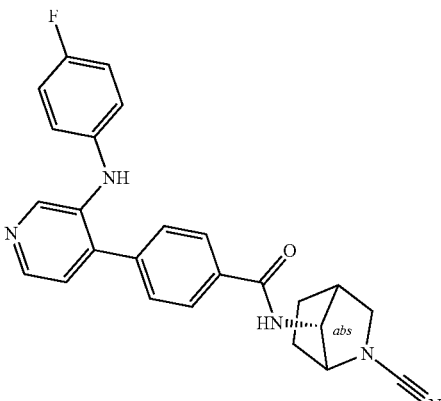<br>N-((7R)-2-cyano-2-azabicyclo[2.2.1]heptan-7-yl)-4-(3-((4-fluorophenyl)amino)pyridin-4-yl)benzamide |

In some embodiments, a compound described herein is provided in non-salt form. In some embodiments, a compound described herein is provided as a pharmaceutically acceptable salt.

In another aspect, the disclosure relates to a compound, or a pharmaceutically acceptable salt thereof, prepared by a method comprising: preparing a compound of the present disclosure as a mixture of stereoisomers; separating the stereoisomers by chiral HPLC according to the procedure described in Example 2, Step 7; isolating one or more stereoisomers that are USP30 Inhibitor Compounds having an $IC_{50}$ value of <1 µM as measured in a Ubiquitin-Rhodamine 110 Assay as described in Example 1; and optionally treating the isolated stereoisomer with an acid or base to afford a pharmaceutically acceptable salt thereof.

In some embodiments, the compound is the $1^{st}$ eluting isomer. In some embodiments, the compound is the $2^{nd}$ eluting isomer. In some embodiments, the compound is the $3^{rd}$ eluting isomer. In some embodiments, the compound is the $4^{th}$ eluting isomer. In some embodiments, the compound is the $5^{th}$, $6^{th}$, $7^{th}$, or $8^{th}$ eluting isomer.

In some embodiments, a compound of the present disclosure, or a pharmaceutically acceptable salt thereof, is a USP30 Inhibitor Compound having an $IC_{50}$ value of ≤1 µM as measured in a Ubiquitin-Rhodamine 110 Assay as described in Example 1. In some embodiments, the $IC_{50}$ value is ≤0.1 µM.

Pharmaceutical Compositions and Routes of Administration

The disclosure also relates to a pharmaceutical composition comprising one or more compounds provided herein, or a pharmaceutically acceptable salt thereof, and a pharmaceutically acceptable carrier. In some embodiments, the pharmaceutical composition comprises a therapeutically effective amount of the one or more compounds, or a pharmaceutically acceptable salt thereof. In some embodiments, the pharmaceutical composition is for use in a method of treating a neurodegenerative disorder, such as Parkinson's Disease.

The compounds and pharmaceutically acceptable salts disclosed herein may be administered via any mode of administration for therapeutic agents, consistent with conventional pharmaceutical practices. In some embodiments, the pharmaceutical compositions reported herein can be provided in a unit dosage form. In some embodiments, the pharmaceutical compositions reported herein can be provided in an oral dosage form. In some embodiments, the pharmaceutical compositions described herein can be provided in a solid oral dosage form, such as a tablet, capsule, powder, or cachet.

The pharmaceutical compositions described herein can be prepared according to conventional mixing, granulating or coating methods. For example, oral dosage forms (e.g., tablets) may be prepared by dry blending or dry granulation. The pharmaceutical compositions described herein can contain from about 0.1% to about 99%, from about 5% to about 90%, or from about 1% to about 20% of the compound or pharmaceutically acceptable salt by weight or volume. The pharmaceutically acceptable carriers employed in the pharmaceutical compositions described herein may include one or more pharmaceutical excipients, such as fillers, disintegrants, lubricants, glidants, anti-adherents, anti-statics, surfactants, or stabilizing additives. Suitable solid carriers are known in the art, e.g., magnesium carbonate, magnesium stearate, talc, sugar or lactose. With some drugs, the presence of such additives promotes the stability and dispersibility of the agent in solution. Suitable, but non-limiting, examples of stabilizing additives include gum acacia, gelatin, methyl cellulose, polyethylene glycol, carboxylic acids and salts thereof, and polylysine. In some embodiments, the stabilizing additives are gum acacia, gelatin and methyl cellulose. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

The pharmaceutical compositions described herein may contain the compound or pharmaceutically acceptable salt in substantially pure form, such as at least 60% pure, more suitably at least 75% pure, preferably at least 85% pure and most preferably at least 98% pure (w/w).

The compounds and pharmaceutically acceptable salts described herein are preferably administered in a therapeutically effective amount (e.g., an amount having a suitable favorable therapeutic index). The amount and frequency of administration will be regulated according to the judgment of the attending clinician considering such factors as the age, gender, condition and size of the patient, as well as severity of the medical condition being treated; the route of administration; the renal or hepatic function of the patient; and the particular compound or pharmaceutically acceptable salt employed. A physician or veterinarian of ordinary skill in the art can readily determine and prescribe the effective amount of the drug required to prevent, counter or arrest the progress of the condition. For convenience, the total daily dosage may be divided and administered in portions during the day as required.

Uses of Compounds Disclosed Herein

The present disclosure also provides uses of compounds of formula (I). Compounds of formula (I) are useful in medicine. For examples, compounds and compositions described herein are inhibitors of USP30. Without wishing to be bound by any particular theory, such inhibition of USP30 can provide treatment of the symptoms and/or underlying causes of diseases or conditions associated with USP30 activity. In some embodiments, inhibitors of USP30 can be used to treat neurodegenerative and neurologic diseases or conditions, such as Parkinson's disease.

Provided herein are methods of treating a disease or disorder associated with a ubiquitin-specific protease (e.g., USP30), comprising administering to a patient in need thereof a therapeutically effective amount of a compound or composition provided herein. In some embodiments, the disease or disorder associated with a ubiquitin-specific protease (e.g., USP30) is a neurodegenerative disease or disorder (e.g., Parkinson's disease).

The present disclosure also provides methods of inhibiting a ubiquitin-specific protease (e.g., USP30) in a patient in need thereof, comprising administering to the patient a therapeutically effective amount of a compound or composition provided herein.

The present disclosure also provides methods of treating a neurodegenerative disease or disorder (e.g., Parkinson's disease) in a patient in need thereof, comprising administering to the patient a therapeutically effective amount of a compound or composition provided herein.

The present disclosure also provides compounds for use in method of inhibiting a ubiquitin-specific protease (e.g., USP30) in a patient in need thereof. In some embodiments, the present disclosure provides compounds for use in a method of treating a neurodegenerative disease or disorder (e.g., Parkinson's disease) in a patient in need thereof.

Synthesis of Compounds Disclosed Herein

The compounds and pharmaceutically acceptable salts disclosed herein may be prepared by methods known in the art of organic synthesis as set forth in part by the following synthetic schemes. In the schemes described below, it is well understood that protecting groups for sensitive or reactive groups are employed where necessary in accordance with general principles of chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art.

In general, the compounds of formula (I) can be synthesized by the methods outlined in Scheme 1, by the specific procedures discussed in Examples 2-4, and/or by methods otherwise known to one skilled in the art. The starting materials for the synthesis described in Scheme 1 are commercially available or can be prepared by methods known to one skilled in the art.

Scheme 1. Synthesis of Compounds of Formula I

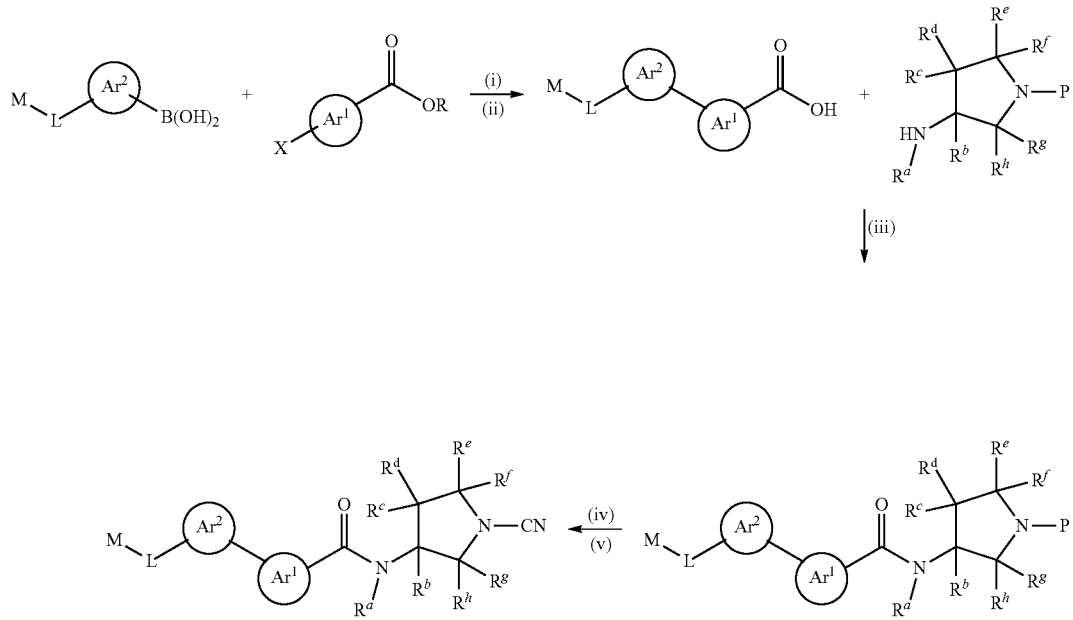

(i) cross coupling catalyst (e.g., XPhos-Pd), base (e.g., $K_3PO_4$), solvent (e.g., dioxane, $H_2O$) (X is a leaving group, e.g., Br; R is an alkyl group, e.g., Me);
(ii) Base (e.g., LiOH), solvent (e.g., THF, $H_2O$); (iii) amide coupling agent (e.g., HATU), base (e.g., DIEA), solvent (e.g., DMF) (P is a protecting group, e.g., Boc); (iv) deprotection conditions (e.g., acid, e.g., $CF_3COOH$), solvent (e.g., $CH_2Cl_2$); (v) cyanation agent (e.g., BrCN), base (e.g., $NaHCO_3$).

Exemplary Embodiments

The following numbered embodiments, while non-limiting, are exemplary of certain aspects of the disclosure:
1. A compound of formula (I):

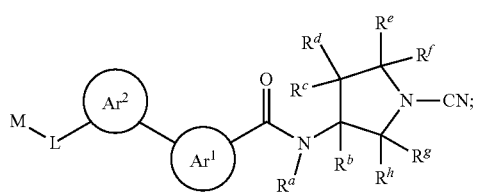

I or a pharmaceutically acceptable salt thereof, wherein:

$Ar^1$ is phenylene or 5-6 membered heteroarylene, wherein said phenylene or heteroarylene is substituted with m $R^1$ groups;

$Ar^2$ is phenylene or 5-6 membered heteroarylene, wherein said phenylene or heteroarylene is substituted with n $R^2$ groups;

L is —O—, —S—, —NR$^3$—, —C(R$^4$)$_2$—, —S(O)$_2$—, or —S(O)—;

M is 3-6 membered cycloalkyl, phenyl, or 5-6 membered heteroaryl, wherein said cycloalkyl, phenyl, or heteroaryl is substituted with p $R^5$ groups;

each occurrence of $R^1$, $R^2$, and $R^5$ is independently halo, cyano, NO$_2$, oxo, hydroxyl, —R$^6$, —OR$^6$, C$_1$-C$_6$ alkyl, C$_1$-C$_6$ haloalkyl, C$_1$-C$_6$ hydroxyalkyl, —C$_1$-C$_6$ alkylene-R$^6$, C$_1$-C$_6$ alkoxy, C$_1$-C$_6$ haloalkoxy, —C$_0$-C$_3$ alkylene-NR$^6$R$^7$, —C$_0$-C$_3$ alkylene-NR$^7$R$^8$, —C$_0$-C$_3$ alkylene-C(O)NR$^6$R$^7$, —C$_0$-C$_3$ alkylene-C(O)NR$^7$R$^8$, —C$_0$-C$_3$ alkylene-NR$^7$C(O)R$^6$, —C$_0$-C$_3$ alkylene-NR$^7$C(O)R$^8$, —C$_0$-C$_3$ alkylene-NR$^7$S(O)$_2$R$^6$, —C$_0$-C$_3$ alkylene-C(O)R$^6$, —C$_0$-C$_3$ alkylene-C(O)R$^7$, —C$_0$-C$_3$ alkylene-SR$^6$, —C$_0$-C$_3$ alkylene-S(O)R$^6$, —C$_0$-C$_3$ alkylene-S(O)$_2$R$^6$, —C$_0$-C$_3$ alkylene-S(O)$_2$R$^7$, —C$_0$-C$_3$ alkylene-S(O)$_2$NR$^6$R$^7$, —C$_0$-C$_3$ alkylene-S(O)$_2$NR$^7$R$^8$, —C$_0$-C$_3$ alkylene-NR$^7$C(O)NR$^8$R$^9$, —C$_0$-C$_3$ alkylene- NR$^7$S(O)$_2$NR$^8$R$^9$, —C$_0$-C$_3$ alkylene-C(O)OR$^7$, —C$_0$-C$_3$ alkylene-C(O)OR$^6$, —C$_0$-C$_3$ alkylene-OC(O)R$^7$, —C$_0$-C$_3$ alkylene-OC(O)R$^6$, —C$_0$-C$_3$ alkylene-NR$^7$C(O)OR$^8$, or —C$_0$-C$_3$ alkylene-NR$^7$S(O)$_2$R$^8$;

$R^3$ is H, C$_1$-C$_6$ alkyl, or C$_1$-C$_6$ haloalkyl;

each $R^4$ is independently H, C$_1$-C$_6$ alkyl, C$_1$-C$_6$ haloalkyl, or two $R^4$ groups together with the carbon atom to which they are attached form a 3-6 membered cycloalkyl or heterocycloalkyl;

each $R^6$ is independently 5-10 membered heteroaryl, 4-10 membered heterocycloalkyl, 6-10 membered aryl, or 3-8 membered cycloalkyl, wherein said heteroaryl, heterocycloalkyl, aryl, or cycloalkyl is optionally substituted with 1-5 substituents independently selected from the group consisting of halo, oxo, C$_1$-C$_6$ alkyl, C$_1$-C$_6$ haloalkyl, C$_1$-C$_6$ hydroxyalkyl, C$_1$-C$_6$ alkoxy, C$_1$-C$_6$ haloalkoxy, C$_2$-C$_6$ alkenyl, C$_2$-C$_6$ alkynyl, 5-10 membered heteroaryl, 4-10 membered heterocycloalkyl, 6-10 membered aryl, 3-8 membered cycloalkyl, —NR$^{10}$C(O)NR$^{11}$R$^{12}$, —NR$^{10}$R$^{11}$, —C(O)R$^{10}$, —NR$^{10}$C(O)R$^{11}$, —NR$^{10}$C(O)OR$^{11}$, —S(O)$_2$R$^{10}$, —C(O)NR$^{10}$R$^{11}$, —C(O)OR$^{10}$, —S(O)$_2$NR$^{10}$R$^{11}$, —NR$^{10}$S(O)$_2$R$^{11}$, —OR$^{10}$, —OC(O)R$^{10}$, —OS(O)$_2$R$^{10}$, —OC(O)NR$^{10}$R$^{11}$, —OC(O)NR$^{10}$R$^{11}$, —OS(O)$_2$NR$^{10}$R$^{11}$, —OC(O)R$^{10}$, —C(O)NR$^{10}$C(O)NR$^{11}$R$^{12}$, —C(O)NR$^{10}$R$^{11}$, —C(O)C(O)R$^{10}$, —C(O)NR$^{10}$C(O)R$^{11}$, —C(O)NR$^{10}$C(O)OR$^{11}$, —C(O)S(O)$_2$R$^{10}$, —C(O)C(O)NR$^{10}$R$^{11}$, —C(O)C(O)OR$^{10}$, —C(O)S(O)$_2$NR$^{10}$R$^{11}$, —C(O)NR$^{10}$S(O)$_2$R$^{11}$, —C$_1$-C$_6$ alkylene-R$^{10}$, —C$_1$-C$_6$ alkylene-NR$^{10}$C(O)NR$^{11}$R$^{12}$, —C$_1$-C$_6$ alkylene-NR$^{10}$R$^{11}$, —C$_1$-C$_6$ alkylene-C(O)R$^{10}$, —C$_1$-C$_6$ alkylene-NR$^{10}$C(O)R$^{11}$, —C$_1$-C$_6$ alkylene-NR$^{10}$C(O)OR$^{11}$, —C$_1$-C$_6$ alkylene-S(O)$_2$R$^{10}$, —C$_1$-C$_6$ alkylene-C(O)NR$^{10}$R$^{11}$, —C$_1$-C$_6$ alkylene-C(O)OR$^{10}$, —C$_1$-C$_6$ alkylene-S(O)$_2$NR$^{10}$R$^{11}$, —C$_1$-C$_6$ alkylene-NR$^{10}$S(O)$_2$R$^{11}$, —C$_1$-C$_6$ alkenylene-R$^{10}$, —C$_1$-C$_6$ alkenylene-NR$^{10}$C(O)NR$^{11}$R$^{12}$, —C$_1$-C$_6$ alkenylene-NR$^{10}$R$^{11}$, —C$_1$-C$_6$ alkenylene-C(O)R$^{10}$, —C$_1$-C$_6$ alkenylene-NR$^{10}$C(O)R$^{11}$, —C$_1$-C$_6$ alkenylene-NR$^{10}$C(O)OR$^{11}$, —C$_1$-C$_6$ alkenylene-S(O)$_2$R$^{10}$, —C$_1$-C$_6$ alkenylene-C(O)NR$^{10}$R$^{11}$, —C$_1$-C$_6$ alkenylene-C(O)OR$^{10}$, —C$_1$-C$_6$ alkenylene-S(O)$_2$NR$^{10}$R$^{11}$, and —C$_1$-C$_6$ alkenylene-NR$^{10}$S(O)$_2$R$^{11}$;

each $R^7$, $R^8$, and $R^9$ is independently hydrogen or C$_1$-C$_6$ alkyl;

each $R^{10}$, $R^{11}$, and $R^{12}$ is independently hydrogen, C$_1$-C$_6$ alkyl, 5-10 membered heteroaryl, 4-10 membered heterocycloalkyl, 6-10 membered aryl, or 3-8 membered cycloalkyl;

m is 0-4;

n is 0-4;

p is 0-4;

$R^a$, $R^b$, $R^c$, $R^d$, $R^e$, $R^f$, $R^g$, and $R^h$ are defined as follows:

(i) $R^a$ and $R^b$ form a C$_1$-C$_4$ alkylene group between the atoms to which they are attached, wherein said C$_1$-C$_4$ alkylene group is substituted with 0-4 substituents selected from the group consisting of halogen, C$_1$-C$_3$ alkyl, and C$_1$-C$_3$ haloalkyl; and $R^c$, $R^d$, $R^e$, $R^f$, $R^g$, and $R^h$ are each independently hydrogen, halogen, C$_1$-C$_3$ alkyl, or C$_1$-C$_3$ haloalkyl; or (ii) $R^a$ and $R^e$ form a C$_1$-C$_2$ alkylene group between the atoms to which they are attached, wherein said C$_1$-C$_2$ alkylene group is substituted with 0-4 substituents selected from the group consisting of halogen, C$_1$-C$_3$ alkyl, and C$_1$-C$_3$ haloalkyl; and $R^b$, $R^c$, $R^d$, $R^f$, $R^g$, and $R^h$ are each independently hydrogen, halogen, C$_1$-C$_3$ alkyl, or C$_1$-C$_3$ haloalkyl; or (iii) $R^a$ and $R^g$ form a C$_1$-C$_3$ alkylene group between the atoms to which they are attached, wherein said C$_1$-C$_3$ alkylene group is substituted with 0-4 substituents selected from the group consisting of halogen, C$_1$-C$_3$ alkyl, and C$_1$-C$_3$ haloalkyl; and $R^b$, $R^c$, $R^d$, $R^e$, $R^f$, and $R^h$ are each independently hydrogen, halogen, C$_1$-C$_3$ alkyl, or C$_1$-C$_3$ haloalkyl; or (iv) $R^b$ and $R^c$ form a C$_1$-C$_4$ alkylene group between the atoms to which they are attached, wherein said C$_1$-C$_4$ alkylene group is substituted with 0-4 substituents selected from the group consisting of halogen, C$_1$-C$_3$ alkyl, and C$_1$-C$_3$ haloalkyl; and $R^a$, $R^d$, $R^e$, $R^f$, $R^g$, and $R^h$ are each independently hydrogen, halogen, C$_1$-C$_3$ alkyl, or C$_1$-C$_3$ haloalkyl; or (v) $R^b$ and $R^e$ form a C$_1$-C$_3$ alkylene group between the atoms to which they are attached, wherein said C$_1$-C$_4$ alkylene group is substituted with 0-4 substituents selected from the group consisting of halogen, C$_1$-C$_3$ alkyl, and C$_1$-C$_3$ haloalkyl; and $R^a$, $R^c$, $R^d$, $R^f$, $R^g$, and $R^h$ are each independently hydrogen, halogen, C$_1$-C$_3$ alkyl, or C$_1$-C$_3$ haloalkyl; or (vi) $R^b$ and $R^g$ form a C$_1$-C$_4$ alkylene group between the atoms to which they are attached, wherein said C$_1$-C$_3$ alkylene group is substituted with 0-4 substituents selected from the group consisting of halogen, C$_1$-C$_3$ alkyl, and C$_1$-C$_3$ haloalkyl; and $R^a$, $R^e$, $R^d$, $R^e$, $R^f$, and $R^h$ are each independently hydrogen, halogen, C$_1$-C$_3$ alkyl, or C$_1$-C$_3$ haloalkyl; or (vii) $R^c$ and $R^d$ together with the atom to which they are attached, form a 3-6 membered cycloalkyl or heterocycloalkyl, wherein said 3-6 membered cycloalkyl or heterocycloalkyl is substituted with 0-4 substituents selected from the group consisting of halogen, $C_1$-$C_3$ alkyl, and $C_1$-$C_3$ haloalkyl; and $R^a$, $R^b$, $R^e$, $R^f$, $R^g$, and $R^h$ are each independently hydrogen, halogen, $C_1$-$C_3$ alkyl, or $C_1$-$C_3$ haloalkyl; or (viii) $R^c$ and $R^d$ together form =O; and $R^a$, $R^b$, $R^e$, $R^f$, $R^g$, and $R^h$ are each independently hydrogen, halogen, $C_1$-$C_3$ alkyl, or $C_1$-$C_3$ haloalkyl; or (ix) $R^c$ and $R^e$ form a $C_1$-$C_4$ alkylene group between the atoms to which they are attached, wherein said $C_1$-$C_4$ alkylene group is substituted with 0-4 substituents selected from the group consisting of halogen, $C_1$-$C_3$ alkyl, and $C_1$-$C_3$ haloalkyl; and $R^a$, $R^b$, $R^d$, $R^f$, $R^g$, and $R^h$ are each independently hydrogen, halogen, $C_1$-$C_3$ alkyl, or $C_1$-$C_3$ haloalkyl; or (x) $R^c$ and $R^g$ form a $C_1$-$C_3$ alkylene group between the atoms to which they are attached, wherein said $C_1$-$C_3$ alkylene group is substituted with 0-4 substituents selected from the group consisting of halogen, $C_1$-$C_3$ alkyl, and $C_1$-$C_3$ haloalkyl; and $R^a$, $R^b$, $R^d$, $R^e$, $R^f$ and $R^h$ are each independently hydrogen, halogen, $C_1$-$C_3$ alkyl, or $C_1$-$C_3$ haloalkyl; or (xi) $R^c$ and $R^f$ together with the atom to which they are attached, form a 3-6 membered cycloalkyl or heterocycloalkyl, wherein said 3-6 membered cycloalkyl or heterocycloalkyl is substituted with 0-4 substituents selected from the group consisting of halogen, $C_1$-$C_3$ alkyl, and $C_1$-$C_3$ haloalkyl; and $R^a$, $R^b$, $R^c$, $R^d$, $R^g$, and $R^h$ are each independently hydrogen, halogen, $C_1$-$C_3$ alkyl, or $C_1$-$C_3$ haloalkyl; or (xii) $R^e$ and $R^f$ together form =O; and $R^a$, $R^b$, $R^c$, $R^d$, $R_g$, and $R^h$ are each independently hydrogen, halogen, $C_1$-$C_3$ alkyl, or $C_1$-$C_3$ haloalkyl; or (xiii) $R^e$ and $R^g$ form a $C_1$-$C_3$ alkylene group between the atoms to which they are attached, wherein said $C_1$-$C_3$ alkylene group is substituted with 0-4 substituents selected from the group consisting of halogen, $C_1$-$C_3$ alkyl, and $C_1$-$C_3$ haloalkyl; and $R^a$, $R^b$, $R^c$, $R^d$, $R^f$, and $R^h$ are each independently hydrogen, halogen, $C_1$-$C_3$ alkyl, or $C_1$-$C_3$ haloalkyl; or (xiv) $R^g$ and $R^h$ together with the atom to which they are attached, form a 3-6 membered cycloalkyl or heterocycloalkyl, wherein said 3-6 membered cycloalkyl or heterocycloalkyl is substituted with 0-4 substituents selected from the group consisting of halogen, $C_1$-$C_3$ alkyl, and $C_1$-$C_3$ haloalkyl; and $R^a$, $R^b$, $R^c$, $R^d$, $R^e$, and $R^f$ are each independently hydrogen, halogen, $C_1$-$C_3$ alkyl, or $C_1$-$C_3$ haloalkyl; or (xv) $R^g$ and $R^h$ together form =O; and $R^a$, $R^b$, $R^c$, $R^d$, $R^e$, and $R^f$ are each independently hydrogen, halogen, $C_1$-$C_3$ alkyl, or $C_1$-$C_3$ haloalkyl.

2. The compound of embodiment 1, or a pharmaceutically acceptable salt thereof, wherein $R^c$ and $R^g$ form a $C_1$-$C_3$ alkylene group between the atoms to which they are attached, wherein said $C_1$-$C_3$ alkylene group is substituted with 0-4 substituents selected from the group consisting of halogen, $C_1$-$C_3$ alkyl, and $C_1$-$C_3$ haloalkyl; and $R^a$, $R^b$, $R^d$, $R^e$, $R^f$, and $R^h$ are each independently hydrogen, halogen, $C_1$-$C_3$ alkyl, or $C_1$-$C_3$ haloalkyl.

3. The compound of embodiment 1, or a pharmaceutically acceptable salt thereof, wherein $R^b$ and $R^c$ form a $C_1$-$C_4$ alkylene group between the atoms to which they are attached, wherein said $C_1$-$C_4$ alkylene group is substituted with 0-4 substituents selected from the group consisting of halogen, $C_1$-$C_3$ alkyl, and $C_1$-$C_3$ haloalkyl; and $R^a$, $R^d$, $R^e$, $R^f$, $R^g$, and $R^h$ are each independently hydrogen, halogen, $C_1$-$C_3$ alkyl, or $C_1$-$C_3$ haloalkyl.

4. The compound of embodiment 1, or a pharmaceutically acceptable salt thereof, wherein $R^c$ and $R^d$ together with the atom to which they are attached, form a 3-6 membered cycloalkyl or heterocycloalkyl, wherein said 3-6 membered cycloalkyl or heterocycloalkyl is substituted with 0-4 substituents selected from the group consisting of halogen, $C_1$-$C_3$ alkyl, and $C_1$-$C_3$ haloalkyl; and $R^a$, $R^b$, $R^e$, $R^f$, $R^g$, and $R^h$ are each independently hydrogen, halogen, $C_1$-$C_3$ alkyl, or $C_1$-$C_3$ haloalkyl.

5. The compound of embodiment 1, wherein the compound has formula (I-A):

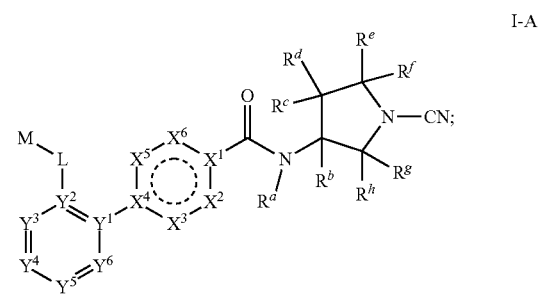

I-A or a pharmaceutically acceptable salt thereof, wherein:
$X^1$ is C or N;
$X^2$ is CH, $CR^1$, O, S, N, NH, or $NR^1$;
$X^3$ is CH, $CR^1$, O, S, N, NH, or $NR^1$;
$X^4$ is C or N;
$X^5$ is a bond, CH, $CR^1$, O, S, N, NH, or $NR^1$;
$X^6$ is CH, $CR^1$, O, S, N, NH, or $NR^1$;
$Y^1$ is C or N;
$Y^2$ is C or N;
$Y^3$ is CH, $CR^2$, O, S, N, NH, or $NR^2$;
$Y^4$ is a bond, CH, $CR^2$, O, S, N, NH, or $NR^2$;
$Y^5$ is CH, $CR^2$, O, S, N, NW;
$Y^6$ is CH, $CR^2$, O, S, N, NH, or $NR^2$;
$R^a$, $R^b$, $R^c$, $R^d$, $R^e$, $R^f$, $R^g$, and $R^h$ are defined as follows:

(ii) $R^a$ and $R^e$ form a $C_1$-$C_2$ alkylene group between the atoms to which they are attached, wherein said $C_1$-$C_2$ alkylene group is substituted with 0-4 substituents selected from the group consisting of halogen, $C_1$-$C_3$ alkyl, and $C_1$-$C_3$ haloalkyl; and $R^b$, $R^c$, $R^d$, $R^f$, $R^g$, and $R^h$ are each independently hydrogen, halogen, $C_1$-$C_3$ alkyl, or $C_1$-$C_3$ haloalkyl; or (iv) $R^b$ and $R^c$ form a $C_1$-$C_4$ alkylene group between the atoms to which they are attached, wherein said $C_1$-$C_4$ alkylene group is substituted with 0-4 substituents selected from the group consisting of halogen, $C_1$-$C_3$ alkyl, and $C_1$-$C_3$ haloalkyl; and $R^a$, $R^d$, $R^e$, $R^f$, $R^g$, and $R^h$ are each independently hydrogen, halogen, $C_1$-$C_3$ alkyl, or $C_1$-$C_3$ haloalkyl; or (vii) $R^c$ and $R^d$ together with the atom to which they are attached, form a 3-6 membered cycloalkyl or heterocycloalkyl, wherein said 3-6 membered cycloalkyl or heterocycloalkyl is substituted with 0-4 substituents selected from the group consisting of halogen, $C_1$-$C_3$ alkyl, and $C_1$-$C_3$ haloalkyl; and $R^a$, $R^b$, $R^e$, $R^f$, $R^g$, and $R^h$ are each independently hydrogen, halogen, $C_1$-$C_3$ alkyl, or $C_1$-$C_3$ haloalkyl; or (viii) $R^c$ and $R^d$ together form =O; and $R^a$, $R^b$, $R^e$, $R^f$, $R^g$, and $R^h$ are each independently hydrogen, halogen, $C_1$-$C_3$ alkyl, or $C_1$-$C_3$ haloalkyl; or (ix) $R^c$ and $R^e$ form a $C_1$-$C_4$ alkylene group between the atoms to which they are attached, wherein said $C_1$-$C_4$ alkylene group is substituted with 0-4 substituents selected from the group consisting of halogen, $C_1$-$C_3$ alkyl, and $C_1$-$C_3$ haloalkyl; and $R^a$, $R^b$, $R^d$, $R^f$, $R^g$, and $R^h$ are each independently hydrogen, halogen, $C_1$-$C_3$ alkyl, or $C_1$-$C_3$ haloalkyl; or (x) $R^c$ and $R^g$ form a $C_1$-$C_3$ alkylene group between the atoms to which they are attached, wherein said $C_1$-$C_3$ alkylene group is substituted with 0-4 substituents selected from the group consisting of halogen, $C_1$-$C_3$ alkyl, and $C_1$-$C_3$ haloalkyl; and $R^a$, $R^b$, $R^d$, $R^e$, $R^f$, and $R^h$ are each independently hydrogen, halogen, $C_1$-$C_3$ alkyl, or $C_1$-$C_3$ haloalkyl; or (xi) $R^e$ and $R^f$ together with the atom to which they are attached, form a 3-6 membered cycloalkyl or heterocycloalkyl, wherein said 3-6 membered cycloalkyl or heterocycloalkyl is substituted with 0-4 substituents selected from the group consisting of halogen, $C_1$-$C_3$ alkyl, and $C_1$-$C_3$ haloalkyl; and $R^a$, $R^b$, $R^c$, $R^d$, $R^g$, and $R^h$ are each independently hydrogen, halogen, $C_1$-$C_3$ alkyl, or $C_1$-$C_3$ haloalkyl; or (xiii) $R^e$ and $R^g$ form a $C_1$-$C_3$ alkylene group between the atoms to which they are attached, wherein said $C_1$-$C_3$ alkylene group is substituted with 0-4 substituents selected from the group consisting of halogen, $C_1$-$C_3$ alkyl, and $C_1$-$C_3$ haloalkyl; and $R^a$, $R^b$, $R^c$, $R^d$, $R^f$, and $R^h$ are each independently hydrogen, halogen, $C_1$-$C_3$ alkyl, or $C_1$-$C_3$ haloalkyl; or (xv) $R^g$ and $R^h$ together form =O; and $R^a$, $R^b$, $R^c$, $R^d$, $R^e$, and $R^f$ are each independently hydrogen, halogen, $C_1$-$C_3$ alkyl, or $C_1$-$C_3$ haloalkyl.

6. The compound of embodiment 5, or a pharmaceutically acceptable salt thereof, wherein $R^c$ and $R^g$ form a $C_1$-$C_3$ alkylene group between the atoms to which they are attached, wherein said $C_1$-$C_3$ alkylene group is substituted with 0-4 substituents selected from the group consisting of halogen, $C_1$-$C_3$ alkyl, and $C_1$-$C_3$ haloalkyl; and $R^a$, $R^b$, $R^d$, $R^e$, $R^f$, and $R^h$ are each independently hydrogen, halogen, $C_1$-$C_3$ alkyl, or $C_1$-$C_3$ haloalkyl.

7. The compound of embodiment 5, or a pharmaceutically acceptable salt thereof, wherein $R^b$ and $R^c$ form a $C_1$-$C_4$ alkylene group between the atoms to which they are attached, wherein said $C_1$-$C_4$ alkylene group is substituted with 0-4 substituents selected from the group consisting of halogen, $C_1$-$C_3$ alkyl, and $C_1$-$C_3$ haloalkyl; and $R^a$, $R^d$, $R^e$, $R^f$, $R^g$, and $R^h$ are each independently hydrogen, halogen, $C_1$-$C_3$ alkyl, or $C_1$-$C_3$ haloalkyl.

8. The compound of embodiment 5, or a pharmaceutically acceptable salt thereof, wherein $R^c$ and $R^d$ together with the atom to which they are attached, form a 3-6 membered cycloalkyl or heterocycloalkyl, wherein said 3-6 membered cycloalkyl or heterocycloalkyl is substituted with 0-4 substituents selected from the group consisting of halogen, $C_1$-$C_3$ alkyl, and $C_1$-$C_3$ haloalkyl; and $R^a$, $R^b$, $R^e$, $R^f$, $R^g$, and $R^h$ are each independently hydrogen, halogen, $C_1$-$C_3$ alkyl, or $C_1$-$C_3$ haloalkyl.

9. The compound of any one of embodiments 5-8, or a pharmaceutically acceptable salt thereof, wherein $X^1$ is C; $X^2$ is N; $X^3$ is NH; $X^4$ is C; $X^5$ is a bond; and $X^6$ is CH.

10. The compound of any one of embodiments 5-9, or a pharmaceutically acceptable salt thereof, wherein $Y^1$ is C; $Y^2$ is C; $Y^3$ is CH; $Y^4$ is CH; $Y^5$ is CH; and $Y^6$ is CH.

11. The compound of any one of embodiments 5-10, or a pharmaceutically acceptable salt thereof, wherein L is O.

12. The compound of any one of embodiments 5-11, or a pharmaceutically acceptable salt thereof, wherein M is phenyl substituted with p $R^5$ groups.

13. The compound of embodiment 1, wherein the compound has formula (I-B):

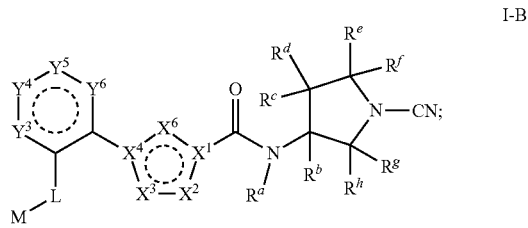

I-B or a pharmaceutically acceptable salt thereof, wherein:

$X^1$ is C or N;

$X^2$ is CH, $CR^1$, O, S, N, NH, or $NR^1$;

$X^3$ is CH, $CR^1$, O, S, N, NH, or $NR^1$;

$X^4$ is C or N;

$X^6$ is CH, $CR^1$, O, S, N, NH, or $NR^1$;

$Y^3$ is CH, $CR^2$, or N, $Y^4$ is CH, $CR^2$, or N;

$Y^5$ is CH, $CR^2$, or N;

$Y^6$ is CH, $CR^2$, or N;

$R^a$, $R^b$, $R^c$, $R^d$, $R^e$, $R^f$, $R^g$, and $R^h$ are defined as follows:

(ii) $R^a$ and $R^e$ form a $C_1$-$C_2$ alkylene group between the atoms to which they are attached, wherein said $C_1$-$C_2$ alkylene group is substituted with 0-4 substituents selected from the group consisting of halogen, $C_1$-$C_3$ alkyl, and $C_1$-$C_3$ haloalkyl; and $R^b$, $R^c$, $R^d$, $R^f$, $R^g$, and $R^h$ are each independently hydrogen, halogen, $C_1$-$C_3$ alkyl, or $C_1$-$C_3$ haloalkyl; or (iv) $R^b$ and $R^c$ form a $C_1$-$C_4$ alkylene group between the atoms to which they are attached, wherein said $C_1$-$C_4$ alkylene group is substituted with 0-4 substituents selected from the group consisting of halogen, $C_1$-$C_3$ alkyl, and $C_1$-$C_3$ haloalkyl; and $R^a$, $R^d$, $R^e$, $R^f$, $R^g$, and $R^h$ are each independently hydrogen, halogen, $C_1$-$C_3$ alkyl, or $C_1$-$C_3$ haloalkyl; or (vii) $R^c$ and $R^d$ together with the atom to which they are attached, form a 3-6 membered cycloalkyl or heterocycloalkyl, wherein said 3-6 membered cycloalkyl or heterocycloalkyl is substituted with 0-4 substituents selected from the group consisting of halogen, $C_1$-$C_3$ alkyl, and $C_1$-$C_3$ haloalkyl; and $R^a$, $R^b$, $R^e$, $R^f$, $R^g$, and $R^h$ are each independently hydrogen, halogen, $C_1$-$C_3$ alkyl, or $C_1$-$C_3$ haloalkyl; or (viii) $R^c$ and $R^d$ together form =O; and $R^a$, $R^b$, $R^e$, $R^g$, and $R^h$ are each independently hydrogen, halogen, $C_1$-$C_3$ alkyl, or $C_1$-$C_3$ haloalkyl; or (ix) $R^c$ and $R^e$ form a $C_1$-$C_4$ alkylene group between the atoms to which they are attached, wherein said $C_1$-$C_4$ alkylene group is substituted with 0-4 substituents selected from the group consisting of halogen, $C_1$-$C_3$ alkyl, and $C_1$-$C_3$ haloalkyl; and $R^a$, $R^b$, $R^d$, $R^f$, $R^g$, and $R^h$ are each independently hydrogen, halogen, $C_1$-$C_3$ alkyl, or $C_1$-$C_3$ haloalkyl; or (x) $R^c$ and $R^g$ form a $C_1$-$C_3$ alkylene group between the atoms to which they are attached, wherein said $C_1$-$C_3$ alkylene group is substituted with 0-4 substituents selected from the group consisting of halogen, $C_1$-$C_3$ alkyl, and $C_1$-$C_3$ haloalkyl; and $R^a$, $R^b$, $R^d$, $R^e$, $R^f$, and $R^h$ are each independently hydrogen, halogen, $C_1$-$C_3$ alkyl, or $C_1$-$C_3$ haloalkyl; or (xi) $R^e$ and $R^f$ together with the atom to which they are attached, form a 3-6 membered cycloalkyl or heterocycloalkyl, wherein said 3-6 membered cycloalkyl or heterocycloalkyl is substituted with 0-4 substituents selected from the group consisting of halogen, $C_1$-$C_3$ alkyl, and $C_1$-$C_3$ haloalkyl; and $R^a$, $R^b$, $R^c$, $R^d$, $R^g$, and $R^h$ are each independently hydrogen, halogen, $C_1$-$C_3$ alkyl, or $C_1$-$C_3$ haloalkyl; or (xiii) $R^e$ and $R^g$ form a $C_1$-$C_3$ alkylene group between the atoms to which they are attached, wherein said $C_1$-$C_3$ alkylene group is substituted with 0-4 substituents selected from the group consisting of halogen, $C_1$-$C_3$ alkyl, and $C_1$-$C_3$ haloalkyl; and $R^a$, $R^b$, $R^c$, $R^d$, $R^f$, and $R^h$ are each independently hydrogen, halogen, $C_1$-$C_3$ alkyl, or $C_1$-$C_3$ haloalkyl; or (xv) $R^g$ and $R^h$ together form =O; and $R^a$, $R^b$, $R^c$, $R^d$, $R^e$, and $R^f$ are each independently hydrogen, halogen, $C_1$-$C_3$ alkyl, or $C_1$-$C_3$ haloalkyl.

14. The compound of embodiment 13, or a pharmaceutically acceptable salt thereof, wherein $R^c$ and $R^g$ form a $C_1$-$C_3$ alkylene group between the atoms to which they are attached, wherein said $C_1$-$C_3$ alkylene group is substituted with 0-4 substituents selected from the group consisting of halogen, $C_1$-$C_3$ alkyl, and $C_1$-$C_3$ haloalkyl; and $R^a$, $R^b$, $R^d$, $R^e$, $R^f$, and $R^h$ are each independently hydrogen, halogen, $C_1$-$C_3$ alkyl, or $C_1$-$C_3$ haloalkyl.

15. The compound of embodiment 13, or a pharmaceutically acceptable salt thereof, wherein $R^b$ and $R^c$ form a $C_1$-$C_4$ alkylene group between the atoms to which they are attached, wherein said $C_1$-$C_4$ alkylene group is substituted with 0-4 substituents selected from the group consisting of halogen, $C_1$-$C_3$ alkyl, and $C_1$-$C_3$ haloalkyl; and $R^a$, $R^d$, $R^e$, $R^f$, $R^g$, and $R^h$ are each independently hydrogen, halogen, $C_1$-$C_3$ alkyl, or $C_1$-$C_3$ haloalkyl.

16. The compound of embodiment 13, or a pharmaceutically acceptable salt thereof, wherein $R^c$ and $R^d$ together with the atom to which they are attached, form a 3-6 membered cycloalkyl or heterocycloalkyl, wherein said 3-6 membered cycloalkyl or heterocycloalkyl is substituted with 0-4 substituents selected from the group consisting of halogen, $C_1$-$C_3$ alkyl, and $C_1$-$C_3$ haloalkyl; and $R^a$, $R^b$, $R^e$, $R^f$, $R^g$, and $R^h$ are each independently hydrogen, halogen, $C_1$-$C_3$ alkyl, or $C_1$-$C_3$ haloalkyl.

17. The compound of any one of embodiments 13-16, or a pharmaceutically acceptable salt thereof, wherein $X^1$ is C; $X^2$ is N; $X^3$ is NH; $X^4$ is C; and $X^6$ is CH.

18. The compound of any one of embodiments 13-17, or a pharmaceutically acceptable salt thereof, wherein $Y^1$ is C; $Y^2$ is C; $Y^3$ is CH; $Y^4$ is CH; $Y^5$ is CH; and $Y^6$ is CH.

19. The compound of any one of embodiments 13-18, or a pharmaceutically acceptable salt thereof, wherein L is O.

20. The compound of any one of embodiments 13-19, or a pharmaceutically acceptable salt thereof, wherein M is phenyl substituted with p $R^5$ groups.

21. The compound of embodiment 1, wherein the compound has formula (I-C):

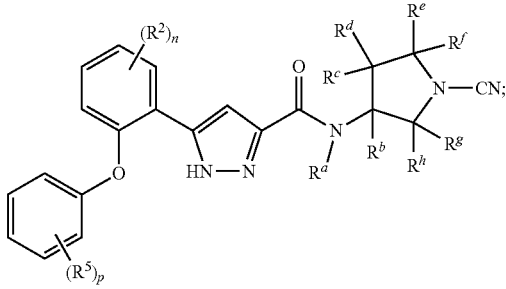

I-C or a pharmaceutically acceptable salt thereof, wherein:
$R^a$, $R^b$, $R^c$, $R^d$, $R^e$, $R^f$, $R^g$, and $R^h$ are defined as follows:
(ii) $R^a$ and $R^e$ form a $C_1$-$C_2$ alkylene group between the atoms to which they are attached; and $R^b$, $R^c$, $R^d$, $R^f$, $R^g$, and $R^h$ are each hydrogen; or (iv) $R^b$ and $R^c$ form a $C_1$-$C_4$ alkylene group between the atoms to which they are attached; and $R^a$, $R^d$, $R^e$, $R^f$, $R^g$, and $R^h$ are each hydrogen; or (vii) $R^c$ and $R^d$ together with the atom to which they are attached, form a 3-6 membered cycloalkyl or heterocycloalkyl; and $R^a$, $R^b$, $R^e$, $R^f$, $R^g$, and $R^h$ are each hydrogen; or (viii) $R^c$ and $R^d$ together form =O; and $R^a$, $R^b$, $R^e$, $R^f$, $R^g$ and $R^h$ are each hydrogen; or (ix) $R^c$ and $R^e$ form a $C_1$-$C_4$ alkylene group between the atoms to which they are attached; and $R^a$, $R^b$, $R^d$, $R^f$, $R^g$, and $R^h$ are each hydrogen; or (x) $R^c$ and $R^g$ form a $C_1$-$C_3$ alkylene group between the atoms to which they are attached; and $R^a$, $R^b$, $R^d$, $R^e$, $R^f$, and $R^h$ are each hydrogen; or (xi) $R^e$ and $R^f$ together with the atom to which they are attached, form a 3-6 membered cycloalkyl or heterocycloalkyl; and $R^a$, $R^b$, $R^c$, $R^d$, $R^g$, and $R^h$ are each hydrogen; or (xiii) $R^e$ and $R^g$ form a $C_1$-$C_3$ alkylene group between the atoms to which they are attached; and $R^a$, $R^b$, $R^c$, $R^d$, $R^f$, and $R^h$ are each independently hydrogen or (xv) $R^g$ and $R^h$ together form =O; and $R^a$, $R^b$, $R^c$, $R^d$, $R^e$, and $R^f$ are each hydrogen.

22. The compound of embodiment 21, or a pharmaceutically acceptable salt thereof, wherein $R^a$, $R^b$, $R^c$, $R^d$, $R^e$, $R^f$, $R^g$, and $R^h$ are defined as follows:
(ii) $R^a$ and $R^e$ form a $C_1$-$C_2$ alkylene group between the atoms to which they are attached; and $R^b$, $R^c$, $R^d$, $R^f$, $R^g$, and $R^h$ are each hydrogen; or (iv) $R^b$ and Re form a $C_1$-$C_3$ alkylene group between the atoms to which they are attached; and $R^a$, $R^d$, $R^e$, $R^f$, $R^g$, and $R^h$ are each hydrogen; or (vii) $R^c$ and $R^d$ together with the atom to which they are attached, form a 3-membered cycloalkyl or a 4-membered heterocycloalkyl; and $R^a$, $R^b$, $R^e$, $R^f$, $R^g$, and $R^h$ are each hydrogen; or (viii) $R^c$ and $R^d$ together form =O; and $R^a$, $R^b$, $R^e$, $R^f$, $R^g$, and $R^h$ are each hydrogen; or (ix) $R^c$ and $R^e$ form a $C_2$ alkylene group between the atoms to which they are attached; and $R^a$, $R^b$, $R^d$, $R^f$, $R^g$, and $R^h$ are each hydrogen; or (x) $R^c$ and $R^g$ form a $C_1$-$C_2$ alkylene group between the atoms to which they are attached; and $R^a$, $R^b$, $R^d$, $R^e$, $R^f$, and $R^h$ are each hydrogen; or (xi) $R^e$ and $R^f$ together with the atom to which they are attached, form a 4-membered heterocycloalkyl; and $R^a$, $R^b$, $R^c$, $R^d$, $R^g$, and $R^h$ are each hydrogen; or (xiii) $R^e$ and $R^g$ form a $C_2$ alkylene group between the atoms to which they are attached; and $R^a$, $R^b$, $R^c$, $R^d$, $R^f$, and $R^h$ are each independently hydrogen or (xv) $R^g$ and $R^h$ together form =O; and $R^a$, $R^b$, $R^c$, $R^d$, $R^e$, and $R^f$ are each hydrogen.

23. The compound of embodiment 22, or a pharmaceutically acceptable salt thereof, wherein $R^c$ and $R^g$ form a $C_1$-$C_2$ alkylene group between the atoms to which they are attached; and $R^a$, $R^b$, $R^d$, $R^e$, $R^f$, and $R^h$ are each hydrogen.

24. The compound of embodiment 22, or a pharmaceutically acceptable salt thereof, wherein $R^b$ and $R^c$ form a $C_1$-$C_3$ alkylene group between the atoms to which they are attached; and $R^a$, $R^d$, $R^e$, $R^f$, $R^g$, and $R^h$ are each hydrogen.

25. The compound of embodiment 22, or a pharmaceutically acceptable salt thereof, wherein $R^e$ and $R^d$ together with the atom to which they are attached, form a 3-membered cycloalkyl or a 4-membered heterocycloalkyl; and $R^a$, $R^b$, $R^e$, $R^f$, $R^g$, and $R^h$ are each hydrogen.

26. The compound of any one of embodiments 21-25, or a pharmaceutically acceptable salt thereof, wherein n and p are 0.

27. The compound of embodiment 1, or a pharmaceutically acceptable salt thereof, wherein the compound is selected from Table 1.

28. The compound of embodiment 1, or a pharmaceutically acceptable salt thereof, wherein the compound is selected from Table 2.

29. The compound of any one of embodiments 1-28, or a pharmaceutically acceptable salt thereof, that is a USP30 Inhibitor Compound having an IC50 value of ≤1 µM as measured in a Ubiquitin-Rhodamine 110 Assay as described in Example 1.

30. The compound of embodiment 29, or a pharmaceutically acceptable salt thereof, wherein the IC50 value is ≤0.1 µM.

31. A compound of formula (I-C)

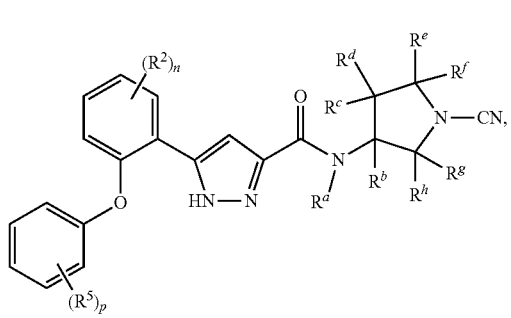

I-C or a pharmaceutically acceptable salt thereof, that is a USP30 Inhibitor Compound having an $IC_{50}$ value of ≤1 µM and >0.001 µM as measured in a Ubiquitin-Rhodamine 110 Assay as described in Example 1, wherein:

each occurrence of $R^2$ and $R^5$ is independently halo, cyano, hydroxyl, $C_1$-$C_6$ alkyl, $C_1$-$C_6$ alkoxyl, $C_1$-$C_6$ haloalkyl, and $C_1$-$C_6$ hydroxyalkyl;

n is 0-4;

p is 0-4;

$R^h$ is hydrogen;

$R^a$, $R^b$, $R^c$, $R^d$, $R^e$, $R^f$, and $R^g$ are defined as follows:

(ii) $R^a$ and $R^e$ form a $C_1$-$C_2$ alkylene group between the atoms to which they are attached; and $R^b$, $R^c$, $R^d$, $R^f$, and $R^g$ are each hydrogen; or (iv) $R^b$ and $R^c$ form a $C_1$-$C_2$ alkylene group between the atoms to which they are attached; and $R^a$, $R^e$, $R^d$, $R^f$, and $R^g$ are each hydrogen; or (vii) $R^c$ and $R^d$ together with the atom to which they are attached, form a 3 membered cycloalkyl; and $R^a$, $R^b$, $R^e$, $R^f$, and $R_g$ are each hydrogen; or (x) $R^c$ and $R^g$ form a $C_1$-$C_2$ alkylene group between the atoms to which they are attached; and $R^a$, $R^b$, $R^d$, $R^e$, and $R^f$ are each hydrogen; or (xi) $R^e$ and $R^f$ together with the atom to which they are attached, form a 4 membered heterocycloalkyl; and $R^a$, $R^b$, $R^c$, $R^d$, and $R^g$ are each hydrogen; or (xiii) $R^c$ and $R^g$ form a $C_2$ alkylene group between the atoms to which they are attached; and $R^a$, $R^b$, $R^c$, $R^d$, and $R^f$ are each independently hydrogen.

32. The compound of embodiment 31, or a pharmaceutically acceptable salt thereof, wherein the compound has the following formula

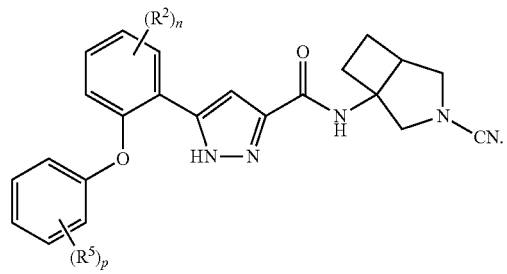

33. The compound of embodiment 31, or a pharmaceutically acceptable salt thereof, wherein the compound has the following formula

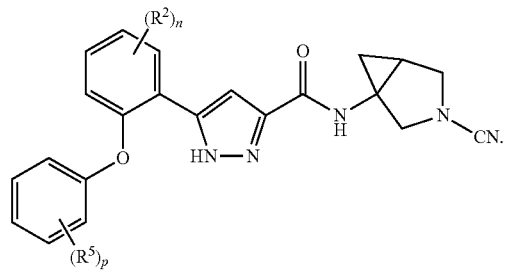

34. The compound of embodiment 31, or a pharmaceutically acceptable salt thereof, wherein the compound has the following formula

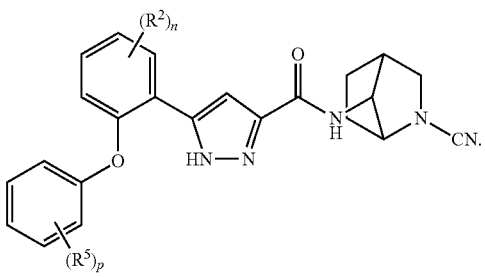

35. The compound of embodiment 31, or a pharmaceutically acceptable salt thereof, wherein the compound has the following formula

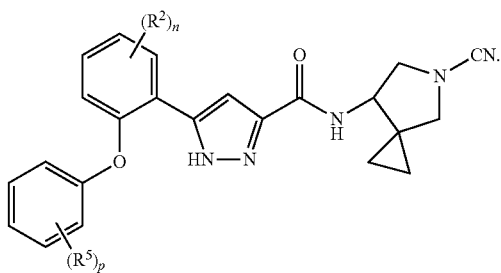

36. The compound of any one of embodiments 31-35, or a pharmaceutically acceptable salt thereof, wherein n and p are 0.
37. A pharmaceutical composition comprising the compound of any one of embodiments 1-36, or a pharmaceutically acceptable salt thereof, and a pharmaceutically acceptable carrier.
38. A method of inhibiting a ubiquitin-specific protease in a patient in need thereof, comprising administering to the patient a therapeutically effective amount of the compound of any one of embodiments 1-36, or a pharmaceutically acceptable salt thereof, or the pharmaceutical composition of embodiment 37.
39. The method of embodiment 38, wherein the ubiquitin-specific protease is USP30.
40. A method of treating a neurodegenerative disorder in a patient in need thereof, comprising administering to the patient a therapeutically effective amount of the compound of any one of embodiments 1-36, or a pharmaceutically acceptable salt thereof, or the pharmaceutical composition of embodiment 37.
41. The method of embodiment 40, wherein the neurodegenerative disorder is Parkinson's Disease.
42. A compound of any one of embodiments 1-36, or a pharmaceutically acceptable salt thereof, for use in a method of inhibiting a ubiquitin-specific protease in a patient in need thereof.
43. The compound or pharmaceutically acceptable salt for use of embodiment 42, wherein the ubiquitin-specific protease is USP30.
44. A compound of any one of embodiments 1-36, or a pharmaceutically acceptable salt thereof, for use in a method of treating a neurodegenerative disorder in a patient in need thereof.
45. The compound or pharmaceutically acceptable salt for use of embodiment 44, wherein the neurodegenerative disorder is Parkinson's Disease.
46. A USP30 Inhibitor Compound of the formula:

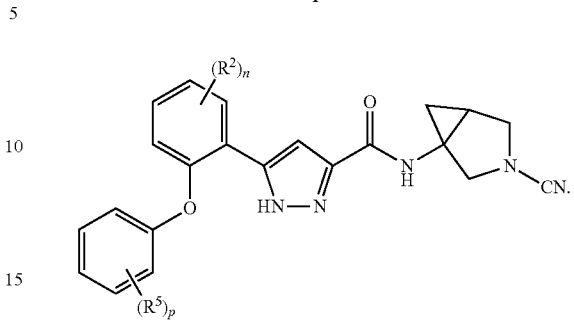

or a pharmaceutically acceptable salt thereof, wherein:
each occurrence of $R^2$ and $R^5$ is independently halo, cyano, hydroxyl, $C_1$-$C_6$ alkyl, $C_1$-$C_6$ alkoxyl, $C_1$-$C_6$ haloalkyl, or $C_1$-$C_6$ hydroxyalkyl;
n is 0-4;
p is 0-4.
47. The compound of any one of embodiments 1-36 or 44-46, having an $IC_{50}$ value of ≤0.5 µM and >0.001 µM as measured in a Ubiquitin-Rhodamine 110 Assay as described in Example 1.
48. The compound of embodiment 47, having an $IC_{50}$ value of ≤0.1 µM and >0.001 µM as measured in a Ubiquitin-Rhodamine 110 Assay as described in Example 1.
49. A USP30 Inhibitor Compound as disclosed and provided herein.
50. The USP30 Inhibitor Compound of embodiment 49, having an $IC_{50}$ value of ≤1 µM and >0.001 µM as measured in a Ubiquitin-Rhodamine 110 Assay as described in Example 1.

EXAMPLES

General Methods

All solvents used were commercially available and were used without further purification. Reactions were typically run using anhydrous solvents under an inert atmosphere of nitrogen.

Proton NMR spectra were recorded using a Broker Plus 400 NMR Spectrometer. The deuterated solvent (DMSO-$d_6$) typically contained 0.03% to 0.05% v/v tetramethylsilane, which was used as the reference signal (set at δ 0.00 for 1H).

LCMS analyses were performed on a SHIMADZU LCMS consisting of an UFLC 20-AD and LCMS 2020 MS detector. The column used was a Shim-pack XR-ODS, 2.2 µm, 3.0×50 mm. The instrument uses reverse-phase conditions (acetonitrile/water, containing 0.05% ammonia).

Abbreviations

Unless otherwise noted, or where the context dictates otherwise, the following abbreviations shall be understood to have the following meanings:
δ chemical shift
ACN Acetonitrile
DIEA N,N-Diisopropylethylamine
DMF N,N-Dimethylformamide
DCM Dichloromethane or methylene chloride
h hour
$^1$H NMR proton nuclear magnetic resonance
HATU 2-(3H-[1,2,3]Triazolo[4,5-b]pyridin-3-yl)-1,1,3,3-tetramethylisouronium hexafluorophosphate HPLC high performance liquid chromatography
Hz Hertz
LCMS liquid chromatography/mass spectrometry
min minutes
MS mass spectrometry
ppm parts per million
RT retention time
SEMCl 2-chloromethyl 2-(trimethylsilyl)ethyl ether
TFA Trifluoroacetic acid
THF Tetrahydrofuran
XPhos-Pd Chloro(2-dicyclohexylphosphino-2',4',6'-triisopropyl-1,1'-biphenyl)[2-(2'-amino-1,1'-biphenyl)]palladium(II) (2-dicyclohexylphosphino-2',4',6'-triisopropyl-1,1'-biphenyl)[2-(2'-amino-1,1'-biphenyl)]palladium(II) methanesulfonate
XPhos-Pd-G3

Example 1

Ubiquitin-Rhodamine 110 Assay for USP30 Activity

The assay was performed in a final volume of 9 μL in assay buffer containing 20 mM Tris-HCl (pH 8.0, (1M Tris-HCl, pH 8.0 solution; Corning 46-031-CM)), 1 mM GSH (L-glutathione reduced, Sigma-Aldrich, G4251-100G), 0.03% BGG (0.22 μM filtered, Sigma, G7516-25G), and 0.01% Triton X-100 (Sigma, T9284-10 L). Nanoliter quantities of 10-point, 3-fold serial dilution in DMSO were pre-dispensed into 1536 assay plates (Corning, #3724BC) for a final test concentration of 25 μM to 1.3 nM, top to lowest dose, respectively. Concentration and incubation times were optimized for the maximal signal-to-background while maintaining initial velocity conditions at a fixed substrate concentration. The final concentration of USP30 (human recombinant USP30, Boston Biochem, cat. #E-582) in the assay was 0.2 nM. Final substrate (Ub-Rh110; Ubiquitin-Rhodamine 110, UbiQ-126) concentration was 25 nM with [Ub-Rh110]<<Km. 3 μL of 2×USP30 was added to assay plates (pre-stamped with compound), preincubated for 30 minutes and then treated with 3 μL of 2×Ub-Rh110. Plates were incubated for 30 minutes at room temperature before addition of 3 μL of stop solution (final concentration of 10 mM citric acid (Sigma, 251275-500G)). Fluorescence was read on the Envision (excitation at 485 nm and emission at 535 nm; Perkin Elmer) or on the PheraSTAR (excitation at 485 nm and emission at 535 nm; BMG Labtech) fluorescence reader.

For all assay formats, data were reported as percent inhibition compared with control wells based on the following equation: % inh=1−((FLU−AveLow)/(AveHigh−AveLow)) where FLU=measured Fluorescence, AveLow=average Fluorescence of no enzyme control (n=16), and AveHigh=average Fluorescence of DMSO control (n=16). $IC_{50}$ values were determined by curve fitting of the standard 4 parameter logistic fitting algorithm included in the Activity Base software package: IDBS XE Designer Model205. Data is fitted using the Levenburg Marquardt algorithm.

The calculated $IC_{50}$ values of the compounds described herein are reported in Table 3, where A represents an $IC_{50}$ of <0.1 μM, B represents an $IC_{50}$ of 0.1 to 1.0 μM, and C represents an $IC_{50}$ of >1.0 μM. Compounds in the USP30 biochemical assay were deemed active if the $IC_{50}$ was ≤1 μM.

TABLE 3

$IC_{50}$ Values of Compounds in Ubiquitin-Rhodamine 110 Assay

| Compound | $IC_{50}$ (μM) |
|---|---|
| 1-a | B |
| 1b | A |
| 2-a | A |
| 2-b | C |
| 3-a | B |
| 3-b | A |
| 4-a | B |
| 4-b | B |
| 5-a | A |
| 5-b | B |
| 6-a | A |
| 6-b | B |
| 7-a | A |
| 7-b | B |
| 8-a | B |
| 8-b | B |
| 9-a | C |
| 9-b | C |
| 13-a | A |
| 13-b | A |
| 20-a | A |
| 20-b | A |

Example 2

Preparation of (1S,5R)-2-(5-(2-phenoxyphenyl)-1H-pyrazole-3-carbonyl)-2,6-diazabicyclo[3.2.1]octane-6-carbonitrile (1-a) and (1R,5S)-2-(5-(2-phenoxyphenyl)-1H-pyrazole-3-carbonyl)-2,6-diazabicyclo[3.2.1]octane-6-carbonitrile (1-b)

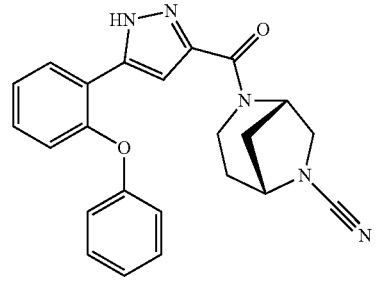

Compound 1-a

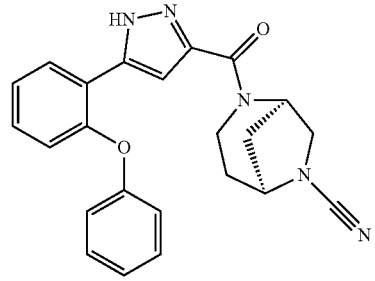

Compound 1-b

Compounds 1-a and 1-b were prepared by the following route:

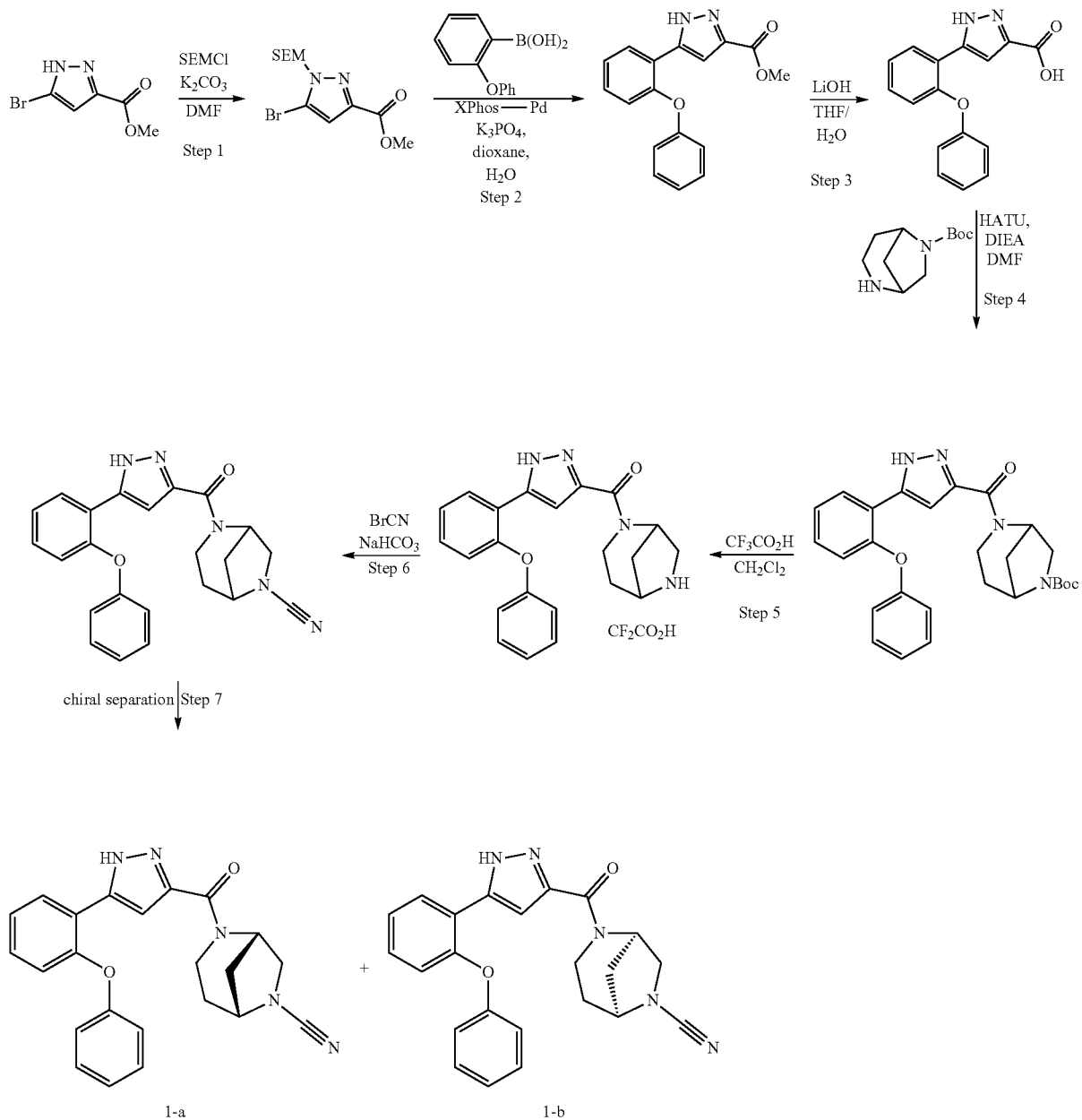

Step 1. Methyl 5-bromo-1-[[2-(trimethylsilyl)ethoxy]methyl]-1H-pyrazole-3-carboxylate 2-Chloromethyl 2-(trimethylsilyl)ethyl ether (12.3 mL, 69.5 mmol) was added to a mixture of methyl 5-bromo-1H-pyrazole-3-carboxylate (5.00 g, 23.2 mmol) and $K_2CO_3$ (18.0 g, 130 mmol) in DMF (50 mL) at 0° C. in an ice/water bath. The resulting solution was stirred for 14 h at 25° C. The reaction was quenched by the addition of water (100 mL). The resulting mixture was extracted with ethyl acetate (3×100 mL). The combined organic layers were washed with brine (100 mL), dried over anhydrous sodium sulfate, filtered, and concentrated under vacuum. The residue was purified by silica gel chromatography (eluting with 15:1 petroleum ether/ethyl acetate) to afford methyl 5-bromo-1-[[2-(trimethylsilyl)ethoxy]methyl]-1H-pyrazole-3-carboxylate as a yellow oil (6.20 g, 79%). LCMS (ES, m/z) 335, 337 $[M+H]^+$.

Step 2. Methyl 5-(2-phenoxyphenyl)-1-[[2-(trimethylsilyl)ethoxy]methyl]-1H-pyrazole-3-carboxylate A solution of methyl 5-bromo-1-[[2-(trimethylsilyl)ethoxy]methyl]-1H-pyrazole-3-carboxylate (6.20 g, 18.4 mmol), (2-phenoxyphenyl)boronic acid (4.96 g, 23.2 mmol), XPhos-Pd (2.90 g, 3.68 mmol) and $K_3PO_4$ (11.7 g, 55.2 mmol) in dioxane (120 mL) and $H_2O$ (24 mL) was stirred for 15 h at 100° C. in an oil bath. After cooling to 25° C., the solids were filtered out. The filtrate was concentrated under vacuum. The residue was diluted with water (50 mL). The resulting mixture was extracted with ethyl acetate (3×50 mL). The combined organic layer was dried over anhydrous sodium sulfate, filtered, and concentrated under vacuum. The residue was purified by reverse phase chromatography (Column:)(Bridge Shield RP18 OBD Column, 5 µm, 30×150 mm; Mobile phase, A: water (containing 10 mmol/L $NH_4HCO_3$) and B: ACN (5% B to 72% over 20 min); Detector: UV:220 and 254 nm) to afford methyl 5-(2-phenoxyphenyl)-1-[[2-(trimethylsilyl)ethoxy]methyl]-1H-pyrazole-3-carboxylate as a yellow solid (3.20 g, 41%). LCMS (ES, m/z) 425 $[M+H]^+$.

Step 3. 5-(2-Phenoxyphenyl)-1-[[2-(trimethylsilyl) ethoxy]methyl]-1H-pyrazole-3-carboxylic acid A solution of methyl 5-(2-phenoxyphenyl)-1-[[2-(trimethylsilyl)ethoxy]methyl]-1H-pyrazole-3-carboxylate (1.40 g, 3.30 mmol) and LiOH (0.810 g, 33.8 mmol) in THF (60 mL) and $H_2O$ (15 mL) was stirred for 4 h at 50° C. The mixture was allowed to cool to 25° C. and concentrated under vacuum. The pH value of the residue was adjusted to 5-6 with 3 N hydrochloric acid. The solids were collected by filtration and dried in an oven to afford 5-(2-phenoxyphenyl)-1-[[2-(trimethylsilyl)ethoxy] methyl]-1H-pyrazole-3-carboxylic acid as an off-white solid (1.05 g, 78%). LCMS (ES, m/z) 411 $[M+H]^+$.

Step 4. tert-butyl 2-[5-(2-phenoxyphenyl)-1-[[2-(trimethylsilyl)ethoxy]methyl]-1H-pyrazole-3-carbonyl]-2,6-diazabicyclo[3.2.1]octane-6-carboxylate A solution of 5-(2-phenoxyphenyl)-1-[[2-(trimethylsilyl) ethoxy]methyl]-1H-pyrazole-3-carboxylic acid (150 mg, 0.366 mmol), HATU (210 mg, 0.541 mmol), tert-butyl 2,6-diazabicyclo[3.2.1]octane-6-carboxylate (75.0 mg, 0.346 mmol) and DIEA (0.2 mL, 1.40 mmol) in DMF (2 mL) was stirred for 3 h at 25° C. The reaction was quenched by the addition of water (10 mL). The resulting mixture was extracted with ethyl acetate (3×20 mL). The combined organic layer was washed with brine (20 mL), dried over anhydrous sodium sulfate, filtered, and concentrated under reduced pressure. The residue was purified by silica gel column chromatography (eluting with 1/1 petroleum ether/ ethyl acetate) to afford tert-butyl 2-[5-(2-phenoxyphenyl)-1-[[2-(trimethylsilyl)ethoxy]methyl]-1H-pyrazole-3-carbonyl]-2,6-diazabicyclo[3.2.1]octane-6-carboxylate as a white solid (100 mg, 45%). LCMS (ES, m/z): 605 $[M+H]^+$.

Step 5. 2-[5-(2-phenoxyphenyl)-1H-pyrazole-3-carbonyl]-2,6-diazabicyclo[3.2.1]octane 2,2,2-trifluoroacetate A solution of tert-butyl 2-[5-(2-phenoxyphenyl)-1-[[2-(trimethylsilyl)ethoxy]methyl]-1H-pyrazole-3-carbonyl]-2,6-diazabicyclo[3.2.1]octane-6-carboxylate (100 mg, 0.157 mmol) and TFA (1 mL) in DCM (2 mL) was stirred for 2 h at 25° C. The resulting mixture was concentrated under vacuum to afford 2-[5-(2-phenoxyphenyl)-1H-pyrazole-3-carbonyl]-2,6-diazabicyclo[3.2.1]octane 2,2,2-trifluoroacetate as a colorless oil (110 mg, crude). LCMS (ES, m/z): 375 $[M+H]^+$.

Step 6. 2-[5-(2-phenoxyphenyl)-1H-pyrazole-3-carbonyl]-2,6-diazabicyclo[3.2.1]octane-6-carbonitrile Cyanogen bromide (17.8 mg, 0.170 mmol) was added to a 0° C. mixture of 2-[5-(2-phenoxyphenyl)-1H-pyrazole-3-carbonyl]-2,6-diazabicyclo[3.2.1]octane 2,2,2-trifluoroacetate (80.0 mg, 0.170 mmol) and $NaHCO_3$ (82.0 mg, 0.957 mmol) in DMF (2 mL). The resulting mixture stirred for 16 h at 25° C. The reaction was quenched by the addition of water (10 mL). The resulting mixture was extracted with ethyl acetate (3×20 mL). The combined organic layer was dried over anhydrous sodium sulfate, filtered, and concentrated under reduced pressure. The residue was purified by Prep-HPLC (Column: XBridge Shield RP18 OBD Column, 5 µm,19×150 mm; Mobile Phase A: water (containing 10 mmol/L $NH_4HCO_3$) and B: $CH_3CN$ (30% to 55% in 8 min); Flow rate: 25 mL/min; Detector: 220 nm) to afford 2-[5-(2-phenoxyphenyl)-1H-pyrazole-3-carbonyl]-2,6-diazabicyclo [3.2.1]octane-6-carbonitrile as a white solid (40.0 mg, 59%). LCMS (ES, m/z): 400 $[M+H]^+$.

Step 7. (1S,5R)-2-(5-(2-phenoxyphenyl)-1H-pyrazole-3-carbonyl)-2,6-diazabicyclo[3.2.1]octane-6-carbonitrile and (1R,5S)-2-(5-(2-phenoxyphenyl)-1H-pyrazole-3-carbonyl)-2,6-diazabicyclo[3.2.1] octane-6-carbonitrile 2-[5-(2-Phenoxyphenyl)-1H-pyrazole-3-carbonyl]-2,6-diazabicyclo[3.2.1]octane-6-carbonitrile (40.0 mg, 0.100 mmol) was separated by chiral-HPLC (Column: CHIRAL ART Cellulose-SB, 2×25 cm, 5um; Mobile Phase A: n-hexane and B: EtOH (hold 50% in 15 min); Flow rate: 20 mL/min; Detector: 254/220 nm; $RT_1$: 8.911 min and $RT_2$: 11.119 min). The first eluting isomer ($RT_1$=8.911 min) was collected and concentrated under vacuum, then lyophilized to obtain a compound for which the absolute stereochemistry was arbitrarily assigned as (1S,5R)-2-(5-(2-phenoxyphenyl)-1H-pyrazole-3-carbonyl)-2,6-diazabicyclo[3.2.1]octane-6-carbonitrile (1-a) as a white solid (13.8 mg, 35%). LCMS (ES, m/z): 400 $[M+H]^+$; $^1$H-NMR (DMSO-$d_6$, 400 MHz) δ (ppm): 13.63 (br s, 1H), 7.86-7.85 (m, 1H), 7.44-7.29 (m, 4H), 7.13-6.90 (m, 5H), 5.49-5.18 (m, 1H), 4.65-4.31 (m, 1H), 4.18-4.17 (m, 1H), 3.65-3.46 (m, 3H), 3.08-3.03 (m, 1H), 1.86-1.72 (m, 4H). The second eluting isomer ($RT_2$=11.119 min) was collected and concentrated under vacuum, then lyophilized to obtain a compound for which the absolute stereochemistry was arbitrarily assigned as (1R,5S)-2-(5-(2-phenoxyphenyl)-1H-pyrazole-3-carbonyl)-2,6-diazabicyclo[3.2.1]octane-6-carbonitrile (1-b) as a white solid (14.8 mg, 37%). LCMS (ES, m/z): 400 $[M+H]^+$; $^1$H-NMR (DMSO-$d_6$, 400 MHz) δ (ppm): 13.63 (br s, 1H), 7.88-7.85 (m, 1H), 7.44-7.29 (m, 4H), 7.14-6.90 (m, 5H), 5.48-5.17 (m, 1H), 4.65-4.31 (m, 1H), 4.18-4.17 (m, 1H), 3.65-3.48 (m, 3H), 3.08-3.03 (m, 1H), 1.86-1. 72 (m, 4H).

The compounds set forth in Table 4 were prepared by methods analogous to the preparation of compounds 1-a and 1-b. Each pair of compounds listed in Table 4 (i.e., compounds 2-a and 2-b, compounds 3-a and 3-b, etc.) was obtained as a racemic mixture, and were then separated by chiral HPLC according to the procedure described in Example 2, Step 7, to obtain the individual compounds in substantially enantiomerically pure form. The first and second eluting enantiomer of each enantiomer pair is identified in Table 4. The absolute stereochemistry of each enantiomer was arbitrarily assigned.

TABLE 4

Additional Compounds Prepared By Analogous Methods

| Cmpd No. | Structure | IUPAC name | MS (ESI, m/z) [M + H]+ | ¹H-NMR δ (ppm) |
|---|---|---|---|---|
| 2-a | first eluting isomer | N-((1S,4S,7S)-2-cyano-2-azabicyclo[2.2.1]heptan-7-yl)-5-(2-phenoxyphenyl)-1H-pyrazole-3-carboxamide | 400 | ¹HNMR (DMSO-d$_6$, 400 MHz) δ (ppm): 13.7-13.6 (m, 1H), 8.42-8.15 (m, 1H), 8.04-7.85 (m, 1H), 7.42-7.29 (m, 4H), 7.15-7.10 (m, 1H), 7.02-6.95 (m, 4H), 4.06-4.04 (m, 1H), 3.84-3.82 (m, 1H), 3.52-3.49 (m, 1H), 3.10-3.06 (m, 1H), 2.67-2.62 (m, 1H), 1.97-1.88 (m, 1H), 1.84-1.71 (m, 2H), 1.54-1.48 (m, 1H). |
| 2-b | second eluting isomer | N-((1R,4R,7R)-2-cyano-2-azabicyclo[2.2.1]heptan-7-yl)-5-(2-phenoxyphenyl)-1H-pyrazole-3-carboxamide | 400 | ¹HNMR (DMSO-d$_6$, 400 MHz) δ (ppm): 13.8-13.6 (m, 1H), 8.57-8.15 (m, 1H), 8.02-7.86 (m, 1H), 7.40-7.22 (m, 4H), 7.15-7.11 (m, 1H), 7.01-6.97 (m, 4H), 4.06-4.04 (m, 1H), 3.83-3.81 (m, 1H), 3.53-3.50 (m, 1H), 3.09-3.06 (m, 1H), 2.71-2.60 (m, 1H), 1.97-1.88 (m, 1H), 1.84-1.71 (m, 2H), 1.54-1.48 (m, 1H). |
| 4-a | first eluting isomer | (1S,4S)-5-(5-(2-phenoxyphenyl)-1H-pyrazole-3-carbonyl)-2,5-diazabicyclo[2.2.1]heptane-2-carbonitrile | 386 | ¹HNMR (DMSO-d$_6$, 400 MHz) δ (ppm): 13.7 (br s, 1H), 7.91-7.89 (m, 1H), 7.44-7.37 (m, 3H), 7.32-7.29 (m, 1H), 7.15-7.12 (m, 1H), 7.03-6.99 (m, 4H), 5.50-5.40 (m, 0.5H), 4.87-4.86 (m, 0.5H), 4.46-4.43 (m, 1H), 4.06-3.88 (m, 1H), 3.65-3.51 (m, 2H), 3.36-3.34 (m, 1H), 1.99-1.85 (m, 2H). |

TABLE 4-continued

Additional Compounds Prepared By Analogous Methods

| Cmpd No. | Structure | IUPAC name | MS (ESI, m/z) [M + H]⁺ | ¹H-NMR δ (ppm) |
|---|---|---|---|---|
| 4-b | 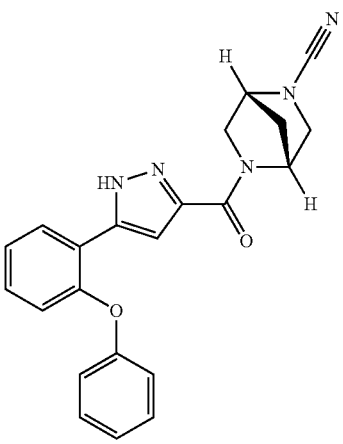<br>second eluting isomer | (1R,4R)-5-(5-(2-phenoxyphenyl)-1H-pyrazole-3-carbonyl)-2,5-diazabicyclo[2.2.1]heptane-2-carbonitrile | 386 | ¹HNMR (DMSO-d₆, 400 MHz) δ (ppm): 13.7 (br s, 1H), 7.91-7.89 (m, 1H), 7.44-7.37(m, 3H), 7.32-7.29 (m, 1H), 7.15-7.12 (m, 1H), 7.03-6.99 (m, 4H), 5.50-5.40 (m, 0.5H), 4.87-4.86 (m, 0.5H), 4.46-4.43 (m, 1H), 3.99-3.88 (m, 1H), 3.65-3.51 (m, 2H), 3.44-3.34 (m, 1H), 1.99-1.81 (m, 2H). |
| 5-a | 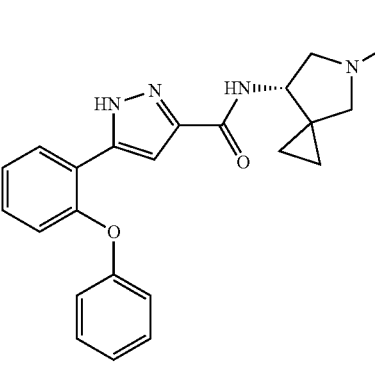<br>first eluting isomer | (S)-N-(5-cyano-5-azaspiro[2.4]heptan-7-yl)-5-(2-phenoxyphenyl)-1H-pyrazole-3-carboxamide | 400 | ¹HNMR (DMSO-d₆, 400 MHz) δ (ppm): 13.6 (br s, 1H), 8.41-8.38 (m, 1H), 7.92-7.85(m, 1H), 7.41-7.29 (m, 4H), 7.15-7.12 (m, 1H), 7.02-6.91 (m, 4H), 4.25-4.20 (m, 1H), 3.82-3.78 (m, 1H), 3.68-3.65 (m, 1H), 3.52-3.44 (m, 1H), 3.25-3.24 (m, 1H), 0.80-0.59 (m, 4H). |
| 5-b | 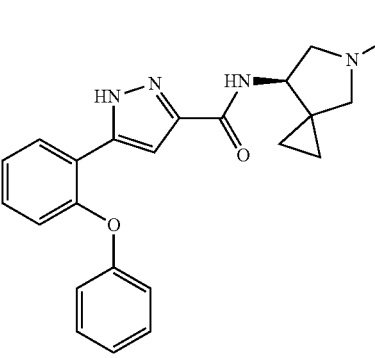<br>second eluting isomer | (R)-N-(5-cyano-5-azaspiro[2.4]heptan-7-yl)-5-(2-phenoxyphenyl)-1H-pyrazole-3-carboxamide | 400 | ¹HNMR (DMSO-d₆, 400 MHz) δ (ppm): 13.6 (br s, 1H), 8.41-8.38 (m, 1H), 7.92-7.85(m, 1H), 7.41-7.29 (m, 4H), 7.15-7.12 (m, 1H), 7.02-6.91 (m, 4H), 4.25-4.20 (m, 1H), 3.82-3.78 (m, 1H), 3.68-3.65 (m, 1H), 3.48-3.40 (m, 1H), 3.26-3.24 (m, 1H), 0.80-0.59 (m, 4H). |

TABLE 4-continued

Additional Compounds Prepared By Analogous Methods

| Cmpd No. | Structure | IUPAC name | MS (ESI, m/z) [M + H]+ | 1H-NMR δ (ppm) |
|---|---|---|---|---|
| 7-a | first eluting isomer | N-((1S,2S,4R)-7-cyano-7-azabicyclo[2.2.1]heptan-2-yl)-5-(2-phenoxyphenyl)-1H-pyrazole-3-carboxamide | 400 | 1HNMR (DMSO-$d_6$, 400 MHz) δ (ppm): 13.7-13.6 (m, 1H), 8.62-8.51 (m, 1H), 8.05-7.87 (m, 1H) 7.45-7.25 (m, 4H), 7.19-7.12 (m, 1H), 7.04-6.95 (m, 4H), 4.27-4.13 (m, 3H), 2.22-2.08 (m, 1H), 1.83-1.65 (m, 4H). |
| 7-b | second eluting isomer | N-((1R,2R,4S)-7-cyano-7-azabicyclo[2.2.1]heptan-2-yl)-5-(2-phenoxyphenyl)-1H-pyrazole-3-carboxamide | 400 | 1HNMR (DMSO-$d_6$, 400 MHz) δ (ppm): 13.7-13.6 (m, 1H), 8.62-8.51 (m, 1H), 8.03-7.86(m, 1H), 7.47-7.25 (m, 4H), 7.15-7.10 (m, 1H), 7.01-6.95 (m, 4H), 4.30-4.15 (m, 3H), 2.22-2.10 (m, 1H), 1.88-1.62 (m, 4H). |
| 8-a | first eluting isomer | N-((1R,4R,5S)-2-cyano-2-azabicyclo[2.1.1]hexan-5-yl)-5-(2-phenoxyphenyl)-1H-pyrazole-3-carboxamide | 386 | 1HNMR (DMSO-$d_6$, 400 MHz) δ (ppm): 13.7 (br s, 1H), 7.94-7.88 (m, 2H), 7.41-7.28 (m, 4H), 7.16-7.12 (m, 1H), 7.03-6.92 (m, 4H), 4.20-4.19 (m, 1H), 3.83-3.82 (m, 1H), 3.45-3.43 (m, 1H), 2.94-2.92 (m, 1H), 1.78-1.76 (m, 1H), 1.32-1.29 (m, 1H). |

TABLE 4-continued

Additional Compounds Prepared By Analogous Methods

| Cmpd No. | Structure | IUPAC name | MS (ESI, m/z) [M + H]⁺ | ¹H-NMR δ (ppm) |
|---|---|---|---|---|
| 8-b | second eluting isomer | N-((1S,4S,5R)-2-cyano-2-azabicyclo[2.1.1]hexan-5-yl)-5-(2-phenoxyphenyl)-1H-pyrazole-3-carboxamide | 386 | ¹HNMR (DMSO-d₆, 400 MHz) δ (ppm): 13.6 (br s, 1H), 7.94-7.88 (m, 2H), 7.41-7.29 (m, 4H), 7.16-7.12 (m, 1H), 7.03-6.98 (m, 4H), 4.20-4.19 (m, 1H), 3.83-3.82 (m, 1H), 3.45-3.43 (m, 1H), 2.94-2.92 (m, 1H), 1.78-1.76 (m, 1H), 1.32-1.29 (m, 1H). |
| 9-a | first eluting isomer | N-[(7S)-5-cyano-2-oxa-5-azaspiro[3.4]octan-7-yl]-5-(2-phenoxyphenyl)-1H-pyrazole-3-carboxamide | 416 | ¹H-NMR (CD₃OD, 400 MHz) δ (ppm): 7.80-7.77 (m, 1H), 7.39-7.35 (m, 3H), 7.28-7.25 (m, 1H), 7.16-7.13 (m, 2H), 7.03-6.97 (m, 3H), 4.97-4.93 (m, 2H), 4.74-4.70 (m, 2H), 4.55-4.50 (m, 1H), 3.86-3.81 (m, 1H), 3.54-3.50 (m, 1H), 2.68-2.63 (m, 1H), 2.53-2.48 (m, 1H). |
| 9-b | second eluting isomer | N-[(7R)-5-cyano-2-oxa-5-azaspiro[3.4]octan-7-yl]-5-(2-phenoxyphenyl)-1H-pyrazole-3-carboxamide | 416 | ¹H-NMR (CD30D, 400 MHz) δ (ppm): 7.80-7.77 (m, 1H), 7.39-7.35 (m, 3H), 7.28-7.25 (m, 1H), 7.16-7.13 (m, 2H), 7.03-6.97 (m, 3H), 4.97-4.90 (m, 2H), 4.74-4.70 (m, 2H), 4.55-4.51 (m, 1H), 3.86-3.82 (m, 1H), 3.54-3.50 (m, 1H), 2.68-2.63 (m, 1H), 2.53-2.48 (m, 1H). |
| 13-a | 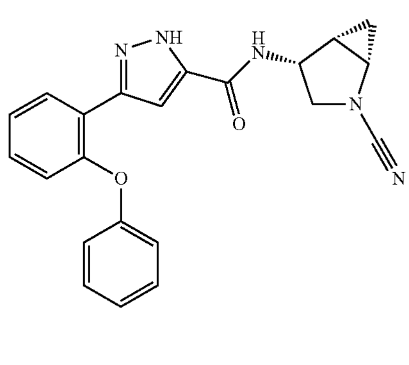 [SMILES: N#CN1C[C@H](NC(=O)c2cc(-c3ccccc3Oc3ccccc3)n[nH]2)[C@@H]2C[C@@H]21] | N-((1S,4R,5S)-2-cyano-2-azabicyclo[3.1.0]hexan-4-yl)-3-(2-phenoxyphenyl)-1H-pyrazole-5-carboxamide | 386 | ¹H-NMR (DMSO-d₆, 400 MHz) δ (ppm): ¹H-NMR (DMSO-d₆, 400 MHz) δ (ppm): 13.75-13.61 (m, 1H), 8.55-8.20 (m, 1H), 8.05-7.87 (m, 1H), 7.45-7.30 (m, 4H), 7.16-7.14 (m, 1H), 7.03-6.97 (m, 3H), 6.95-6.85 (m, 1H), 4.80-4.77 (m, 1H), 3.72-3.67 (m, 1H), 3.51-3.49 (m, 1H), 3.12-3.08 (m, 1H), 1.90-1.80 (m, 1H), 1.40-1.20 (m, 1H), 0.75-0.60 (m, 1H). |

TABLE 4-continued

Additional Compounds Prepared By Analogous Methods

| Cmpd No. | Structure | IUPAC name | MS (ESI, m/z) [M + H]+ | ¹H-NMR δ (ppm) |
|---|---|---|---|---|
| 13-b | 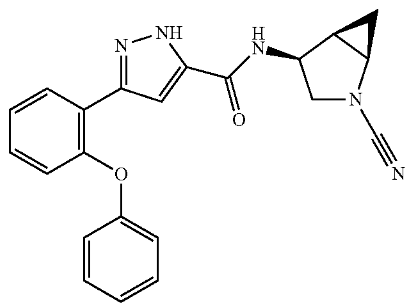 [SMILES: N#CN1C[C@@H](NC(=O)c2cc(-c3ccccc3Oc3ccccc3)n[nH]2)[C@H]2C[C@H]21] | N-((1R,4S,5R)-2-cyano-2-azabicyclo[3.1.0]hexan-4-yl)-3-(2-phenoxyphenyl)-1H-pyrazole-5-carboxamide | | |
| 20-a | 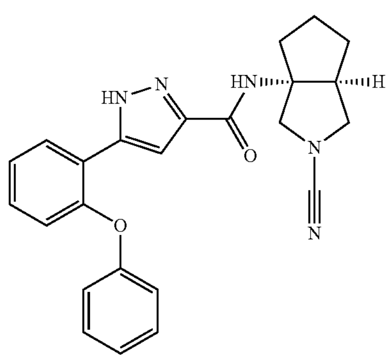 [SMILES: N#CN1C[C@@H]2CCC[C@]2(NC(=O)c2cc(-c3ccccc3Oc3ccccc3)[nH]n2)C1] | N-((3aR,6aS)-2-cyanohexahydrocyclopenta[c]pyrrol-3a(1H)-yl)-5-(2-phenoxyphenyl)-1H-pyrazole-3-carboxamide | 414 | ¹H-NMR (DMSO-$d_6$, 400 MHz) δ (ppm): 13.70-13.58 (m, 1H), 8.55-8.21 (m, 1H), 8.03-7.86 (m, 1H), 7.45-7.13 (m, 5H), 7.04-6.92 (m, 3H), 3.70-3.66 (m, 2H), 3.54-3.49 (m, 1H), 3.16-3.14 (m, 1H), 1.78-1.74 (m, 1H), 2.93-2.81 (m, 1H), 2.09-1.90 (m, 3H), 1.71-1.63 (m, 2H), 1.41-1.37 (m, 1H). |
| 20-b | 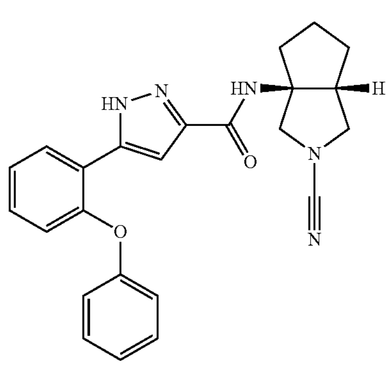 [SMILES: N#CN1C[C@H]2CCC[C@@]2(NC(=O)c2cc(-c3ccccc3Oc3ccccc3)[nH]n2)C1] | N-((3aS,6aR)-2-cyanohexahydrocyclopenta[c]pyrrol-3a(1H)-yl)-5-(2-phenoxyphenyl)-1H-pyrazole-3-carboxamide | 414 | ¹H-NMR (DMSO-$d_6$, 400 MHz) δ (ppm): 13.62 (br s, 1H), 8.33 (br s, 1H), 7.94-7.93 (m, 1H), 7.42-7.30 (m, 3H), 7.28-7.26 (m, 1H), 7.16-7.14 (m, 1H), 7.12 (br s, 1H), 7.08-6.98 (m, 3H), 3.70-3.64 (m, 2H), 3.52-3.50 (m, 1H), 3.16-3.13 (m, 1H), 2.91-2.89 (m, 1H), 2.05-1.89 (m, 3H), 1.73-1.63 (m, 2H), 1.41-1.37 (m, 1H). |

Example 3
Preparation of N-((1R,5S)-3-cyano-3-azabicyclo[3.2.0]heptan-1-yl)-5-(2-phenoxyphenyl)-1H-pyrazole-3-carboxamide (6-a) and N-((1S,5R)-3-cyano-3-azabicyclo[3.2.0]heptan-1-yl)-5-(2-phenoxyphenyl)-1H-pyrazole-3-carboxamide (6-b)
Compound 6-a
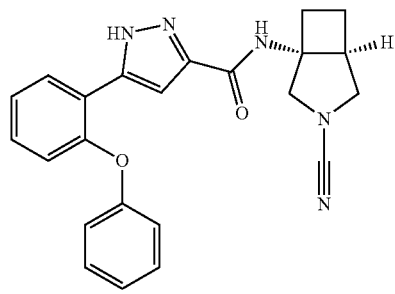
Compound 6-b
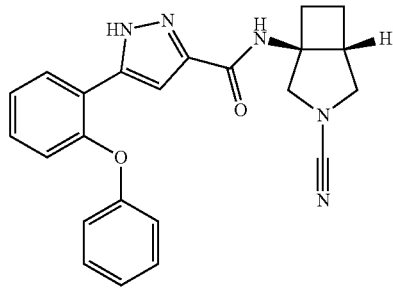
Compounds 6-a and 6-b were prepared by the following route:
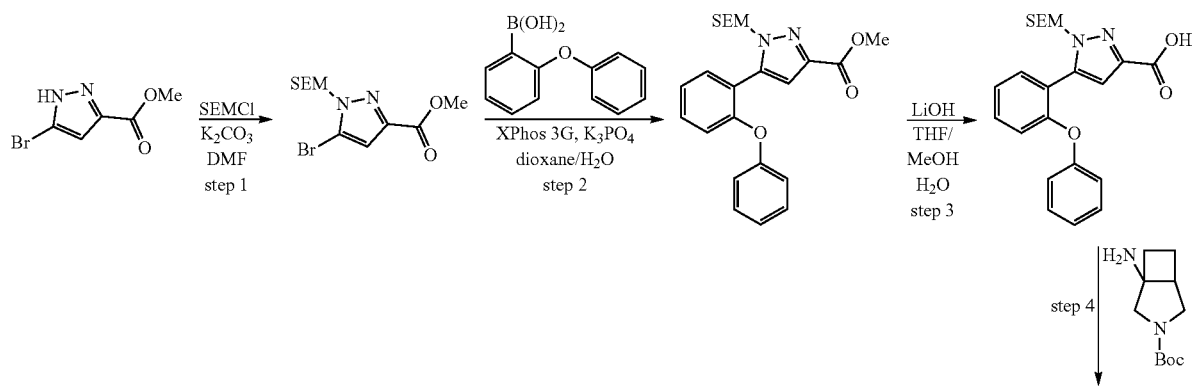
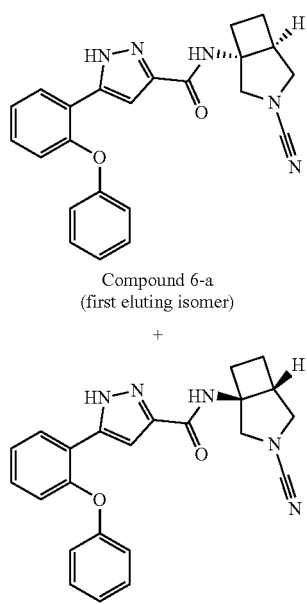
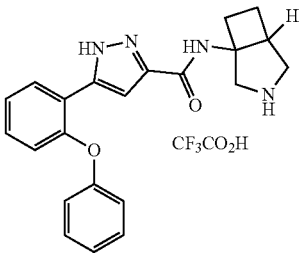
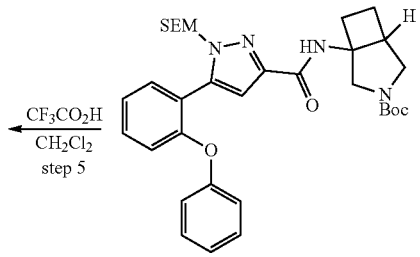

Step 1. Methyl 5-bromo-1-[[2-(trimethylsilyl)ethoxy]methyl]-1H-pyrazole-3-carboxylate 2-(Trimethylsilyl)ethoxymethyl chloride (12.2 mL, 68.8 mmol) was added dropwise to a 0° C. solution of methyl 5-bromo-1H-pyrazole-3-carboxylate (5.00 g, 24.5 mmol) and potassium carbonate (18.0 g, 130 mmol) in DMF (10 mL). The resulting mixture was stirred for 14 h at 25° C. The reaction was quenched with water (20 mL) at 0° C. The resulting mixture was extracted with ethyl acetate (3×30 mL). The combined organic layers were washed with brine (2×100 mL), dried over anhydrous sodium sulfate, and filtered. The filtrate was concentrated under vacuum. The residue was purified by silica gel chromatography (eluting with 15:1 petroleum ether/ethyl acetate) to afford methyl 5-bromo-1-[[2-(trimethylsilyl)ethoxy]methyl]-1H-pyrazole-3-carboxylate (6.20 g, 76%) as a yellow oil. LCMS (ES, m/z): 335, 337 $[M+H]^+$.

Step 2. Methyl 5-(2-phenoxyphenyl)-1-[[2-(trimethylsilyl)ethoxy]methyl]-1H-pyrazole-3-carboxylate A solution of methyl 5-bromo-1-[[2-(trimethylsilyl)ethoxy]methyl]-1H-pyrazole-3-carboxylate (6.20 g, 18.5 mmol), (2-phenoxyphenyl)boronic acid (4.96 g, 23.2 mmol), XPhos-Pd-G3 (3.12 g, 36.9 mmol) and potassium phosphate tribasic (25.4 mg, 37.1 mmol) in dioxane (120 mL) and water (24 mL) was stirred for 15 h at 100° C. in an oil bath. The mixture was cooled to 25° C. The resulting mixture was concentrated under vacuum. The residue was diluted with water (30 mL). The resulting mixture was extracted with ethyl acetate (3×30 mL). The combined organic layers were dried over anhydrous sodium sulfate, filtered, and concentrated. The residue was purified by reverse phase chromatography (Column:)(Bridge Shield RP18 OBD Column, 5 μm, 30×150 mm; Mobile phase, A: water (containing 0.05% ammonium hydrogen) and B: acetonitrile (5% B to 72% over 20 min); Detector: UV 220 and 254 nm) to afford methyl 5-(2-phenoxyphenyl)-1-[[2-(trimethylsilyl)ethoxy]methyl]-1H-pyrazole-3-carboxylate as a yellow solid (3.20 g, 41%). LCMS (ES, m/z): 425 $[M+H]^+$.

Step 3. 5-(2-Phenoxyphenyl)-1-[[2-(trimethylsilyl)ethoxy]methyl]-1H-pyrazole-3-carboxylic acid A solution of methyl 5-(2-phenoxyphenyl)-1-[[2-(trimethylsilyl)ethoxy]methyl]-1H-pyrazole-3-carboxylate (1.40 g, 3.30 mmol) and lithium hydroxide (810 mg, 34.0 mmol) in THF (60.0 mL), water (15.0 mL), and methanol (30.0 mL) was stirred for 4 h at 50° C. The mixture was cooled to 25° C. and concentrated under vacuum. The pH value of the residue was adjusted to 3-4 with 3 N aqueous hydrochloric acid solution. The resulting mixture was extracted with ethyl acetate (3×30 mL). The combined organic layers were washed with brine (2×100 mL), dried over anhydrous sodium sulfate, filtered, and concentrated. The residue was purified by silica gel chromatography (eluting with 2:1 petroleum ether/ethyl acetate) to afford 5-(2-phenoxyphenyl)-1-[[2-(trimethylsilyl)ethoxy]methyl]-1H-pyrazole-3-carboxylic acid as an off-white solid (1.00 g, 74%). LCMS (ES, m/z): 411 $[M+H]^+$.

Step 4. tert-Butyl 1-(5-(2-phenoxyphenyl)-1-((2-(trimethylsilyl)ethoxy)methyl)-1H-pyrazole-3-carboxamido)-3-azabicyclo[3.2.0]heptane-3-carboxylate A solution of 5-(2-phenoxyphenyl)-1-[[2-(trimethylsilyl)ethoxy]methyl]-1H-pyrazole-3-carboxylic acid (300 mg, 0.723 mmol), tert-butyl 1-amino-3-azabicyclo[3.2.0]heptane-3-carboxylate (154 mg, 0.723 mmol), HATU (275 mg, 0.723 mmol) and N,N-diisopropylethylamine (0.239 mL, 1.45 mmol) in DMF (2 mL) was stirred for 40 min at 25° C. The reaction was quenched with water (5 mL). The resulting mixture was extracted with ethyl acetate (3×15 mL). The combined organic layers were washed with brine (2×30 mL), dried over anhydrous sodium sulfate, filtered, and concentrated. The residue was purified by silica gel chromatography (eluting with 4:1 petroleum ether/ethyl acetate) to afford tert-butyl 1-(5-(2-phenoxyphenyl)-1-((2-(trimethylsilyl)ethoxy)methyl)-1H-pyrazole-3-carboxamido)-3-azabicyclo[3.2.0]heptane-3-carboxylate as an off-white solid (350 mg, 80%). LCMS (ES, m/z): 605 $[M+H]^+$.

Step 5. N-(3-azabicyclo[3.2.0]heptan-1-yl)-5-(2-phenoxyphenyl)-1H-pyrazole-3-carboxamide 2,2,2-trifluoroacetate A solution of tert-butyl 1-(5-(2-phenoxyphenyl)-1-((2-(trimethylsilyl)ethoxy)methyl)-1H-pyrazole-3-carboxamido)-3-azabicyclo[3.2.0]heptane-3-carboxylate (350 mg, 0.579 mmol) in trifluoroacetic acid (1 mL) and dichloromethane (3 mL) was stirred for 30 min at 25° C. The resulting mixture was concentrated under vacuum to afford N-(3-azabicyclo[3.2.0]heptan-1-yl)-5-(2-phenoxyphenyl)-1H-pyrazole-3-carboxamide 2,2,2-trifluoroacetate as a brown oil (360 mg, crude). LCMS (ES, m/z): 375 $[M+H]t$

Step 6. N-((1R,5 S)-3-cyano-3-azabicyclo[3.2.0]heptan-1-yl)-5-(2-phenoxyphenyl)-1H-pyrazole-3-carboxamide (6-a) and N-((1S,5R)-3-cyano-3-azabicyclo[3.2.0]heptan-1-yl)-5-(2-phenoxyphenyl)-1H-pyrazole-3-carboxamide (6-b)

Cyanogen bromide (72.8 mg, 0.687 mmol) was added dropwise to a 0° C. solution of N-(3-azabicyclo[3.2.0]heptan-1-yl)-5-(2-phenoxyphenyl)-1H-pyrazole-3-carboxamide 2,2,2-trifluoroacetate (350 mg, 0.763 mmol) and sodium bicarbonate (785 mg, 9.25 mmol) in DMF (2 mL). The mixture was stirred for 1 h at 25° C. The solids were filtered out. The filtrate was directly purified by Prep-HPLC (Column:)(Bridge Shield RP18 OBD Column, 5 μm, 30×150 mm; Mobile phase, A: water (containing 0.05% ammonium hydrogen) and B: acetonitrile (35% B to 65% over 7 min); Detector: UV 220 and 254 nm) to afford N-(3-cyano-3-azabicyclo[3.2.0]heptan-1-yl)-5-(2-phenoxyphenyl)-1H-pyrazole-3-carboxamide as a white solid (70.0 mg). This material was separated by chiral-HPLC (Column: Chiralpak IG, 2*25 cm, 5 μm; Mobile Phase, A: MTBE and B: EtOH (hold 15% in 24 min); Flow rate: 20 mL/min; Detector: 220/254 nm). The first eluting isomer was collected, and the absolute stereochemistry was arbitrarily assigned as (1R,5S): N-((1R,5S)-3-cyano-3-azabicyclo[3.2.0]heptan-1-yl)-5-(2-phenoxyphenyl)-1H-pyrazole-3-carboxamide ($RT_1$=10.9 min) as a white solid (6-a, 28.5 mg, 10%). LCMS (ES, m/z): 400 $[M+H]^+$. $^1$H-NMR (DMSO-$d_6$, 400 MHz) δ (ppm): 13.68-13.62 (m, 1H), 8.92-8.61 (m, 1H), 8.03-7.86 (m, 1H), 7.42-7.23 (m, 4H), 7.21-7.12 (m, 1H), 7.03-6.89 (m, 4H), 3.73-3.70 (m, 1H), 3.68-3.56 (m, 1H), 3.39-3.31 (m, 2H), 3.08-3.05 (m, 1H), 2.34-2.31 (m, 1H), 2.20-2.08 (m, 2H), 1.61-1.58 (m, 1H). The second eluting isomer was collected, and the absolute stereochemistry was arbitrarily assigned as (1S,5R): N-((1S,5R)-3-cyano-3-azabicyclo[3.2.0]heptan-1-yl)-5-(2-phenoxyphenyl)-1H-pyrazole-3-carboxamide ($RT_2$=12.7 min) as a white solid (6-b, 20.6 mg, 8%). LCMS (ES, m/z): 400 $[M+H]^+$. $^1$H-NMR (DMSO-$d_6$, 400 MHz) δ (ppm): 13.68-13.62 (m, 1H), 8.92-8.61 (m, 1H), 8.03-7.86 (m, 1H), 7.42-7.29 (m, 4H), 7.21-7.12 (m, 1H), 7.04-6.89 (m, 4H), 3.73-3.70 (m, 1H), 3.68-3.54 (m, 1H), 3.39-3.31 (m, 2H), 3.08-3.05 (m, 1H), 2.34-2.31 (m, 1H), 2.20-2.08 (m, 2H), 1.61-1.58 (m, 1H). Alternatively, the absolute stereochemistry of the first and second eluting isomers could have been arbitrarily assigned as (1S,5R) and (1R,5S), respectively.

Example 4
Preparation of N-((1S,5R)-3-cyano-3-azabicyclo[3.1.0]hexan-1-yl)-5-(2-phenoxyphenyl)-1H-pyrazole-3-carboxamide (3-a) and N-((1R,5S)-3-cyano-3-azabicyclo[3.1.0]hexan-1-yl)-5-(2-phenoxyphenyl)-1H-pyrazole-3-carboxamide (3-b)
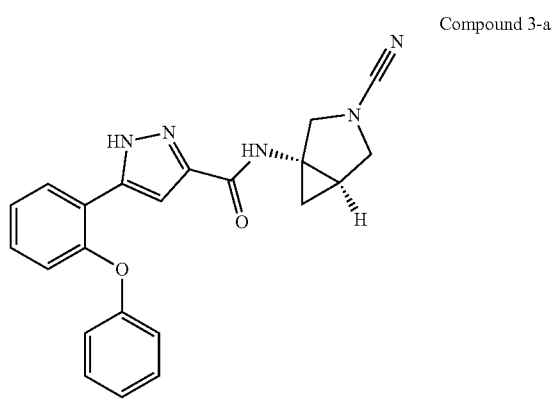
Compound 3-a
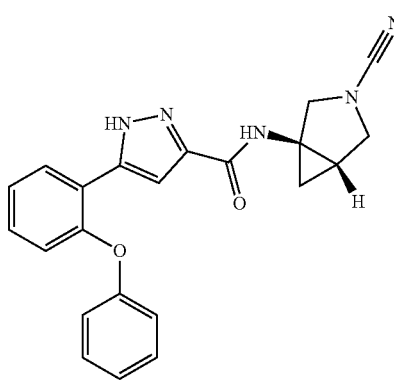
Compound 3-b
Compounds 3-a and 3-b were prepared by the following route:
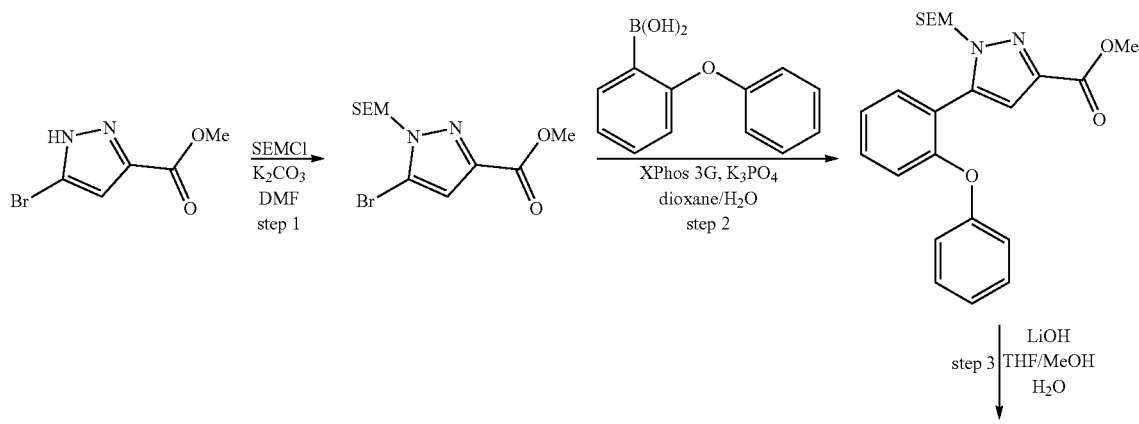
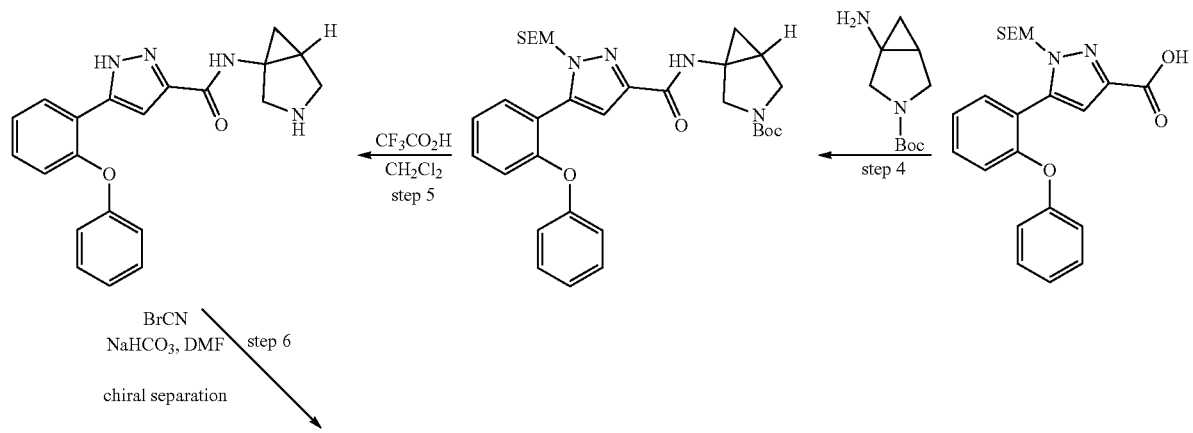

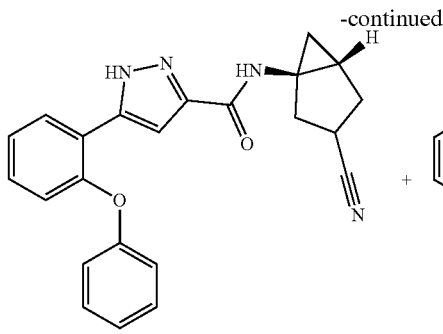

Coupound 3-a
(first eluting isomer)

+

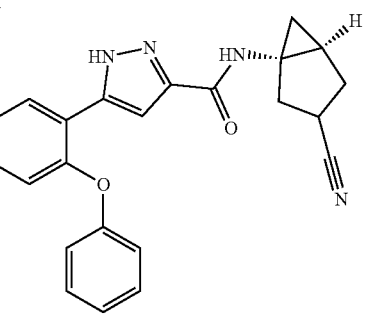

Coupound 3-b
(second eluting isomer)

Step 1. Methyl 5-bromo-1-[[2-(trimethylsilyl)ethoxy]methyl]-1H-pyrazole-3-carboxylate 2-(Trimethylsilyl)ethoxymethyl chloride (12.2 mL, 68.8 mmol) was added dropwise to a 0° C. solution of methyl 5-bromo-1H-pyrazole-3-carboxylate (5.00 g, 24.5 mmol) and potassium carbonate (18.0 g, 130 mmol) in DMF (10 mL). The resulting mixture stirred for 14 h at 25° C. The reaction was quenched with water (20 mL) at 0° C. The resulting mixture was extracted with ethyl acetate (3×30 mL). The combined organic layers were washed with brine (2×100 mL), dried over anhydrous sodium sulfate, and filtered. The filtrate was concentrated under vacuum. The residue was purified by silica gel chromatography (eluting with 15:1 petroleum ether/ethyl acetate) to afford methyl 5-bromo-1-[[2-(trimethylsilyl)ethoxy]methyl]-1H-pyrazole-3-carboxylate (6.20 g, 76%) as a yellow oil. LCMS (ES, m/z): 335, 337 [M+H]$^+$.

Step 2. Methyl 5-(2-phenoxyphenyl)-1-[[2-(trimethylsilyl)ethoxy]methyl]-1H-pyrazole-3-carboxylate A solution of methyl 5-bromo-1-[[2-(trimethylsilyl)ethoxy]methyl]-1H-pyrazole-3-carboxylate (6.20 g, 18.5 mmol), (2-phenoxyphenyl)boronic acid (4.96 g, 23.2 mmol), XPhos-Pd-G3 (3.12 g, 36.9 mmol) and potassium phosphate tribasic (25.4 mg, 37.1 mmol) in dioxane (120 mL) and water (24 mL) was stirred for 15 h at 100° C. in an oil bath. The mixture was cooled to 25° C. The resulting mixture was concentrated under vacuum. The residue was diluted with water (30 mL). The resulting mixture was extracted with ethyl acetate (3×30 mL). The combined organic layers were dried over anhydrous sodium sulfate, filtered, and concentrated. The residue was purified by reverse phase chromatography (Column:)(Bridge Shield RP18 OBD Column, 5 μm, 30×150 mm; Mobile phase, A: water (containing 0.05% ammonium hydrogen) and B: acetonitrile (5% B to 72% over 20 min); Detector: UV 220 and 254 nm) to afford methyl 5-(2-phenoxyphenyl)-1-[[2-(trimethylsilyl)ethoxy]methyl]-1H-pyrazole-3-carboxylate as a yellow solid (3.20 g, 41%). LCMS (ES, m/z): 425 [M+H]$^+$.

Step 3. 5-(2-Phenoxyphenyl)-1-[[2-(trimethylsilyl)ethoxy]methyl]-1H-pyrazole-3-carboxylic acid A solution of methyl 5-(2-phenoxyphenyl)-1-[[2-(trimethylsilyl)ethoxy]methyl]-1H-pyrazole-3-carboxylate (1.40 g, 3.30 mmol) and lithium hydroxide (810 mg, 34.0 mmol) in THF (60.0 mL), water (15.0 mL), and methanol (30.0 mL) was stirred for 4 h at 50° C. The mixture was cooled to 25° C. and concentrated under vacuum. The pH value of the residue was adjusted to 3-4 with 3 N aqueous hydrochloric acid solution. The resulting mixture was extracted with ethyl acetate (3×30 mL). The combined organic layers were washed with brine (2×100 mL), dried over anhydrous sodium sulfate, filtered, and concentrated. The residue was purified by silica gel chromatography (eluting with 2:1 petroleum ether/ethyl acetate) to afford 5-(2-phenoxyphenyl)-1-[[2-(trimethylsilyl)ethoxy]methyl]-1H-pyrazole-3-carboxylic acid as an off-white solid (1.00 g, 74%). LCMS (ES, m/z): 411 [M+H]$^+$.

Step 4. tert-butyl-(5-(2-phenoxyphenyl)-14(2-(trimethylsilyl)ethoxy)methyl)-1H-pyrazole-3-carboxamido)-3-azabicyclo[3.1.0]hexane-3-carboxylate A solution of 5-(2-phenoxyphenyl)-1-[[2-(trimethylsilyl)ethoxy]methyl]-1H-pyrazole-3-carboxylic acid (300 mg, 0.723 mmol), tert-butyl 1-amino-3-azabicyclo[3.1.0]hexane-3-carboxylate (145 mg, 0.723 mmol), HATU (278 mg, 0.723 mmol) and N,N-diisopropylethylamine (0.242 mL, 1.47 mmol) in DMF (3 mL) was stirred for 30 min at 25° C. The reaction was quenched with water (10 mL) at 25° C. The resulting mixture was extracted with ethyl acetate (3×10 mL). The combined organic layers were washed with brine (2×30 mL), dried over anhydrous sodium sulfate, filtered, and concentrated. The residue was purified by silica gel chromatography (eluting with 4:1 petroleum ether/ethyl acetate) to afford tert-butyl 1-(5-(2-phenoxyphenyl)-1-((2-(trimethylsilyl)ethoxy)methyl)-1H-pyrazole-3-carboxamido)-3-azabicyclo[3.1.0]hexane-3-carboxylate as an off-white solid (280 mg, 67%). LCMS (ES, m/z): 591 [M+H]$^+$.

Step 5. N-(3-azabicyclo[3.1.0]hexan-1-yl)-5-(2-phenoxyphenyl)-1H-pyrazole-3-carboxamide 2,2,2-trifluoroacetate A solution of tert-butyl 1-(5-(2-phenoxyphenyl)-1-((2-(trimethylsilyl)ethoxy)methyl)-1H-pyrazole-3-carboxamido)-3-azabicyclo[3.1.0]hexane-3-carboxylate (280 mg, 0.475 mmol) in trifluoroacetic acid (1 mL) and dichloromethane (3 mL) was stirred for 2 h at 25° C. The resulting mixture was concentrated under vacuum to afford N-(3-azabicyclo[3.1.0]hexan-1-yl)-5-(2-phenoxyphenyl)-1H-pyrazole-3-carboxamide 2,2,2-trifluoroacetate as a yellow oil (285 mg, crude). LCMS (ES, m/z): 361 [M+H]$^+$.

Step 6. N-((1S,5R)-3-cyano-3-azabicyclo[3.1.0]hexan-1-yl)-5-(2-phenoxyphenyl)-1H-pyrazole-3-carboxamide (3-a) and N-((1R,5S)-3-cyano-3-azabicyclo[3.1.0]hexan-1-yl)-5-(2-phenoxyphenyl)-1H-pyrazole-3-carboxamide (3-b)

Cyanogen bromide (58.5 mg, 0.552 mmol) was added dropwise to a 0° C. solution of N-(3-azabicyclo[3.1.0]hexan-1-yl)-5-(2-phenoxyphenyl)-1H-pyrazole-3-carboxamide 2,2,2-trifluoroacetate (280 mg, 0.613 mmol) and sodium bicarbonate (653 mg, 7.69 mmol) in DMF (2 mL). The mixture was stirred for 1 h at 25° C. The reaction was cooled to 0° C. and quenched with water (10 mL). The resulting mixture was extracted with ethyl acetate (3×10 mL). The combined organic layers were washed with brine (20 mL), dried over anhydrous sodium sulfate, filtered, and concentrated. The residue was purified by Prep-HPLC (Column:)(Bridge Shield RP18 OBD Column, 5 μm, 30×150 mm; Mobile phase, A: water (containing 0.05% ammonium hydrogen) and B: acetonitrile (28% B to 48% over 7 min); Detector: UV 220 and 254 nm) to afford N-(3-cyano-3-azabicyclo[3.1.0]hexan-1-yl)-5-(2-phenoxyphenyl)-1H-pyrazole-3-carboxamide as a white solid (60.0 mg). This material was separated by chiral-HPLC (Column: Chiralpak IG, 2*25 cm, 5 μm; Mobile Phase, A: MTBE and B: EtOH (hold 30% in 10.5 min); Flow rate: 13 mL/min; Detector: 220/254 nm). The first eluting isomer was collected, and the absolute stereochemistry was arbitrarily assigned as (1S,5R): N-((1S,5R)-3-cyano-3-azabicyclo[3.1.0]hexan-1-yl)-5-(2-phenoxyphenyl)-1H-pyrazole-3-carboxamide (RT$_1$=6.45 min) as a pink solid (3-a, 30.3 mg, 14%). LCMS (ES, m/z): 386 [M+H]$^+$. $^1$H-NMR (DMSO-d$_6$, 400 MHz) δ (ppm): 13.72-13.64 (m, 1H), 9.08-8.70 (m, 1H), 8.05-7.85 (m, 1H), 7.44-7.29 (m, 4H), 7.20-7.12 (m, 1H), 7.04-6.87 (m, 4H), 3.69-3.66 (m, 1H), 3.57-3.48 (m, 3H), 1.78-1.74 (m, 1H), 1.17-1.14 (m, 1H), 0.87-0.82 (m, 1H). The second eluting isomer was collected, and the absolute stereochemistry was arbitrarily assigned as (1R,5S); N-((1R,5S)-3-cyano-3-azabicyclo[3.1.0]hexan-1-yl)-5-(2-phenoxyphenyl)-1H-pyrazole-3-carboxamide (RT$_2$=8.97 min) (3-b, 29.9 mg, 14%) as a white solid. LCMS (ES, m/z): 386 [M+H]$^+$. $^1$H-NMR (DMSO-d$_6$, 400 MHz) δ (ppm): 13.72-13.64 (m, 1H), 9.08-8.70 (m, 1H), 8.05-7.85 (m, 1H), 7.44-7.29 (m, 4H), 7.22-7.12 (m, 1H), 7.04-6.87 (m, 4H), 3.69-3.66 (m, 1H), 3.57-3.51 (m, 3H), 1.78-1.74 (m, 1H), 1.17-1.14 (m, 1H), 0.87-0.82 (m, 1H). Alternatively, the absolute stereochemistry of the first and second eluting isomers could have been arbitrarily assigned as (1R,5S) and (1S,5R), respectively.

Many modifications and variations of the embodiments described herein may be made without departing from the scope, as is apparent to those skilled in the art. The specific embodiments described herein are offered by way of example only.

What is claimed is:

1. A compound of formula (I):

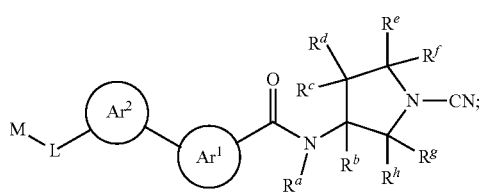

I or a pharmaceutically acceptable salt thereof, wherein R$^a$, R$^b$, R$^c$, R$^d$, R$^e$, R$^f$, R$^g$, and R$^h$ are defined as follows:

(i) R$^a$ and R$^b$ form a C$_1$-C$_4$ alkylene group between the atoms to which they are attached, wherein said C$_1$-C$_4$ alkylene group is substituted with 0-4 substituents selected from the group consisting of halogen, C$_1$-C$_3$ alkyl, and C$_1$-C$_3$ haloalkyl; and R$^c$, R$^d$, R$^e$, R$^f$, R$^g$, and R$^h$ are each independently hydrogen, halogen, C$_1$-C$_3$ alkyl, or C$_1$-C$_3$ haloalkyl; or (ii) R$^a$ and R$^e$ form a C$_1$-C$_2$ alkylene group between the atoms to which they are attached, wherein said C$_1$-C$_2$ alkylene group is substituted with 0-4 substituents selected from the group consisting of halogen, C$_1$-C$_3$ alkyl, and C$_1$-C$_3$ haloalkyl; and R$^b$, R$^c$, R$^d$, R$^f$, R$^g$, and R$^h$ are each independently hydrogen, halogen, C$_1$-C$_3$ alkyl, or C$_1$-C$_3$ haloalkyl; or (iii) R$^a$ and R$^g$ form a C$_1$-C$_3$ alkylene group between the atoms to which they are attached, wherein said C$_1$-C$_3$ alkylene group is substituted with 0-4 substituents selected from the group consisting of halogen, C$_1$-C$_3$ alkyl, and C$_1$-C$_3$ haloalkyl; and R$^b$, R$^c$, R$^d$, R$^e$, R$^f$, and R$^h$ are each independently hydrogen, halogen, C$_1$-C$_3$ alkyl, or C$_1$-C$_3$ haloalkyl; or (iv) R$^b$ and R$^c$ form a C$_1$-C$_4$ alkylene group between the atoms to which they are attached, wherein said C$_1$-C$_4$ alkylene group is substituted with 0-4 substituents selected from the group consisting of halogen, C$_1$-C$_3$ alkyl, and C$_1$-C$_3$ haloalkyl; and R$^a$, R$^d$, R$^e$, R$^f$, R$^g$, and R$^h$ are each independently hydrogen, halogen, C$_1$-C$_3$ alkyl, or C$_1$-C$_3$ haloalkyl; or (v) R$^b$ and R$^e$ form a C$_1$-C$_3$ alkylene group between the atoms to which they are attached, wherein said C$_1$-C$_3$ alkylene group is substituted with 0-4 substituents selected from the group consisting of halogen, C$_1$-C$_3$ alkyl, and C$_1$-C$_3$ haloalkyl; and R$^a$, R$^c$, R$^d$, R$^f$, R$^g$, and R$^h$ are each independently hydrogen, halogen, C$_1$-C$_3$ alkyl, or C$_1$-C$_3$ haloalkyl; or (vi) R$^b$ and R$^g$ form a C$_1$-C$_4$ alkylene group between the atoms to which they are attached, wherein said C$_1$-C$_4$ alkylene group is substituted with 0-4 substituents selected from the group consisting of halogen, C$_1$-C$_3$ alkyl, and C$_1$-C$_3$ haloalkyl; and R$^a$, R$^c$, R$^d$, R$^e$, R$^f$, and R$^h$ are each independently hydrogen, halogen, C$_1$-C$_3$ alkyl, or C$_1$-C$_3$ haloalkyl; or (vii) R$^c$ and R$^d$, together with the atom to which they are attached, form a 3-6 membered cycloalkyl or heterocycloalkyl, wherein said 3-6 membered cycloalkyl or heterocycloalkyl is substituted with 0-4 substituents selected from the group consisting of halogen, C$_1$-C$_3$ alkyl, and C$_1$-C$_3$ haloalkyl; and R$^a$, R$^b$, R$^e$, R$^f$, R$^g$, and R$^h$ are each independently hydrogen, halogen, C$_1$-C$_3$ alkyl, or C$_1$-C$_3$ haloalkyl; or (viii) R$^c$ and R$^d$ together form =O; and R$^a$, R$^b$, R$^e$, R$^f$, R$^g$, and R$^h$ are each independently hydrogen, halogen, C$_1$-C$_3$ alkyl, or C$_1$-C$_3$ haloalkyl; or (ix) R$^c$ and R$^e$ form a C$_1$-C$_4$ alkylene group between the atoms to which they are attached, wherein said C$_1$-C$_4$ alkylene group is substituted with 0-4 substituents selected from the group consisting of halogen, C$_1$-C$_3$ alkyl, and C$_1$-C$_3$ haloalkyl; and R$^a$, R$^b$, R$^d$, R$^f$, R$^g$, and R$^h$ are each independently hydrogen, halogen, C$_1$-C$_3$ alkyl, or C$_1$-C$_3$ haloalkyl; or (x) R$^c$ and R$^g$ form a C$_1$-C$_3$ alkylene group between the atoms to which they are attached, wherein said C$_1$-C$_3$ alkylene group is substituted with 0-4 substituents selected from the group consisting of halogen, C$_1$-C$_3$ alkyl, and C$_1$-C$_3$ haloalkyl; and R$^a$, R$^b$, $R^d$, $R^e$, $R^f$, and $R^h$ are each independently hydrogen, halogen, $C_1$-$C_3$ alkyl, or $C_1$-$C_3$ haloalkyl; or (xi) $R^e$ and $R^f$, together with the atom to which they are attached, form a 3-6 membered cycloalkyl or heterocycloalkyl, wherein said 3-6 membered cycloalkyl or heterocycloalkyl is substituted with 0-4 substituents selected from the group consisting of halogen, $C_1$-$C_3$ alkyl, and $C_1$-$C_3$ haloalkyl; and $R^a$, $R^b$, $R^c$, $R^d$, $R^g$, and $R^h$ are each independently hydrogen, halogen, $C_1$-$C_3$ alkyl, or $C_1$-$C_3$ haloalkyl; or (xii) $R^e$ and $R^f$ together form =O; and $R^a$, $R^b$, $R^c$, $R^d$, $R^g$ and $R^h$ are each independently hydrogen, halogen, $C_1$-$C_3$ alkyl, or $C_1$-$C_3$ haloalkyl; or (xiii) $R^e$ and $R^g$ form a $C_1$-$C_3$ alkylene group between the atoms to which they are attached, wherein said $C_1$-$C_3$ alkylene group is substituted with 0-4 substituents selected from the group consisting of halogen, $C_1$-$C_3$ alkyl, and $C_1$-$C_3$ haloalkyl; and $R^a$, $R^b$, $R^c$, $R^d$, $R^f$, and $R^h$ are each independently hydrogen, halogen, $C_1$-$C_3$ alkyl, or $C_1$-$C_3$ haloalkyl; or (xiv) $R^g$ and $R^h$, together with the atom to which they are attached, form a 3-6 membered cycloalkyl or heterocycloalkyl, wherein said 3-6 membered cycloalkyl or heterocycloalkyl is substituted with 0-4 substituents selected from the group consisting of halogen, $C_1$-$C_3$ alkyl, and $C_1$-$C_3$ haloalkyl; and $R^a$, $R^b$, $R^c$, $R^d$, $R^e$, and $R^f$ are each independently hydrogen, halogen, $C_1$-$C_3$ alkyl, or $C_1$-$C_3$ haloalkyl; or (xv) $R^g$ and $R^h$ together form =O; and $R^a$, $R^b$, $R^c$, $R^d$, $R^e$, and $R^f$ are each independently hydrogen, halogen, $C_1$-$C_3$ alkyl, or $C_1$-$C_3$ haloalkyl; and $Ar^1$ is phenylene or 5-6 membered heteroarylene, wherein said phenylene or heteroarylene is substituted with m $R^1$ groups; and $Ar^2$ is phenylene or 5-6 membered heteroarylene, wherein said phenylene or heteroarylene is substituted with n $R^2$ groups;

L is —O—, —S—, —$NR^3$—, —$C(R^4)_2$—, —$S(O)_2$—, or —S(O)—;

M is 3-6 membered cycloalkyl, phenyl, or 5-6 membered heteroaryl, wherein said cycloalkyl, phenyl, or heteroaryl is substituted with p $R^5$ groups;

each occurrence of $R^1$, $R^2$, and $R^5$ is independently halo, cyano, $NO_2$, oxo, hydroxyl, —$R^6$, —$OR^6$, $C_1$-$C_6$ alkyl, $C_1$-$C_6$ haloalkyl, $C_1$-$C_6$ hydroxyalkyl, —$C_1$-$C_6$ alkylene-$R^6$, $C_1$-$C_6$ alkoxy, $C_1$-$C_6$ haloalkoxy, —$C_0$-$C_3$ alkylene-$NR^6R^7$, —$C_0$-$C_3$ alkylene-$NR^7R^8$, —$C_0$-$C_3$ alkylene-$C(O)NR^6R^7$, —$C_0$-$C_3$ alkylene-$C(O)NR^7R^8$, —$C_0$-$C_3$ alkylene-$NR^7C(O)R^6$, —$C_0$-$C_3$ alkylene-$NR^7C(O)R^8$, —$C_0$-$C_3$ alkylene-$NR^7S(O)_2R^6$, —$C_0$-$C_3$ alkylene-$C(O)R^6$, —$C_0$-$C_3$ alkylene-$C(O)R^7$, —$C_0$-$C_3$ alkylene-$SR^6$, —$C_0$-$C_3$ alkylene-$S(O)R^6$, —$C_0$-$C_3$ alkylene-$S(O)_2R^6$, —$C_0$-$C_3$ alkylene-$S(O)_2R^7$, —$C_0$-$C_3$ alkylene-$S(O)_2NR^6R^7$, —$C_0$-$C_3$ alkylene-$S(O)_2NR^7R^8$, —$C_0$-$C_3$ alkylene-$NR^7C(O)NR^8R^9$, —$C_0$-$C_3$ alkylene-$NR^7S(O)_2NR^8R^9$, —$C_0$-$C_3$ alkylene-$C(O)OR^7$, —$C_0$-$C_3$ alkylene-$C(O)OR^6$, —$C_0$-$C_3$ alkylene-$OC(O)R^7$, —$C_0$-$C_3$ alkylene-$OC(O)R^6$, —$C_0$-$C_3$ alkylene-$NR^7C(O)OR^8$, or —$C_0$-$C_3$ alkylene-$NR^7S(O)_2R^8$;

$R^3$ is H, $C_1$-$C_6$ alkyl, or $C_1$-$C_6$ haloalkyl;

each $R^4$ is independently H, $C_1$-$C_6$ alkyl, or $C_1$-$C_6$ haloalkyl, or two $R^4$ groups together with the carbon atom to which they are attached form a 3-6 membered cycloalkyl or heterocycloalkyl;

each $R^6$ is 5-10 membered heteroaryl, 4-10 membered heterocycloalkyl, 6-10 membered aryl, or 3-8 membered cycloalkyl, wherein said heteroaryl, heterocycloalkyl, aryl, or cycloalkyl is optionally substituted with 1-5 substituents independently selected from the group consisting of halo, oxo, $C_1$-$C_6$ alkyl, $C_1$-$C_6$ haloalkyl, $C_1$-$C_6$ hydroxyalkyl, $C_1$-$C_6$ alkoxy, $C_1$-$C_6$ haloalkoxy, $C_2$-$C_6$ alkenyl, $C_2$-$C_6$ alkynyl, 5-10 membered heteroaryl, 4-10 membered heterocycloalkyl, 6-10 membered aryl, 3-8 membered cycloalkyl, —$NR^{10}C(O)NR^{11}R^{12}$, —$NR^{10}R^{11}$, —$C(O)R^{10}$, —$NR^{10}C(O)R^{11}$, —$NR^{10}C(O)OR^{11}$, —$S(O)_2R^{10}$, —$C(O)NR^{10}R^{11}$, —$C(O)OR^{10}$, —$S(O)_2NR^{10}R^{11}$, —$NR^{10}S(O)_2R^{11}$, —$OR^{10}$, —$OC(O)R^{10}$, —$OS(O)_2R^{10}$, —$OC(O)NR^{10}R^{11}$, —$OC(O)OR^{10}$, —$OS(O)_2NR^{10}R^{11}$, —$C(O)NR^{10}C(O)NR^{11}R^{12}$, —$C(O)C(O)R^{10}$, —$C(O)NR^{10}C(O)R^{11}$, —$C(O)NR^{10}C(O)OR^{11}$, —$C(O)S(O)_2R^{10}$, —$C(O)C(O)NR^{10}R^{11}$, —$C(O)C(O)OR^{10}$, —$C(O)S(O)_2NR^{10}R^{11}$, —$C(O)NR^{10}S(O)_2R^{11}$, —$C_1$-$C_6$ alkylene-$R^{10}$, —$C_1$-$C_6$ alkylene-$NR^{10}C(O)NR^{11}R^{12}$, —$C_1$-$C_6$ alkylene-$NR^{10}NR^{11}$, —$C_1$-$C_6$ alkylene-$C(O)R^{10}$, —$C_1$-$C_6$ alkylene-$NR^{10}C(O)R^{11}$, —$C_1$-$C_6$ alkylene-$NR^{10}C(O)OR^{11}$, —$C_1$-$C_6$ alkylene-$S(O)_2R^{10}$, —$C_1$-$C_6$ alkylene-$C(O)NR^{10}R^{11}$, —$C_1$-$C_6$ alkylene-$C(O)OR^{10}$, —$C_1$-$C_6$ alkylene-$S(O)_2NR^{10}R^{11}$, —$C_1$-$C_6$ alkylene-$NR^{10}S(O)_2R^{11}$, —$C_1$-$C_6$ alkenylene-$R^{10}$, —$C_1$-$C_6$ alkenylene-$NR^{10}C(O)NR^{11}R^{12}$, —$C_1$-$C_6$ alkenylene-$NR^{10}R^{11}$, —$C_1$-$C_6$ alkenylene-$C(O)R^{10}$, —$C_1$-$C_6$ alkenylene-$NR^{10}C(O)R^{11}$, —$C_1$-$C_6$ alkenylene-$NR^{10}C(O)OR^{11}$, —$C_1$-$C_6$ alkenylene-$S(O)_2R^{10}$, —$C_1$-$C_6$ alkenylene-$C(O)NR^{10}R^{11}$, —$C_1$-$C_6$ alkenylene-$C(O)OR^{10}$, —$C_1$-$C_6$ alkenylene-$S(O)_2NR^{10}R^{11}$, and —$C_1$-$C_6$ alkenylene-$NR^{10}S(O)_2R^{11}$;

each $R^7$, $R^8$, and $R^9$ is independently hydrogen or $C_1$-$C_6$ alkyl;

each $R^{10}$, $R^{11}$, and $R^{12}$ is independently hydrogen, $C_1$-$C_6$ alkyl, 5-10 membered heteroaryl, 4-10 membered heterocycloalkyl, 6-10 membered aryl, or 3-8 membered cycloalkyl;

m is 0-4;

n is 0-4; and p is 0-4.

2. The compound of claim 1, wherein the compound is of formula (I-C):

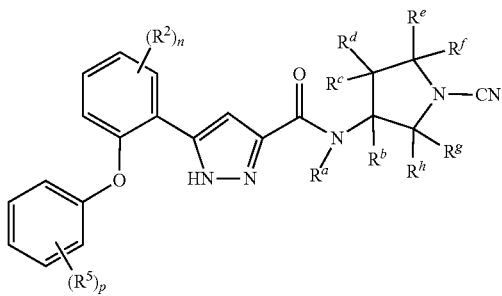

I-C or a pharmaceutically acceptable salt thereof.

3. The compound of claim 1, wherein $R^b$ and $R^c$ form a $C_1$-$C_4$ alkylene group between the atoms to which they are attached, and $R^a$, $R^d$, $R^e$, $R^f$, $R^g$, and $R^h$ are each hydrogen.

4. The compound of claim 1, wherein the compound is of formula (I-1):

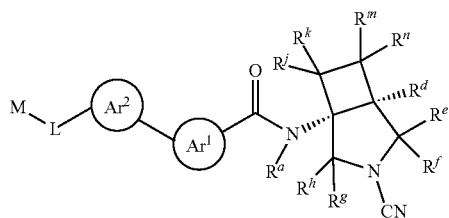

I-1 or a pharmaceutically acceptable salt thereof, wherein $R^j$, $R^k$, $R^m$, and $R^n$ are each independently hydrogen, halogen, $C_1$-$C_3$ alkyl, or $C_1$-$C_3$ haloalkyl.

5. The compound of claim 1, wherein the compound is of formula (I-2):

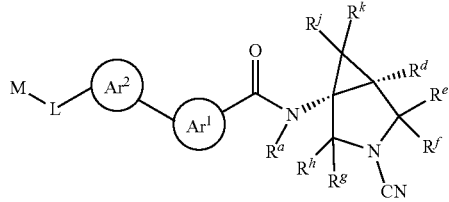

I-2 or a pharmaceutically acceptable salt thereof, wherein $R^j$ and $R^k$ are each independently hydrogen, halogen, $C_1$-$C_3$ alkyl, or $C_1$-$C_3$ haloalkyl.

6. The compound of claim 1, wherein the compound is of formula (I-3):

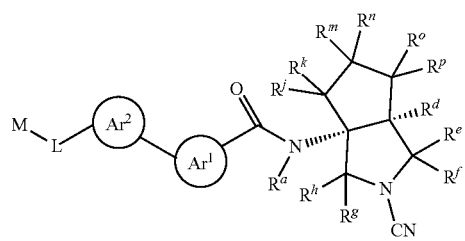

I-3 or a pharmaceutically acceptable salt thereof, wherein $R^j$, $R^k$, $R^m$, $R^n$, $R^o$, and $R^p$ are each independently hydrogen, halogen, $C_1$-$C_3$ alkyl, or $C_1$-$C_3$ haloalkyl.

7. The compound of claim 1, wherein $R^c$ and $R^e$ form a $C_1$-$C_4$ alkylene group between the atoms to which they are attached; and $R^a$, $R^b$, $R^d$, $R^f$, $R^g$, and $R^h$ are each hydrogen.

8. The compound of claim 1, wherein the compound is of formula (I-4):

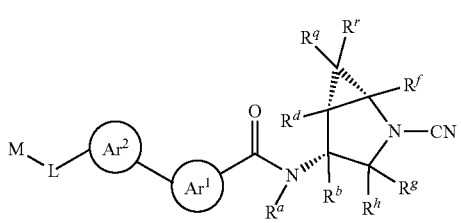

I-4 or a pharmaceutically acceptable salt thereof, wherein $R^q$ and $R^r$ are each independently hydrogen, halogen, $C_1$-$C_3$ alkyl, or $C_1$-$C_3$ haloalkyl.

9. The compound of claim 1, wherein $R^a$ and $R^e$ form a $C_1$-$C_2$ alkylene group between the atoms to which they are attached; and $R^b$, $R^c$, $R^d$, $R^f$, $R^g$, and $R^h$ are each hydrogen.

10. The compound of claim 1, wherein $R^c$ and $R^d$, together with the atom to which they are attached, form a 3-6 membered cycloalkyl or heterocycloalkyl; and $R^a$, $R^b$, $R^e$, $R^f$, $R^g$, and $R^h$ are each hydrogen.

11. The compound of claim 1, wherein $R^c$ and $R^g$ form a $C_1$-$C_3$ alkylene group between the atoms to which they are attached; and $R^a$, $R^b$, $R^d$, $R^e$, $R^f$, and $R^h$ are each hydrogen.

12. The compound of claim 1, wherein $R^e$ and $R^f$, together with the atom to which they are attached, form a 3-6 membered cycloalkyl or heterocycloalkyl; and $R^a$, $R^b$, $R^c$, $R^d$, $R^g$, and $R^h$ are each hydrogen.

13. The compound of claim 1, wherein $R^e$ and $R^g$ form a $C_1$-$C_3$ alkylene group between the atoms to which they are attached; and $R^a$, $R^b$, $R^c$, $R^d$, $R^f$, and $R^h$ are each hydrogen.

14. The compound of claim 1, wherein $Ar^1$ is 5-6 membered heteroarylene.

15. The compound of claim 14, wherein $Ar^2$ is phenylene.

16. The compound of claim 15, wherein L is —O—, —S—, or —NH—.

17. The compound of claim 15, wherein L is —O—.

18. The compound of claim 17, wherein M is phenyl substituted with p $R^5$ groups.

19. The compound of claim 1, wherein each occurrence of $R^1$, $R^2$, and $R^5$ is independently halo, cyano, hydroxyl, $C_{1-6}$ alkyl, $C_{1-6}$ alkoxy, $C_{1-6}$ haloalkyl, and $C_{1-6}$ hydroxyalkyl.

20. A compound, or pharmaceutically acceptable salt thereof, selected from:

| Compound Number | Compound Structure and Chemical Name |
|---|---|
| 1-a | 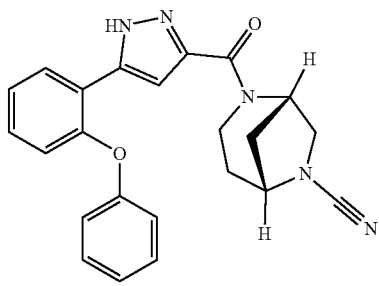 [SMILES: N#CN1C[C@@H]2C[C@H]1CCN2C(=O)c1cc(-c2ccccc2Oc2ccccc2)[nH]n1] (1S,5R)-2-(5-(2-phenoxyphenyl)-1H-pyrazole-3-carbonyl)-2,6-diazabicyclo[3.2.1]octane-6-carbonitrile |
| 1-b | 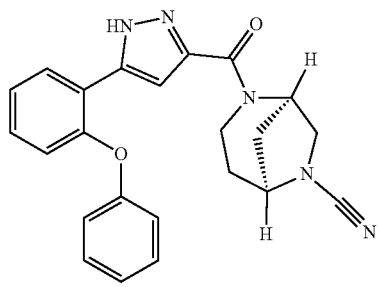 [SMILES: N#CN1C[C@H]2C[C@@H]1CCN2C(=O)c1cc(-c2ccccc2Oc2ccccc2)[nH]n1] (1R,5S)-2-(5-(2-phenoxyphenyl)-1H-pyrazole-3-carbonyl)-2,6-diazabicyclo[3.2.1]octane-6-carbonitrile |
| 2-a | 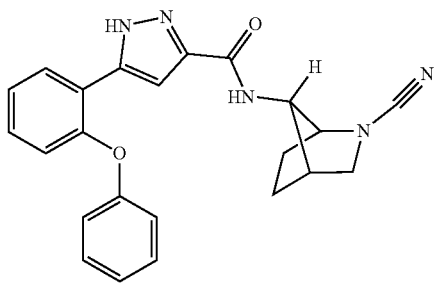 [SMILES: N#CN1CC2CCC1C2NC(=O)c1cc(-c2ccccc2Oc2ccccc2)[nH]n1] N-((1S,4S,7S)-2-cyano-2-azabicyclo[2.2.1]heptan-7-yl)-5-(2-phenoxyphenyl)-1H-pyrazole-3-carboxamide |
| 2-b | 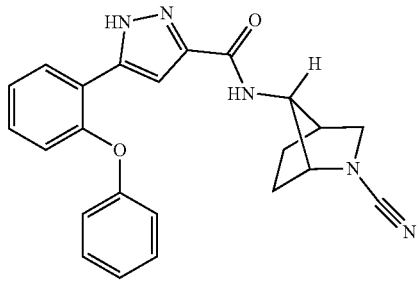 [SMILES: N#CN1CC2CCC1C2NC(=O)c1cc(-c2ccccc2Oc2ccccc2)[nH]n1] N-((1R,4R,7R)-2-cyano-2-azabicyclo[2.2.1]heptan-7-yl)-5-(2-phenoxyphenyl)-1H-pyrazole-3-carboxamide |

| Compound Number | Compound Structure and Chemical Name |
|---|---|
| 3-a | 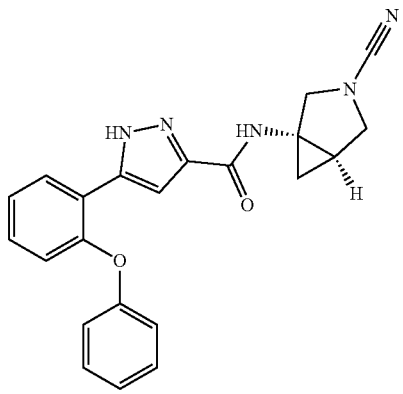 [SMILES: N#CN1C[C@H]2C[C@@]2(NC(=O)c2cc(-c3ccccc3Oc3ccccc3)[nH]n2)C1]<br>N-((1S, 5R)-3-cyano-3-azabicyclo[3.1.0]hexan-1-yl)-5-(2-phenoxyphenyl)-1H-pyrazole-3-carboxamide |
| 3-b | 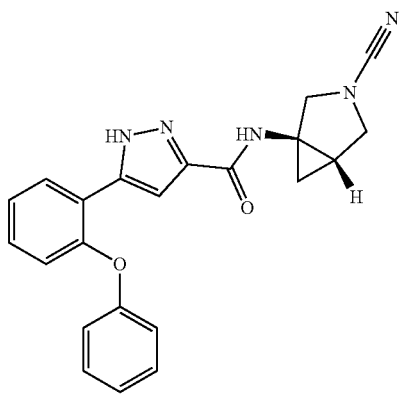 [SMILES: N#CN1C[C@@H]2C[C@]2(NC(=O)c2cc(-c3ccccc3Oc3ccccc3)[nH]n2)C1]<br>N-((1R, 5S)-3-cyano-3-azabicyclo[3.1.0]hexan-1-yl)-5-(2-phenoxyphenyl)-1H-pyrazole-3-carboxamide |
| 4-a | 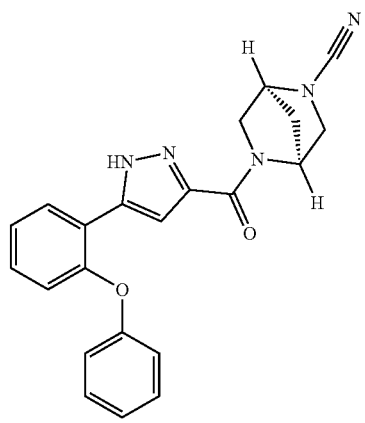 [SMILES: N#CN1C[C@@H]2C[C@H]1CN2C(=O)c1cc(-c2ccccc2Oc2ccccc2)[nH]n1]<br>(1S,4S)-5-(5-(2-phenoxyphenyl)-1H-pyrazole-3-carbonyl)-2,5-diazabicyclo[2.2.1]heptane-2-carbonitrile |

| Compound Number | Compound Structure and Chemical Name |
|---|---|
| 4-b | 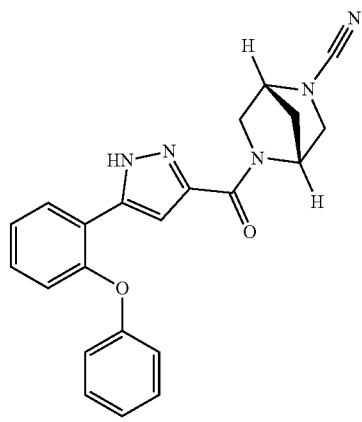 [SMILES: N#CN1C[C@H]2C[C@@H]1CN2C(=O)c1cc(-c2ccccc2Oc2ccccc2)[nH]n1]<br>(1R,4R)-5-(5-(2-phenoxyphenyl)-1H-pyrazole-3-carbonyl)-2,5-diazabicyclo[2.2.1]heptane-2-carbonitrile |
| 5-a | 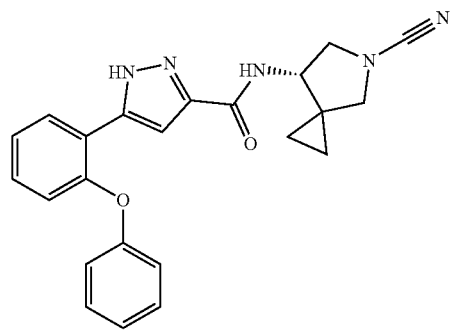 [SMILES: N#CN1C[C@@H](NC(=O)c2cc(-c3ccccc3Oc3ccccc3)[nH]n2)C2(CC2)C1]<br>(S)-N-(5-cyano-5-azaspiro[2.4]heptan-7-yl)-5-(2-phenoxyphenyl)-1H-pyrazole-3-carboxamide |
| 5-b | 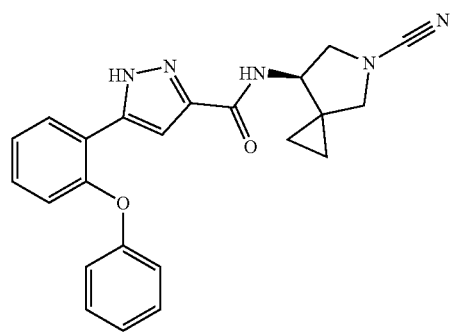 [SMILES: N#CN1C[C@H](NC(=O)c2cc(-c3ccccc3Oc3ccccc3)[nH]n2)C2(CC2)C1]<br>(R)-N-(5-cyano-5-azaspiro[2.4]heptan-7-yl)-5-(2-phenoxyphenyl)-1H-pyrazole-3-carboxamide |

| Compound Number | Compound Structure and Chemical Name |
|---|---|
| 6-a | 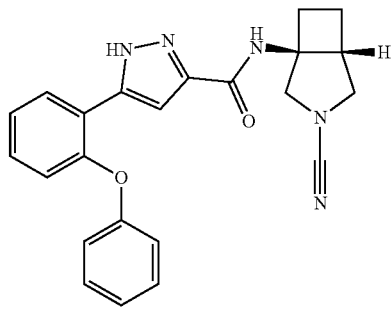 [SMILES: N#CN1C[C@H]2CC[C@@]2(NC(=O)c2cc(-c3ccccc3Oc3ccccc3)[nH]n2)C1]<br>N-((1R,5S)-3-cyano-3-azabicyclo[3.2.0]heptan-1-yl)-5-(2-phenoxyphenyl)-1H-pyrazole-3-carboxamide |
| 6-b | 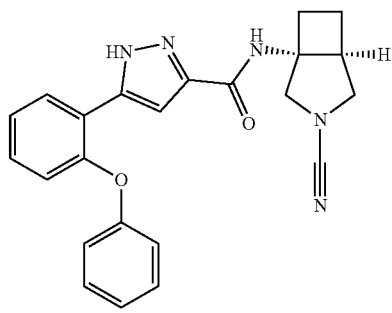 [SMILES: N#CN1C[C@@H]2CC[C@]2(NC(=O)c2cc(-c3ccccc3Oc3ccccc3)[nH]n2)C1]<br>N-((1S,5R)-3-cyano-3-azabicyclo[3.2.0]heptan-1-yl)-5-(2-phenoxyphenyl)-1H-pyrazole-3-carboxamide |
| 7-a | 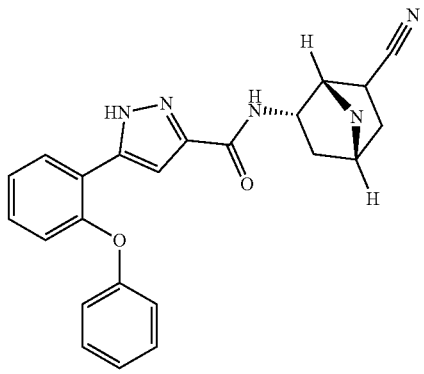 [SMILES: N#CC1C[C@@H]2C[C@H](NC(=O)c3cc(-c4ccccc4Oc4ccccc4)[nH]n3)[C@H]1N2]<br>N-((1S,2S,4R)-7-cyano-7-azabicyclo[2.2.1]heptan-2-yl)-5-(2-phenoxyphenyl)-1H-pyrazole-3-carboxamide |

-continued

| Compound Number | Compound Structure and Chemical Name |
|---|---|
| 7-b | 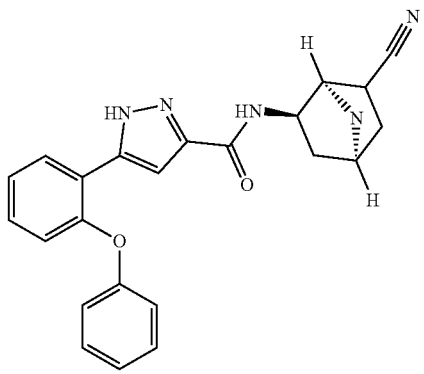 [SMILES: N#CC1C[C@H]2C[C@@H](NC(=O)c3cc(-c4ccccc4Oc4ccccc4)[nH]n3)[C@@H]1N2]<br>N-((1R,2R,4S)-7-cyano-7-azabicyclo[2.2.1]heptan-2-yl)-5-(2-phenoxyphenyl)-1H-pyrazole-3-carboxamide |
| 8-a | 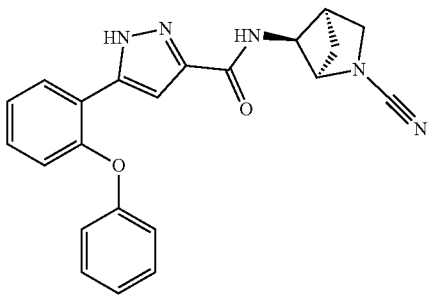 [SMILES: N#CN1C[C@H]2C[C@@H]1[C@H]2NC(=O)c1cc(-c2ccccc2Oc2ccccc2)[nH]n1]<br>N-[(1R,4R,5S)-2-cyano-2-azabicyclo[2.1.1]hexan-5-yl]-5-(2-phenoxyphenyl)-1H-pyrazole-3-carboxamide |
| 8-b | 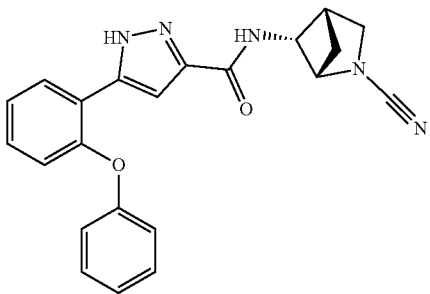 [SMILES: N#CN1C[C@@H]2C[C@H]1[C@@H]2NC(=O)c1cc(-c2ccccc2Oc2ccccc2)[nH]n1]<br>N-((1S,4S,5R)-2-cyano-2-azabicyclo[2.1.1]hexan-5-yl)-5-(2-phenoxyphenyl)-1H-pyrazole-3-carboxamide |
| 9-a | 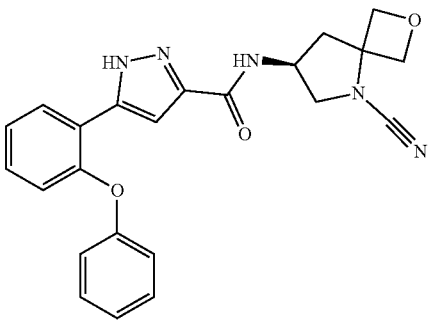 [SMILES: N#CN1C[C@@H](NC(=O)c2cc(-c3ccccc3Oc3ccccc3)[nH]n2)CC12COC2]<br>(S)-N-(5-cyano-2-oxa-5-azaspiro[3.4]octan-7-yl)-5-(2-phenoxyphenyl)-1H-pyrazole-3-carboxamide |

-continued

| Compound Number | Compound Structure and Chemical Name |
|---|---|
| 9-b | 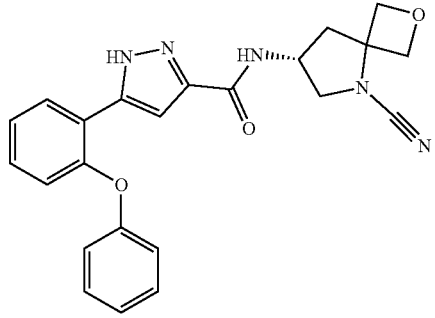 [SMILES: N#CN1C[C@H](NC(=O)c2cc(-c3ccccc3Oc3ccccc3)[nH]n2)CC12COC2]<br>(R)-N-(5-cyano-2-oxa-5-azaspiro[3.4]octan-7-yl)-5-(2-phenoxyphenyl)-1H-arazole-3-carboxamide |
| 13-a | 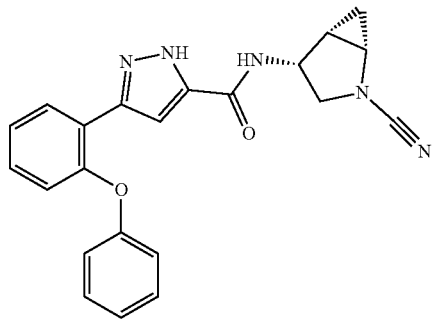 [SMILES: N#CN1C[C@H](NC(=O)c2cc(-c3ccccc3Oc3ccccc3)n[nH]2)[C@@H]2C[C@@H]21]<br>N-((1S,4R,5S)-2-cyano-2-azabicyclo[3.1.0]hexan-4-yl)-3-(2-phenoxyphenyl)-1H-pyrazole-5-carboxamide |
| 13-b | 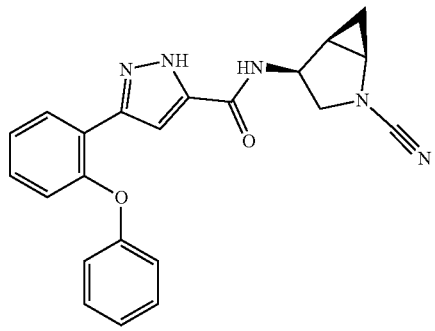 [SMILES: N#CN1C[C@@H](NC(=O)c2cc(-c3ccccc3Oc3ccccc3)n[nH]2)[C@H]2C[C@H]21]<br>N-((1R,4S,5R)-2-cyano-2-azabicyclo[3.1.0]hexan-4-yl)-3-(2-phenoxyphenyl)-1H-pyrazole-5-carboxamide |
| 20-a | 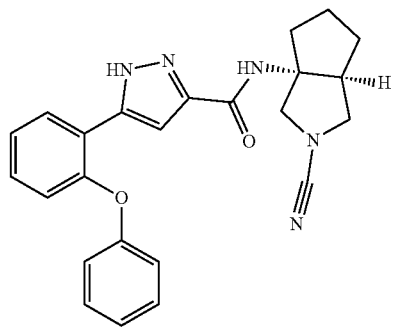 [SMILES: N#CN1C[C@@H]2CCC[C@]2(NC(=O)c2cc(-c3ccccc3Oc3ccccc3)[nH]n2)C1]<br>N-((3aR,6aS)-2-cyanohexahydrocyclopenta[c]pyrrol-3a(1H)-yl)-5-(2-phenoxyphenyl)-1H-pyrazole-3-carboxamide |

-continued

| Compound Number | Compound Structure and Chemical Name |
|---|---|
| 20-b | 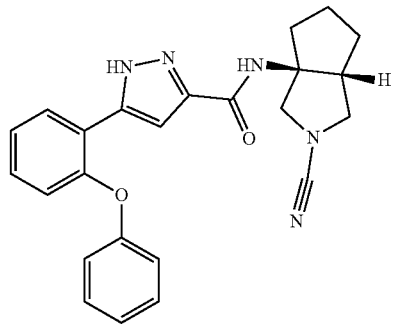 [SMILES: N#CN1C[C@H]2CCC[C@@]2(NC(=O)c2cc(-c3ccccc3Oc3ccccc3)[nH]n2)C1]<br>N-((3aS,6aR)-2-cyanohexahydrocyclopenta[c]pyrrol-3a(1H)-yl)-5-(2-phenoxyphenyl)-1H-pyrazole-3-carboxamide |
| 10 | 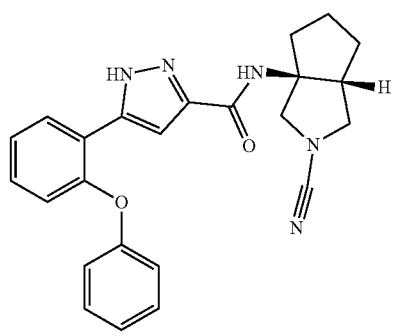 [SMILES: N#CN1C[C@H]2CCC[C@@]2(NC(=O)c2cc(-c3ccccc3Oc3ccccc3)[nH]n2)C1]<br>(S)-N-(1-cyano-4-oxopyrrolidin-3-yl)-5-(2-phenoxyphenyl)-1H-pyrazole-3-carboxamide |
| 11 | 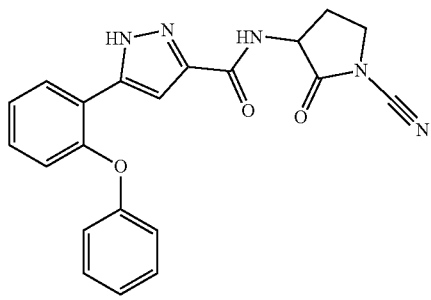 [SMILES: N#CN1CCC(NC(=O)c2cc(-c3ccccc3Oc3ccccc3)[nH]n2)C1=O]<br>N-(1-cyano-2-oxopyrrolidin-3-yl)-5-(2-phenoxyphenyl)-1H-pyrazole-3-carboxamide |
| 12 | 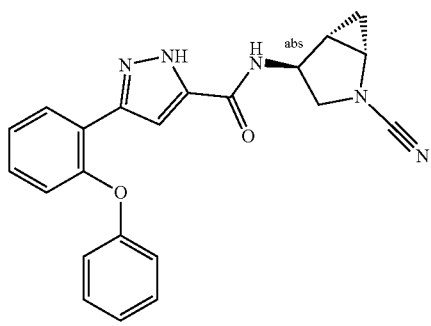 [SMILES: N#CN1C[C@@H](NC(=O)c2cc(-c3ccccc3Oc3ccccc3)n[nH]2)[C@@H]2C[C@@H]21]<br>N-((1S,4S,5S)-2-cyano-2-azabicyclo[3.1.0]hexan-4-yl)-3-(2-phenoxyphenyl)-1H-pyrazole-5-carboxamide |

| Compound Number | Compound Structure and Chemical Name |
|---|---|
| 13 | 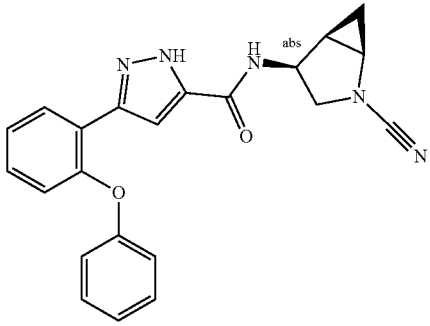 [SMILES: N#CN1C[C@@H](NC(=O)c2cc(-c3ccccc3Oc3ccccc3)n[nH]2)[C@H]2C[C@H]21]<br>N-((1R,4S,5R)-2-cyano-2-azabicyclo[3.1.0]hexan-4-yl)-3-(2-phenoxyphenyl)-1H-pyrazole-5-carboxamide |
| 14 | 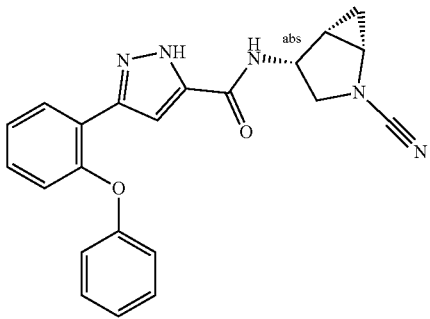 [SMILES: N#CN1C[C@H](NC(=O)c2cc(-c3ccccc3Oc3ccccc3)n[nH]2)[C@@H]2C[C@@H]21]<br>N-((1S,4R,5S)-2-cyano-2-azabicyclo[3.1.0]hexan-4-yl)-3-(2-phenoxyphenyl)-1H-pyrazole-5-carboxamide |
| 15 | 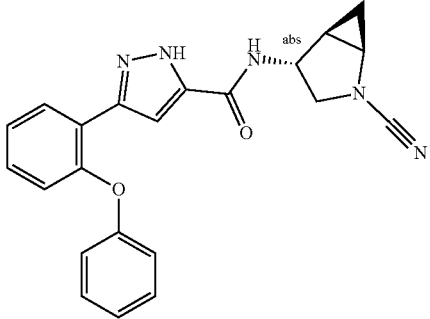 [SMILES: N#CN1C[C@H](NC(=O)c2cc(-c3ccccc3Oc3ccccc3)n[nH]2)[C@H]2C[C@H]21]<br>N-((1R,4R,5R)-2-cyano-2-azabicyclo[3.1.0]hexan-4-yl)-3-(2-phenoxyphenyl)-1H-pyrazole-5-carboxamide |
| 16 | 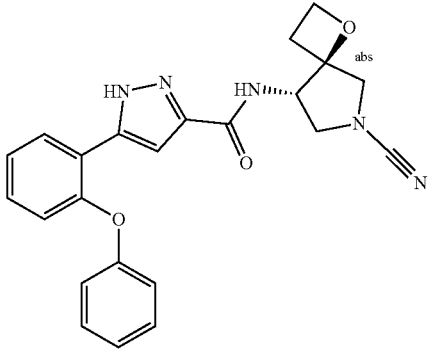 [SMILES: N#CN1C[C@H](NC(=O)c2cc(-c3ccccc3Oc3ccccc3)[nH]n2)[C@]2(CCO2)C1]<br>N-((4S,8S)-6-cyano-1-oxa-6-azaspiro[3.4]octan-8-yl)-5-(2-phenoxyphenyl)-1H-pyrazole-3-carboxamide |

| Compound Number | Compound Structure and Chemical Name |
|---|---|
| 17 | 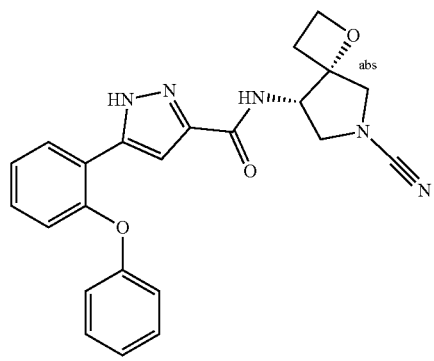 [SMILES: N#CN1C[C@H](NC(=O)c2cc(-c3ccccc3Oc3ccccc3)[nH]n2)[C@@]2(CCO2)C1]<br>N-((4R,8S)-6-cyano-1-oxa-6-azaspiro[3.4]octan-8-yl)-5-(2-phenoxyphenyl)-1H-pyrazole-3-carboxamide |
| 18 | 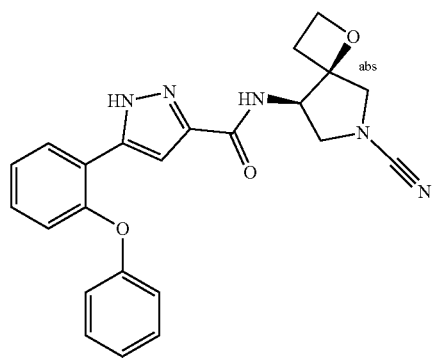 [SMILES: N#CN1C[C@@H](NC(=O)c2cc(-c3ccccc3Oc3ccccc3)[nH]n2)[C@]2(CCO2)C1]<br>N-((4S,8R)-6-cyano-1-oxa-6-azaspiro[3.4]octan-8-yl)-5-(2-phenoxyphenyl)-1H-pyrazole-3-carboxamide |
| 19 | 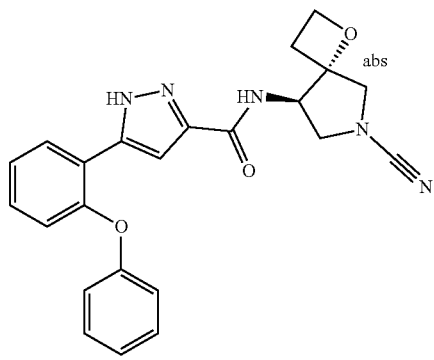 [SMILES: N#CN1C[C@@H](NC(=O)c2cc(-c3ccccc3Oc3ccccc3)[nH]n2)[C@@]2(CCO2)C1]<br>N-((4R,8R)-6-cyano-1-oxa-6-azaspiro[3.4]octan-8-yl)-5-(2-phenoxyphenyl)-1H-byrazole-3-carboxamide |

| Compound Number | Compound Structure and Chemical Name |
|---|---|
| 20 | 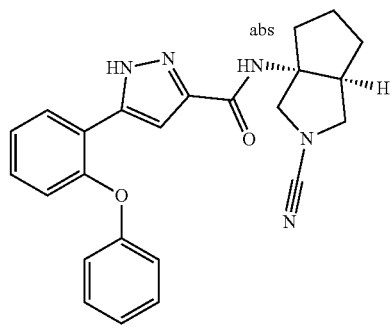 [SMILES: N#CN1C[C@@H]2CCC[C@]2(NC(=O)c2cc(-c3ccccc3Oc3ccccc3)[nH]n2)C1]<br>N-((3aR,6aS)-2-cyanohexahydrocyclopenta[c]pyrrol-3a(1H)-yl)-5-(2-phenoxyphenyl)-1H-pyrazole-3-carboxamide |
| 21 | 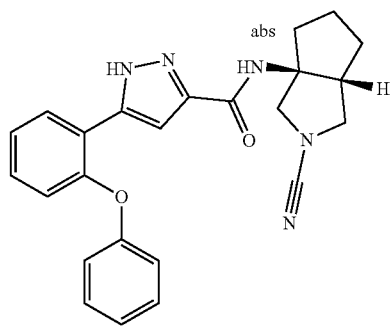 [SMILES: N#CN1C[C@H]2CCC[C@@]2(NC(=O)c2cc(-c3ccccc3Oc3ccccc3)[nH]n2)C1]<br>N-((3aS,6aR)-2-cyanohexahydrocyclopenta[c]pyrrol-3a(1H)-yl)-5-(2-phenoxyphenyl)-1H-pyrazole-3-carboxamide |
| 22 | 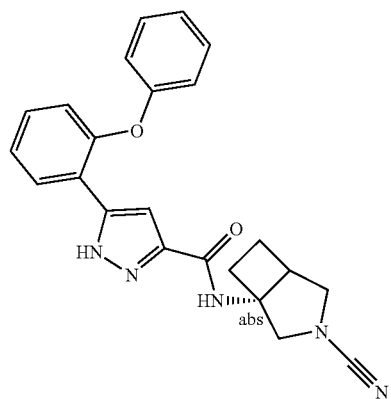 [SMILES: N#CN1CC2CC[C@]2(NC(=O)c2cc(-c3ccccc3Oc3ccccc3)[nH]n2)C1]<br>N-((1R)-3-cyano-3-azabicyclo[3.2.0]heptan-1-yl)-5-(2-phenoxyphenyl)-1H-pyrazole-3-carboxamide |

| Compound Number | Compound Structure and Chemical Name |
|---|---|
| 23 | 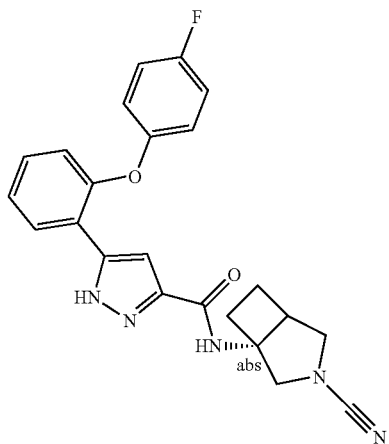 [SMILES: N#CN1CC2CC[C@]2(NC(=O)c2cc(-c3ccccc3Oc3ccc(F)cc3)[nH]n2)C1]<br>N-((1R)-3-cyano-3-azabicyclo[3.2.0]heptan-1-yl)-5-(2-(4-fluorophenoxy)phenyl)-1H-pyrazole-3-carboxamide |
| 24 | 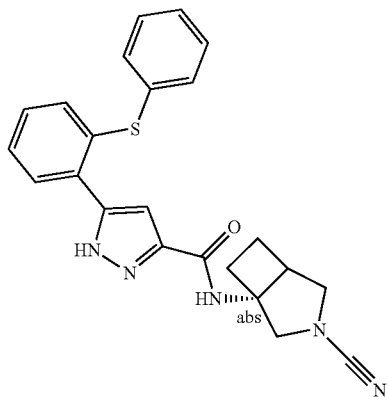 [SMILES: N#CN1CC2CC[C@]2(NC(=O)c2cc(-c3ccccc3Sc3ccccc3)[nH]n2)C1]<br>N-((1R)-3-cyano-3-azabicyclo[3.2.0]heptan-1-yl)-5-(2-(phenylthio)phenyl)-1H-pyrazole-3-carboxamide |
| 25 | 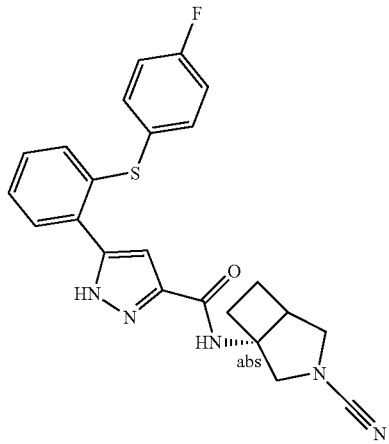 [SMILES: N#CN1CC2CC[C@]2(NC(=O)c2cc(-c3ccccc3Sc3ccc(F)cc3)[nH]n2)C1]<br>N-((1R)-3-cyano-3-azabicyclo[3.2.0]heptan-1-yl)-5-(2-((4-fluorophenyl)thio)phenyl)-1H-pyrazole-3-carboxamide |

| Compound Number | Compound Structure and Chemical Name |
|---|---|
| 26 | 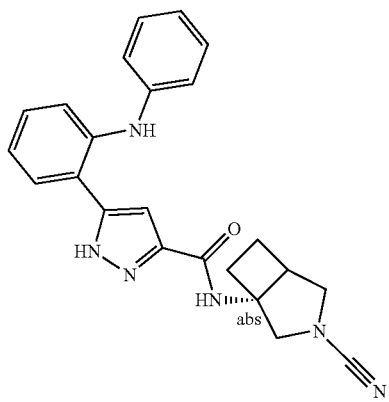 [SMILES: N#CN1CC2CC[C@]2(NC(=O)c2cc(-c3ccccc3Nc3ccccc3)[nH]n2)C1]<br>N-((1R)-3-cyano-3-azabicyclo[3.2.0]heptan-1-yl)-5-(2-(phenylamino)phenyl)-1H-pyrazole-3-carboxamide |
| 27 | 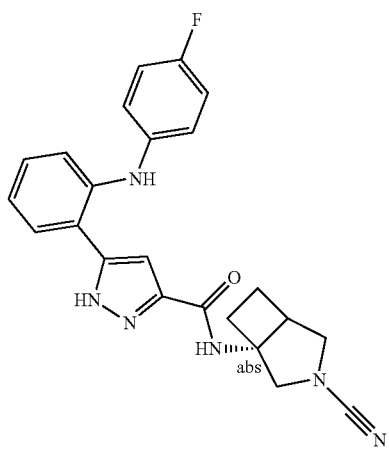<br>N-((1R)-3-cyano-3-azabicyclo[3.2.0]heptan-1-yl)-5-(2-((4-fluorophenyl)amino)phenyl)-1H-pyrazole-3-carboxamide |
| 28 | 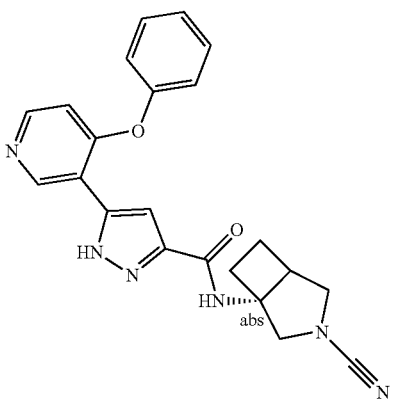 [SMILES: N#CN1CC2CC[C@]2(NC(=O)c2cc(-c3cnccc3Oc3ccccc3)[nH]n2)C1]<br>N-((1R)-3-cyano-3-azabicyclo[3.2.0]heptan-1-yl)-5-(4-phenoxypyridin-3-yl)-1H-pyrazole-3-carboxamide |

| Compound Number | Compound Structure and Chemical Name |
|---|---|
| 29 | 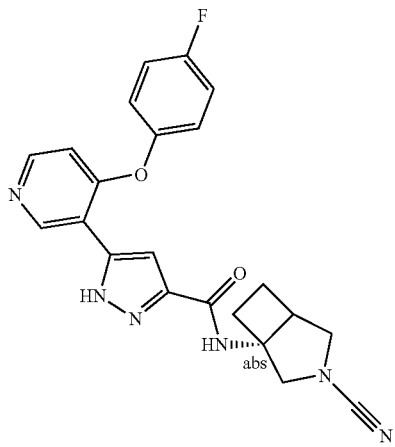 [SMILES: N#CN1CC2CC[C@]2(NC(=O)c2cc(-c3cnccc3Oc3ccc(F)cc3)[nH]n2)C1]<br>N-((1R)-3-cyano-3-azabicyclo[3.2.0]heptan-1-yl)-5-(4-(4-fluorophenoxy)pyridin-3-yl)-1H-pyrazole-3-carboxamide |
| 30 | 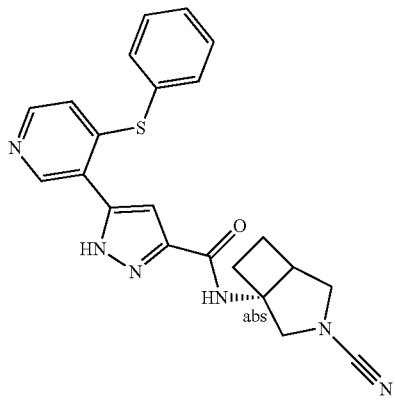<br>N-((1R)-3-cyano-3-azabicyclo[3.2.0]heptan-1-yl)-5-(4-(phenylthio)pyridin-3-yl)-1H-pyrazole-3-carboxamide |
| 31 | 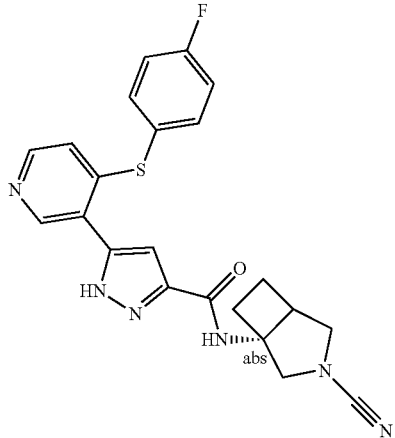<br>N-((1R)-3-cyano-3-azabicyclo[3.2.0]heptan-1-yl)-5-(4-((4-fluorophenyl)thio)pyridin-3-yl)-1H-pyrazole-3-carboxamide |

| Compound Number | Compound Structure and Chemical Name |
|---|---|
| 32 | 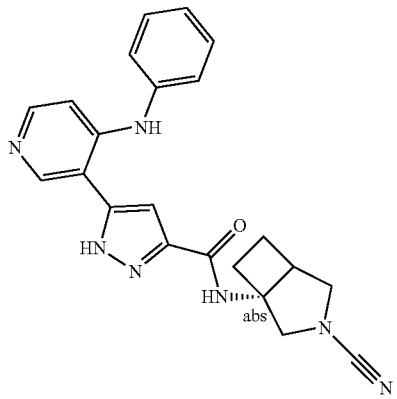 [SMILES: N#CN1CC2CC[C@]2(NC(=O)c2cc(-c3cnccc3Nc3ccccc3)[nH]n2)C1]<br>N-((1R)-3-cyano-3-azabicyclo[3.2.0]heptan-1-yl)-5-(4-(phenylamino)pyridin-3-yl)-1H-pyrazole-3-carboxamide |
| 33 | 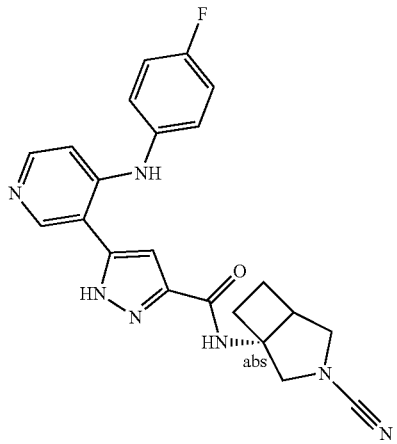 [SMILES: N#CN1CC2CC[C@]2(NC(=O)c2cc(-c3cnccc3Nc3ccc(F)cc3)[nH]n2)C1]<br>N-((1R)-3-cyano-3-azabicyclo[3.2.0]heptan-1-yl)-5-(4-((4-fluorophenyl)amino)pyridin-3-yl)-1H-pyrazole-3-carboxamide |
| 34 | 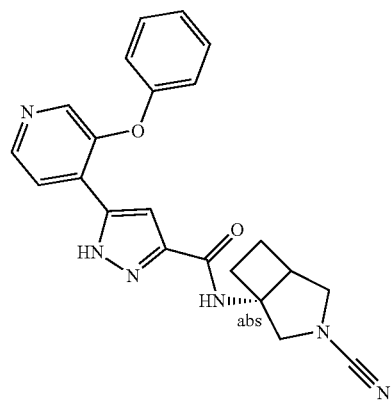 [SMILES: N#CN1CC2CC[C@]2(NC(=O)c2cc(-c3ccncc3Oc3ccccc3)[nH]n2)C1]<br>N-((1R)-3-cyano-3-azabicyclo[3.2.0]heptan-1-yl)-5-(3-phenoxypyridin-4-yl)-1H-pyrazole-3-carboxamide |

| Compound Number | Compound Structure and Chemical Name |
|---|---|
| 35 | 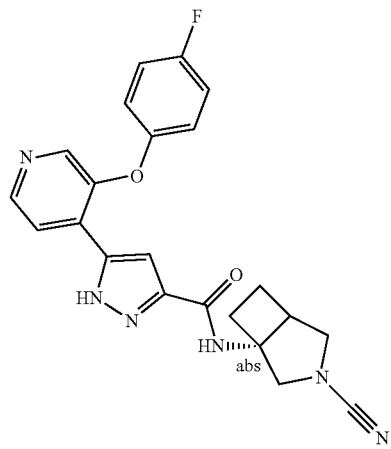 [SMILES: N#CN1CC2CC[C@]2(NC(=O)c2cc(-c3ccncc3Oc3ccc(F)cc3)[nH]n2)C1]<br>N-((1R)-3-cyano-3-azabicyclo[3.2.0]heptan-1-yl)-5-(3-(4-fluoraphenoxy)pyridin-4-yl)-1H-pyrazole-3-carboxamide |
| 36 | 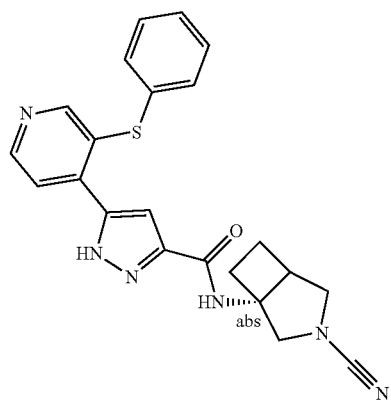<br>N-((1R)-3-cyano-3-azabicyclo[3.2.0]heptan-1-yl)-5-(3-(phenylthio)pyridin-4-yl)-1H-pyrazole-3-carboxamide |
| 37 | 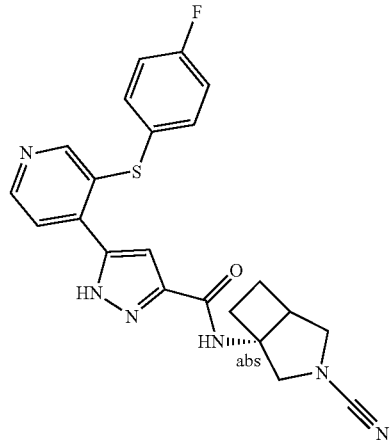<br>N-((1R)-3-cyano-3-azabicyclo[3.2.0]heptan-1-yl)-5-(3-((4-fluorophenyl)thio)pyridin-4-1)-1H-pyrazole-3-carboxamide |

| Compound Number | Compound Structure and Chemical Name |
|---|---|
| 38 | 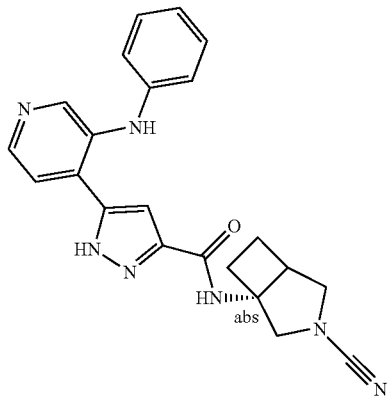 [SMILES: N#CN1CC2CC[C@]2(NC(=O)c2cc(-c3ccncc3Nc3ccccc3)[nH]n2)C1]<br>N-((1R)-3-cyano-3-azabicyclo[3.2.0]heptan-1-yl)-5-(3-(phenylamino)pyridin-4-yl)-1H-pyrazole-3-carboxamide |
| 39 | 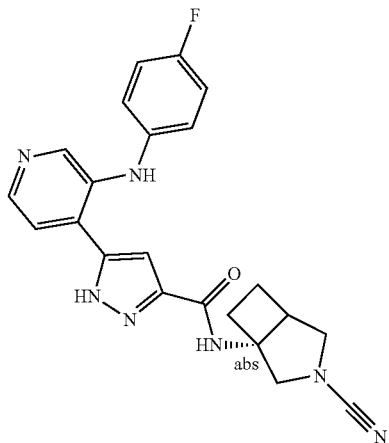 [SMILES: N#CN1CC2CC[C@]2(NC(=O)c2cc(-c3ccncc3Nc3ccc(F)cc3)[nH]n2)C1]<br>N-((1R)-3-cyano-3-azabicyclo[3.2.0]heptan-1-yl)-5-(3-((4-fluorophenyl)amino)pyridin-4-yl)-1H-pyrazole-3-carboxamide |
| 40 | 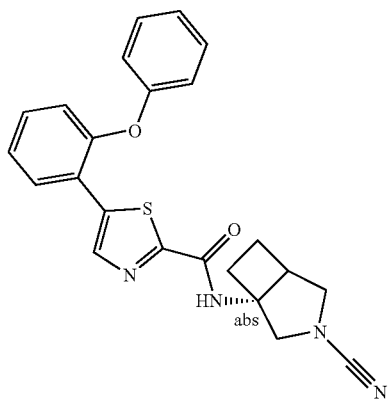<br>N-((1R)-3-cyano-3-azabicyclo[3.2.0]heptan-1-yl)-5-(2-phenoxyphenyl)thiazole-2-carboxamide |

| Compound Number | Compound Structure and Chemical Name |
|---|---|
| 41 | 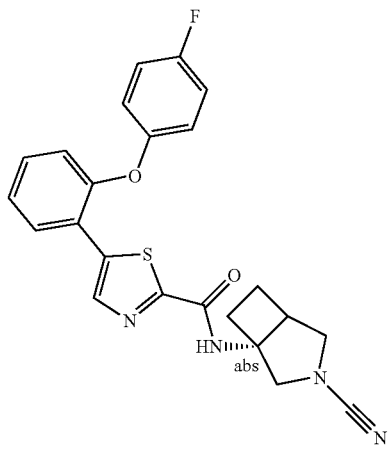<br>N-((1R)-3-cyano-3-azabicyclo[3.2.0]heptan-1-yl)-5-(2-(4-fluorophenoxy)phenyl)thiazole-2-carboxamide |
| 42 | 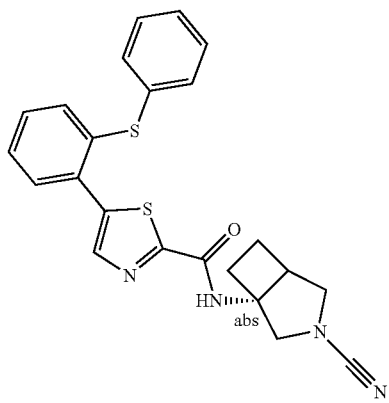 [SMILES: N#CN1CC2CC[C@]2(NC(=O)c2ncc(-c3ccccc3Sc3ccccc3)s2)C1]<br>N-((1R)-3-cyano-3-azabicyclo[3.2.0]heptan-1-yl)-5-(2-(phenylthio)phenyl)thiazole-2-carboxamide |
| 43 | 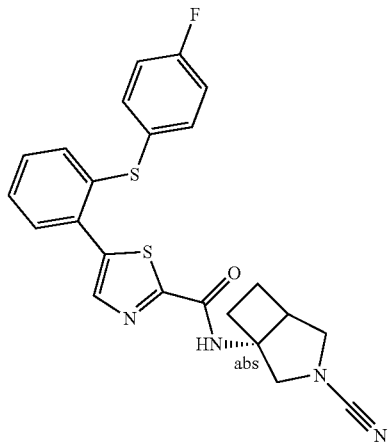 [SMILES: N#CN1CC2CC[C@]2(NC(=O)c2ncc(-c3ccccc3Sc3ccc(F)cc3)s2)C1]<br>N-((1R)-3-cyano-3-azabicyclo[3.2.0]heptan-1-yl)-5-(2-((4-fluorophenyl)thio)phenyl)thiazole-2-carboxamide |

| Compound Number | Compound Structure and Chemical Name |
|---|---|
| 44 | 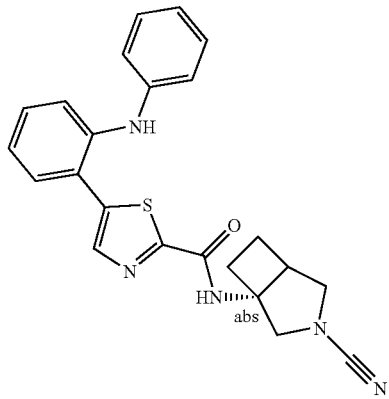 [SMILES: N#CN1CC2CC[C@]2(NC(=O)c2ncc(-c3ccccc3Nc3ccccc3)s2)C1]<br>N-((1R)-3-cyano-3-azabicyclo[3.2.0]heptan-1-yl)-5-(2-(phenylamino)phenyl)thiazole-2-carboxamide |
| 45 | 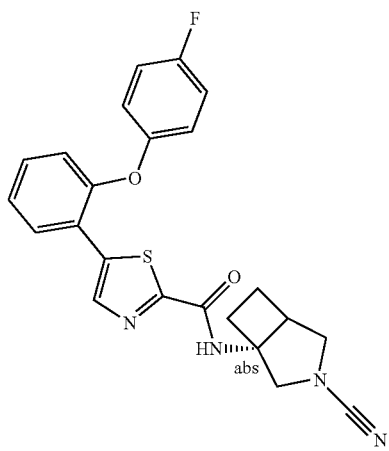 [SMILES: N#CN1CC2CC[C@]2(NC(=O)c2ncc(-c3ccccc3Oc3ccc(F)cc3)s2)C1]<br>N-((1R)-3-cyano-3-azabicyclo[3.2.0]heptan-1-yl)-5-(2-((4-fluorophenyl)amino)phenyl)thiazole-2-carboxamide |
| 46 | 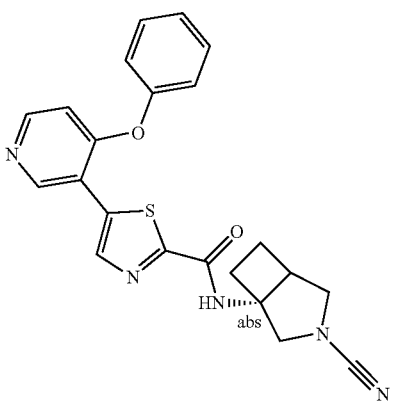 [SMILES: N#CN1CC2CC[C@]2(NC(=O)c2ncc(-c3cnccc3Oc3ccccc3)s2)C1]<br>N-((1R)-3-cyano-3-azabicyclo[3.2.0]heptan-1-yl)-5-(4-phenoxypyridin-3-yl)thiazole-2-carboxamide |

| Compound Number | Compound Structure and Chemical Name |
|---|---|
| 47 | 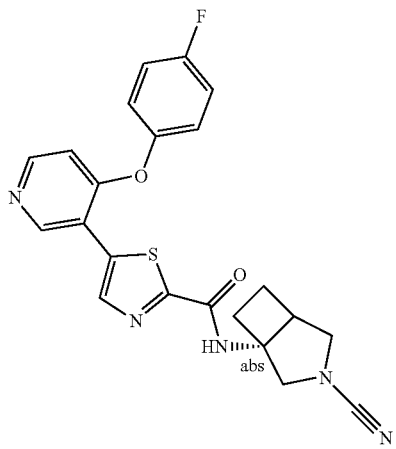 [SMILES: N#CN1CC2CC[C@]2(NC(=O)c2ncc(-c3cnccc3Oc3ccc(F)cc3)s2)C1]<br>N-((1R)-3-cyano-3-azabicyclo[3.2.0]heptan-1-yl)-5-(4-(4-fluorophenoxy)pyridin-3-yl)thiazole-2-carboxamide |
| 48 | 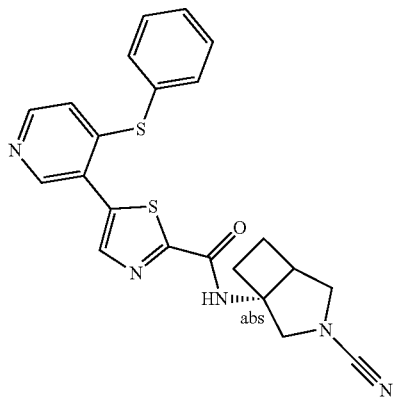 [SMILES: N#CN1CC2CC[C@]2(NC(=O)c2ncc(-c3cnccc3Sc3ccccc3)s2)C1]<br>N-((1R)-3-cyano-3-azabicyclo[3.2.0]heptan-1-yl)-5-(4-(phenylthio)pyridin-3-yl)thiazole-2-carboxamide |
| 49 | 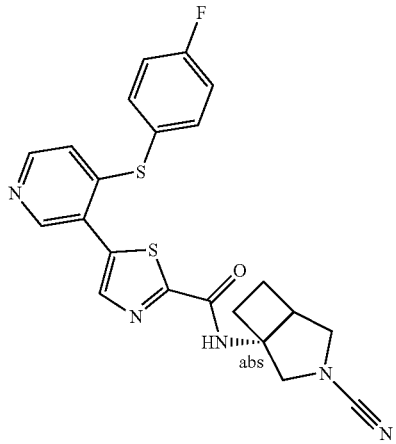<br>N-((1R)-3-cyano-3-azabicyclo[3.2.0]heptan-1-yl)-5-(4-((4-fluorophenyl)thio)pyridin-3-yl)thiazole-2-carboxamide |

| Compound Number | Compound Structure and Chemical Name |
|---|---|
| 50 | 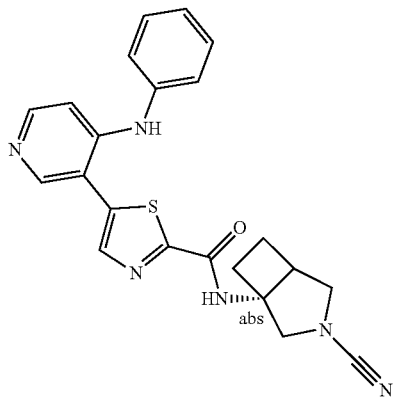 [SMILES: N#CN1CC2CC[C@]2(NC(=O)c2ncc(-c3cnccc3Nc3ccccc3)s2)C1]<br>N-((1R)-3-cyano-3-azabicyclo[3.2.0]heptan-1-yl)-5-(4-(phenylamino)pyridin-3-yl)thiazole-2-carboxamide |
| 51 | 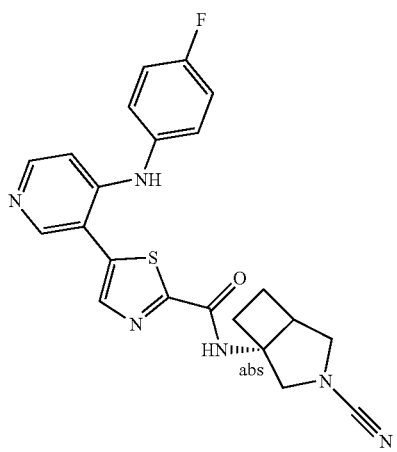 [SMILES: N#CN1CC2CC[C@]2(NC(=O)c2ncc(-c3cnccc3Nc3ccc(F)cc3)s2)C1]<br>N-((1R)-3-cyano-3-azabicyclo[3.2.0]heptan-1-yl)-5-(4-((4-fluorophenyl)amino)pyridin-3-yl)thiazole-2-carboxamide |
| 52 | 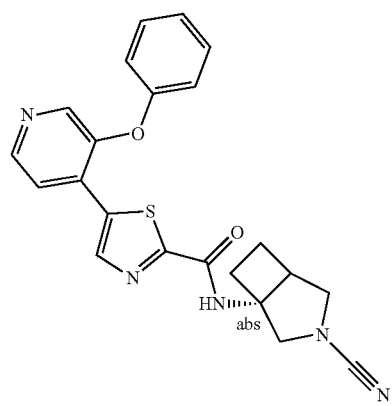<br>N-((1R)-3-cyano-3-azabicyclo[3.2.0]heptan-1-yl)-5-(3-phenoxypyridin-4-yl)thiazole-2-carboxamide |

-continued
| Compound Number | Compound Structure and Chemical Name |
|---|---|
| 53 | 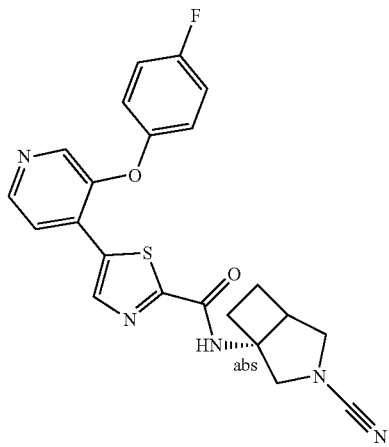 [SMILES: N#CN1CC2CC[C@]2(NC(=O)c2ncc(-c3ccncc3Oc3ccc(F)cc3)s2)C1]<br>N-((1R)-3-cyano-3-azabicyclo[3.2.0]heptan-1-yl)-5-(3-(4-fluorophenoxy)pyridin-4-yl)thiazole-2-carboxamide |
| 54 | 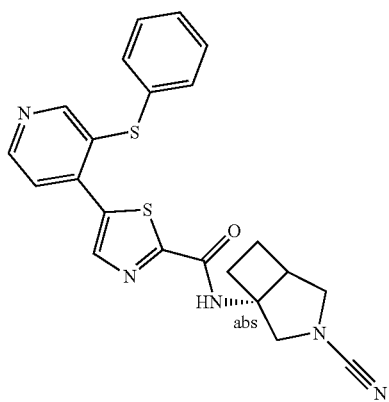 [SMILES: N#CN1CC2CC[C@]2(NC(=O)c2ncc(-c3ccncc3Sc3ccccc3)s2)C1]<br>N-((1R)-3-cyano-3-azabicyclo[3.2.0]heptan-1-yl)-5-(3-(phenylthio)pyridin-4-yl)thiazole-2-carboxamide |
| 55 | 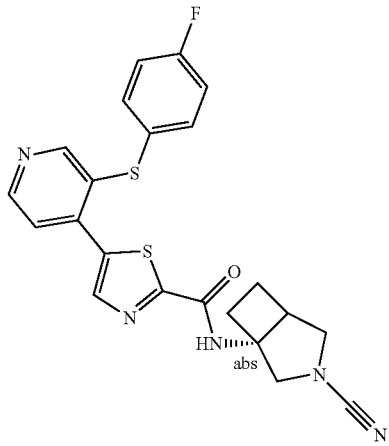<br>N-((1R)-3-cyano-3-azabicyclo[3.2.0]heptan-1-yl)-5-(3-((4-fluorophenyl)thio)pyridin-4-yl)thiazole-2-carboxamide |

| Compound Number | Compound Structure and Chemical Name |
|---|---|
| 56 | 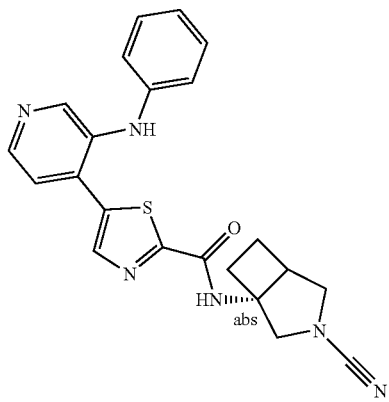 [SMILES: N#CN1CC2CC[C@]2(NC(=O)c2ncc(-c3ccncc3Nc3ccccc3)s2)C1]<br>N-((1R)-3-cyano-3-azabicyclo[3.2.0]heptan-1-yl)-5-(3-(phenylamino)pyridin-4-yl)thiazole-2-carboxamide |
| 57 | 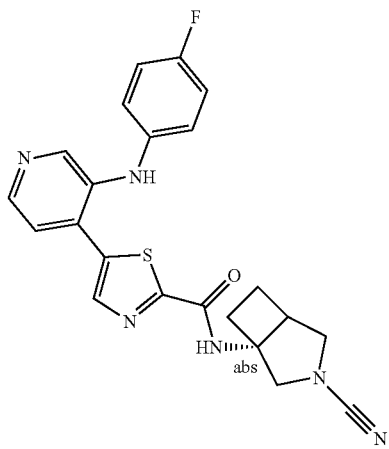 [SMILES: N#CN1CC2CC[C@]2(NC(=O)c2ncc(-c3ccncc3Nc3ccc(F)cc3)s2)C1]<br>N-((1R)-3-cyano-3-azabicyclo[3.2.0]heptan-1-yl)-5-(3-((4-fluorophenyl)amino)pyridin-4-yl)thiazole-2-carboxamide |
| 58 | 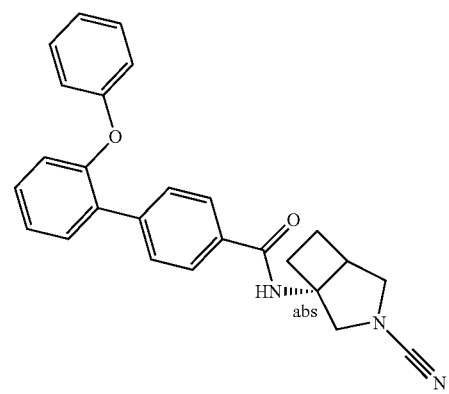<br>N-((1R)-3-cyano-3-azabicyclo[3.2.0]heptan-1-yl)-2'-phenoxy-[1,1'-biphenyl]-4-carboxamide |

| Compound Number | Compound Structure and Chemical Name |
|---|---|
| 59 | 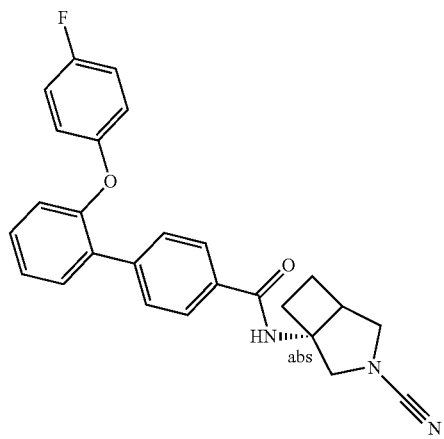<br>N-((1R)-3-cyano-3-azabicyclo[3.2.0]heptan-1-yl)-2'-(4-fluorophenoxy)-[1,1'-biphenyl]-4-carboxamide |
| 60 | 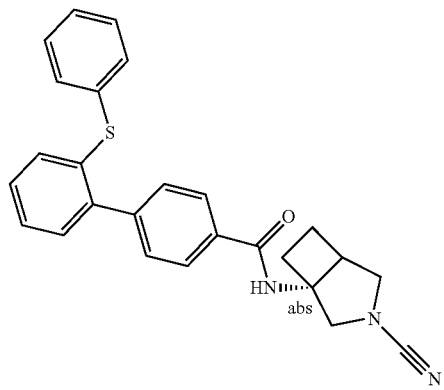 [SMILES: N#CN1CC2CC[C@]2(NC(=O)c2ccc(-c3ccccc3Oc3ccccc3)cc2)C1]<br>N-((1R)-3-cyano-3-azabicyclo[3.2.0]heptan-1-yl)-2'-(phenylthio)-[1,1'-biphenyl]-4-carboxamide |
| 61 | 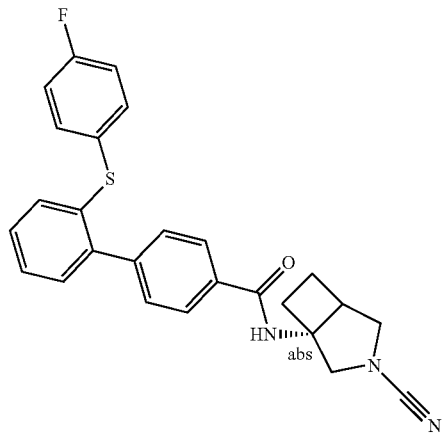 [SMILES: N#CN1CC2CC[C@]2(NC(=O)c2ccc(-c3ccccc3Sc3ccc(F)cc3)cc2)C1]<br>N-((1R)-3-cyano-3-azabicyclo[3.2.0]heptan-1-yl)-2'-((4-fluorophenyl)thio)-[1,1'-biphenyl]-4-carboxamide |

-continued
| Compound Number | Compound Structure and Chemical Name |
|---|---|
| 62 | 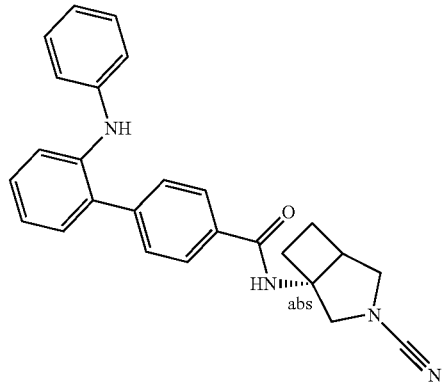 [SMILES: N#CN1CC2CC[C@]2(NC(=O)c2ccc(-c3ccccc3Nc3ccccc3)cc2)C1]<br>N-((1R)-3-cyano-3-azabicyclo[3.2.0]heptan-1-yl)-2'-(phenylamino)-[1,1'-biphenyl]-4-carboxamide |
| 63 | 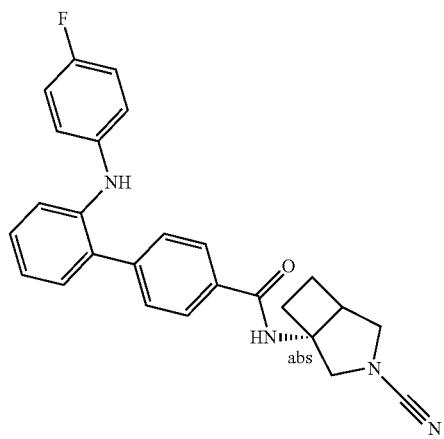 [SMILES: N#CN1CC2CC[C@]2(NC(=O)c2ccc(-c3ccccc3Nc3ccc(F)cc3)cc2)C1]<br>N-((1R)-3-cyano-3-azabicyclo[3.2.0]heptan-1-yl)-2'-((4-fluorophenyl)amino)-[1,1'-biphenyl]-4-carboxamide |
| 64 | 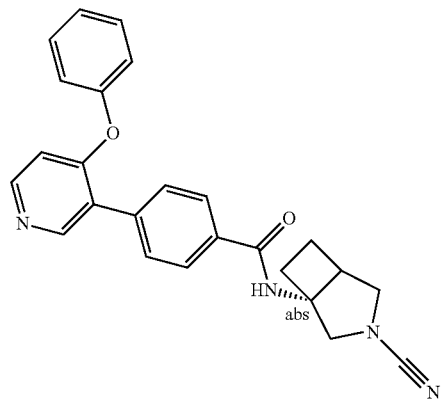 [SMILES: N#CN1CC2CC[C@]2(NC(=O)c2ccc(-c3cnccc3Oc3ccccc3)cc2)C1]<br>N-((1R)-3-cyano-3-azabicyclo[3.2.0]heptan-1-yl)-4-(4-phenoxypyridin-3-yl)benzamide |

| Compound Number | Compound Structure and Chemical Name |
|---|---|
| 65 | 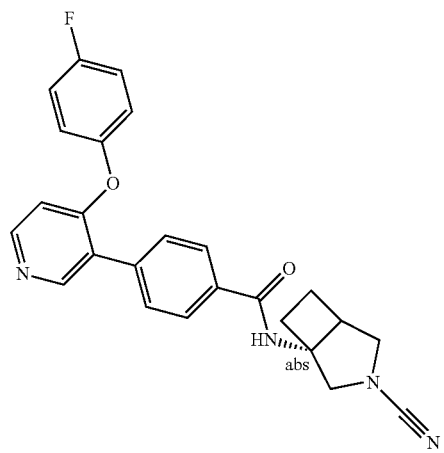 [SMILES: N#CN1CC2CC[C@]2(NC(=O)c2ccc(-c3cnccc3Oc3ccc(F)cc3)cc2)C1]<br>N-((1R)-3-cyano-3-azabicyclo[3.2.0]heptan-1-yl)-4-(4-(4-fluorophenoxy)pyridin-3-yl)benzamide |
| 66 | 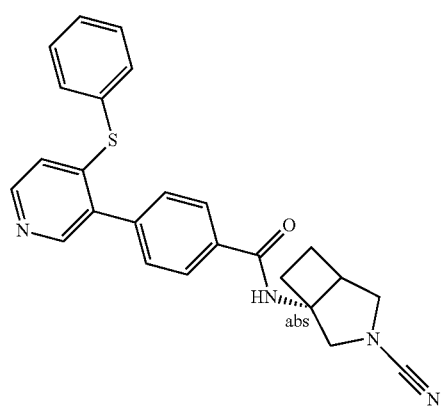 [SMILES: N#CN1CC2CC[C@]2(NC(=O)c2ccc(-c3cnccc3Sc3ccccc3)cc2)C1]<br>N-((1R)-3-cyano-3-azabicyclo[3.2.0]heptan-1-yl)-4-(4-(phenylthio)pyridin-3-yl)benzamide |
| 67 | 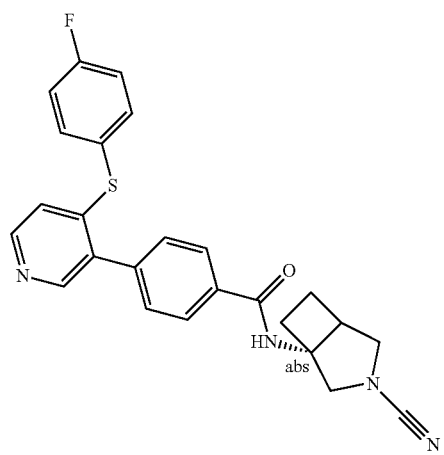<br>N-((1R)-3-cyano-3-azabicyclo[3.2.0]heptan-1-yl)-4-(4-((4-fluorophenyl)thio)pyridin-3-yl)benzamide |

| Compound Number | Compound Structure and Chemical Name |
|---|---|
| 68 | 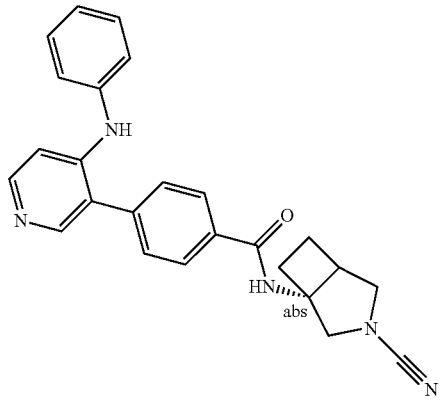 [SMILES: N#CN1CC2CC[C@]2(NC(=O)c2ccc(-c3cnccc3Nc3ccccc3)cc2)C1]<br>N-((1R)-3-cyano-3-azabicyclo[3.2.0]heptan-1-yl)-4-(4-(phenylamino)pyridin-3-yl)benzamide |
| 69 | 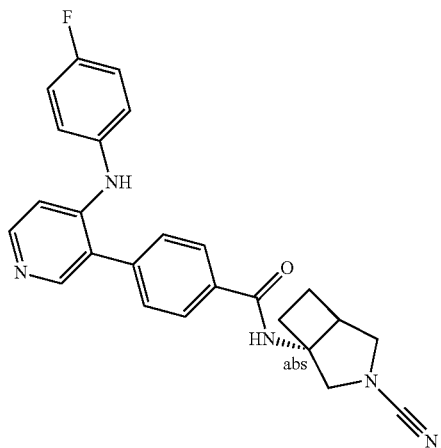 [SMILES: N#CN1CC2CC[C@]2(NC(=O)c2ccc(-c3cnccc3Nc3ccc(F)cc3)cc2)C1]<br>N-((1R)-3-cyano-3-azabicyclo[3.2.0]heptan-1-yl)-4-(4-((4-fluorophenyl)amino)pyridin-3-yl)benzamide |
| 70 | 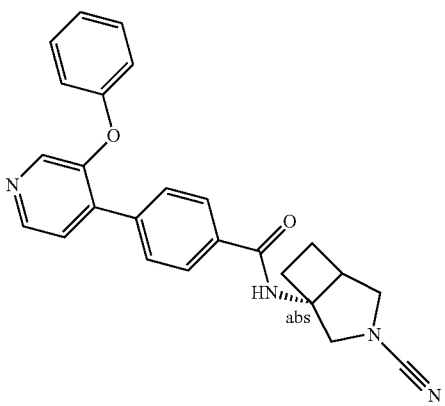<br>N-((1R)-3-cyano-3-azabicyclo[3.2.0]heptan-1-yl)-4-(3-phenoxypyridin-4-yl)benzamide |

| Compound Number | Compound Structure and Chemical Name |
|---|---|
| 71 | 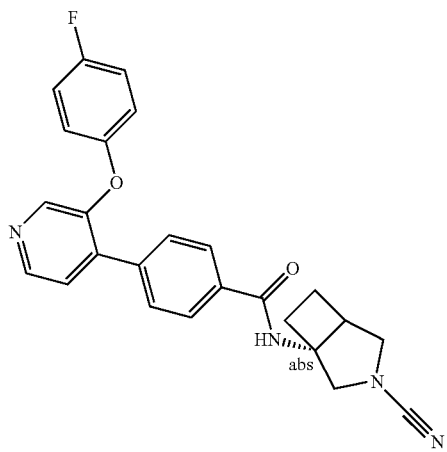 [SMILES: N#CN1CC2CC[C@]2(NC(=O)c2ccc(-c3ccncc3Oc3ccc(F)cc3)cc2)C1]<br>N-((1R)-3-cyano-3-azabicyclo[3.2.0]heptan-1-yl)-4-(3-(4-fluorophenoxy)pyridin-4-yl)benzamide |
| 72 | 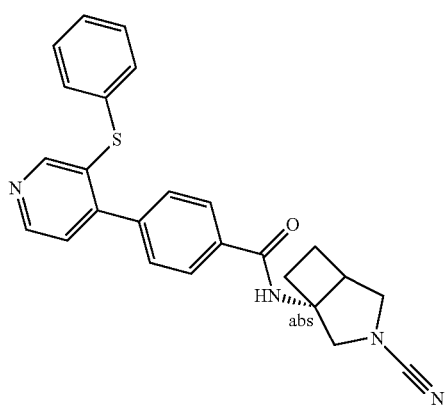 [SMILES: N#CN1CC2CC[C@]2(NC(=O)c2ccc(-c3ccncc3Sc3ccccc3)cc2)C1]<br>N-((1R)-3-cyano-3-azabicyclo[3.2.0]heptan-1-yl)-4-(3-(phenylthio)pyridin-4-yl)benzamide |
| 73 | 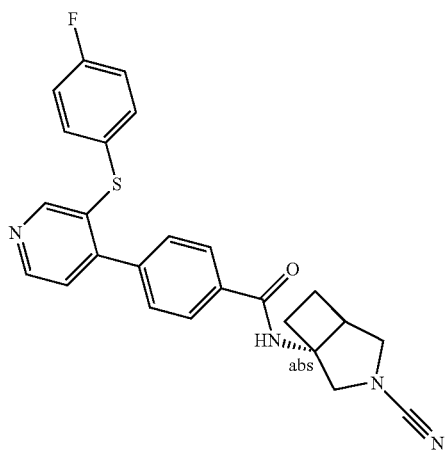<br>N-((1R)-3-cyano-3-azabicyclo[3.2.0]heptan-1-yl)-4-(3-((4-fluorophenyl)thio)pyridin-4-yl)benzamide |

| Compound Number | Compound Structure and Chemical Name |
|---|---|
| 74 | 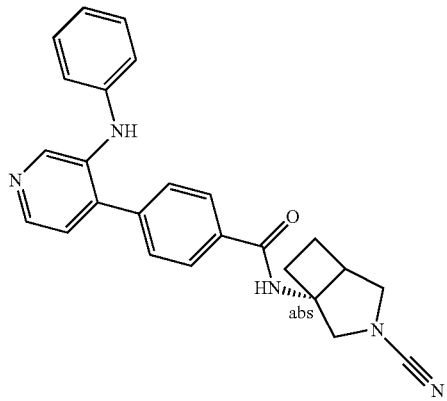 [SMILES: N#CN1CC2CC[C@]2(NC(=O)c2ccc(-c3ccncc3Nc3ccccc3)cc2)C1]<br>N-((1R)-3-cyano-3-azabicyclo[3.2.0]heptan-1-yl)-4-(3-(phenylamino)pyridin-4-yl)benzamide |
| 75 | 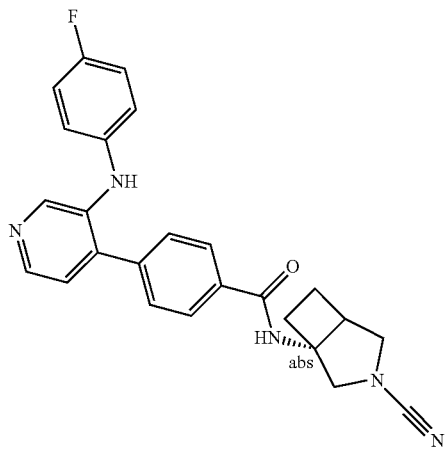 [SMILES: N#CN1CC2CC[C@]2(NC(=O)c2ccc(-c3ccncc3Nc3ccc(F)cc3)cc2)C1]<br>N-((1R)-3-cyano-3-azabicyclo[3.2.0]heptan-1-yl)-4-(3-((4-fluorophenyl)amino)pyridin-4-yl)benzamide |
| 76 | 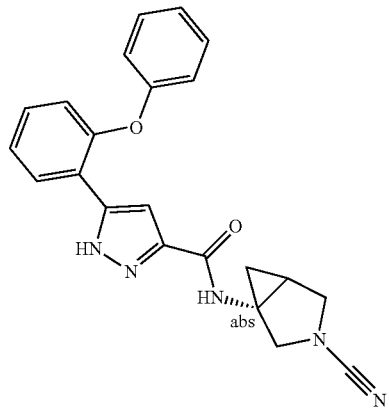 [SMILES: N#CN1CC2C[C@]2(NC(=O)c2cc(-c3ccccc3Oc3ccccc3)[nH]n2)C1]<br>N-((1R)-3-cyano-3-azabicyclo[3.1.0]hexan-1-yl)-5-(2-phenoxyphenyl)-1H-pyrazole-3-carboxamide |

| Compound Number | Compound Structure and Chemical Name |
|---|---|
| 77 | 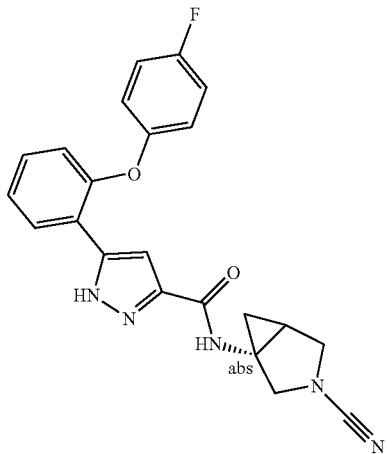 [SMILES: N#CN1CC2C[C@]2(NC(=O)c2cc(-c3ccccc3Oc3ccc(F)cc3)[nH]n2)C1]<br>N-((1R)-3-cyano-3-azabicyclo[3.1.0]hexan-1-yl)-5-(2-(4-fluorophenoxy)phenyl)-1H-pyrazole-3-carboxamide |
| 78 | 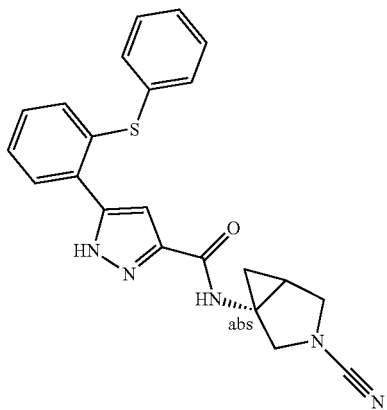 [SMILES: N#CN1CC2C[C@]2(NC(=O)c2cc(-c3ccccc3Sc3ccccc3)[nH]n2)C1]<br>N-((1R)-3-cyano-3-azabicyclo[3.1.0]hexan-1-yl)-5-(2-(phenylthio)phenyl)-1H-arazole-3-carboxamide |
| 79 | 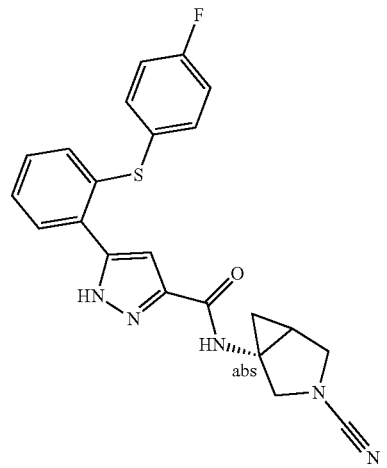 [SMILES: N#CN1CC2C[C@]2(NC(=O)c2cc(-c3ccccc3Sc3ccc(F)cc3)[nH]n2)C1]<br>N-((1R)-3-cyano-3-azabicyclo[3.1.0]hexan-1-yl)-5-(2-((4-fluorophenyl)thio)phenyl)-1H-pyrazole-3-carboxamide |

273
-continued
| Compound Number | Compound Structure and Chemical Name |
|---|---|
| 80 | 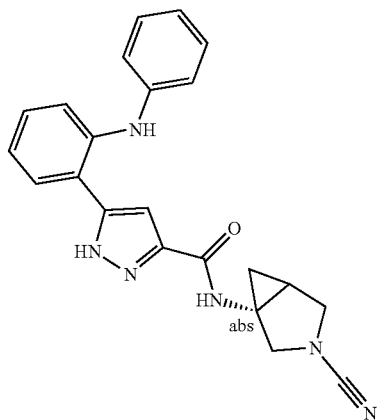 [SMILES: N#CN1CC2C[C@]2(NC(=O)c2cc(-c3ccccc3Nc3ccccc3)[nH]n2)C1]<br>N-((1R)-3-cyano-3-azabicyclo[3.1.0]hexan-1-yl)-5-(2-(phenylamino)phenyl)-1H-pyrazole-3-carboxamide |
| 81 | 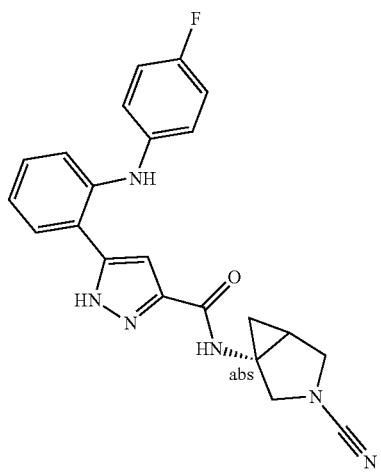 [SMILES: N#CN1CC2C[C@]2(NC(=O)c2cc(-c3ccccc3Nc3ccc(F)cc3)[nH]n2)C1]<br>N-((1R)-3-cyano-3-azabicyclo[3.1.0]hexan-1-yl)-5-(2-((4-fluorophenyl)amino)phenyl)-1H-pyrazole-3-carboxamide |
| 82 | 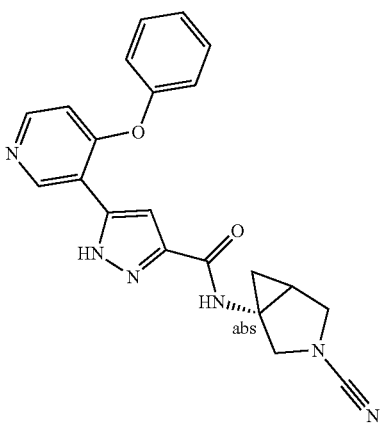 [SMILES: N#CN1CC2C[C@]2(NC(=O)c2cc(-c3cnccc3Oc3ccccc3)[nH]n2)C1]<br>N-((1R)-3-cyano-3-azabicyclo[3.1.0]hexan-1-yl)-5-(4-phenoxypyridin-3-yl)-1H-pyrazole-3-carboxamide |

| Compound Number | Compound Structure and Chemical Name |
|---|---|
| 83 | 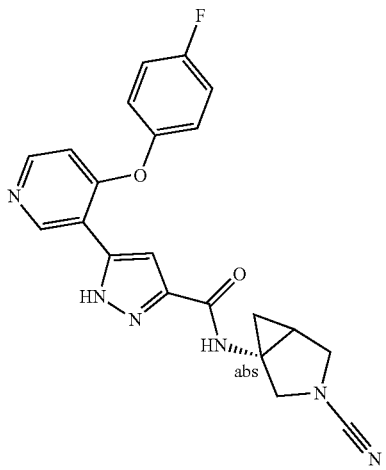 [SMILES: N#CN1CC2C[C@]2(NC(=O)c2cc(-c3cnccc3Oc3ccc(F)cc3)[nH]n2)C1]<br>N-((1R)-3-cyano-3-azabicyclo[3.1.0]hexan-1-yl)-5-(4-(4-fluorophenoxy)pyridin-3-yl)-1H-pyrazole-3-carboxamide |
| 84 | 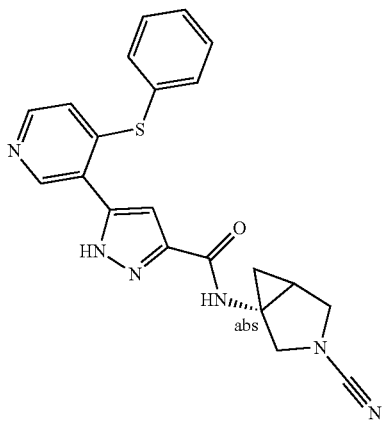 [SMILES: N#CN1CC2C[C@]2(NC(=O)c2cc(-c3cnccc3Sc3ccccc3)[nH]n2)C1]<br>N-((1R)-3-cyano-3-azabicyclo[3.1.0]hexan-1-yl)-5-(4-(phenylthio)pyridin-3-yl)-1H-pyrazole-3-carboxamide |
| 85 | 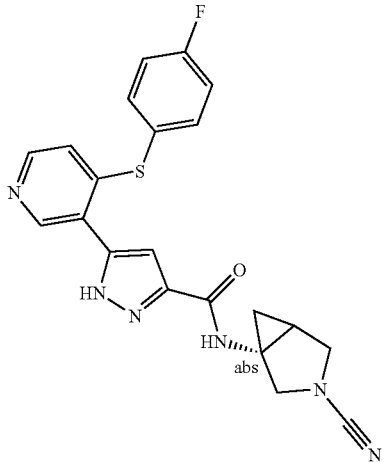 [SMILES: N#CN1CC2C[C@]2(NC(=O)c2cc(-c3cnccc3Sc3ccc(F)cc3)[nH]n2)C1]<br>N-((1R)-3-cyano-3-azabicyclo[3.1.0]hexan-1-yl)-5-(4-((4-fluorophenyl)thio)pyridin-3-1)-1H-pyrazole-3-carboxamide |

| Compound Number | Compound Structure and Chemical Name |
|---|---|
| 86 | 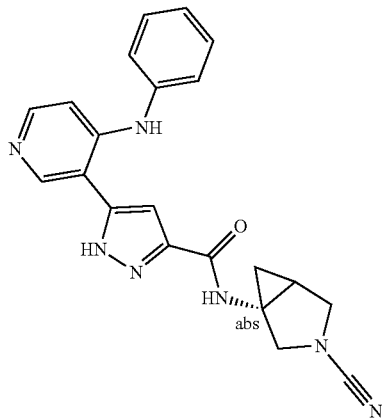 [SMILES: N#CN1CC2C[C@]2(NC(=O)c2cc(-c3cnccc3Nc3ccccc3)[nH]n2)C1]<br>N-((1R)-3-cyano-3-azabicyclo[3.1.0]hexan-1-yl)-5-(4-(phenylamino)pyridin-3-yl)-1H-pyrazole-3-carboxamide |
| 87 | 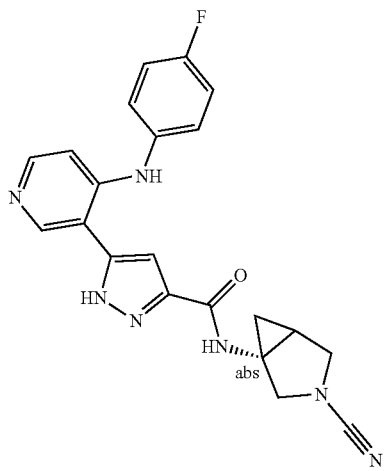 [SMILES: N#CN1CC2C[C@]2(NC(=O)c2cc(-c3cnccc3Nc3ccc(F)cc3)[nH]n2)C1]<br>N-((1R)-3-cyano-3-azabicyclo[3.1.0]hexan-1-yl)-5-(4-((4-fluorophenyl)amino)pyridin-3-yl)-1H-pyrazole-3-carboxamide |
| 88 | 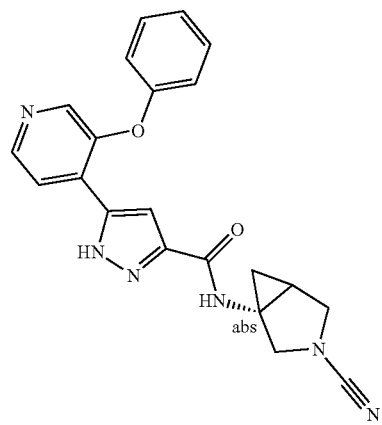 [SMILES: N#CN1CC2C[C@]2(NC(=O)c2cc(-c3ccncc3Oc3ccccc3)[nH]n2)C1]<br>N-((1R)-3-cyano-3-azabicyclo[3.1.0]hexan-1-yl)-5-(3-phenoxypyridin-4-yl)-1H-pyrazole-3-carboxamide |

| Compound Number | Compound Structure and Chemical Name |
|---|---|
| 89 | 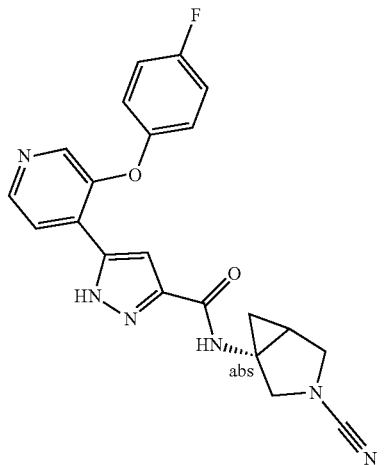 [SMILES: N#CN1CC2C[C@]2(NC(=O)c2cc(-c3ccncc3Oc3ccc(F)cc3)[nH]n2)C1]<br>N-((1R)-3-cyano-3-azabicyclo[3.1.0]hexan-1-yl)-5-(3-(4-fluorophenoxy)pyridin-4-yl)-1H-pyrazole-3-carboxamide |
| 90 | 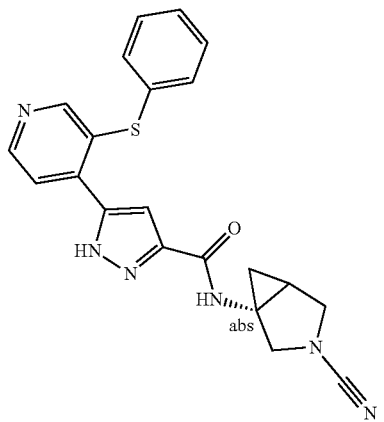 [SMILES: N#CN1CC2C[C@]2(NC(=O)c2cc(-c3ccncc3Sc3ccccc3)[nH]n2)C1]<br>N-((1R)-3-cyano-3-azabicyclo[3.1.0]hexan-1-yl)-5-(3-(phenylthio)pyridin-4-yl)-1H-pyrazole-3-carboxamide |
| 91 | 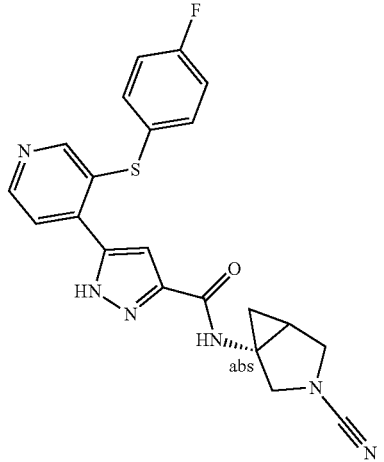<br>N-((1R)-3-cyano-3-azabicyclo[3.1.0]hexan-1-yl)-5-(3-((4-fluorophenyl)thio)pyridin-4-yl)-1H-pyrazole-3-carboxamide |

-continued
| Compound Number | Compound Structure and Chemical Name |
|---|---|
| 92 | 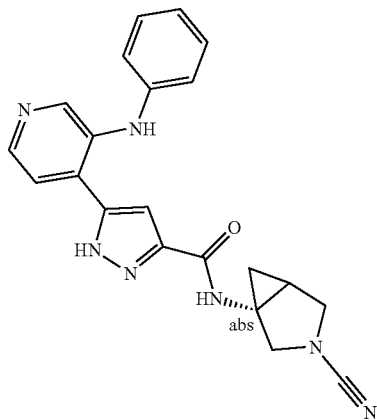 [SMILES: N#CN1CC2C[C@]2(NC(=O)c2cc(-c3ccncc3Nc3ccccc3)[nH]n2)C1]<br>N-((1R)-3-cyano-3-azabicyclo[3.1.0]hexan-1-yl)-5-(3-(phenylamino)pyridin-4-yl)-1H-pyrazole-3-carboxamide |
| 93 | 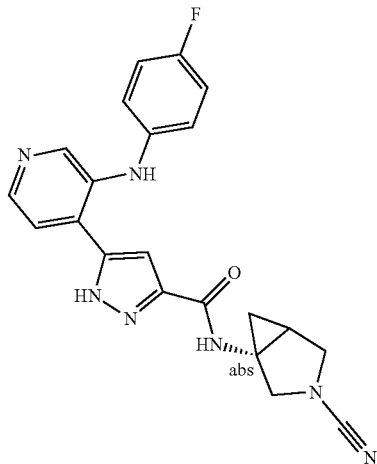 [SMILES: N#CN1CC2C[C@]2(NC(=O)c2cc(-c3ccncc3Nc3ccc(F)cc3)[nH]n2)C1]<br>N-((1R)-3-cyano-3-azabicyclo[3.1.0]hexan-1-yl)-5-(3-((4-fluorophenyl)amino)pyridin-4-yl)-1H-pyrazole-3-carboxamide |
| 94 | 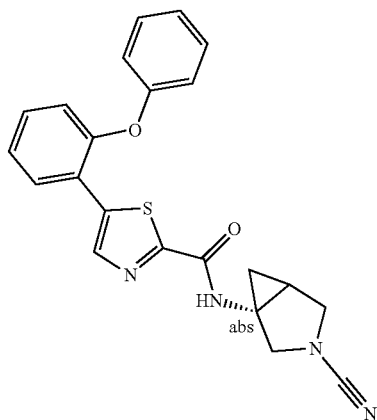 [SMILES: N#CN1CC2C[C@]2(NC(=O)c2ncc(-c3ccccc3Oc3ccccc3)s2)C1]<br>N-((1R)-3-cyano-3-azabicyclo[3.1.0]hexan-1-yl)-5-(2-phenoxyphenyl)thiazole-2-carboxamide |

| Compound Number | Compound Structure and Chemical Name |
|---|---|
| 95 | 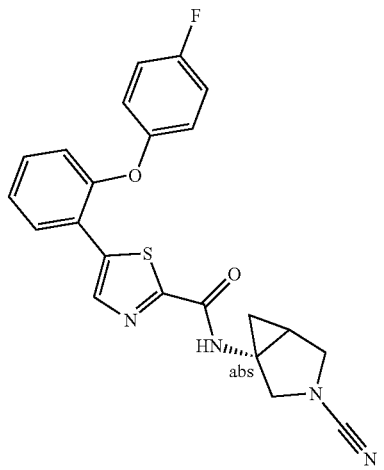<br>N-((1R)-3-cyano-3-azabicyclo[3.1.0]hexan-1-yl)-5-(2-(4-fluorophenoxy)phenyl)thiazole-2-carboxamide |
| 96 | 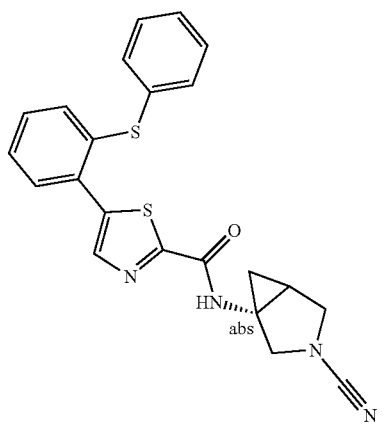<br>N-((1R)-3-cyano-3-azabicyclo[3.1.0]hexan-1-yl)-5-(2-(phenylthio)phenyl)thiazole-2-carboxamide |
| 97 | 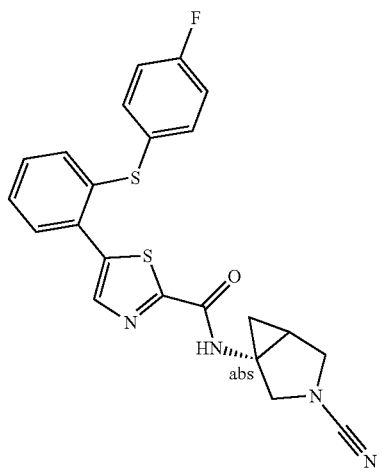 [SMILES: N#CN1CC2C[C@]2(NC(=O)c2ncc(-c3ccccc3Oc3ccc(F)cc3)s2)C1]<br>N-((1R)-3-cyano-3-azabicyclo[3.1.0]hexan-1-yl)-5-(2-((4-fluorophenyl)thio)phenyl)thiazole-2-carboxamide |

-continued
| Compound Number | Compound Structure and Chemical Name |
|---|---|
| 98 | 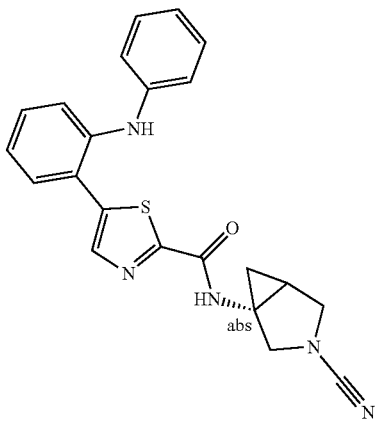 [SMILES: N#CN1CC2C[C@]2(NC(=O)c2ncc(-c3ccccc3Nc3ccccc3)s2)C1]<br>N-((1R)-3-cyano-3-azabicyclo[3.1.0]hexan-1-yl)-5-(2-(phenylamino)phenyl)thiazole-2-carboxamide |
| 99 | 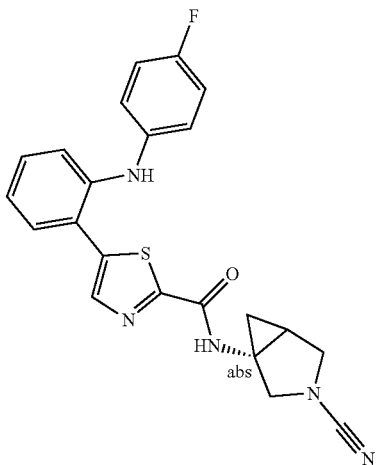 [SMILES: N#CN1CC2C[C@]2(NC(=O)c2ncc(-c3ccccc3Nc3ccc(F)cc3)s2)C1]<br>N-((1R)-3-cyano-3-azabicyclo[3.1.0]hexan-1-yl)-5-(2-((4-fluorophenyl)amino)phenyl)thiazole-2-carboxamide |
| 100 | 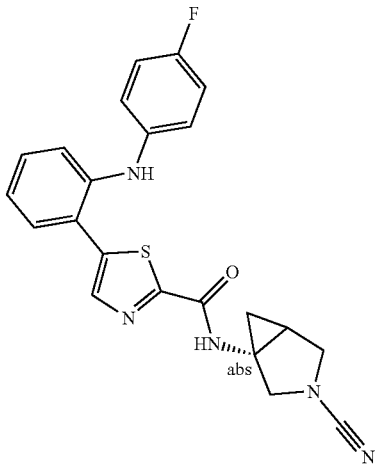 [SMILES: N#CN1CC2C[C@]2(NC(=O)c2ncc(-c3ccccc3Nc3ccc(F)cc3)s2)C1]<br>N-((1R)-3-cyano-3-azabicyclo[3.1.0]hexan-1-yl)-5-(4-phenoxypyridin-3-yl)thiazole-2-carboxamide |

| Compound Number | Compound Structure and Chemical Name |
|---|---|
| 101 | 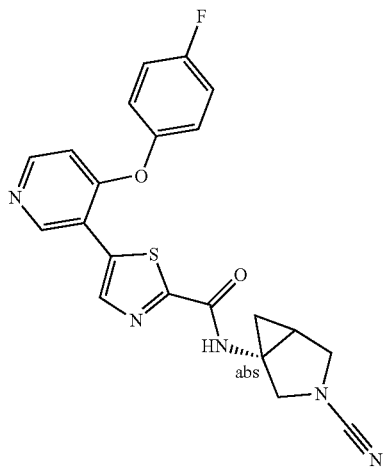 [SMILES: N#CN1CC2C[C@]2(NC(=O)c2ncc(-c3cnccc3Oc3ccc(F)cc3)s2)C1]<br>N-((1R)-3-cyano-3-azabicyclo[3.1.0]hexan-1-yl)-5-(4-(4-fluorophenoxy)pyridin-3-yl)thiazole-2-carboxamide |
| 102 | 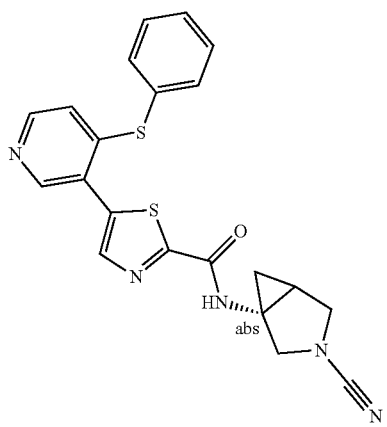 [SMILES: N#CN1CC2C[C@]2(NC(=O)c2ncc(-c3cnccc3Sc3ccccc3)s2)C1]<br>N-((1R)-3-cyano-3-azabicyclo[3.1.0]hexan-1-yl)-5-(4-(phenylthio)pyridin-3-yl)thiazole-2-carboxamide |
| 103 | 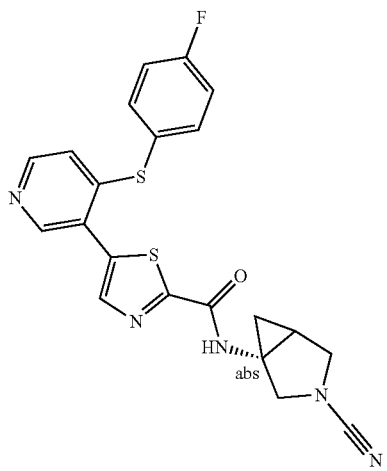 [SMILES: N#CN1CC2C[C@]2(NC(=O)c2ncc(-c3cnccc3Sc3ccc(F)cc3)s2)C1]<br>N-((1R)-3-cyano-3-azabicyclo[3.1.0]hexan-1-yl)-5-(4-((4-fluorophenyl)thio)pyridin-3-yl)thiazole-2-carboxamide |

| Compound Number | Compound Structure and Chemical Name |
|---|---|
| 104 | 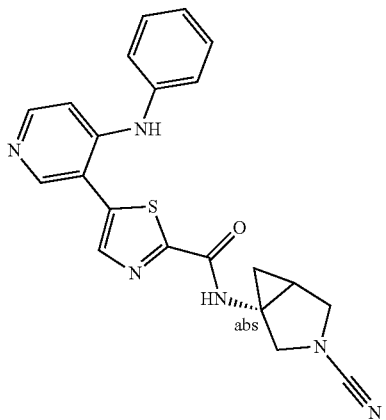 [SMILES: N#CN1CC2C[C@]2(NC(=O)c2ncc(-c3cnccc3Nc3ccccc3)s2)C1]
N-((1R)-3-cyano-3-azabicyclo[3.1.0]hexan-1-yl)-5-(4-(phenylamino)pyridin-3-yl)thiazole-2-carboxamide |
| 105 | 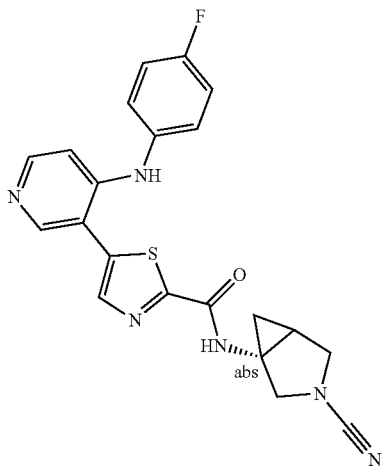 [SMILES: N#CN1CC2C[C@]2(NC(=O)c2ncc(-c3cnccc3Nc3ccc(F)cc3)s2)C1]
N-((1R)-3-cyano-3-azabicyclo[3.1.0]hexan-1-yl)-5-(4-((4-fluorophenyl)amino)pyridin-3-yl)thiazole-2-carboxamide |
| 106 | 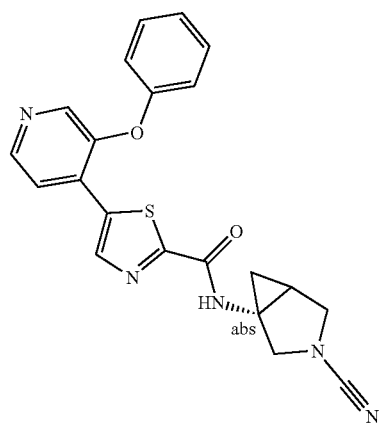 [SMILES: N#CN1CC2C[C@]2(NC(=O)c2ncc(-c3ccncc3Oc3ccccc3)s2)C1]
N-((1R)-3-cyano-3-azabicyclo[3.1.0]hexan-1-yl)-5-(3-phenoxypyridin-4-yl)thiazole-2-carboxamide |

| Compound Number | Compound Structure and Chemical Name |
|---|---|
| 107 | 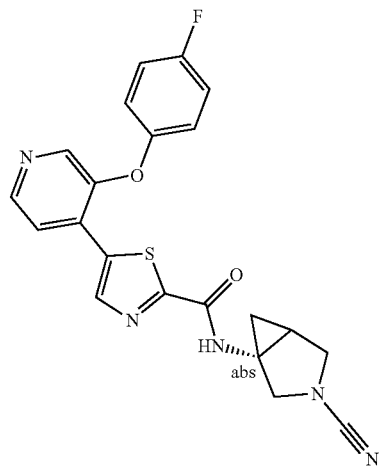 [SMILES: N#CN1CC2C[C@]2(NC(=O)c2ncc(-c3ccncc3Oc3ccc(F)cc3)s2)C1]<br>N-((1R)-3-cyano-3-azabicyclo[3.1.0]hexan-1-yl)-5-(3-(4-fluorophenoxy)pyridin-4-yl)thiazole-2-carboxamide |
| 108 | 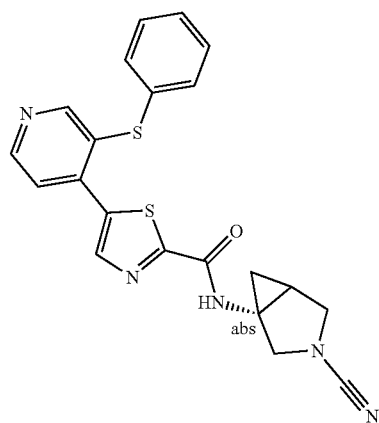<br>N-((1R)-3-cyano-3-azabicyclo[3.1.0]hexan-1-yl)-5-(3-(phenylthio)pyridin-4-yl)thiazole-2-carboxamide |
| 109 | 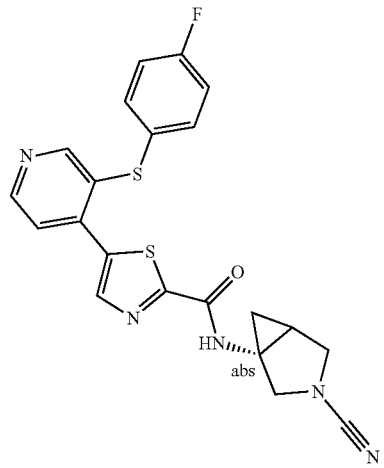 [SMILES: N#CN1CC2C[C@]2(NC(=O)c2ncc(-c3ccncc3Sc3ccc(F)cc3)s2)C1]<br>N-((1R)-3-cyano-3-azabicyclo[3.1.0]hexan-1-yl)-5-(3-((4-fluorophenyl)thio)pyridin-4-yl)thiazole-2-carboxamide |

| Compound Number | Compound Structure and Chemical Name |
|---|---|
| 110 | 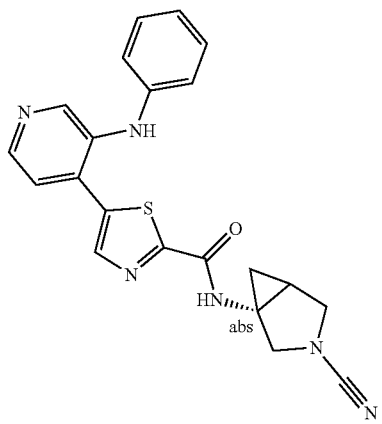 [SMILES: N#CN1CC2C[C@]2(NC(=O)c2ncc(-c3ccncc3Nc3ccccc3)s2)C1]<br>N-((1R)-3-cyano-3-azabicyclo[3.1.0]hexan-1-yl)-5-(3-(phenylamino)pyridin-4-yl)thiazole-2-carboxamide |
| 111 | 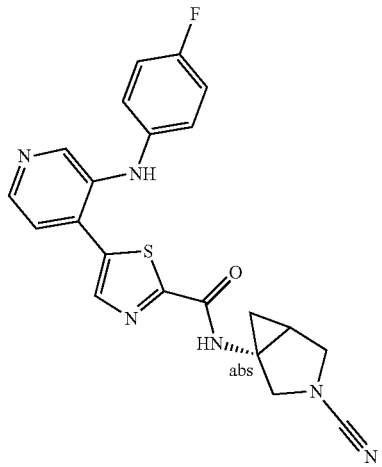 [SMILES: N#CN1CC2C[C@]2(NC(=O)c2ncc(-c3ccncc3Nc3ccc(F)cc3)s2)C1]<br>N-((1R)-3-cyano-3-azabicyclo[3.1.0]hexan-1-yl)-5-(3-((4-fluorophenyl)amino)pyridin-4-yl)thiazole-2-carboxamide |
| 112 | 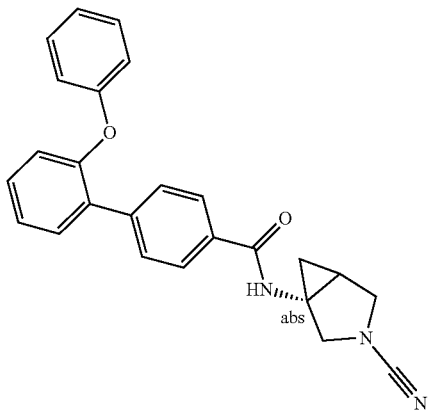<br>N-((1R)-3-cyano-3-azabicyclo[3.1.0]hexan-1-yl)-2'-phenoxy-[1,1'-biphenyl]-4-carboxamide |

-continued
| Compound Number | Compound Structure and Chemical Name |
|---|---|
| 113 | 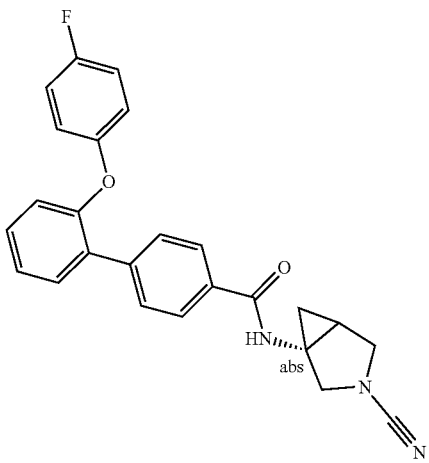<br>N-((1R)-3-cyano-3-azabicyclo[3.1.0]hexan-1-yl)-2'-(4-fluorophenoxy)-[1,1'-biphenyl]-4-carboxamide |
| 114 | 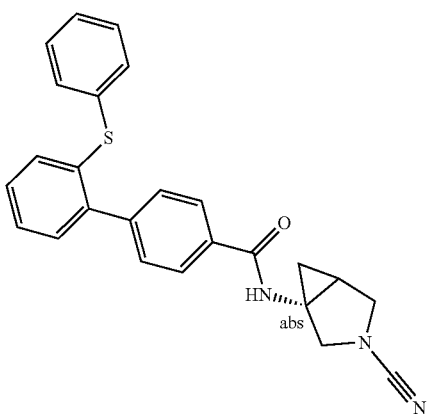 [SMILES: N#CN1CC2C[C@]2(NC(=O)c2ccc(-c3ccccc3Oc3ccccc3)cc2)C1]<br>N-((1R)-3-cyano-3-azabicyclo[3.1.0]hexan-1-yl)-2'-(phenylthio)-[1,1'-biphenyl]-4-carboxamide |
| 115 | 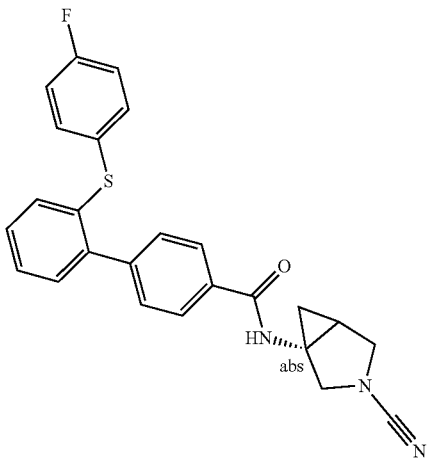 [SMILES: N#CN1CC2C[C@]2(NC(=O)c2ccc(-c3ccccc3Sc3ccc(F)cc3)cc2)C1]<br>N-((1R)-3-cyano-3-azabicyclo[3.1.0]hexan-1-yl)-2'-((4-fluorophenyl)thio)-[1,1'-biphenyl]-4-carboxamide |

| Compound Number | Compound Structure and Chemical Name |
|---|---|
| 116 | 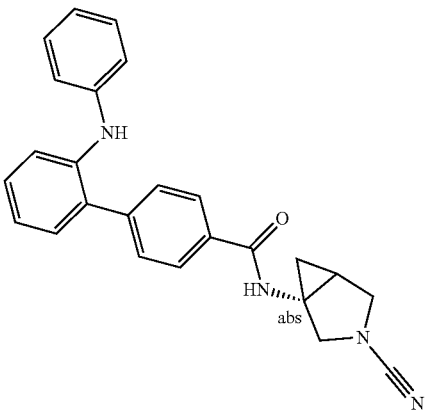 [SMILES: N#CN1CC2C[C@]2(NC(=O)c2ccc(-c3ccccc3Nc3ccccc3)cc2)C1]<br>N-((1R)-3-cyano-3-azabicyclo[3.1.0]hexan-1-yl)-2'-(phenylamino)-[1,1'-biphenyl]-4-carboxamide |
| 117 | 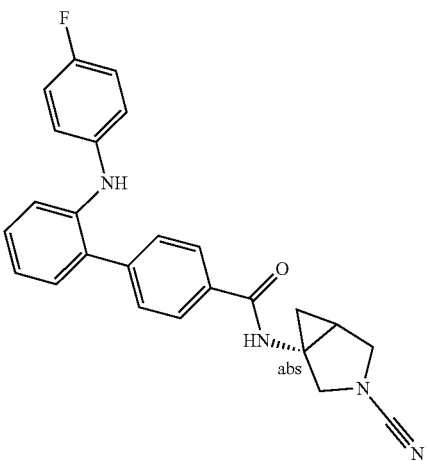<br>N-((1R)-3-cyano-3-azabicyclo[3.1.0]hexan-1-yl)-2'-(4-fluorophenyl)amino)-[1,1'-biphenyl]-4-carboxamide |
| 118 | 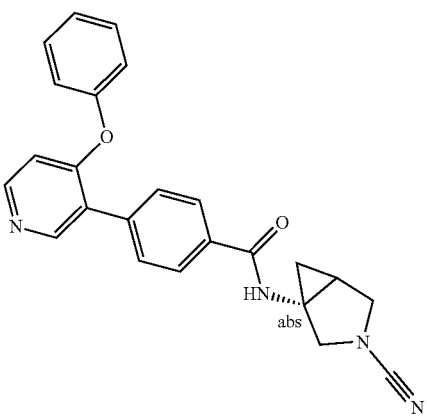 [SMILES: N#CN1CC2C[C@]2(NC(=O)c2ccc(-c3cnccc3Sc3ccccc3)cc2)C1]<br>N-((1R)-3-cyano-3-azabicyclo[3.1.0]hexan-1-yl)-4-(4-phenoxypyridin-3-yl)benzamide |

| Compound Number | Compound Structure and Chemical Name |
|---|---|
| 119 | 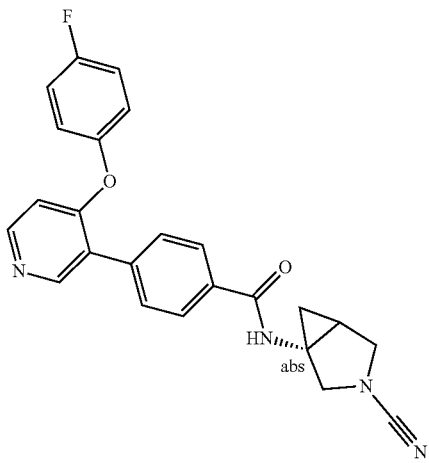<br>N-((1R)-3-cyano-3-azabicyclo[3.1.0]hexan-1-yl)-4-(4-((4-fluorophenoxy)pyridin-3-yl)benzamide |
| 120 | 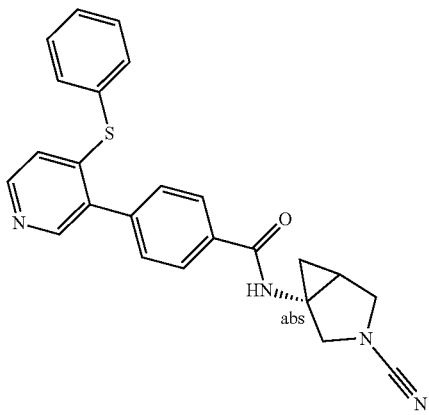<br>N-((1R)-3-cyano-3-azabicyclo[3.1.0]hexan-1-yl)-4-(4-(phenylthio)pyridin-3-yl)benzamide |
| 121 | 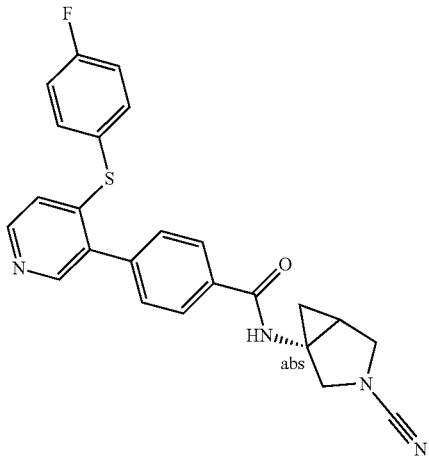 [SMILES: N#CN1CC2C[C@]2(NC(=O)c2ccc(-c3cnccc3Sc3ccc(F)cc3)cc2)C1]<br>N-((1R)-3-cyano-3-azabicyclo[3.1.0]hexan-1-yl)-4-(4-((4-fluorophenyl)thio)pyridin-3-yl)benzamide |

| Compound Number | Compound Structure and Chemical Name |
|---|---|
| 122 | 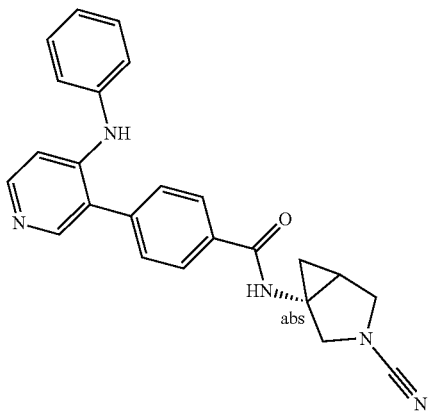<br>N-((1R)-3-cyano-3-azabicyclo[3.1.0]hexan-1-yl)-4-(4-(phenylamino)pyridin-3-yl)benzamide |
| 123 | 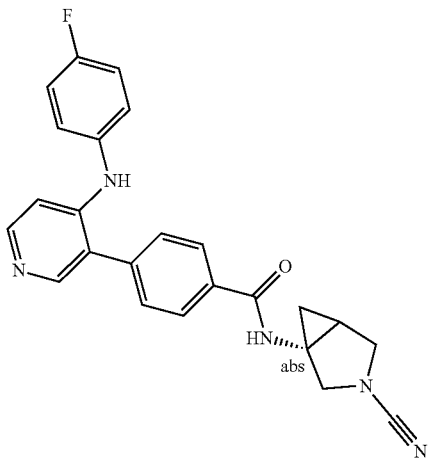 [SMILES: N#CN1CC2C[C@]2(NC(=O)c2ccc(-c3cnccc3Nc3ccc(F)cc3)cc2)C1]<br>N-((1R)-3-cyano-3-azabicyclo[3.1.0]hexan-1-yl)-4-(4-((4-fluorophenyl)amino)pyridin-3-yl)benzamide |
| 124 | 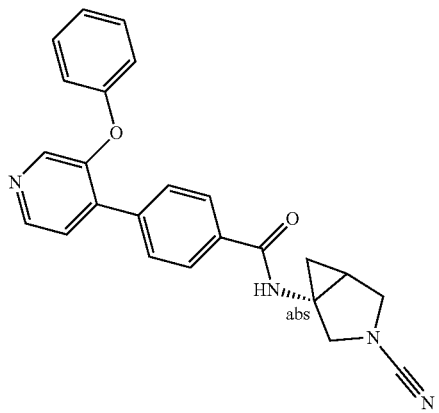<br>N-((1R)-3-cyano-3-azabicyclo[3.1.0]hexan-1-yl)-4-(3-phenoxypyridin-4-yl)benzamide |

-continued
| Compound Number | Compound Structure and Chemical Name |
|---|---|
| 125 | 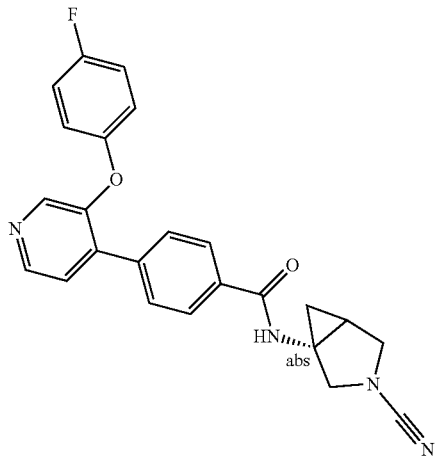<br>N-((1R)-3-cyano-3-azabicyclo[3.1.0]hexan-1-yl)-4-(3-(4-fluorophenoxy)pyridin-4-yl)benzamide |
| 126 | 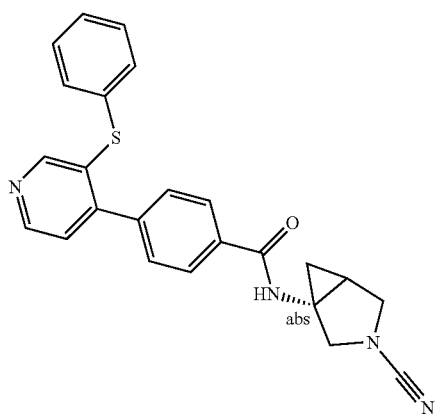 [SMILES: N#CN1CC2C[C@]2(NC(=O)c2ccc(-c3ccncc3Oc3ccccc3)cc2)C1]<br>N-((1R)-3-cyano-3-azabicyclo[3.1.0]hexan-1-yl)-4-(3-(phenylthio)pyridin-4-yl)benzamide |
| 127 | 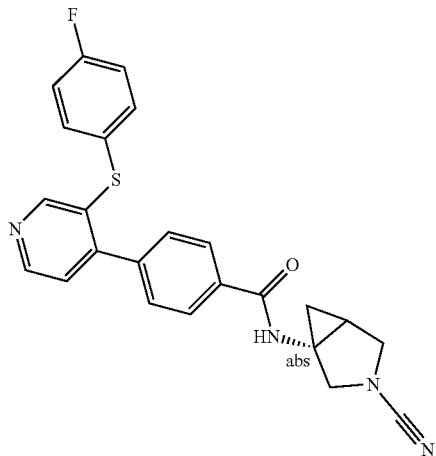 [SMILES: N#CN1CC2C[C@]2(NC(=O)c2ccc(-c3ccncc3Sc3ccc(F)cc3)cc2)C1]<br>N-((1R)-3-cyano-3-azabicyclo[3.1.0]hexan-1-yl)-4-(3-((4-fluorophenyl)thio)pyridin-4-yl)benzamide |

| Compound Number | Compound Structure and Chemical Name |
|---|---|
| 128 | 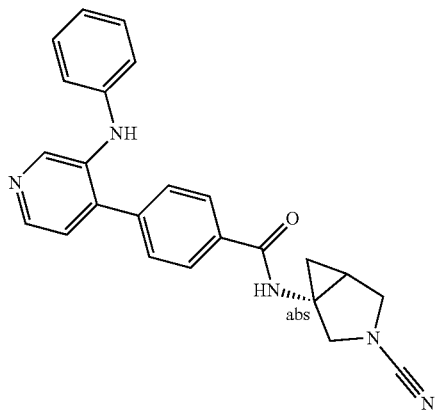 [SMILES: N#CN1CC2C[C@]2(NC(=O)c2ccc(-c3ccncc3Nc3ccccc3)cc2)C1]<br>N-((1R)-3-cyano-3-azabicyclo[3.1.0]hexan-1-yl)-4-(3-(phenylamino)pyridin-4-yl)benzamide |
| 129 | 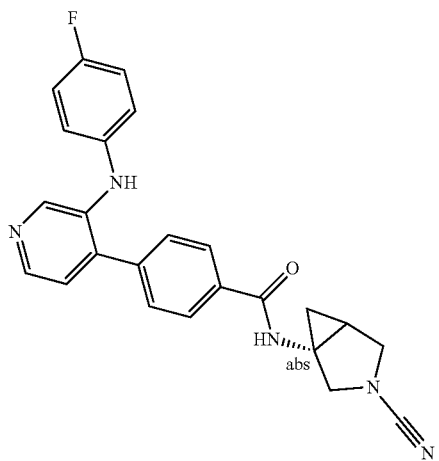 [SMILES: N#CN1CC2C[C@]2(NC(=O)c2ccc(-c3ccncc3Nc3ccc(F)cc3)cc2)C1]<br>N-((1R)-3-cyano-3-azabicyclo[3.1.0]hexan-1-yl)-4-(3-((4-fluorophenyl)amino)pyridin-4-yl)benzamide |
| 130 | 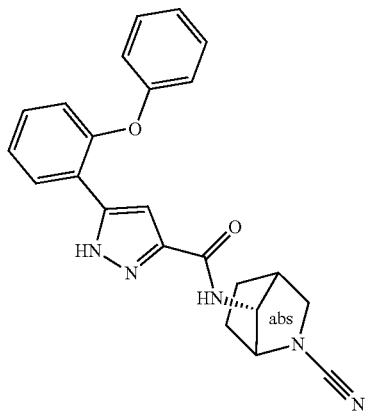 [SMILES: N#CN1CC2CCC1[C@@H]2NC(=O)c1cc(-c2ccccc2Oc2ccccc2)[nH]n1]<br>N-((7R)-2-cyano-2-azabicyclo[2.2.1]heptan-7-yl)-5-(2-phenoxyphenyl)-1H-pyrazole-3-carboxamide |

| Compound Number | Compound Structure and Chemical Name |
|---|---|
| 131 | 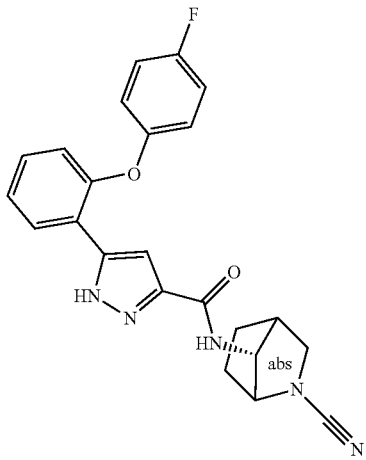 [SMILES: N#CN1CC2CCC1[C@@H]2NC(=O)c1cc(-c2ccccc2Oc2ccc(F)cc2)[nH]n1]<br>N-((7R)-2-cyano-2-azabicyclo[2.2.1]heptan-7-yl)-5-(2-(4-fluorophenoxy)phenyl)-1H-pyrazole-3-carboxamide |
| 132 | 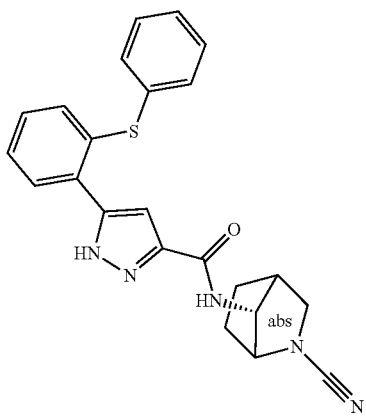 [SMILES: N#CN1CC2CCC1[C@@H]2NC(=O)c1cc(-c2ccccc2Sc2ccccc2)[nH]n1]<br>N-((7R)-2-cyano-2-azabicyclo[2.2.1]heptan-7-yl)-5-(2-(phenylthio)phenyl)-1H-pyrazole-3-carboxamide |
| 133 | 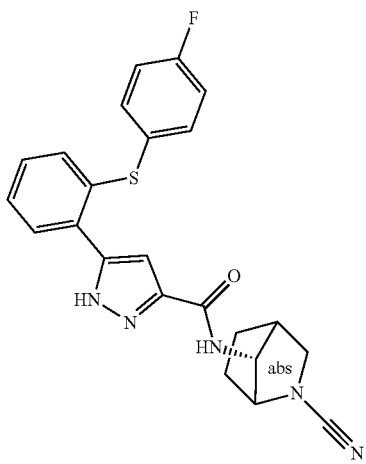<br>N-((7R)-2-cyano-2-azabicyclo[2.2.1]heptan-7-yl)-5-(2-((4-fluorophenyl)thio)phenyl)-1H-pyrazole-3-carboxamide |

| Compound Number | Compound Structure and Chemical Name |
|---|---|
| 134 | 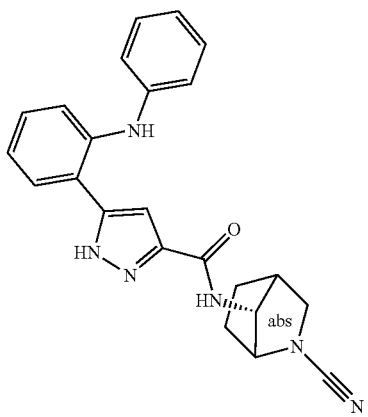 [SMILES: N#CN1CC2CCC1[C@@H]2NC(=O)c1cc(-c2ccccc2Nc2ccccc2)[nH]n1]<br>N-((7R)-2-cyano-2-azabicyclo[2.2.1]heptan-7-yl)-5-(2-(phenylamino)phenyl)-1H-pyrazole-3-carboxamide |
| 135 | 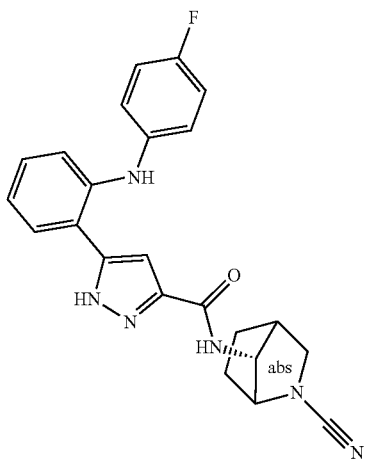 [SMILES: N#CN1CC2CCC1[C@@H]2NC(=O)c1cc(-c2ccccc2Nc2ccc(F)cc2)[nH]n1]<br>N-((7R)-2-cyano-2-azabicyclo[2.2.1]heptan-7-yl)-5-(2-((4-fluorophenyl)amino)phenyl)-1H-pyrazole-3-carboxamide |
| 136 | 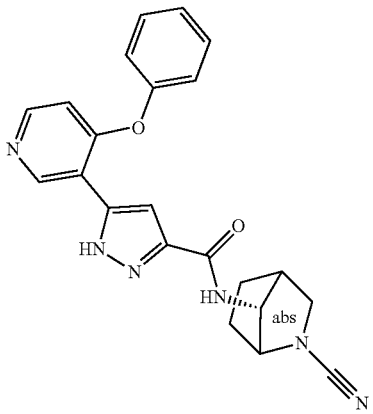 [SMILES: N#CN1CC2CCC1[C@@H]2NC(=O)c1cc(-c2cnccc2Oc2ccccc2)[nH]n1]<br>N-((7R)-2-cyano-2-azabicyclo[2.2.1]heptan-7-yl)-5-(4-phenoxypyridin-3-yl)-1H-pyrazole-3-carboxamide |

| Compound Number | Compound Structure and Chemical Name |
|---|---|
| 137 | 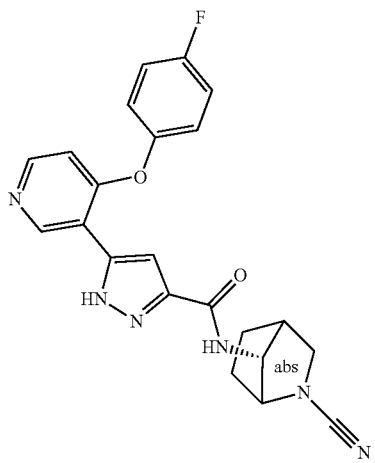 [SMILES: N#CN1CC2CCC1[C@@H]2NC(=O)c1cc(-c2cnccc2Oc2ccc(F)cc2)[nH]n1]<br>N-((7R)-2-cyano-2-azabicyclo[2.2.1]heptan-7-yl)-5-(4-(4-fluorophenoxy)pyridin-3-yl)-1H-pyrazole-3-carboxamide |
| 138 | 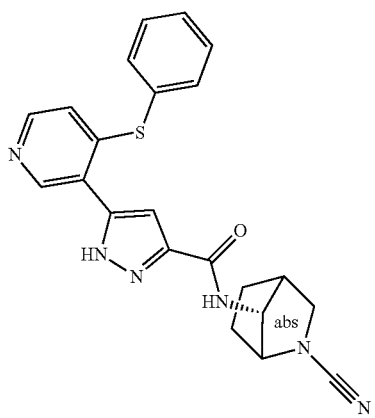 [SMILES: N#CN1CC2CCC1[C@@H]2NC(=O)c1cc(-c2cnccc2Sc2ccccc2)[nH]n1]<br>N-((7R)-2-cyano-2-azabicyclo[2.2.1]heptan-7-yl)-5-(4-(phenylthio)pyridin-3-yl)-1H-pyrazole-3-carboxamide |
| 139 | 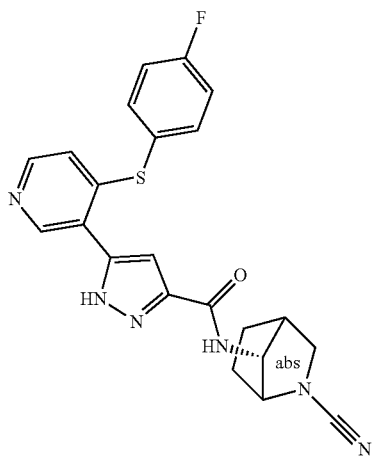 [SMILES: N#CN1CC2CCC1[C@@H]2NC(=O)c1cc(-c2cnccc2Sc2ccc(F)cc2)[nH]n1]<br>N-((7R)-2-cyano-2-azabicyclo[2.2.1]heptan-7-yl)-5-(4-((4-fluorophenyl)thio)pyridin-3-yl)-1H-pyrazole-3-carboxamide |

| Compound Number | Compound Structure and Chemical Name |
|---|---|
| 140 | 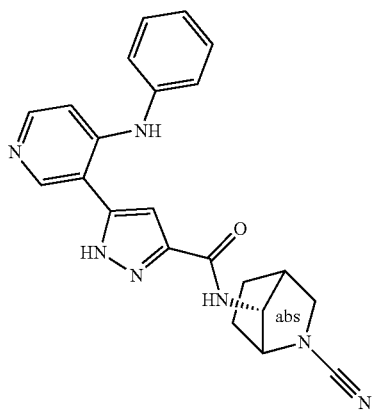 [SMILES: N#CN1CC2CCC1[C@@H]2NC(=O)c1cc(-c2cnccc2Nc2ccccc2)[nH]n1]<br>N-((7R)-2-cyano-2-azabicyclo[2.2.1]heptan-7-yl)-5-(4-(phenylamino)pyridin-3-yl)-1H-pyrazole-3-carboxamide |
| 141 | 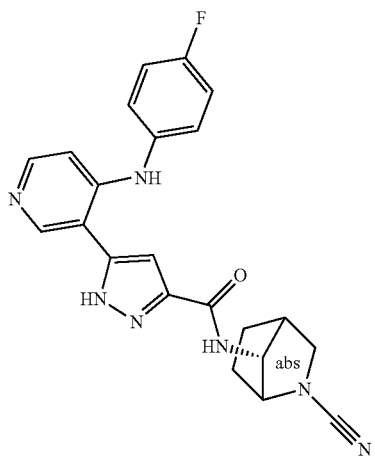 [SMILES: N#CN1CC2CCC1[C@@H]2NC(=O)c1cc(-c2cnccc2Nc2ccc(F)cc2)[nH]n1]<br>N-((7R)-2-cyano-2-azabicyclo[2.2.1]heptan-7-yl)-5-(4-((4-fluorophenyl)amino)pyridin-3-yl)-1H-pyrazole-3-carboxamide |
| 142 | 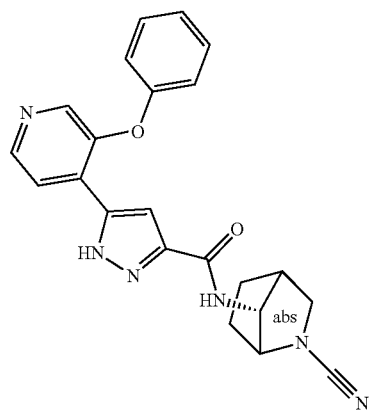<br>N-((7R)-2-cyano-2-azabicyclo[2.2.1]heptan-7-yl)-5-(3-phenoxypyridin-4-yl)-1H-pyrazole-3-carboxamide |

| Compound Number | Compound Structure and Chemical Name |
|---|---|
| 143 | 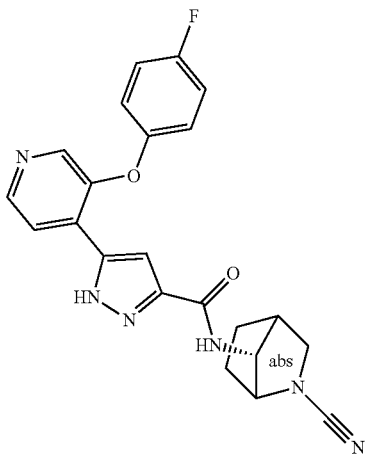 [SMILES: N#CN1CC2CCC1[C@@H]2NC(=O)c1cc(-c2ccncc2Oc2ccc(F)cc2)[nH]n1]<br>N-((7R)-2-cyano-2-azabicyclo[2.2.1]heptan-7-yl)-5-(3-(4-fluorophenoxy)pyridin-4-yl)-1H-pyrazole-3-carboxamide |
| 144 | 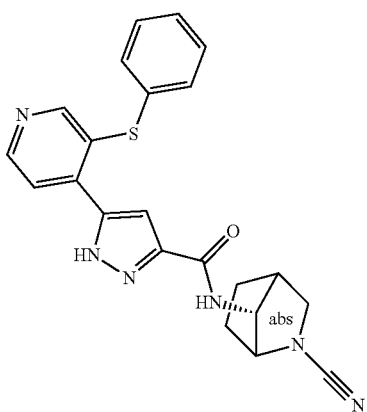 [SMILES: N#CN1CC2CCC1[C@@H]2NC(=O)c1cc(-c2ccncc2Sc2ccccc2)[nH]n1]<br>N-((7R)-2-cyano-2-azabicyclo[2.2.1]heptan-7-yl)-5-(3-(phenylthio)pyridin-4-yl)-1H-pyrazole-3-carboxamide |
| 145 | 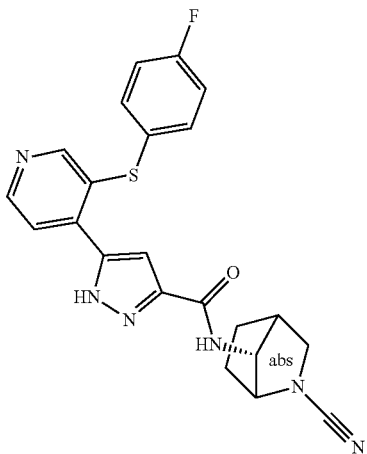<br>N-((7R)-2-cyano-2-azabicyclo[2.2.1]heptan-7-yl)-5-(3-((4-fluorophenyl)thio)pyridin-4-1)-1H-pyrazole-3-carboxamide |

| Compound Number | Compound Structure and Chemical Name |
|---|---|
| 146 | 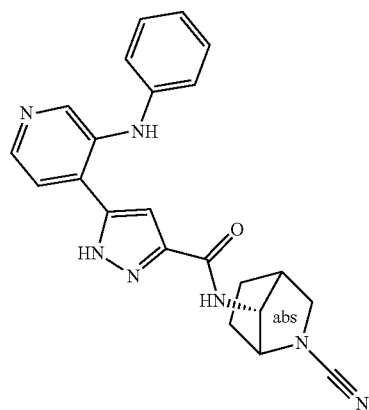 [SMILES: N#CN1CC2CCC1[C@@H]2NC(=O)c1cc(-c2ccncc2Nc2ccccc2)[nH]n1]<br>N-((7R)-2-cyano-2-azabicyclo[2.2.1]heptan-7-yl)-5-(3-(phenylamino)pyridin-4-yl)-1H-pyrazole-3-carboxamide |
| 147 | 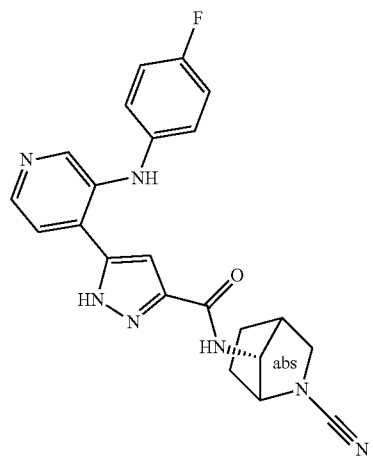 [SMILES: N#CN1CC2CCC1[C@@H]2NC(=O)c1cc(-c2ccncc2Nc2ccc(F)cc2)[nH]n1]<br>N-((7R)-2-cyano-2-azabicyclo[2.2.1]heptan-7-yl)-5-(3-((4-fluorophenyl)amino)pyridin-4-yl)-1H-pyrazole-3-carboxamide |
| 148 | 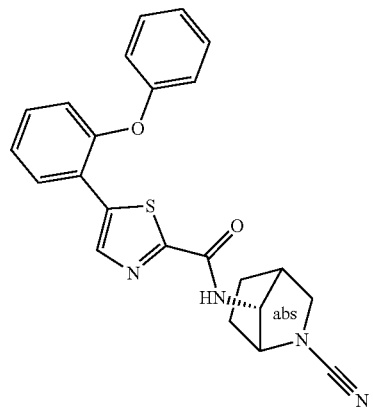 [SMILES: N#CN1CC2CCC1[C@@H]2NC(=O)c1ncc(-c2ccccc2Oc2ccccc2)s1]<br>N-((7R)-2-cyano-2-azabicyclo[2.2.1]heptan-7-yl)-5-(2-phenoxyphenyl)thiazole-2-carboxamide |

| Compound Number | Compound Structure and Chemical Name |
|---|---|
| 149 | 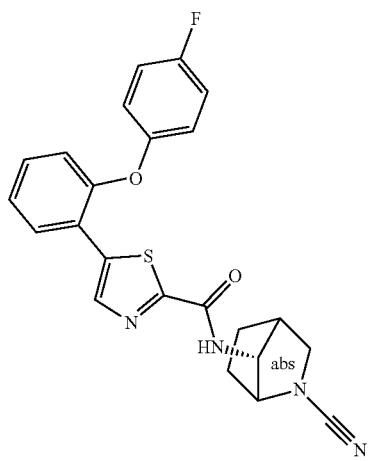 [SMILES: N#CN1CC2CCC1[C@@H]2NC(=O)c1ncc(-c2ccccc2Oc2ccc(F)cc2)s1]<br>N-((7R)-2-cyano-2-azabicyclo[2.2.1]heptan-7-yl)-5-(2-(4-fluorophenoxy)phenyl)thiazole-2-carboxamide |
| 150 | 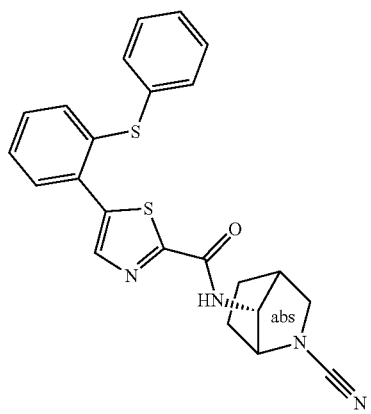<br>N-((7R)-2-cyano-2-azabicyclo[2.2.1]heptan-7-yl)-5-(2-(phenylthio)phenyl)thiazole-2-carboxamide |
| 151 | 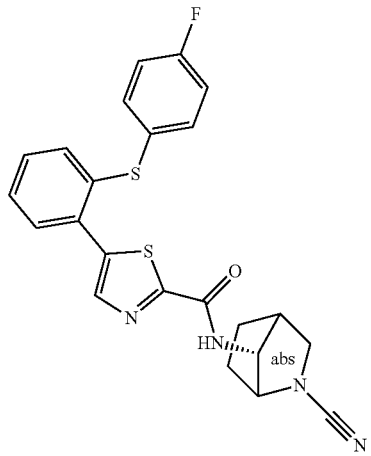 [SMILES: N#CN1CC2CCC1[C@@H]2NC(=O)c1ncc(-c2ccccc2Sc2ccc(F)cc2)s1]<br>N-((7R)-2-cyano-2-azabicyclo[2.2.1]heptan-7-yl)-5-(2-((4-fluorophenyl)thio)phenyl)thiazole-2-carboxamide |

| Compound Number | Compound Structure and Chemical Name |
|---|---|
| 152 | 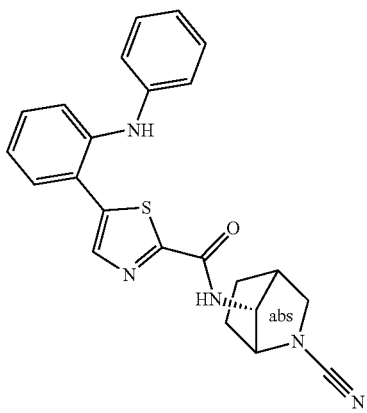 [SMILES: N#CN1CC2CCC1[C@@H]2NC(=O)c1ncc(-c2ccccc2Nc2ccccc2)s1]<br>N-((7R)-2-cyano-2-azabicyclo[2.2.1]heptan-7-yl)-5-(2-(phenylamino)phenyl)thiazole-2-carboxamide |
| 153 | 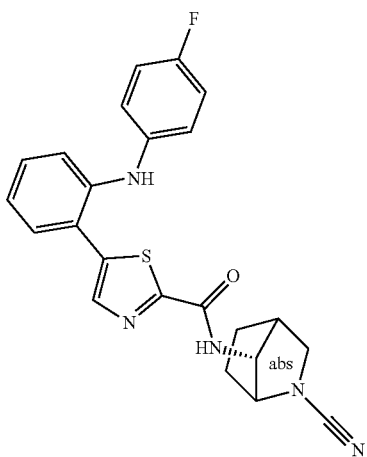 [SMILES: N#CN1CC2CCC1[C@@H]2NC(=O)c1ncc(-c2ccccc2Nc2ccc(F)cc2)s1]<br>N-((7R)-2-cyano-2-azabicyclo[2.2.1]heptan-7-yl)-5-(2-((4-fluorophenyl)amino)phenyl)thiazole-2-carboxamide |
| 154 | 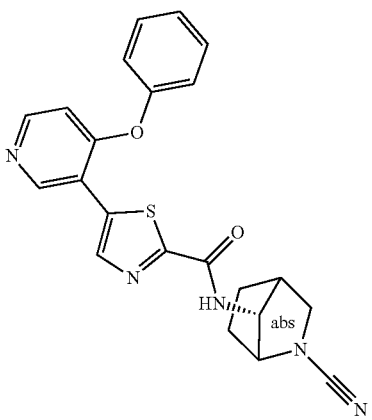 [SMILES: N#CN1CC2CCC1[C@@H]2NC(=O)c1ncc(-c2cnccc2Oc2ccccc2)s1]<br>N-((7R)-2-cyano-2-azabicyclo[2.2.1]heptan-7-yl)-5-(4-phenoxypyridin-3-yl)thiazole-2-carboxamide |

-continued
| Compound Number | Compound Structure and Chemical Name |
|---|---|
| 155 | 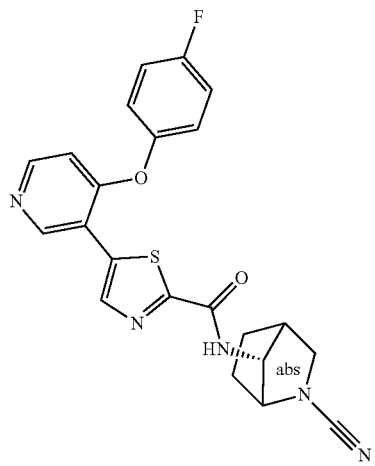 [SMILES: N#CN1CC2CCC1[C@@H]2NC(=O)c1ncc(-c2cnccc2Oc2ccc(F)cc2)s1]<br>N-((7R)-2-cyano-2-azabicyclo[2.2.1]heptan-7-yl)-5-(4-(4-fluorophenoxy)pyridin-3-yl)thiazole-2-carboxamide |
| 156 | 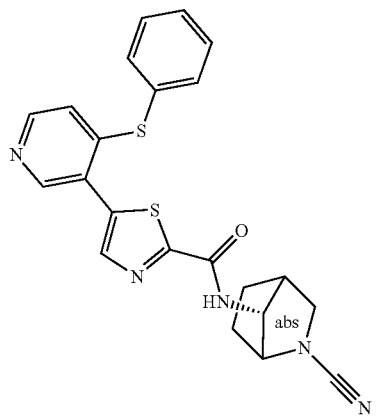<br>N-((7R)-2-cyano-2-azabicyclo[2.2.1]heptan-7-yl)-5-(4-(phenylthio)pyridin-3-yl)thiazole-2-carboxamide |
| 157 | 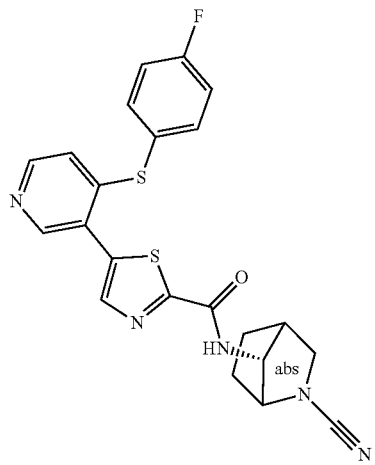<br>N-((7R)-2-cyano-2-azabicyclo[2.2.1]heptan-7-yl)-5-(4-((4-fluorophenyl)thio)pyridin-3-yl)thiazole-2-carboxamide |

| Compound Number | Compound Structure and Chemical Name |
|---|---|
| 158 | 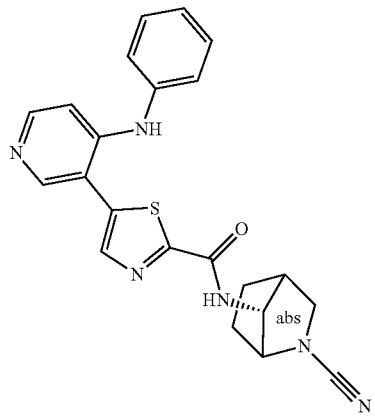<br>N-((7R)-2-cyano-2-azabicyclo[2.2.1]heptan-7-yl)-5-(4-(phenylamino)pyridin-3-yl)thiazole-2-carboxamide |
| 159 | 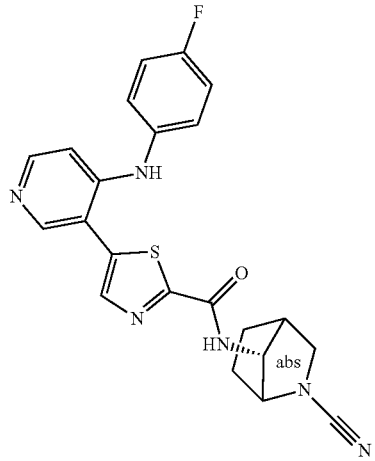 [SMILES: N#CN1CC2CCC1[C@@H]2NC(=O)c1ncc(-c2cnccc2Nc2ccc(F)cc2)s1]<br>N-((7R)-2-cyano-2-azabicyclo[2.2.1]heptan-7-yl)-5-(4-((4-fluorophenyl)amino)pyridin-3-yl)thiazole-2-carboxamide |
| 160 | 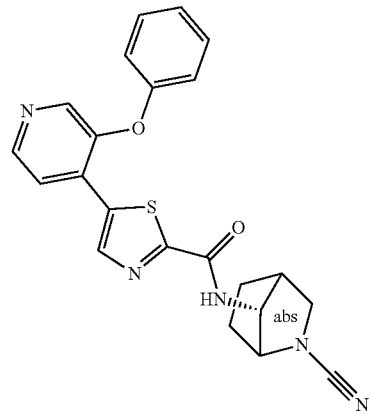 [SMILES: N#CN1CC2CCC1[C@@H]2NC(=O)c1ncc(-c2ccncc2Oc2ccccc2)s1]<br>N-((7R)-2-cyano-2-azabicyclo[2.2.1]heptan-7-yl)-5-(3-phenoxypyridin-4-yl)thiazole-2-carboxamide |

| Compound Number | Compound Structure and Chemical Name |
|---|---|
| 161 | 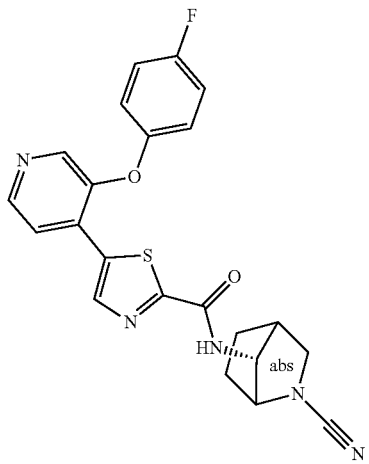 [SMILES: N#CN1CC2CCC1[C@@H]2NC(=O)c1ncc(-c2ccncc2Oc2ccc(F)cc2)s1]<br>N-((7R)-2-cyano-2-azabicyclo[2.2.1]heptan-7-yl)-5-(3-(4-fluorophenoxy)pyridin-4-yl)thiazole-2-carboxamide |
| 162 | 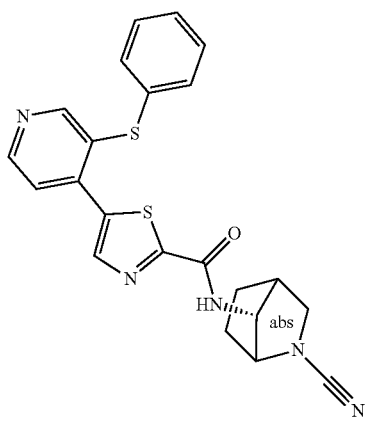<br>N-((7R)-2-cyano-2-azabicyclo[2.2.1]heptan-7-yl)-5-(3-(phenylthio)pyridin-4-yl)thiazole-2-carboxamide |
| 163 | 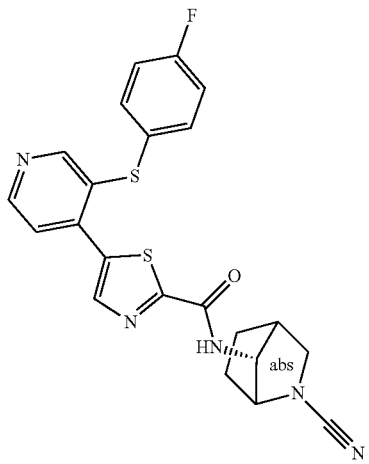 [SMILES: N#CN1CC2CCC1[C@@H]2NC(=O)c1ncc(-c2ccncc2Sc2ccc(F)cc2)s1]<br>N-((7R)-2-cyano-2-azabicyclo[2.2.1]heptan-7-yl)-5-(3-((4-fluorophenyl)thio)pyridin-4-yl)thiazole-2-carboxamide |

| Compound Number | Compound Structure and Chemical Name |
|---|---|
| 164 | 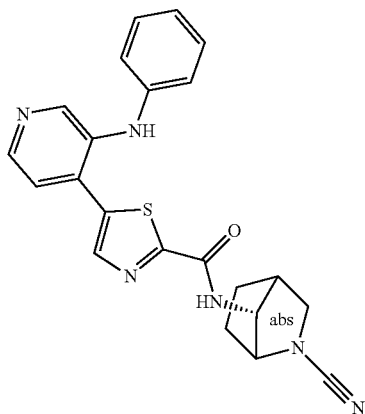 [SMILES: N#CN1CC2CCC1[C@@H]2NC(=O)c1ncc(-c2ccncc2Nc2ccccc2)s1]<br>N-((7R)-2-cyano-2-azabicyclo[2.2.1]heptan-7-yl)-5-(3-(phenylamino)pyridin-4-yl)thiazole-2-carboxamide |
| 165 | 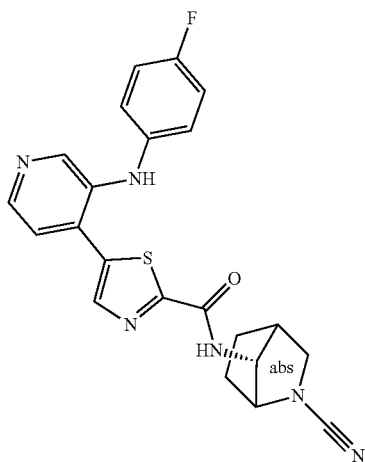 [SMILES: N#CN1CC2CCC1[C@@H]2NC(=O)c1ncc(-c2ccncc2Nc2ccc(F)cc2)s1]<br>N-((7R)-2-cyano-2-azabicyclo[2.2.1]heptan-7-yl)-5-(3-((4-fluorophenyl)amino)pyridin-4-yl)thiazole-2-carboxamide |
| 166 | 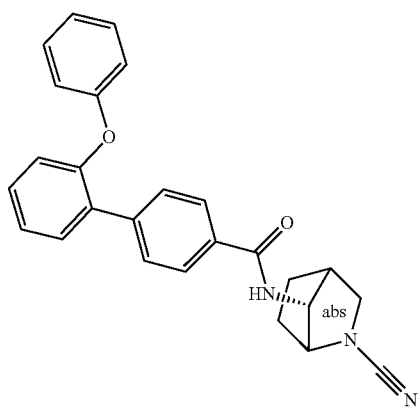<br>N-((7R)-2-cyano-2-azabicyclo[2.2.1]heptan-7-yl)-2'-phenoxy-[1,1'-biphenyl]-4-carboxamide |

| Compound Number | Compound Structure and Chemical Name |
|---|---|
| 167 | 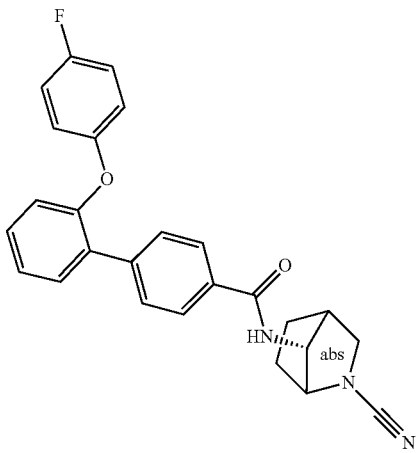 [SMILES: N#CN1CC2CCC1[C@@H]2NC(=O)c1ccc(-c2ccccc2Oc2ccc(F)cc2)cc1]<br>N-((7R)-2-cyano-2-azabicyclo[2.2.1]heptan-7-yl)-2'-(4-fluorophenoxy)-[1,1'-biphenyl]-4-carboxamide |
| 168 | 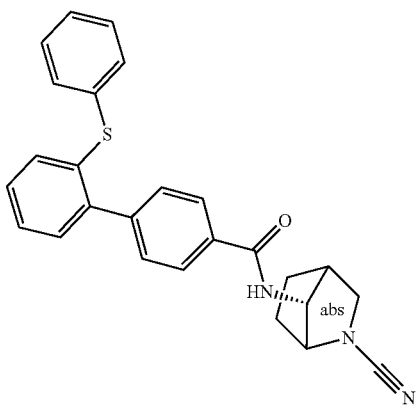 [SMILES: N#CN1CC2CCC1[C@@H]2NC(=O)c1ccc(-c2ccccc2Sc2ccccc2)cc1]<br>N-((7R)-2-cyano-2-azabicyclo[2.2.1]heptan-7-yl)-2'-(phenylthio)-[1,1'-biphenyl]-4-carboxamide |
| 169 | 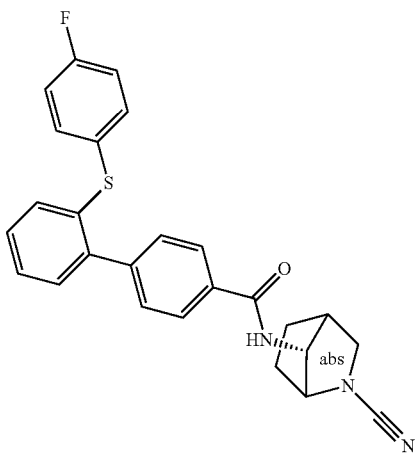 [SMILES: N#CN1CC2CCC1[C@@H]2NC(=O)c1ccc(-c2ccccc2Sc2ccc(F)cc2)cc1]<br>N-((7R)-2-cyano-2-azabicyclo[2.2.1]heptan-7-yl)-2'-(4-fluorophenyl)thio)-[1,1'-biphenyl]-4-carboxamide |

| Compound Number | Compound Structure and Chemical Name |
|---|---|
| 170 | 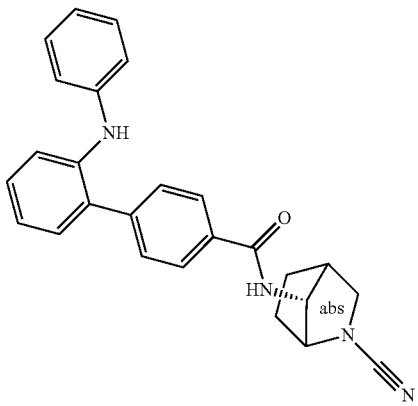 [SMILES: N#CN1CC2CCC1[C@@H]2NC(=O)c1ccc(-c2ccccc2Nc2ccccc2)cc1]<br>N-((7R)-2-cyano-2-azabicyclo[2.2.1]heptan-7-yl)-2'-(phenylamino)-[1,1'-biphenyl]-4-carboxamide |
| 171 | 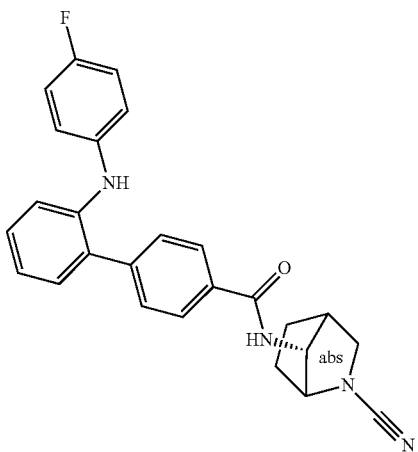 [SMILES: N#CN1CC2CCC1[C@@H]2NC(=O)c1ccc(-c2ccccc2Nc2ccc(F)cc2)cc1]<br>N-((7R)-2-cyano-2-azabicyclo[2.2.1]heptan-7-yl)-2'-(4-fluorophenyl)amino)-[1,1'-biphenyl]-4-carboxamide |
| 172 | 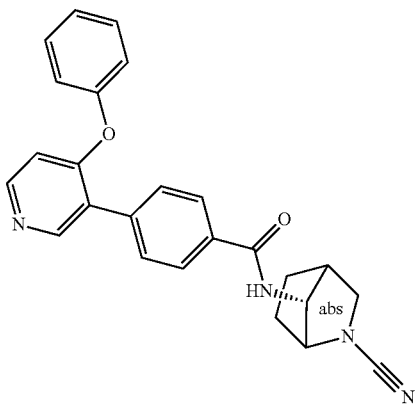 [SMILES: N#CN1CC2CCC1[C@@H]2NC(=O)c1ccc(-c2cnccc2Sc2ccccc2)cc1]<br>N-((7R)-2-cyano-2-azabicyclo[2.2.1]heptan-7-yl)-4-(4-phenoxypyridin-3-yl)benzamide |

-continued
| Compound Number | Compound Structure and Chemical Name |
|---|---|
| 173 | 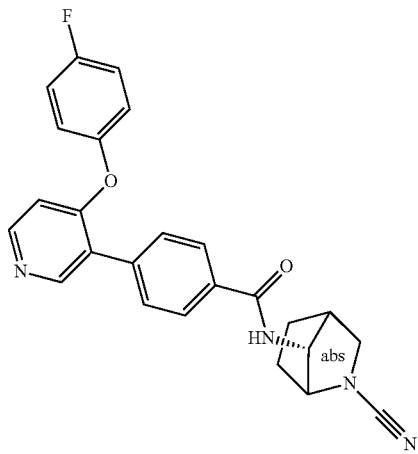 [SMILES: N#CN1CC2CCC1[C@@H]2NC(=O)c1ccc(-c2cnccc2Sc2ccc(F)cc2)cc1]<br>N-((7R)-2-cyano-2-azabicyclo[2.2.1]heptan-7-yl)-4-(4-(4-fluorophenoxy)pyridin-3-yl)benzamide |
| 174 | 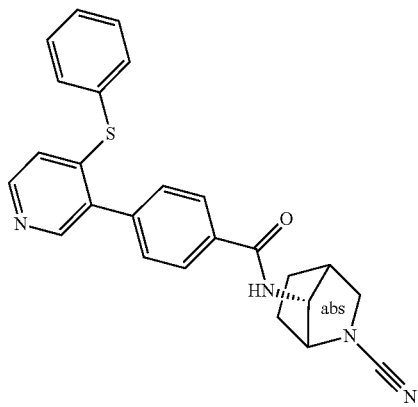<br>N-((7R)-2-cyano-2-azabicyclo[2.2.1]heptan-7-yl)-4-(4-(phenylthio)pyridin-3-yl)benzamide |
| 175 | 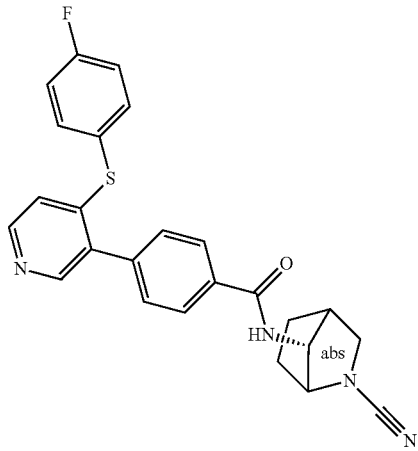<br>N-((7R)-2-cyano-2-azabicyclo[2.2.1]heptan-7-yl)-4-(4-((4-fluorophenyl)thio)pyridin-3-yl)benzamide |

| Compound Number | Compound Structure and Chemical Name |
|---|---|
| 176 | 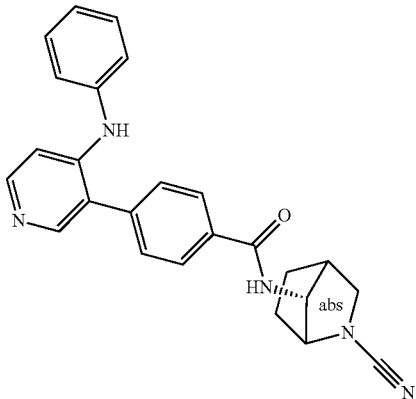 [SMILES: N#CN1CC2CCC1[C@@H]2NC(=O)c1ccc(-c2cnccc2Nc2ccccc2)cc1]<br>N-((7R)-2-cyano-2-azabicyclo[2.2.1]heptan-7-yl)-4-(4-(phenylamino)pyridin-3-yl)benzamide |
| 177 | 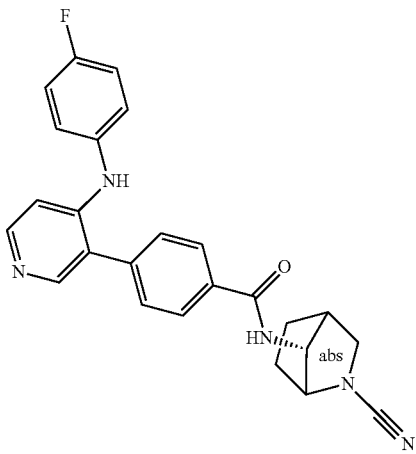 [SMILES: N#CN1CC2CCC1[C@@H]2NC(=O)c1ccc(-c2cnccc2Nc2ccc(F)cc2)cc1]<br>N-((7R)-2-cyano-2-azabicyclo[2.2.1]heptan-7-yl)-4-(4-((4-fluorophenyl)amino)pyridin-3-yl)benzamide |
| 178 | 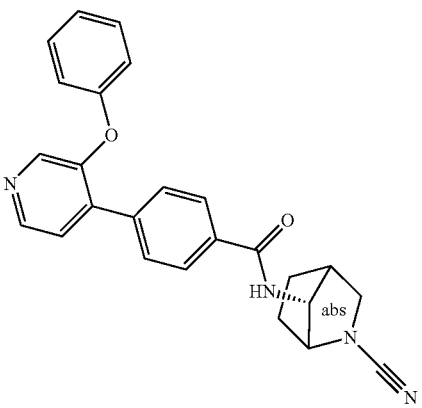 [SMILES: N#CN1CC2CCC1[C@@H]2NC(=O)c1ccc(-c2ccncc2Oc2ccccc2)cc1]<br>N-((7R)-2-cyano-2-azabicyclo[2.2.1]heptan-7-yl)-4-(3-phenoxypyridin-4-yl)benzamide |

| Compound Number | Compound Structure and Chemical Name |
|---|---|
| 179 | 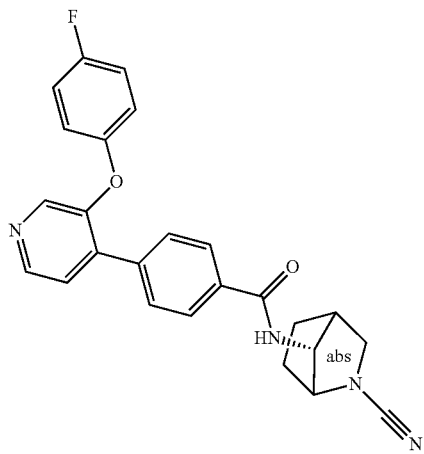 [SMILES: N#CN1CC2CCC1[C@@H]2NC(=O)c1ccc(-c2ccncc2Oc2ccc(F)cc2)cc1]<br>N-((7R)-2-cyano-2-azabicyclo[2.2.1]heptan-7-yl)-4-(3-(4-fluorophenoxy)pyridin-4-yl)benzamide |
| 180 | 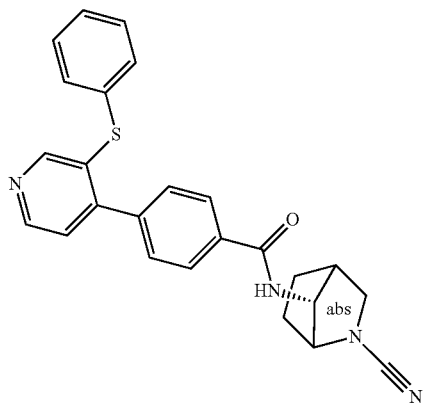<br>N-((7R)-2-cyano-2-azabicyclo[2.2.1]heptan-7-yl)-4-(3-(phenylthio)pyridin-4-yl)benzamide |
| 181 | 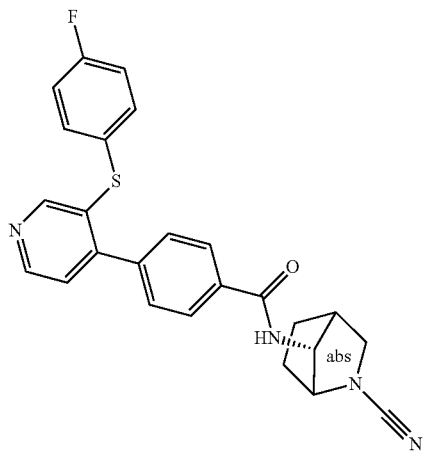<br>N-((7R)-2-cyano-2-azabicyclo[2.2.1]heptan-7-yl)-4-(3-((4-fluorophenyl)thio)pyridin-4-yl)benzamide |

| Compound Number | Compound Structure and Chemical Name |
|---|---|
| 182 | 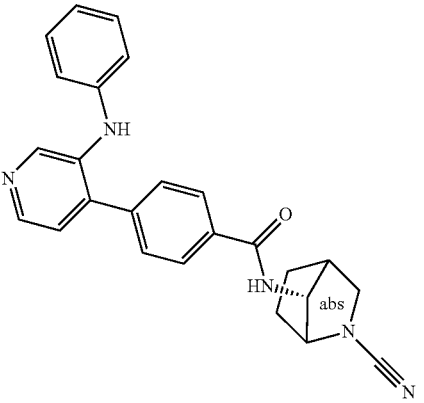 [SMILES: N#CN1CC2CCC1[C@@H]2NC(=O)c1ccc(-c2ccncc2Nc2ccccc2)cc1]<br>N-((7R)-2-cyano-2-azabicyclo[2.2.1]heptan-7-yl)-4-(3-(phenylamino)pyridin-4-yl)benzamide |
| 183 | 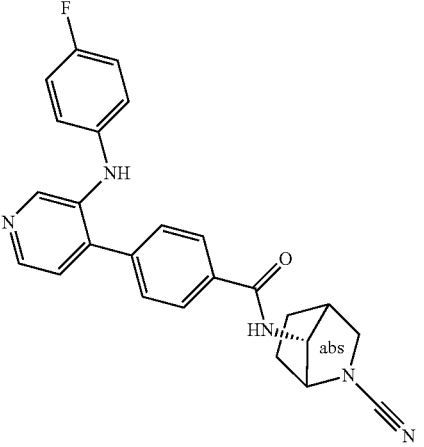 [SMILES: N#CN1CC2CCC1[C@@H]2NC(=O)c1ccc(-c2ccncc2Nc2ccc(F)cc2)cc1]<br>N-((7R)-2-cyano-2-azabicyclo[2.2.1]heptan-7-yl)-4-(3-((4-fluorophenyl)amino)pyridin-4-yl)benzamide. |
21. A pharmaceutical composition comprising the compound of claim 1, or a pharmaceutically acceptable salt thereof, and a pharmaceutically acceptable carrier.
* * * * *

UNITED STATES PATENT AND TRADEMARK OFFICE
CERTIFICATE OF CORRECTION

PATENT NO. : 11,535,618 B2  Page 1 of 5
APPLICATION NO. : 17/282521
DATED : December 27, 2022
INVENTOR(S) : Alex J. Buckmelter et al.

It is certified that error appears in the above-identified patent and that said Letters Patent is hereby corrected as shown below:

In the Specification

In Column 188, beginning around Line 20 and ending around Line 40, please delete the structure:

"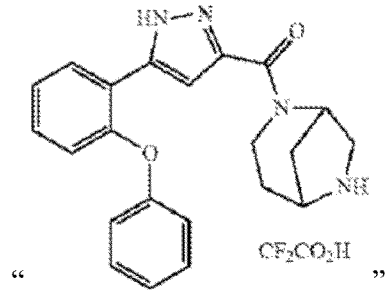"

And insert the structure:

--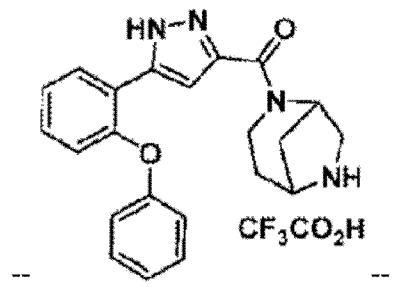--

Signed and Sealed this
Eighteenth Day of April, 2023

Katherine Kelly Vidal
*Director of the United States Patent and Trademark Office*

CERTIFICATE OF CORRECTION (continued)
U.S. Pat. No. 11,535,618 B2

In Column 205, beginning around Line 45 and ending around Line 60, please delete the structure:

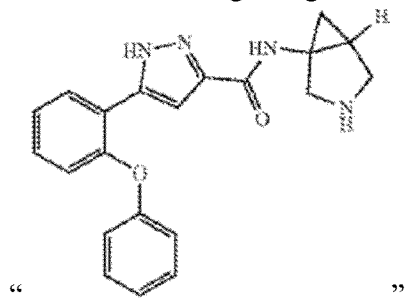

" "

And insert the structure:

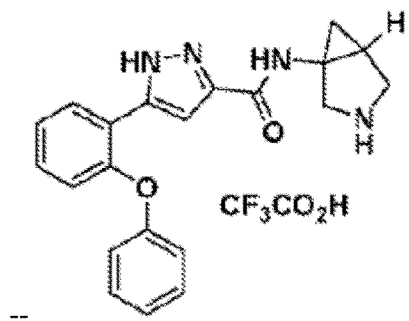

-- --

In Column 207, beginning at Line 1 and ending around Line 15, please delete the structure:

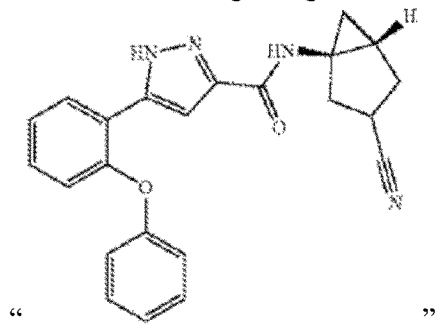

" "

And insert the structure:

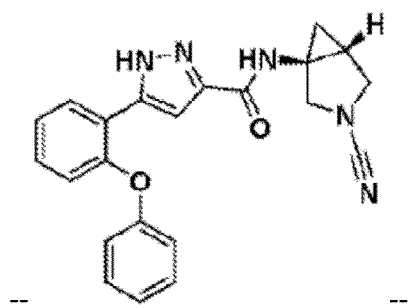

-- --

CERTIFICATE OF CORRECTION (continued)
U.S. Pat. No. 11,535,618 B2

In Column 208, beginning at the Line 1 and ending around Line 15, please delete the structure:

"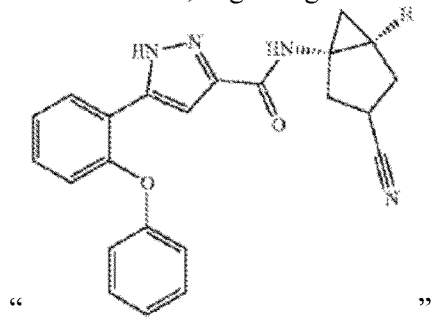"

And insert the structure:

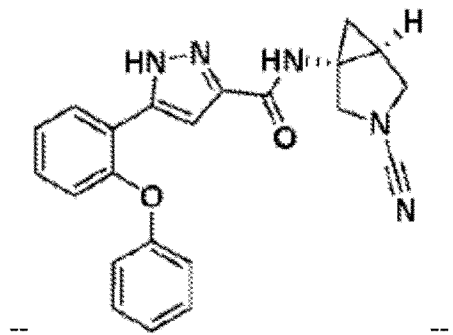

-- --

In the Claims

In Claim 1, Column 212, beginning at Line 22 and ending at Line 23, please delete:
"-$C_{1-6}$ alkylene-$NR^{10}NR^{11}$"
And insert:
-- -$C_{1-6}$ alkylene-$NR^{10}R^{11}$ --

In Claim 20, Column 221, third structure, please delete:

"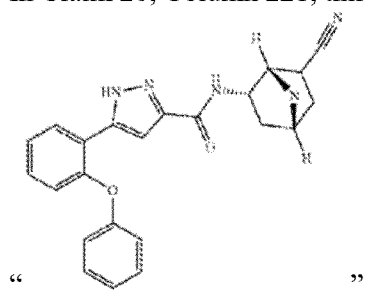"

And insert:

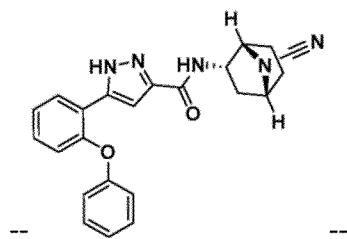

-- --

In Claim 20, Column 223, first structure, please delete:

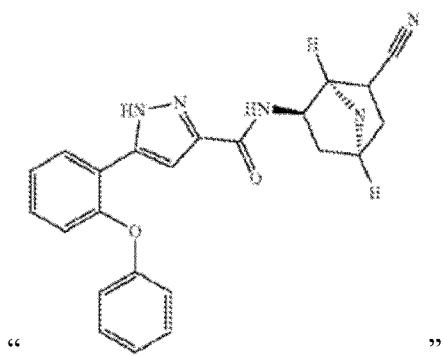
"                    "
And insert:
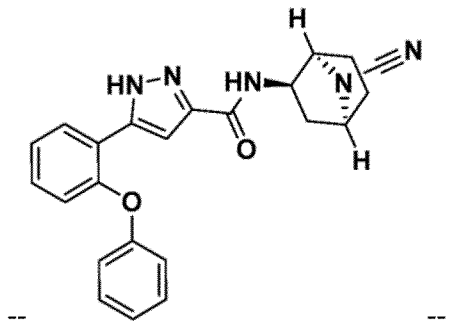
--                    --
In Claim 20, Column 227, second structure, please delete:
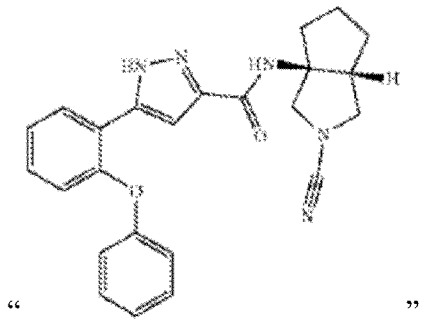
"                    "
And insert:
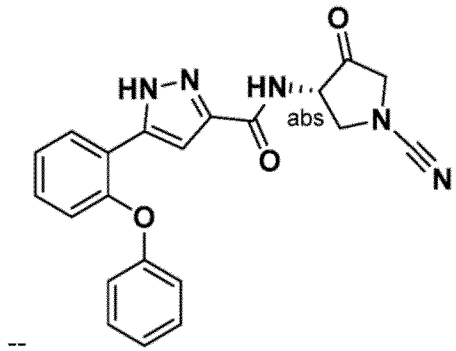
--                    --
In Claim 20, Column 249, second structure, please delete:

CERTIFICATE OF CORRECTION (continued)
U.S. Pat. No. 11,535,618 B2

Page 5 of 5

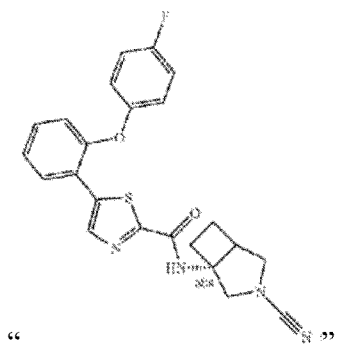

"

And insert:

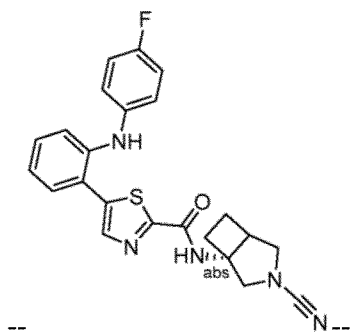

--

In Claim 20, Column 285, last structure, please delete:

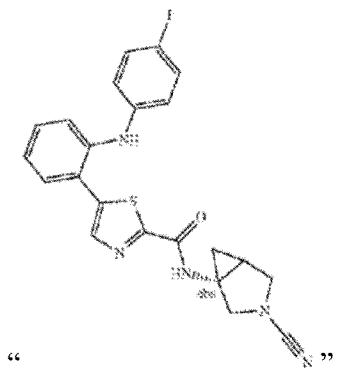

"

And insert:

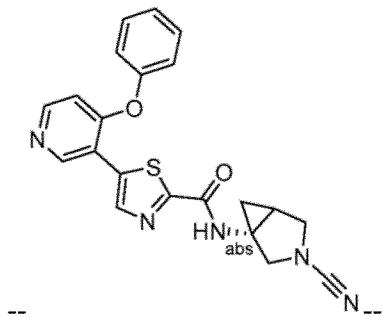

--